United States Patent
Buettelmann et al.

(10) Patent No.: US 10,435,407 B2
(45) Date of Patent: Oct. 8, 2019

(54) TRIAZA-SPIRODECANONES AS DDR1 INHIBITORS

(71) Applicant: Hoffmann-La Roche Inc., Little Falls, NJ (US)

(72) Inventors: Bernd Buettelmann, Basel (CH); Buelent Kocer, Basel (CH); Bernd Kuhn, Basel (CH); Marco Prunotto, Basel (CH); Hans Richter, Basel (CH); Martin Ritter, Basel (CH); Markus Rudolph, Basel (CH); Alexander Lee Satz, Basel (CH)

(73) Assignee: Hoffmann-La Roche Inc., Little Falls, NY (US)

(*) Notice: Subject to any disclaimer, the term of this patent is extended or adjusted under 35 U.S.C. 154(b) by 0 days.

(21) Appl. No.: 16/266,782

(22) Filed: Feb. 4, 2019

(65) Prior Publication Data

US 2019/0169189 A1  Jun. 6, 2019

Related U.S. Application Data

(60) Division of application No. 15/850,826, filed on Dec. 21, 2017, now Pat. No. 10,239,876, which is a continuation of application No. PCT/EP2016/065231, filed on Jun. 30, 2016.

(30) Foreign Application Priority Data

Jul. 3, 2015 (EP) .................................. 15175259.9

(51) Int. Cl.
| | | |
|---|---|---|
| C07D 471/10 | (2006.01) |
| A61P 35/00 | (2006.01) |
| A61P 13/12 | (2006.01) |
| A61P 37/06 | (2006.01) |
| A61P 9/00 | (2006.01) |
| A61P 1/16 | (2006.01) |
| C07D 519/00 | (2006.01) |

(52) U.S. Cl.
CPC .............. *C07D 471/10* (2013.01); *A61P 1/16* (2018.01); *A61P 9/00* (2018.01); *A61P 13/12* (2018.01); *A61P 35/00* (2018.01); *A61P 37/06* (2018.01); *C07D 519/00* (2013.01)

(58) Field of Classification Search
CPC ...................................................... C07D 471/10
USPC ............................................. 546/20; 514/278
See application file for complete search history.

(56) References Cited

U.S. PATENT DOCUMENTS

| | | | |
|---|---|---|---|
| 3,839,340 A | 10/1974 | Scharpf et al. | |
| 3,839,342 A | 10/1974 | Scharpf et al. | |
| 4,329,353 A | 5/1982 | Stokbroekx et al. | |
| 5,635,510 A | 6/1997 | Burkholder et al. | |
| 6,326,379 B1 * | 12/2001 | Macor ................. | C07D 471/04 514/212.08 |

FOREIGN PATENT DOCUMENTS

| | | |
|---|---|---|
| EP | 0 921 125 A1 | 6/1999 |
| EP | 1 329 451 A1 | 7/2003 |
| WO | 99/65494 A1 | 12/1999 |
| WO | 01 94346 A1 | 12/2001 |
| WO | 2007/039438 A1 | 4/2007 |
| WO | 2010/037081 A1 | 4/2010 |
| WO | 2011/160084 A1 | 12/2011 |

OTHER PUBLICATIONS

ISR and Written Opinion of PCT/EP2016/065231, dated as of actual completion of the international search dated Aug. 1, 2016.

* cited by examiner

*Primary Examiner* — Patricia L Morris
(74) *Attorney, Agent, or Firm* — Brian L. Buckwalter

(57) ABSTRACT

The present invention relates to compounds of formula (I):

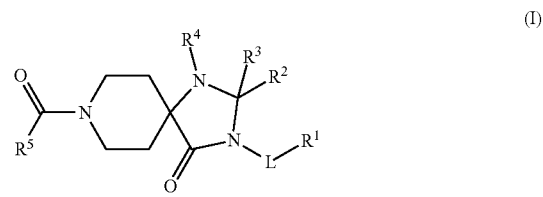

or pharmaceutically acceptable salts thereof, wherein L and $R^1$ to $R^5$ are as described herein, as well as processes for their manufacture, pharmaceutical compositions comprising them, and their use as medicaments.

23 Claims, No Drawings

TRIAZA-SPIRODECANONES AS DDR1 INHIBITORS

CROSS REFERENCE TO RELATED APPLICATIONS

This application is a divisional application of U.S. application Ser. No. 15/850,826 having a filing date of Dec. 21, 2017 and which claims the benefit of priority to International Application No. PCT/EP2016/065231 having an international filing date of Jun. 30, 2016 which is a continuation of and which claims benefit under 35 U.S.C. § 119 to European Patent Application No. 15175259.9 having an international filing date of Jul. 3, 2015. The entire contents of each are incorporated herein by reference.

FIELD OF THE INVENTION

The present invention relates to a compound of formula (I): or a pharmaceutically

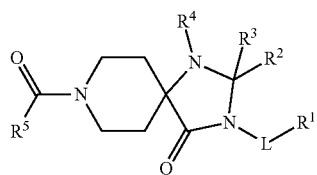

acceptable salt thereof, wherein L, $R^1$ to $R^5$ are as described herein, as well as processes for their manufacture, pharmaceutical compositions comprising them, and their use as medicaments.

BACKGROUND OF THE INVENTION

Discoidin Domain Receptors (DDRs) are type I transmembrane glycoproteins, which are represented by two receptors DDR1 and DDR2. DDR1 is mainly expressed in epithelial cells and DDR2 in stroma. The DDR1 subfamily includes five isoforms generated by alternative splicing with DDR1a and DDR1b as the most common isoforms and DDR1d and DDR1e being either truncated or inactive kinases, respectively. A single protein represents the DDR2 subtype. DDR1 is a collagen-activated receptor tyrosine kinase (RTK). DDR1 is widely expressed during embryonic development and in adult tissues, particularly in epithelia of skin, lung, liver, kidney, gut, colon and brain. Among the collagen-receptor families, the DDRs are the only RTKs that undergo autophosphorylation in response to various collagens.

Structurally, the ectodomain of DDRs is composed of a discoidin (DS) domain, a DS-like domain, and an extracellular juxtamembrane (EJXM) region, which are followed by a single-pass transmembrane segment. The intracellular portion of the receptor is composed of a relatively long intracellular juxtamembrane (UXM) region and a C-terminal kinase domain (KD). DDRs display an atypical activation kinetics manifested by a slow and sustained phosphorylation, which suggests a unique mechanism of receptor activation that differentiates DDRs from other members of the RTK family. DDRs initiate signaling pathways that are critical for cell-collagen interactions and thus play key roles in many physiological and pathological conditions involving collagen remodeling [Leitinger, B., *Discoidin domain receptor functions in physiological and pathological conditions. International review of cell and molecular biology*, 2014. 310: p. 39-87; Hohenester, E., *Signaling complexes at the cell-matrix interface. Current opinion in structural biology*, 2014. 29C: p. 10-16].

Some light on the physiological function of DDR1 can be indirectly deduced by the DDR1-knockout mouse phenotype [Vogel, W. F., et al., *Discoidin domain receptor 1 tyrosine kinase has an essential role in mammary gland development. Molecular and cellular biology*, 2001. 21(8): p. 2906-17]. DDR1-knockout mice survived gestation but are smaller in size than control littermates showing defects in the development of certain organs, such as impaired mammary gland development, poorly calcified fibula bone, and a narrower pelvis. In addition to the above defects present in DDR1-knockout mice, mutant females are unable to lactate because of the failure of alveolar epithelium to secrete milk proteins. DDR1-null female mice during pregnancy showed hyperproliferation and aberrant differentiation of lobulo-alveolar epithelial cells. At birth, the alveoli showed intracellular lipid production and deposition but failure to secrete milk into the central lumen. In the early pubertal stage, the mammary gland development defect was manifest as a delay in mammary duct outgrowth, enlargement in primary ducts, and the terminal end buds due to a marked increase in cell proliferation rate in the mutant mice. In addition, a substantial deposition of collagen was shown in and around mammary gland epithelial cells in DDR1-knockout mice.

The DDR1-knockout adult mice exhibit proteinuria and urinary acanthocytes. Results from electron microscopy demonstrate thickening of subepithelial glomerular basement membrane as well as a focal loss of the podocyte slit diaphragms. These data suggest that the loss of cell-matrix communication in DDR1-deficient podocytes appears to result in excess accumulation of basement membrane proteins, which leads to disturbed anchorage of foot processes and disruption of the slit diaphragm. In other words, the interaction between type IV collagen and DDR1 plays an important role in maintaining the structural integrity of the glomerular basement membrane [Gross, O., et al., *DDR1-deficient mice show localized subepithelial GBM thickening with focal loss of slit diaphragms and proteinuria. Kidney International*, 2004. 66(1): p. 102-11].

Despite some of the developmental defects found in DDR1-null mice, these mice have been valuable in understating the role of these receptors in various diseases, including cancer, atherosclerosis, lung and liver fibrosis, renal injury, and osteoarthritis.

Many cancers are characterized by dysregulated kinome expression and activation. DDRs play a key role in cancer progression and metastatisation processes, in part by regulating the interaction of cancer cells with collagens [Valiathan, R. R., et al., *Discoidin domain receptor tyrosine kinases: new players in cancer progression. Cancer metastasis reviews*, 2012. 31(1-2): p. 295-321]. Both DDRs are overexpressed in a large number of different types of cancer, ranging from lung, breast, brain, esophagus, head and neck, liver, and prostate cancers to lymphomas and leukemias. Dysregulated DDR expression has been shown in a number of studies to correlate with unfavorable outcomes for patients and altered functions of DDR1 and DDR2 likely contribute to tumorigenesis. Moreover, DDR1 can confer resistance to chemotherapy and mediate prosurvival signals in breast cancer and lymphoma cell lines [Cader, F. Z., et al., *The EBV oncogene LMP1 protects lymphoma cells from cell death through the collagen-mediated activation of DDR1.*

*Blood*, 2013, 122(26): p. 4237-45; Ongusaha, P. P., et al., *p53 induction and activation of DDR1 kinase counteract p53-mediated apoptosis and influence p53 regulation through a positive feedback loop. The EMBO journal*, 2003. 22(6): p. 1289-301] and may be involved in the recurrence of certain types of cancer [Dian, Z. X., et al., *Involvement of discoidin domain 1 receptor in recurrence of hepatocellular carcinoma by genome-wide analysis. Medical oncology*, 2012. 29(5): p. 3077-82]. However, the molecular mechanisms underlying the roles of the DDRs in various steps of cancer progression are largely undefined.

Screening of non-small cell lung carcinoma (NSCLC) tissue samples showed that DDR1 is significantly upregulated in these patients and that expression of DDR1 is significantly associated with overall and disease-free survival. Multivariate analysis revealed that expression of DDR1 is independent of tumor differentiation, stage, histology, and patient age. A screening for DDR mutations revealed one polymorphism with synonymous change at S495, unlikely to be of functional importance [Ford, C. E., et al., *Expression and mutation analysis of the discoidin domain receptors 1 and 2 in non-small cell lung carcinoma. British journal of cancer*, 2007. 96(5): p. 808-14]. Other studies underlined the relevance and role of DDR1 in metastatisation process. Screening of NSCLC samples, encompassing 86 squamous cell carcinomas, 69 adenocarcinomas, and 16 pure bronchioloalveolar carcinomas (BAC), indicated that DDR1 upregulation was more frequent in invasive adenocarcinoma (64%) compared with BAC (38%; 83). In addition, DDR1 expression was significantly correlated with lymph node metastasis in invasive NSCLC. Overexpression of DDR1 in lung cancer cells resulted in a significant increase in cell motility and invasiveness, which may correlate with the induction of matrix metalloproteinase-9 [Yang, S. H., et al., *Discoidin domain receptor 1 is associated with poor prognosis of non-small cell lung carcinomas. Oncology reports*, 2010. 24(2): p. 3114; Miao, L., et al., *Discoidin domain receptor 1 is associated with poor prognosis of non-small cell lung cancer and promotes cell invasion via epithelial-to-mesenchymal transition. Medical oncology*, 2013. 30(3): p. 626]. These results indicate that up-regulation of DDR1 may contribute to the progression and poor prognosis of certain types of NSCLC and that this effect may be attributed to increased invasiveness.

Even if not totally understood, DDR1 seems to play a central role in modulation of inflammation and fibrosis. As fibrosis is frequently the result of an earlier inflammation event, it's not clear if the main role of DDR1 resides in the direct blockage of fibrosis processes (e.g., myofibroblast activation, collagen deposition) or more in inflammation modulation. Unfortunately, in vivo experiments performed using the DDR1 null mice do not allow to untangle these two biological processes. Modulation of fibrosis and inflammation has been demonstrated in several organs, namely lung and kidney. DDR1-deficient mice show reduced bleomycin-induced pulmonary injury characterized by reduced collagen and tenascin-C levels [Avivi-Green, C., M. Singal, and W. F. Vogel, *Discoidin domain receptor 1-deficient mice are resistant to bleomycin-induced lung fibrosis. American journal of respiratory and critical care medicine*, 2006. 174(4): p. 420-7]. Authors reported two possible reasons for the decreased fibrotic response in DDR1-null mice are decreased inflammation, with reduced CD3-positive lymphocytes and F4/80-positive cells infiltrating the lungs, and decreased activation of the p38 MAPK, a kinase involved in lung fibrosis. In kidney, DDR1 expression is elevated in patients with lupus nephritis and Goodpasture's syndrome as well as in a mouse model of crescentic glomerulonephritis [Kerroch, M., et al., *Genetic inhibition of discoidin domain receptor 1 protects mice against crescentic glomerulonephritis. FASEB journal: official publication of the Federation of American Societies for Experimental Biology*, 2012. 26(10): p. 4079-91]. Similarly, DDR1 expression increases in the glomeruli of rats that have undergone partial renal ablation [Lee, R., et al., *Localization of discoidin domain receptors in rat kidney. Nephron Exp Nephrol*, 2004. 97(2): p. e62-70] and in tubules of mice that have undergone unilateral ureteral obstruction [Guerrot, D., et al., *Discoidin domain receptor 1 is a major mediator of inflammation and fibrosis in obstructive nephropathy. Am J Pathol*, 2011. 179(1): p. 83-91]. Use of DDR1-null mice in several mouse models of kidney injury showed that compared to wild type mice DDR1-null mice have improved renal function, reduced fibrosis and reduced inflammation. In this context, DDR1-null mice are protected from angiotensin II-mediated proteinuria, glomerular fibrosis, and inflammation, and show reduced collagen deposition, tubular macrophage infiltration and pro-inflammatory cytokine levels following unilateral ureteral obstruction. Moreover, COL4A3 KO mice, the mouse model for human Alport syndrome, crossed onto the DDR1-null mice have reduced renal fibrosis and inflammation due to reduced TGF-β-mediated signaling and reduced levels of the pro-inflammatory cytokine IL6 [Gross, O., et al., *Loss of collagen-receptor DDR1 delays renal fibrosis in hereditary type IV collagen disease. Matrix Biol.* 29(5): p. 346-56]. Finally, DDR1-null mice have increased survival and improved renal function in a model of crescentic glomerulonephritis induced by injection of alloimmune sheep nephrotoxic serum. In that respect, finding that older DDR1-null mice show focal swelling of the glomerular basement membrane (GBM) and mild proteinuria [Gross, O., et al., *DDR1-deficient mice show localized subepithelial GBM thickening with focal loss of slit diaphragms and proteinuria. Kidney Int*, 2004. 66(1): p. 102-11] suggests that DDR1 might play a very different role in physiological conditions. Again, as we mentioned before in the case of the lung fibrosis, hallmark of protection conferred by DDR1 deletion in all these renal experimental studies showed reduced macrophage infiltration supporting the pro-inflammatory role of DDR1.

Despite the progress made in understanding the role of DDR1, there remains an unmet need of potent and selective compounds suitable to modulate the DDR1 receptor to treat diseases related to DDR1 overexpression. Present invention provides novel compounds which exhibit high affinity and selectivity to the DDR1 receptor and are thus suitable for the treatment or prevention of diseases related to DDR1 upregulation.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl. The combination heterocycloalkyl-$CH_2$-phenyl refers to a phenyl-radical bound to the rest of the molecule, the phenyl being substituted via a $CH_2$-linker by a heterocycloalkyl moiety.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts. The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Int. Ed. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "stereoisomer" denotes a compound that possesses identical molecular connectivity and bond multiplicity, but which differs in the arrangement of its atoms in space.

The terms "racemate" and "racemic mixture" can be used interchangeably and denote an equimolar mixture of two enantiomeric species, devoid of optical activity.

The term "halo", "halogen", and "halide" are used interchangeably herein and denote fluoro, chloro, bromo, or iodo. Particular examples for halogen are fluoro and chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples for $C_{1-7}$ alkyl are methyl, ethyl, iso-propyl and tert-butyl.

The term "alkoxy" denotes a group of the formula —O—R', wherein R' is an alkyl group. Examples of alkoxy moieties include methoxy, ethoxy, isopropoxy, and tert-butoxy. Particular example for $C_{1-7}$ alkoxy is methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples for halo-$C_{1-7}$ alkyl are trifluoromethyl and trifluoroethyl, most particularly trifluoromethyl and 2,2,2-trifluoroethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms. Particular example for halo-$C_{1-7}$ alkoxy is trifluoromethoxy.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl. Particular example for alkoxyalkyl is methoxymethyl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular example for cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples for heterocycloalkyl are azetidinyl, pyrrolidinyl, piperidinyl, piperazinyl, morpholinyl, thiomorpholinyl, azaspiro[2.4]heptanyl, 1,3,3a,4,6,6a-hexahydropyrrolo[3,4-c]pyrrolyl, diazaspiro[3.3]heptane-6-yl and 2-oxa-5-azaspiro[3.4]octanyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl. Particular example for aryl is phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples for heteroaryl are pyridinyl, pyrimidinyl, imidazolyl, pyrazolyl, triazolyl, oxazolyl, oxadiazolyl, thiazolyl, thiadiazol, indazolyl, benzo[d][1,2,3]triazolyl, imidazo[1,5-a]pyridinyl, pyrazolo[3,4-b]pyridinyl, pyrazolo[4,3-b]pyridinyl, and tetrazolo[1,5-a]pyridinyl. Particular examples for monocyclic heteroaryl are pyridinyl, pyrimidinyl, imidazolyl, pyrazolyl, triazolyl, oxazolyl, oxadiazolyl, thiazolyl, and thiadiazol.

Particular examples for bicyclic heteroaryl are indazolyl, benzo[d][1,2,3]triazolyl, imidazo[1,5-a]pyridinyl, pyrazolo[3,4-b]pyridinyl, pyrazolo[3,4-c]pyridinyl, pyrazolo[4,3-b]pyridinyl, and tetrazolo[1,5-a]pyridinyl.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine. Particular examples for amino are —NH$_2$ and diethylamine.

The term "alkylamino" denotes a group —NR'R", wherein R' is hydrogen and R" is a alkyl. The term "dialkylamino" as used herein denotes a group —NR'R", wherein R' and R" are both alkyl. Examples of alkylamino groups include methylamino and ethylamino. Examples of alkylamino groups include dimethyl amino, methyl ethyl amino, diethylamino and di(1-methylethyl)amino. Particular example for alkylamino is diethylamine.

The term "oxo" denotes a divalent oxygen atom =O.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point.

Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "leaving group" denotes the group with the meaning conventionally associated with it in synthetic organic chemistry, i.e., an atom or group displaceable under substitution reaction conditions. Examples of leaving groups include halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "inhibitor" denotes a compound which competes with, reduces or prevents the binding of a particular ligand to a particular receptor or enzyme and/or which reduces or prevents the activity of a particular protein, e.g. of a receptor or an enzyme.

The term "binding selectivity" denotes the ratio between the binding affinities of a particular compound to two or more different receptor subtypes. A particular compound is characterized as "binding selective" to a specific receptor subtype if its binding affinity to that receptor subtype is at least 10-fold, particularly at least 50-fold, higher than its binding affinity to other receptor subtype(s).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse. In one embodiment, a non-human animal is a mouse.

The term "half maximal inhibitory concentration" (IC50) denotes the concentration of a particular compound or molecule required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

In detail, the present invention relates to a compound of formula (I)

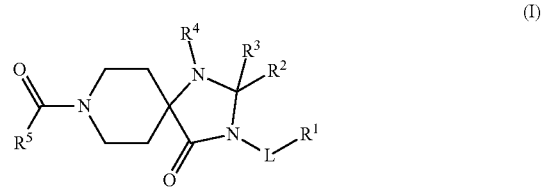

wherein

L is —(CHR$^8$)$_m$—(CHR$^9$)$_n$—(CO)$_q$—

R$^1$ is —NR$^6$R$^7$, aryl, heteroaryl, C$_{3-7}$ cyloalkyl, or heterocycloalkyl, wherein each of aryl, heteroaryl, C$_{3-7}$ cyloalkyl and heterocycloalkyl are optionally substituted with one or more R$^{1'}$;

each $R^{1'}$ is independently selected from halogen, cyano, $C_{1-7}$ alkyl, halo-$C_{1-7}$ alkyl, $C_{3-7}$ cycloalkyl, $C_{3-7}$ cycloalkyl-$C_{1-7}$ alkyl, phenyl, benzyl, heteroaryl, amino, hydroxy, $C_{1-7}$ alkoxy, halo-$C_{1-7}$ alkoxy, $C_{1-7}$ alkoxy-$C_{1-7}$ alkyl, oxo, —$CH_2$—$OR^{16}$, —$C(O)$—$OR^{16}$, —$CH_2$—$NHR^{16}$, —$CH_2$—$CH_2$—$NR^{17}R^{18}$, —$CH_2$—$C(O)$—$NHR^{16}$ and —$C(O)$—$NHR^{16}$;

or two $R^{1'}$ together are forming —$(CR^{12}R^{13})_s$— or —$(CR^{12}R^{13})_t$—O—$(CR^{14}R^{15})_u$—;

$R^2$ is hydrogen, fluorine, $C_{1-7}$ alkyl, or halo-$C_{1-7}$ alkyl;

$R^3$ is hydrogen or $C_{1-7}$ alkyl;

$R^4$ is aryl or heteroaryl, each optionally substituted by one or more $R^{4'}$;

each $R^{4'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy and halo-$C_{1-7}$ alkoxy;

$R^5$ is mono- or bicyclic heteroaryl comprising 2 to 5 heteroatoms selected from N, O or S, wherein $R^5$ is optionally substituted with one or more $R^{5'}$;

each $R^{5'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy and —$C(O)NH_2$;

$R^6$ is $C_{1-7}$ alkyl, halo-$C_{1-7}$ alkyl, hydroxy-$C_{1-7}$ alkyl, $C_{1-7}$ alkoxy-$C_{1-7}$ alkyl, $C_{3-7}$ cycloalkyl, heterocycloalkyl, aryl, heteroaryl, —$CH_2$—$CH_2$—$NR^{17}R^{18}$, wherein $C_{1-7}$ alkyl, $C_{3-7}$ cycloalkyl, heterocycloalkyl, aryl, benzyl, and heteroaryl are optionally substituted with one or more $R^{6'}$;

each $R^{6'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, halo-$C_{1-7}$ alkoxy, $C_{1-7}$ alkoxy-$C_{1-7}$ alkyl, oxo, —$CH_2$—$C(O)$—$NHR^{16}$, heterocycloalkyl, —$CH_2$-heterocycloalkyl, phenyl, heterocycloalkyl-$CH_2$-phenyl optionally substituted with $C_{1-7}$ alkyl, benzyl, heteroaryl and $C_{1-7}$ alkyl-heteroaryl;

$R^7$ is hydrogen, $C_{1-7}$ alkyl, $C_{3-7}$ cycloalkyl or is halo-$C_{1-7}$ alkyl;

$R^8$ is hydrogen, $C_{1-7}$ alkyl, hydroxy-$C_{1-7}$ alkyl, $C_{1-7}$ alkoxy-$C_{1-7}$ alkyl, halo-$C_{1-7}$ alkoxy-$C_{1-7}$ alkyl, —$(CH_2)_r$-phenyl, —$(CH_2)_r$-heteroaryl, —$(CH_2)_r$$NR^{10}R^{11}$;

$R^9$ is hydrogen, $C_{1-7}$ alkyl, or halo-$C_{1-7}$ alkyl;

$R^{10}$ and $R^{11}$ are independently selected from hydrogen and $C_{1-7}$ alkyl or $R^{10}$ and $R^{11}$ together with the nitrogen to which they are bound form heterocycloalkyl;

$R^{12}$, $R^{13}$, $R^{14}$ and $R^{15}$ are each independently selected from hydrogen, halogen and $C_{1-7}$ alkyl;

$R^{16}$ is hydrogen, $C_{1-7}$alkyl, halo-$C_{1-7}$ alkyl, $C_{3-7}$ cycloalkyl, or heterocycloalkyl;

$R^{17}$ and $R^{18}$ are independently selected from hydrogen and $C_{1-7}$ alkyl or $R^{17}$ and $R^{18}$ together with the nitrogen to which they are bound form heterocycloalkyl;

m is 0, 1 or 2;

n is 0, 1 or 2;

q is 0 or 1;

r is 0, 1 or 2;

s is 2, 3 or 4;

t is 1 or 2;

u is 1 or 2;

or a pharmaceutically acceptable salt thereof;

with the proviso that if $R^1$ is heterocycloalkyl bound to L via a nitrogen ring atom, or $R^1$ is —$NR^6R^7$ then:
if q=0 then m+n≥2, or
if q=1 then m+n≥1.

In a particular embodiment of the invention $R^8$ is hydrogen.

In a particular embodiment of the invention $R^9$ is hydrogen.

In a particular embodiment of the invention n is 0.

In a particular embodiment of the invention m is 0 or 1.

In a particular embodiment of the invention q is 0 or 1.

In a particular embodiment of the invention L is void (i.e. n=0, m=0, q=0), —$CH_2$— (i.e. n=0, m=1, $R^8$ is H, q=0), or —$CH_2$—CO— (i.e. n=0, m=1, $R^8$ is H, q=1).

In a particular embodiment of the invention L is void.

In a particular embodiment of the invention n is 0, m is 0 and q is 0.

In a particular embodiment of the invention L is —$CH_2$—.

In a particular embodiment of the invention n is 0, m is 1 and q is 0.

In a particular embodiment of the invention L is —$CH_2$—CO—.

In a particular embodiment of the invention n is 0, m is 1 and q is 0.

In a particular embodiment of the invention L is —CH($CH_3$)—CO—.

In a particular embodiment of the invention n is 0, m is 1 and q is 1.

In one embodiment of the invention $R^1$ is —$NR^6R^7$, aryl, monocyclic heteroaryl, or heterocycloalkyl, wherein each of aryl, monocyclic heteroaryl, and heterocycloalkyl are optionally substituted with one or more $R^{1'}$.

In one embodiment of the invention $R^1$ is —$NR^6R^7$, aryl, monocyclic heteroaryl, $C_{3-7}$ cyloalkyl, 2-oxo-pyrrolidin-3-yl or 2-oxo-3-piperidyl, wherein each of aryl, monocyclic heteroaryl, $C_{3-7}$ cyloalkyl, 2-oxo-pyrrolidin-3-yl and 2-oxo-3-piperidyl are optionally substituted with one or more $R^{1'}$.

In a particular embodiment of the invention $R^1$ is:
—$NR^6R^7$;
phenyl;
monocyclic heteroaryl selected from imidazolyl, pyrazolyl, oxazolyl, oxadiazolyl, thiazolyl, and thiadiazol; or
heterocycloalkyl selected from azetidinyl, pyrrolidinyl, piperidinyl, piperazinyl, morpholinyl, thiomorpholinyl, azaspiro[2.4]heptanyl, 1,3,3a,4,6,6a-hexahydropyrrolo[3,4-c]pyrrolyl, diazaspiro[3.3]heptane-6-yl, 2-oxa-5-azaspiro[3.4]octanyl, 2-oxo-pyrrolidin-3-yl and 2-oxo-3-piperidyl;

wherein each of phenyl, monocyclic heteroaryl, and heterocycloalkyl are optionally substituted with one, two or three $R^{1'}$.

In a particular embodiment of the invention $R^1$ is:
—$NR^6R^7$;
phenyl;
monocyclic heteroaryl selected from imidazolyl, pyrazolyl, oxazolyl, oxadiazolyl, thiazolyl, and thiadiazol; or
heterocycloalkyl selected from 2-oxo-pyrrolidin-3-yl and 2-oxo-3-piperidyl;

wherein each of phenyl, monocyclic heteroaryl, and heterocycloalkyl are optionally substituted with one, two or three $R^{1'}$.

In a particular embodiment of the invention $R^1$ is:
—$NR^6R^7$;
phenyl;
monocyclic heteroaryl selected from imidazol-2-yl, pyrazol-3-yl, pyrazol-4-yl, 1,3-oxazol-4-yl, 1,2,4-oxadiazol-5-yl, 1,3,4-oxadiazol-2-yl, 1,3-thiazol-4-yl, 1,3-thiazol-5-yl, 1,2,4-thiadiazol-5-yl and 1,3,4-thiadiazol-2-yl; or
heterocycloalkyl selected from azetidinyl, pyrrolidinyl, piperidinyl, piperazinyl, morpholinyl, thiomorpholinyl, 5-azaspiro[2.4]heptan-5-yl, 1,3,3a,4,6,6a-hexahydropyrrolo[3,4-c]pyrrol-5-yl, diazaspiro[3.3]heptane-6-yl, and 2-oxa-5-azaspiro[3.4]octan-5-yl, 2-oxo-pyrrolidin-3-yl and 2-oxo-3-piperidyl;

wherein each of phenyl, monocyclic heteroaryl, and heterocycloalkyl are optionally substituted with one, two or three $R^{1'}$.

In a particular embodiment of the invention $R^1$ is:
—$NR^6R^7$;
phenyl;
monocyclic heteroaryl selected from imidazol-2-yl, pyrazol-3-yl, pyrazol-4-yl, 1,3-oxazol-4-yl, 1,2,4-oxadiazol-5-yl, 1,3,4-oxadiazol-2-yl, 1,3-thiazol-4-yl, 1,3-thiazol-5-yl, 1,2,4-thiadiazol-5-yl and 1,3,4-thiadiazol-2-yl; or
heterocycloalkyl selected from 2-oxo-pyrrolidin-3-yl and 2-oxo-3-piperidyl;

wherein each of phenyl, monocyclic heteroaryl, and heterocycloalkyl are optionally substituted with one, two or three $R^{1'}$.

In a particular embodiment of the invention $R^1$ is —$NR^6R^7$.

In a particular embodiment of the invention $R^1$ is phenyl optionally substituted with one, two or three $R^{1'}$.

In a particular embodiment of the invention $R^1$ is monocyclic heteroaryl selected from imidazolyl, pyrazolyl, oxazolyl, oxadiazolyl, thiazolyl, and thiadiazol, each optionally substituted with one, two or three $R^{1'}$.

In a particular embodiment of the invention $R^1$ is heterocycloalkyl selected from azetidinyl, pyrrolidinyl, piperidinyl, piperazinyl, morpholinyl, thiomorpholinyl, azaspiro[2.4]heptanyl, 1,3,3a,4,6,6a-hexahydropyrrolo[3,4-c]pyrrolyl, diazaspiro[3.3]heptane-6-yl, and 2-oxa-5-azaspiro[3.4]octanyl, each optionally substituted with one, two or three $R^{1'}$.

In a particular embodiment of the invention $R^1$ is heterocycloalkyl selected from 2-oxo-pyrrolidin-3-yl and 2-oxo-3-piperidyl, each optionally substituted with one, two or three $R^{1'}$.

In a particular embodiment of the invention $R^1$ is heterocycloalkyl selected from 2-oxo-pyrrolidin-3-yl and 2-oxo-3-piperidyl, each optionally substituted with one $R^{1'}$ wherein $R^{1'}$ is selected from $C_{1-7}$ alkyl, halo-$C_{1-7}$ alkyl, $C_{3-7}$ cycloalkyl, $C_{3-7}$ cycloalkyl-$C_{1-7}$ alkyl, phenyl, benzyl and heteroaryl.

In a particular embodiment of the invention $R^1$ is unsubstituted.

In a particular embodiment of the invention each $R^{1'}$ is independently selected from halogen, cyano, $C_{1-7}$ alkyl, halo-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, $C_{1-7}$ alkoxy-$C_{1-7}$ alkyl, oxo, phenyl, benzyl, heteroaryl, —$CH_2$—$OR^{16}$, —$C(O)$—$OR^{16}$, —$CH_2$—$NHR^{16}$, —$CH_2$—$CH_2$—$NR^{17}R^{18}$, —$CH_2$—$C(O)$—$NHR^{16}$ and —$C(O)$—$NHR^{16}$.

In a particular embodiment of the invention $R^{1'}$ is selected from $C_{1-7}$ alkyl, halo-$C_{1-7}$ alkyl, $C_{3-7}$ cycloalkyl, $C_{3-7}$ cycloalkyl-$C_{1-7}$ alkyl, phenyl, benzyl, heteroaryl, $CH_2$—$OR^{16}$, —$C(O)$—$OR^{16}$, —$CH_2$—$NHR^{16}$, —$CH_2$—$CH_2$—$NR^{17}R^{18}$, —$CH_2$—$C(O)$—$NHR^{16}$ and —$C(O)$—$NHR^{16}$.

In a particular embodiment of the invention $R^{1'}$ is selected from $C_{1-7}$ alkyl, halo-$C_{1-7}$ alkyl, $C_{3-7}$ cycloalkyl, $C_{3-7}$ cycloalkyl-$C_{1-7}$ alkyl, phenyl, benzyl and heteroaryl.

In a particular embodiment of the invention each $R^{1'}$ is independently selected from halo-$C_{1-7}$ alkyl, $C_{3-7}$ cycloalkyl-$C_{1-7}$ alkyl and phenyl.

In a particular embodiment of the invention each $R^{1'}$ is independently selected from halogen, halo-$C_{1-7}$ alkyl, $C_{3-7}$ cycloalkyl.

In a particular embodiment of the invention each $R^{1'}$ is independently selected from fluoro, chloro, cyano, methyl, ethyl, tert-butyl, trifluoromethyl, trifluoroethyl, cyclopropyl, cyclopropyl-methyl, dimethylamino, hydroxy, methoxy, methoxymethyl, oxo, aminocarbonyl, methoxycarbonyl, tert-butoxycarbonyl, aminocarbonyl-methyl, amino-methyl, dimethylamino-ethyl, pyrrolidinyl, phenyl, benzyl, and triazolyl.

In a particular embodiment of the invention each $R^{1'}$ is independently selected from fluoro, chloro, cyano, methyl, ethyl, tert-butyl, trifluoromethyl, trifluoroethyl, cyclopropyl, cyclopropyl-methyl, dimethylamino, hydroxy, methoxy, methoxymethyl, oxo, phenyl, benzyl, and triazolyl.

In a particular embodiment of the invention each $R^{1'}$ is independently selected from trifluoroethyl, cyclopropyl-methyl and phenyl.

In one embodiment of the invention $R^2$ is methyl or hydrogen.

In one embodiment of the invention $R^2$ is hydrogen.

In one embodiment of the invention $R^3$ is hydrogen or methyl.

In one embodiment of the invention $R^3$ is hydrogen.

In one embodiment of the invention $R^4$ is aryl or heteroaryl, each optionally substituted by one or more $R^{4'}$.

In a particular embodiment of the invention $R^4$ is phenyl or pyridinyl, each optionally substituted with one or two substituents independently selected from fluoro, chloro, bromo, cyano and trifluoromethyl.

In one embodiment of the invention $R^4$ is aryl optionally substituted by one or more $R^{4'}$.

In a particular embodiment of the invention $R^4$ is phenyl optionally substituted with one or two halogen independently selected from fluoro and chloro.

In a particular embodiment of the invention $R^4$ is pyridinyl optionally substituted with one or two halogen independently selected from fluoro and chloro. In a particular embodiment of the invention $R^4$ is unsubstituted phenyl.

In a particular embodiment of the invention $R^4$ is unsubstituted pyridinyl.

In a particular embodiment of the invention each $R^{4'}$ is independently selected from fluoro, chloro, bromo, cyano and trifluoromethyl.

In a particular embodiment of the invention each $R^{4'}$ is independently selected from fluoro and chloro.

In one embodiment of the invention $R^5$ is an aromatic bicyclic heteroaryl moiety of formula

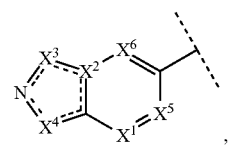

wherein $X^1$ is $CR^{5'}$ or N; $X^2$ is $CR^{5'}$ or N; $X^3$ is $CR^{5'}$, NH or N; $X^4$ is $CR^{5'}$, NH or N; $X^5$ is $CR^{5'}$, N and $X^6$ is $CR^{5'}$, NH with the proviso that at least one of $X^1$, $X^2$, $X^3$, $X^4$, $X^5$ and $X^6$ is N or NH.

In one embodiment of the invention $R^5$ is an aromatic bicyclic heteroaryl moiety of formula

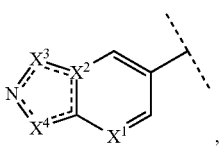

wherein $X^1$ is $CR^{5'}$ or N; $X^2$ is $CR^{5'}$ or N; $X^3$ is $CR^{5'}$, NH or N; and $X^4$ is $CR^{5'}$, NH or N; with the proviso that at least one of $X^1$, $X^2$, $X^3$ and $X^4$ is N or NH.

In one embodiment of the invention $R^5$ is selected from:

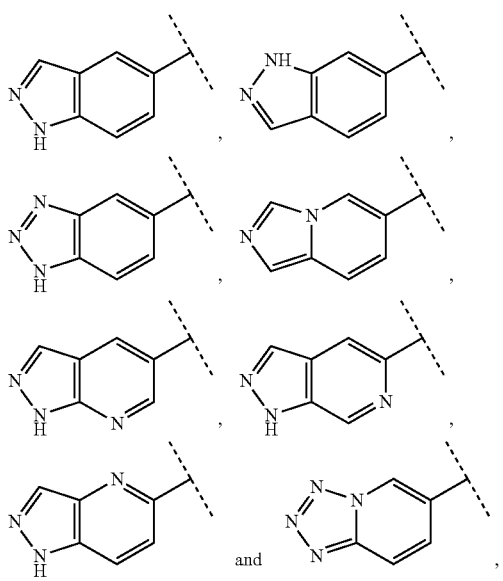

each optionally substituted by with one or more $R^{5'}$.

In a particular embodiment of the invention $R^5$ is selected from pyrimidinyl, indazolyl, benzo[d][1,2,3]triazolyl, imidazo[1,5-a]pyridinyl, pyrazolo[3,4-b]pyridinyl, 1H-pyrazolo[3,4-c]pyridine, 1H-pyrazolo[4,3-b]pyridine and tetrazolo[1,5-a]pyridinyl, each optionally substituted by with one or more $R^{5'}$.

In a particular embodiment of the invention $R^5$ is selected from indazolyl, benzo[d][1,2,3]triazolyl, imidazo[1,5-a]pyridinyl, pyrazolo[3,4-b]pyridinyl, 1H-pyrazolo[3,4-c]pyridine, 1H-pyrazolo[4,3-b]pyridine and tetrazolo[1,5-a]pyridinyl, each optionally substituted by with one or more $R^{5'}$.

In a particular embodiment of the invention $R^5$ is selected from pyrimidinyl, indazolyl, benzo[d][1,2,3]triazolyl, imidazo[1,5-a]pyridinyl, pyrazolo[3,4-b]pyridinyl, 1H-pyrazolo[3,4-c]pyridine, 1H-pyrazolo[4,3-b]pyridine and tetrazolo[1,5-a]pyridinyl, each optionally substituted by with one or more $R^{5'}$.

In a particular embodiment of the invention $R^5$ is selected from indazolyl, benzo[d][1,2,3]triazolyl, imidazo[1,5-a]pyridinyl, pyrazolo[3,4-b]pyridinyl, and tetrazolo[1,5-a]pyridinyl, each optionally substituted by with one or more $R^{5'}$.

In a particular embodiment of the invention $R^5$ is selected from pyrimidine-5-yl, 1H-indazole-5-yl, 1H-indazole-6-yl, 1H-benzo[d][1,2,3]triazole-5-yl, imidazo[1,5-a]pyridine-6-yl, 1H-pyrazolo[3,4-b]pyridine-5-yl, 1H-pyrazolo[3,4-c]pyridine-5-yl, 1H-pyrazolo[4,3-b]pyridine-5-yl and tetrazolo[1,5-a]pyridine-6-yl, each optionally substituted by with one or more $R^{5'}$.

In a particular embodiment of the invention $R^5$ is selected from 1H-indazole-5-yl, 1H-indazole-6-yl, 1H-benzo[d][1,2,3]triazole-5-yl, imidazo[1,5-a]pyridine-6-yl, 1H-pyrazolo[3,4-b]pyridine-5-yl, 1H-pyrazolo[3,4-c]pyridine, 1H-pyrazolo[4,3-b]pyridine and tetrazolo[1,5-a]pyridine-6-yl, each optionally substituted by with one or more $R^{5'}$.

In a particular embodiment of the invention $R^5$ is selected from 1H-indazole-5-yl, 1H-indazole-6-yl, 1H-benzo[d][1,2,3]triazole-5-yl, imidazo[1,5-a]pyridine-6-yl, 1H-pyrazolo[3,4-b]pyridine-5-yl, and tetrazolo[1,5-a]pyridine-6-yl, each optionally substituted by with one or more $R^{5'}$.

In a particular embodiment of the invention $R^5$ is selected from 1H-indazole-5-yl, 1H-indazole-6-yl, 3-amino-1H-indazole-6-yl, 1H-benzo[d][1,2,3]triazole-5-yl, imidazo[1,5-a]pyridine-6-yl, 1H-pyrazolo[3,4-b]pyridine-5-yl, and tetrazolo[1,5-a]pyridine-6-yl.

In a particular embodiment of the invention $R^{5'}$ is methyl or amino, most particularly —$NH_2$.

In a particular embodiment of the invention $R^{5'}$ is amino, most particularly —$NH_2$.

In one embodiment of the invention $R^6$ is $C_{1-7}$ alkyl, halo-$C_{1-7}$ alkyl, $C_{3-7}$ cycloalkyl, heterocycloalkyl, aryl or heteroaryl, each optionally substituted with one $R^{6'}$.

In a particular embodiment of the invention $R^6$ is methyl, ethyl, isopropyl, tert-butyl, trifluoroethyl, cyclopropyl, adamantyl, oxetanyl, pyrrolidinyl, phenyl, thiazolyl, pyrazolyl or pyridinyl, each optionally substituted with one $R^{6'}$.

In a particular embodiment of the invention $R^6$ is trifluoroethyl or pyridinyl.

In a particular embodiment of the invention $R^6$ is unsubstituted.

In a particular embodiment of the invention each $R^{6'}$ is independently selected from halo, cyano, $C_{1-7}$ alkyl, halo-$C_{1-7}$ alkyl, halo-$C_{1-7}$ alkoxy, heterocycloalkyl-$CH_2$-phenyl optionally substituted with $C_{1-7}$ alkyl, heterocycloalkyl, phenyl, and $C_{1-7}$ alkyl-heteroaryl.

In a particular embodiment of the invention each $R^{6'}$ is independently selected from halo-$C_{1-7}$ alkoxy, heterocyclyl phenyl, and $C_{1-7}$ alkyl-heteroaryl.

In a particular embodiment of the invention each $R^{6'}$ is independently selected from halo-$C_{1-7}$ alkoxy, heterocycloalkyl, phenyl, and $C_{1-7}$ alkyl-heteroaryl.

In a particular embodiment of the invention each $R^{6'}$ is independently selected from fluoro, cyano, methyl, trifluoromethyl, trifluoroethyl, trifluoromethoxy, morpholinyl, phenyl, methyl-oxadiazolyl, ((4-methylpiperazin-1-yl)methyl)phenyl, and ((morpholin-3-yl)methyl)phenyl.

In a particular embodiment of the invention each $R^{6'}$ is independently selected from trifluoromethoxy, morpholinyl, phenyl and methyl-oxadiazolyl.

In one embodiment of the invention $R^7$ is hydrogen, $C_{1-7}$ alkyl or $C_{3-7}$ cycloalkyl.

In one embodiment of the invention $R^7$ is hydrogen or $C_{1-7}$ alkyl.

In a particular embodiment of the invention $R^7$ is hydrogen, methyl, isopropyl, cyclopropyl.

In a particular embodiment of the invention $R^7$ is hydrogen, methyl or isopropyl.

In a particular embodiment of the invention $R^7$ is hydrogen or methyl.

In a particular embodiment of the invention $R^{17}$ and $R^{18}$ are independently selected from hydrogen or methyl.

In a particular embodiment of the invention $R^{17}$ and $R^{18}$ are both hydrogen.

In a particular embodiment of the invention $R^{17}$ and $R^{18}$ are both methyl.

Particular compounds of formula (I) of the present invention are those selected from the group consisting of:

2-[1-(4-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(3-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(2-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-(1-(3,4-Dichlorophenyl)-8-(1H-indazole-5-carbonyl)-4-oxo-1,3,8-triazaspiro[4.5]decan-3-yl)-N-(2,2,2-trifluoroethyl)acetamide;

2-(1-(4-Chlorophenyl)-8-(1H-indazole-5-carbonyl)-4-oxo-1,3,8-triazaspiro[4.5]decan-3-yl)-N-(2,2,2-trifluoroethyl)acetamide;

2-(8-(1H-Indazole-5-carbonyl)-4-oxo-1-phenyl-1,3,8-triazaspiro[4.5]decan-3-yl)-N-phenylacetamide;

2-(8-(1H-Indazole-5-carbonyl)-4-oxo-1-phenyl-1,3,8-triazaspiro[4.5]decan-3-yl)-N-(2,2,2-trifluoroethyl)acetamide;

2-(8-(1H-Indazole-5-carbonyl)-4-oxo-1-phenyl-1,3,8-triazaspiro[4.5]decan-3-yl)-N-(2-morpholinoethyl)acetamide;

(rac,trans)-2-(8-(1H-Indazole-5-carbonyl)-4-oxo-1-phenyl-1,3,8-triazaspiro[4.5]decan-3-yl)-N-(2-phenylcyclopropyl)acetamide;

8-(1H-Indazole-5-carbonyl)-3-(2-morpholino-2-oxoethyl)-1-phenyl-1,3,8-triazaspiro[4.5]decan-4-one;

2-(8-(1H-Indazole-5-carbonyl)-4-oxo-1-phenyl-1,3,8-triazaspiro[4.5]decan-3-yl)-N-(pyridin-3-yl)acetamide;

2-(8-(1H-Indazole-5-carbonyl)-4-oxo-1-phenyl-1,3,8-triazaspiro[4.5]decan-3-yl)-N-(pyridin-4-yl)acetamide;

2-(8-(1H-Indazole-5-carbonyl)-4-oxo-1-phenyl-1,3,8-triazaspiro[4.5]decan-3-yl)-N-(3-morpholinophenyl)acetamide;

2-(8-(1H-Indazole-5-carbonyl)-4-oxo-1-phenyl-1,3,8-triazaspiro[4.5]decan-3-yl)-N-(3-(trifluoromethoxy)phenyl)acetamide;

2-(8-(1H-Indazole-5-carbonyl)-4-oxo-1-phenyl-1,3,8-triazaspiro[4.5]decan-3-yl)-N-(pyridin-2-yl)acetamide;

2-(8-(1H-Indazole-6-carbonyl)-4-oxo-1-phenyl-1,3,8-triazaspiro[4.5]decan-3-yl)-N-phenylacetamide;

2-[8-(3-Amino-1H-indazole-6-carbonyl)-4-oxo-1-phenyl-1,3,8-triazaspiro[4.5]decan-3-yl]-N-(2,2,2-trifluoroethyl)acetamide;

2-(4-Oxo-1-phenyl-8-(tetrazolo[1,5-a]pyridine-6-carbonyl)-1,3,8-triazaspiro[4.5]decan-3-yl)-N-(2,2,2-trifluoroethyl)acetamide;

2-[8-(1H-Indazole-6-carbonyl)-4-oxo-1-phenyl-1,3,8-triazaspiro[4.5]decan-3-yl]-N-(2,2,2-trifluoroethyl)acetamide;

2-(4-Oxo-1-phenyl-8-(1H-pyrazolo[3,4-c]pyridine-5-carbonyl)-1,3,8-triazaspiro[4.5]decan-3-yl)-N-(2,2,2-trifluoroethyl)acetamide;

2-(8-(Imidazo[1,5-a]pyridine-6-carbonyl)-4-oxo-1-phenyl-1,3,8-triazaspiro[4.5]decan-3-yl)-N-(2,2,2-trifluoroethyl)acetamide;

2-(4-Oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

2-(4-Oxo-1-phenyl-8-(1H-pyrazolo[3,4-b]pyridine-5-carbonyl)-1,3,8-triazaspiro[4.5]decan-3-yl)-N-phenylacetamide;

2-(4-Oxo-1-phenyl-8-(1H-pyrazolo[3,4-b]pyridine-5-carbonyl)-1,3,8-triazaspiro[4.5]decan-3-yl)-N-(pyridin-2-yl)acetamide;

8-(1H-Benzo[d][1,2,3]triazole-5-carbonyl)-3-(2-morpholino-2-oxoethyl)-1-phenyl-1,3,8-triazaspiro[4.5]decan-4-one;

2-(8-(1H-Benzo[d][1,2,3]triazole-5-carbonyl)-4-oxo-1-phenyl-1,3,8-triazaspiro[4.5]decan-3-yl)-N-(2,2,2-trifluoroethyl)acetamide;

N-Methyl-2-(4-oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

3-(2-(4-Methylpiperazin-1-yl)-2-oxoethyl)-1-phenyl-8-(1H-pyrazolo[3,4-b]pyridine-5-carbonyl)-1,3,8-triazaspiro[4.5]decan-4-one;

3-(2-(1,1-Dioxidothiomorpholino)-2-oxoethyl)-1-phenyl-8-(1H-pyrazolo[3,4-b]pyridine-5-carbonyl)-1,3,8-triazaspiro[4.5]decan-4-one;

N-(Adamantan-1-yl)-2-(4-oxo-1-phenyl-8-(1H-pyrazolo[3,4-b]pyridine-5-carbonyl)-1,3,8-triazaspiro[4.5]decan-3-yl)acetamide;

2-[8-(1H-Indazole-5-carbonyl)-4-oxo-1-phenyl-1,3,8-triazaspiro[4.5]decan-3-yl]-N-methyl-acetamide;

3-(5-Chloro-2-fluorophenyl)-8-(1H-indazole-5-carbonyl)-1-phenyl-1,3,8-triazaspiro[4.5]decan-4-one;

3-[(3-Cyclopropyl-1,2,4-oxadiazol-5-yl)methyl]-8-(1H-indazole-5-carbonyl)-1-phenyl-1,3,8-triazaspiro[4.5]decan-4-one;

8-(1H-Indazole-5-carbonyl)-3-[(2-methyl-1,3-thiazol-4-yl)methyl]-1-phenyl-1,3,8-triazaspiro[4.5]decan-4-one;

8-(1H-Indazole-5-carbonyl)-3-[(1-methylimidazol-2-yl)methyl]-1-phenyl-1,3,8-triazaspiro[4.5]decan-4-one;

8-(1H-Indazole-5-carbonyl)-3-[(2-methylpyrazol-3-yl)methyl]-1-phenyl-1,3,8-triazaspiro[4.5]decan-4-one;

8-(1H-Indazole-5-carbonyl)-3-[(3-methyl-1,2,4-oxadiazol-5-yl)methyl]-1-phenyl-1,3,8-triazaspiro[4.5]decan-4-one;

8-(1H-Indazole-5-carbonyl)-3-[(5-methyl-1,3,4-oxadiazol-2-yl)methyl]-1-phenyl-1,3,8-triazaspiro[4.5]decan-4-one;

3-[[3-(4-Fluorophenyl)-1,2,4-oxadiazol-5-yl]methyl]-8-(1H-indazole-5-carbonyl)-1-phenyl-1,3,8-triazaspiro[4.5]decan-4-one;

3-[(5-Cyclopropyl-1,3,4-thiadiazol-2-yl)methyl]-8-(1H-indazole-5-carbonyl)-1-phenyl-1,3,8-triazaspiro[4.5]decan-4-one;

(3S,4R or 3R,4S)-2-[8-(1H-Indazole-5-carbonyl)-4-oxo-1-phenyl-1,3,8-triazaspiro[4.5]decan-3-yl]-N-(4-phenylpyrrolidin-3-yl)acetamide;

(rac,trans)-2-[8-(1H-Indazole-5-carbonyl)-4-oxo-1-phenyl-1,3,8-triazaspiro[4.5]decan-3-yl]-N-[4-(3-methyl-1,2,4-oxadiazol-5-yl)pyrrolidin-3-yl]acetamide;

(RS)-2-[8-(1H-Indazole-5-carbonyl)-2-methyl-4-oxo-1-phenyl-1,3,8-triazaspiro[4.5]decan-3-yl]-N-(2,2,2-trifluoroethyl)acetamide;

3-[(2-tert-Butyl-5-methyl-1,3-oxazol-4-yl)methyl]-8-(1H-indazole-5-carbonyl)-1-phenyl-1,3,8-triazaspiro[4.5]decan-4-one;

3-[(3-tert-Butyl-1,2,4-thiadiazol-5-yl)methyl]-8-(1H-indazole-5-carbonyl)-1-phenyl-1,3,8-triazaspiro[4.5]decan-4-one;

(3R,4S or 3 S,4R)-2-[8-(1H-Indazole-5-carbonyl)-4-oxo-1-phenyl-1,3,8-triazaspiro[4.5]decan-3-yl]-N-(4-phenylpyrrolidin-3-yl)acetamide;

(RS)-3-[2-Oxo-2-[3-(trifluoromethyl)pyrrolidin-1-yl]ethyl]-1-phenyl-8-(1H-pyrazolo[3,4-b]pyridine-5-carbonyl)-1,3,8-triazaspiro[4.5]decan-4-one;

3-(1-Ethylpyrazol-3-yl)-8-(1H-indazole-5-carbonyl)-1-phenyl-1,3,8-triazaspiro[4.5]decan-4-one;

3-(1-Ethylpyrazol-4-yl)-8-(1H-indazole-5-carbonyl)-1-phenyl-1,3,8-triazaspiro[4.5]decan-4-one;

3-(1,5-Dimethylpyrazol-3-yl)-8-(1H-indazole-5-carbonyl)-1-phenyl-1,3,8-triazaspiro[4.5]decan-4-one;

3-(2,5-Dimethylpyrazol-3-yl)-8-(1H-indazole-5-carbonyl)-1-phenyl-1,3,8-triazaspiro[4.5]decan-4-one;

3-(2,4-Dimethyl-1,3-thiazol-5-yl)-8-(1H-indazole-5-carbonyl)-1-phenyl-1,3,8-triazaspiro[4.5]decan-4-one;

(RS)-1-[2-[8-(1H-Indazole-5-carbonyl)-4-oxo-1-phenyl-1,3,8-triazaspiro[4.5]decan-3-yl]acetyl]pyrrolidine-3-carbonitrile;

(RS)-8-(1H-Indazole-5-carbonyl)-3-[2-oxo-2-[3-(1,2,4-triazol-1-yl)pyrrolidin-1-yl]ethyl]-1-phenyl-1,3,8-triazaspiro[4.5]decan-4-one;

3-[2-(3,3-Dimethylpyrrolidin-1-yl)-2-oxoethyl]-8-(1H-indazole-5-carbonyl)-1-phenyl-1,3,8-triazaspiro[4.5]decan-4-one;

3-[2-(3,3-Difluoroazetidin-1-yl)-2-oxoethyl]-8-(1H-indazole-5-carbonyl)-1-phenyl-1,3,8-triazaspiro[4.5]decan-4-one;

3-[2-[(3R)-3-(Dimethylamino)pyrrolidin-1-yl]-2-oxoethyl]-8-(1H-indazole-5-carbonyl)-1-phenyl-1,3,8-triazaspiro[4.5]decan-4-one;

(rac,cis)-3-[2-(2-Benzyl-1,3,3a,4,6,6a-hexahydropyrrolo[3,4-c]pyrrol-5-yl)-2-oxoethyl]-8-(1H-indazole-5-carbonyl)-1-phenyl-1,3,8-triazaspiro[4.5]decan-4-one;

8-(1H-Indazole-5-carbonyl)-3-[2-[(2R)-2-(methoxymethyl)pyrrolidin-1-yl]-2-oxoethyl]-1-phenyl-1,3,8-triazaspiro[4.5]decan-4-one;

(RS)-3-(2-Oxo-1-phenylpyrrolidin-3-yl)-1-phenyl-8-(1H-pyrazolo[3,4-b]pyridine-5-carbonyl)-1,3,8-triazaspiro[4.5]decan-4-one;

N-(Oxetan-3-yl)-2-[4-oxo-1-phenyl-8-(1H-pyrazolo[3,4-b]pyridine-5-carbonyl)-1,3,8-triazaspiro[4.5]decan-3-yl]acetamide;

(RS)-3-(1-Methyl-2-oxopiperidin-3-yl)-1-phenyl-8-(1H-pyrazolo[3,4-b]pyridine-5-carbonyl)-1,3,8-triazaspiro[4.5]decan-4-one;

(rac,cis)-3-[2-(2-Benzyl-1,3,3a,4,6,6a-hexahydropyrrolo[3,4-c]pyrrol-5-yl)-2-oxoethyl]-1-phenyl-8-(1H-pyrazolo[3,4-b]pyridine-5-carbonyl)-1,3,8-triazaspiro[4.5]decan-4-one;

3-[2-[(3S)-3-Fluoropyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[(3R)-3-Fluoropyrrolidin-1-yl]-2-oxoethyl]-1-phenyl-8-(1H-pyrazolo[3,4-b]pyridine-5-carbonyl)-1,3,8-triazaspiro[4.5]decan-4-one;

(RS)-3-[2-(3-Methoxypyrrolidin-1-yl)-2-oxoethyl]-1-phenyl-8-(1H-pyrazolo[3,4-b]pyridine-5-carbonyl)-1,3,8-triazaspiro[4.5]decan-4-one;

3-[2-(3-Fluoro-3-methylpyrrolidin-1-yl)-2-oxoethyl]-1-phenyl-8-(1H-pyrazolo[3,4-b]pyridine-5-carbonyl)-1,3,8-triazaspiro[4.5]decan-4-one;

3-[2-(3,3-Difluoropyrrolidin-1-yl)-2-oxoethyl]-1-phenyl-8-(1H-pyrazolo[3,4-b]pyridine-5-carbonyl)-1,3,8-triazaspiro[4.5]decan-4-one;

(RS)-3-[2-(2,2-Difluoro-5-azaspiro[2.4]heptan-5-yl)-2-oxoethyl]-1-phenyl-8-(1H-pyrazolo[3,4-b]pyridine-5-carbonyl)-1,3,8-triazaspiro[4.5]decan-4-one;

(RS)-3-[2-(3-Hydroxy-3-methylpyrrolidin-1-yl)-2-oxoethyl]-1-phenyl-8-(1H-pyrazolo[3,4-b]pyridine-5-carbonyl)-1,3,8-triazaspiro[4.5]decan-4-one;

3-[2-(2-Oxa-5-azaspiro[3.4]octan-5-yl)-2-oxoethyl]-1-phenyl-8-(1H-pyrazolo[3,4-b]pyridine-5-carbonyl)-1,3,8-triazaspiro[4.5]decan-4-one;

3-[2-[(3R)-3-Hydroxypyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[(3S)-3-Hydroxypyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[(3S)-3-(Dimethylamino)pyrrolidin-1-yl]-2-oxoethyl]-1-phenyl-8-(1H-pyrazolo[3,4-b]pyridine-5-carbonyl)-1,3,8-triazaspiro[4.5]decan-4-one;

2-[4-Oxo-1-phenyl-8-(1H-pyrazolo[3,4-b]pyridine-5-carbonyl)-1,3,8-triazaspiro[4.5]decan-3-yl]-N-propan-2-yl-N-(2,2,2-trifluoroethyl)acetamide;

N,N-Dimethyl-2-[4-oxo-1-phenyl-8-(1H-pyrazolo[3,4-b]pyridine-5-carbonyl)-1,3,8-triazaspiro[4.5]decan-3-yl]acetamide;

(RS)-3-[2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one;

(RS)-3-(1-Cyclopropyl-2-oxopyrrolidin-3-yl)-1-phenyl-8-(1H-pyrazolo[3,4-b]pyridine-5-carbonyl)-1,3,8-triazaspiro[4.5]decan-4-one;

8-(1H-Indazole-5-carbonyl)-1,3-diphenyl-1,3,8-triazaspiro[4.5]decan-4-one;

3-[2-Fluoro-5-(trifluoromethyl)phenyl]-8-(1H-indazole-5-carbonyl)-1-phenyl-1,3,8-triazaspiro[4.5]decan-4-one;

3-[2-Chloro-5-(trifluoromethyl)phenyl]-8-(1H-indazole-5-carbonyl)-1-phenyl-1,3,8-triazaspiro[4.5]decan-4-one;

3-(2-Fluorophenyl)-8-(1H-indazole-5-carbonyl)-1-phenyl-1,3,8-triazaspiro[4.5]decan-4-one;

1-Phenyl-8-(1H-pyrazolo[3,4-b]pyridine-5-carbonyl)-3-[3-(trifluoromethyl)phenyl]-1,3,8-triazaspiro[4.5]decan-4-one;

3-[2-Fluoro-4-(trifluoromethyl)phenyl]-1-phenyl-8-(1H-pyrazolo[3,4-b]pyridine-5-carbonyl)-1,3,8-triazaspiro[4.5]decan-4-one;

3-(2-Fluoro-4-methylphenyl)-1-phenyl-8-(1H-pyrazolo[3,4-b]pyridine-5-carbonyl)-1,3,8-triazaspiro[4.5]decan-4-one;

4-[4-Oxo-1-phenyl-8-(1H-pyrazolo[3,4-b]pyridine-5-carbonyl)-1,3,8-triazaspiro[4.5]decan-3-yl]benzonitrile;

3-(3-Chlorophenyl)-1-phenyl-8-(1H-pyrazolo[3,4-b]pyridine-5-carbonyl)-1,3,8-triazaspiro[4.5]decan-4-one;

3-(4-Chloro-2-fluorophenyl)-1-phenyl-8-(1H-pyrazolo[3,4-b]pyridine-5-carbonyl)-1,3,8-triazaspiro[4.5]decan-4-one;

3-(5-Chloro-2-fluoro-4-methyl-phenyl)-1-phenyl-8-(1H-pyrazolo[3,4-b]pyridine-5-carbonyl)-1,3,8-triazaspiro[4.5]decan-4-one;

2-(3-((2-(8-(1H-indazole-5-carbonyl)-4-oxo-1-phenyl-1,3,8-triazaspiro[4.5]decan-3-yl)acetamido)methyl)phenyl)-N-methylacetamide;

2-(4-Oxo-1-phenyl-8-(1H-pyrazolo[4,3-b]pyridine-5-carbonyl)-1,3,8-triazaspiro[4.5]decan-3-yl)-N-(2,2,2-trifluoroethyl)acetamide;

2-[8-(2-Aminopyrimidine-5-carbonyl)-4-oxo-1-phenyl-1,3,8-triazaspiro[4.5]decan-3-yl]-N-(2,2,2-trifluoroethyl)acetamide;

N-(2-fluoroethyl)-2-[4-oxo-1-phenyl-8-(1H-pyrazolo[3,4-b]pyridine-5-carbonyl)-1,3,8-triazaspiro[4.5]decan-3-yl]acetamide;

N-(2,2-difluoroethyl)-2-[4-oxo-1-phenyl-8-(1H-pyrazolo[3,4-b]pyridine-5-carbonyl)-1,3,8-triazaspiro[4.5]decan-3-yl]acetamide;

3-(2-Oxo-2-pyrrolidin-1-ylethyl)-1-phenyl-8-(1H-pyrazolo[3,4-b]pyridine-5-carbonyl)-1,3,8-triazaspiro[4.5]decan-4-one;

3-[2-[(3R)-3-(Dimethylamino)pyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-(2-Morpholino-2-oxoethyl)-1-phenyl-8-(1H-pyrazolo[3,4-b]pyridine-5-carbonyl)-1,3,8-triazaspiro[4.5]decan-4-one;

2-[4-Oxo-8-(1H-pyrazolo[3,4-b]pyridine-5-carbonyl)-1-pyridin-3-yl-1,3,8-triazaspiro[4.5]decan-3-yl]-N-(2,2,2-trifluoroethyl)acetamide;

tert-Butyl (3S)-3-[[2-[4-oxo-1-phenyl-8-(1H-pyrazolo[3,4-b]pyridine-5-carbonyl)-1,3,8-triazaspiro[4.5]decan-3-yl]acetyl]amino]pyrrolidine-1-carboxylate;

tert-butyl (3R)-3-[[2-[4-oxo-1-phenyl-8-(1H-pyrazolo[3,4-b]pyridine-5-carbonyl)-1,3,8-triazaspiro[4.5]decan-3-yl]acetyl]amino]pyrrolidine-1-carboxylate;

2-(8-(1H-indazole-5-carbonyl)-4-oxo-1-phenyl-1,3,8-triazaspiro[4.5]decan-3-yl)-N-methyl-N-(2,2,2-trifluoroethyl)acetamide;

N-methyl-2-(4-oxo-1-phenyl-8-(1H-pyrazolo[3,4-c]pyridine-5-carbonyl)-1,3,8-triazaspiro[4.5]decan-3-yl)-N-(2,2,2-trifluoroethyl)acetamide;

2-(8-(3-Methyl-1H-indazole-5-carbonyl)-4-oxo-1-phenyl-1,3,8-triazaspiro[4.5]decan-3-yl)-N-(2,2,2-trifluoroethyl)acetamide;

2-(8-(3-Amino-1H-indazole-5-carbonyl)-4-oxo-1-phenyl-1,3,8-triazaspiro[4.5]decan-3-yl)-N-(2,2,2-trifluoroethyl)acetamide;

2-[8-(1H-indazole-5-carbonyl)-4-oxo-1-phenyl-1,3,8-triazaspiro[4.5]decan-3-yl]-N-(2,2,2-trifluoroethyl)propanamide;

(+)-3-[2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one;

(−)-3-[2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one;

N-(6-cyanopyridin-2-yl)-2-[4-oxo-1-phenyl-8-(1H-pyrazolo[3,4-b]pyridine-5-carbonyl)-1,3,8-triazaspiro[4.5]decan-3-yl]acetamide;

3-[(6-Methylpyridin-2-yl)methyl]-1-phenyl-8-(1H-pyrazolo[3,4-b]pyridine-5-carbonyl)-1,3,8-triazaspiro[4.5]decan-4-one;

6-[[4-Oxo-1-phenyl-8-(1H-pyrazolo[3,4-b]pyridine-5-carbonyl)-1,3,8-triazaspiro[4.5]decan-3-yl]methyl]pyridine-2-carbonitrile;

N-cyclopropyl-2-[4-oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide;

1-[2-[4-Oxo-1-phenyl-8-(1H-pyrazolo[3,4-b]pyridine-5-carbonyl)-1,3,8-triazaspiro[4.5]decan-3-yl]acetyl]pyrrolidine-3-carbonitrile;

(−)-2-[8-(1H-indazole-5-carbonyl)-4-oxo-1-phenyl-1,3,8-triazaspiro[4.5]decan-3-yl]-N-(2,2,2-trifluoroethyl)propanamide;

(+)-2-[8-(1H-indazole-5-carbonyl)-4-oxo-1-phenyl-1,3,8-triazaspiro[4.5]decan-3-yl]-N-(2,2,2-trifluoroethyl)propanamide;

(S)-3-(2-oxo-2-(2-(trifluoromethyl)pyrrolidin-1-yl)ethyl)-1-phenyl-8-(1H-pyrazolo[3,4-b]pyridine-5-carbonyl)-1,3,8-triazaspiro[4.5]decan-4-one;

(R)-3-(2-oxo-2-(2-(trifluoromethyl)pyrrolidin-1-yl)ethyl)-1-phenyl-8-(1H-pyrazolo[3,4-b]pyridine-5-carbonyl)-1,3,8-triazaspiro[4.5]decan-4-one;

tert-Butyl 1-(2-(4-oxo-1-phenyl-8-(1H-pyrazolo[3,4-b]pyridine-5-carbonyl)-1,3,8-triazaspiro[4.5]decan-3-yl)acetyl)-1,6-diazaspiro[3.3]heptane-6-carboxylate;

N-((rac,trans)-2-(3-((4-methylpiperazin-1-yl)methyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide;

2-[8-(1H-indazole-5-carbonyl)-2,2-dimethyl-4-oxo-1-phenyl-1,3,8-triazaspiro[4.5]decan-3-yl]-N-(2,2,2-trifluoroethyl)acetamide;

N-(5-cyano-1,3-thiazol-2-yl)-2-[4-oxo-1-phenyl-8-(1H-pyrazolo[3,4-b]pyridine-5-carbonyl)-1,3,8-triazaspiro[4.5]decan-3-yl]acetamide;

N-[2-methyl-5-(trifluoromethyl)pyrazol-3-yl]-2-[4-oxo-1-phenyl-8-(1H-pyrazolo[3,4-b]pyridine-5-carbonyl)-1,3,8-triazaspiro[4.5]decan-3-yl]acetamide;

N-(2-(3-(morpholinomethyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide;

N-((trans)-2-(2-((4-methylpiperazin-1-yl)methyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide;

3-(2-Oxo-2-(2-(trifluoromethyl)morpholino)ethyl)-1-phenyl-8-(1H-pyrazolo[3,4-b]pyridine-5-carbonyl)-1,3,8-triazaspiro[4.5]decan-4-one;

2-(1-(3-Chlorophenyl)-4-oxo-8-(1H-pyrazolo[3,4-b]pyridine-5-carbonyl)-1,3,8-triazaspiro[4.5]decan-3-yl)-N-(2,2,2-trifluoroethyl)acetamide;

3-[2-(4-Cyclopropylpiperazin-1-yl)-2-oxoethyl]-1-phenyl-8-(1H-pyrazolo[3,4-b]pyridine-5-carbonyl)-1,3,8-triazaspiro[4.5]decan-4-one;

3-[2-Oxo-2-(3,3,4-trimethylpiperazin-1-yl)ethyl]-1-phenyl-8-(1H-pyrazolo[3,4-b]pyridine-5-carbonyl)-1,3,8-triazaspiro[4.5]decan-4-one;

3-[2-Oxo-2-(3-pyrrolidin-1-ylpyrrolidin-1-yl)ethyl]-1-phenyl-8-(1H-pyrazolo[3,4-b]pyridine-5-carbonyl)-1,3,8-triazaspiro[4.5]decan-4-one;

3-[2-(4-Cyclopropyl-3-oxopiperazin-1-yl)-2-oxoethyl]-1-phenyl-8-(1H-pyrazolo[3,4-b]pyridine-5-carbonyl)-1,3,8-triazaspiro[4.5]decan-4-one;

3-[2-[(rac,cis)-3-Hydroxy-4-methylpyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[(rac,trans)-3-Hydroxy-4-methylpyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[4-Methyl-3-(trifluoromethyl)piperazin-1-yl]-2-oxoethyl]-1-phenyl-8-(1H-pyrazolo[3,4-b]pyridine-5-carbonyl)-1,3,8-triazaspiro[4.5]decan-4-one;

8-(1H-indazole-5-carbonyl)-3-[2-[4-methyl-3-(trifluoromethyl)piperazin-1-yl]-2-oxoethyl]-1-phenyl-1,3,8-triazaspiro[4.5]decan-4-one;

2-(4-Oxo-1-phenyl-8-(1H-pyrazolo[3,4-b]pyridine-5-carbonyl)-1,3,8-triazaspiro[4.5]decan-3-yl)-N-(6-(trifluoromethyl)pyridin-2-yl)acetamide;

3-[2-[3-(Aminomethyl)pyrrolidin-1-yl]-2-oxoethyl]-1-phenyl-8-(1H-pyrazolo[3,4-b]pyridine-5-carbonyl)-1,3,8-triazaspiro[4.5]decan-4-one;

3-[2-[3-[2-(Dimethylamino)ethyl]pyrrolidin-1-yl]-2-oxoethyl]-1-phenyl-8-(1H-pyrazolo[3,4-b]pyridine-5-carbonyl)-1,3,8-triazaspiro[4.5]decan-4-one;

N-(2-(morpholinomethyl)phenyl)-2-(4-oxo-1-phenyl-8-(1H-pyrazolo[3,4-b]pyridine-5-carbonyl)-1,3,8-triazaspiro[4.5]decan-3-yl)acetamide;

N-[2-(dimethylamino)ethyl]-2-[4-oxo-1-phenyl-8-(1H-pyrazolo[3,4-b]pyridine-5-carbonyl)-1,3,8-triazaspiro[4.5]decan-3-yl]acetamide;

N-[2-(dimethylamino)ethyl]-2-[4-oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide;

(R)- or (S)-3-(2-Oxo-2-(2-(trifluoromethyl)morpholino)ethyl)-1-phenyl-8-(1H-pyrazolo[4,3-b]pyridine-5-carbonyl)-1,3,8-triazaspiro[4.5]decan-4-one;

2-[4-Oxo-1-phenyl-8-(1H-pyrazolo[3,4-b]pyridine-5-carbonyl)-1,3,8-triazaspiro[4.5]decan-3-yl]-N-[1-(2,2,2-trifluoroethyl)pyrazol-3-yl]acetamide;

(R)- or (S)-8-(1H-indazole-5-carbonyl)-3-(2-oxo-2-(2-(trifluoromethyl)morpholino)ethyl)-1-phenyl-1,3,8-triazaspiro[4.5]decan-4-one;

(R)- or (S)-8-(1H-indazole-5-carbonyl)-3-(2-oxo-2-(2-(trifluoromethyl)morpholino)ethyl)-1-phenyl-1,3,8-triazaspiro[4.5]decan-4-one;

(S)- or (R)-3-(2-Oxo-2-(2-(trifluoromethyl)morpholino)ethyl)-1-phenyl-8-(1H-pyrazolo[3,4-b]pyridine-5-carbonyl)-1,3,8-triazaspiro[4.5]decan-4-one;

(S)- or (R)-3-(2-Oxo-2-(2-(trifluoromethyl)morpholino)ethyl)-1-phenyl-8-(1H-pyrazolo[4,3-b]pyridine-5-carbonyl)-1,3,8-triazaspiro[4.5]decan-4-one;

(R)- or (S)-3-(2-Oxo-2-(2-(trifluoromethyl)morpholino)ethyl)-1-phenyl-8-(1H-pyrazolo[3,4-c]pyridine-5-carbonyl)-1,3,8-triazaspiro[4.5]decan-4-one;

(S)- or (R)-3-(2-Oxo-2-(2-(trifluoromethyl)morpholino)ethyl)-1-phenyl-8-(1H-pyrazolo[3,4-c]pyridine-5-carbonyl)-1,3,8-triazaspiro[4.5]decan-4-one;

(S)- or (R)-8-(1H-indazole-5-carbonyl)-3-(2-oxo-2-(2-(trifluoromethyl)morpholino)ethyl)-1-phenyl-1,3,8-triazaspiro[4.5]decan-4-one;

(R)- or (S)-tert-Butyl 4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate;

(S)- or (R)-tert-Butyl 4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate;

(R)- or (S)-8-(1H-indazole-5-carbonyl)-3-[2-[4-methyl-3-(trifluoromethyl)piperazin-1-yl]-2-oxoethyl]-1-phenyl-1,3,8-triazaspiro[4.5]decan-4-one;

(S)- or (R)-8-(1H-indazole-5-carbonyl)-3-[2-[4-methyl-3-(trifluoromethyl)piperazin-1-yl]-2-oxoethyl]-1-phenyl-1,3,8-triazaspiro[4.5]decan-4-one;

(R)- or (S)-8-(1H-indazole-5-carbonyl)-3-[2-oxo-2-[3-(trifluoromethyl)piperazin-1-yl]ethyl]-1-phenyl-1,3,8-triazaspiro[4.5]decan-4-one;

(S)- or (R)-8-(1H-indazole-5-carbonyl)-3-[2-oxo-2-[3-(trifluoromethyl)piperazin-1-yl]ethyl]-1-phenyl-1,3,8-triazaspiro[4.5]decan-4-one;

N-[2-(dimethylamino)ethyl]-2-[8-(1H-indazole-5-carbonyl)-4-oxo-1-phenyl-1,3,8-triazaspiro[4.5]decan-3-yl]-N-(2,2,2-trifluoroethyl)acetamide;

N-(2-hydroxyethyl)-2-[8-(1H-indazole-5-carbonyl)-4-oxo-1-phenyl-1,3,8-triazaspiro[4.5]decan-3-yl]-N-(2,2,2-trifluoroethyl)acetamide;

1-[2-[8-(1H-indazole-5-carbonyl)-4-oxo-1-phenyl-1,3,8-triazaspiro[4.5]decan-3-yl]acetyl]pyrrolidine-3-carboxamide;

N-(1-hydroxy-2-methylpropan-2-yl)-2-[8-(1H-indazole-5-carbonyl)-4-oxo-1-phenyl-1,3,8-triazaspiro[4.5]decan-3-yl]acetamide;

2-[8-(1H-indazole-5-carbonyl)-4-oxo-1-phenyl-1,3,8-triazaspiro[4.5]decan-3-yl]-N-[1-(trifluoromethyl)cyclopropyl]acetamide;

N-(2-cyanopropan-2-yl)-2-[8-(1H-indazole-5-carbonyl)-4-oxo-1-phenyl-1,3,8-triazaspiro[4.5]decan-3-yl]acetamide;

N-(1-hydroxy-2-methylpropan-2-yl)-2-[4-oxo-1-phenyl-8-(1H-pyrazolo[3,4-b]pyridine-5-carbonyl)-1,3,8-triazaspiro[4.5]decan-3-yl]acetamide;

2-(8-(7-Methyl-1H-indazole-5-carbonyl)-4-oxo-1-phenyl-1,3,8-triazaspiro[4.5]decan-3-yl)-N-(2,2,2-trifluoroethyl)acetamide;

2-[1-(3-Bromophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

8-(1H-indazole-5-carbonyl)-3-[2-oxo-2-[2-(trifluoromethyl)piperazin-1-yl]ethyl]-1-phenyl-1,3,8-triazaspiro[4.5]decan-4-one;

3-[2-[4-Benzyl-2-(trifluoromethyl)piperazin-1-yl]-2-oxoethyl]-8-(1H-indazole-5-carbonyl)-1-phenyl-1,3,8-triazaspiro[4.5]decan-4-one;

8-(1H-indazole-5-carbonyl)-3-[2-[4-methyl-2-(trifluoromethyl)piperazin-1-yl]-2-oxoethyl]-1-phenyl-1,3,8-triazaspiro[4.5]decan-4-one;

(S)-Methyl 4,4-difluoro-1-(2-(4-oxo-1-phenyl-8-(1H-pyrazolo[3,4-b]pyridine-5-carbonyl)-1,3,8-triazaspiro[4.5]decan-3-yl)acetyl)pyrrolidine-2-carboxylate;

2-[4-Oxo-8-(1H-pyrazolo[3,4-b]pyridine-5-carbonyl)-1-[3-(trifluoromethyl)phenyl]-1,3,8-triazaspiro[4.5]decan-3-yl]-N-(2,2,2-trifluoroethyl)acetamide;

2-[1-(3-Chloro-5-fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(3-Cyanophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide; and and pharmaceutically acceptable salts thereof.

Particular compounds of formula (I) of the present invention are those selected from the group consisting of:

2-(8-(1H-Indazole-5-carbonyl)-4-oxo-1-phenyl-1,3,8-triazaspiro[4.5]decan-3-yl)-N-(2,2,2-trifluoroethyl)acetamide;

8-(1H-Indazole-5-carbonyl)-3-(2-morpholino-2-oxoethyl)-1-phenyl-1,3,8-triazaspiro[4.5]decan-4-one;

2-(8-(1H-indazole-5-carbonyl)-4-oxo-1-phenyl-1,3,8-triazaspiro[4.5]decan-3-yl)-N-(pyridin-2-yl)acetamide;

2-(4-Oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

2-(4-Oxo-1-phenyl-8-(1H-pyrazolo[3,4-b]pyridine-5-carbonyl)-1,3,8-triazaspiro[4.5]decan-3-yl)-N-(pyridin-2-yl)acetamide;

N-Methyl-2-(4-oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

2-(4-Oxo-1-phenyl-8-(1H-pyrazolo[4,3-b]pyridine-5-carbonyl)-1,3,8-triazaspiro[4.5]decan-3-yl)-N-(2,2,2-trifluoroethyl)acetamide;

2-(8-(3-Amino-1H-indazole-5-carbonyl)-4-oxo-1-phenyl-1,3,8-triazaspiro[4.5]decan-3-yl)-N-(2,2,2-trifluoroethyl)acetamide;

(R)- or (S)-3-(2-Oxo-2-(2-(trifluoromethyl)morpholino)ethyl)-1-phenyl-8-(1H-pyrazolo[4,3-b]pyridine-5-carbonyl)-1,3,8-triazaspiro[4.5]decan-4-one; and and pharmaceutically acceptable salts thereof.

Compounds of formula (III) are suitable as intermediates in the manufacture of compounds of formula (I).

Another embodiment of the invention relates to a compound of formula (III)

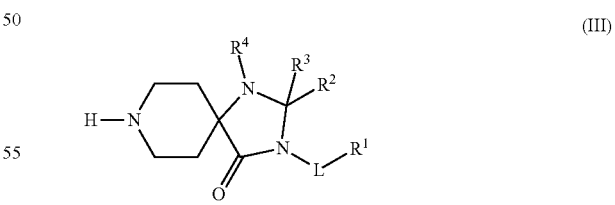

wherein L, $R^1$, $R^2$, $R^3$ and $R^4$ are as described herein; and salts thereof.

Manufacturing Process

One embodiment of the invention relates to a process for the manufacture of a compound of formula (I) comprising the amide coupling of a compound of formula (III) with an optionally protected carboxylic acid of formula $R^5COOH$ to yield a compound of formula (I), wherein L and $R^1$ to $R^5$ are as described herein.

One embodiment of the invention relates to a process for the manufacture of a compound of formula (I) comprising the deprotection step of a compound of formula (II) to a compound of formula (III) followed by the amide coupling step of a compound of formula (III) with an optionally protected carboxylic acid of formula R⁵COOH to yield a compound of formula (I), wherein PG is a protecting group, particularly an amino-protecting group, most particularly a benzyl or tert-butyloxycarbonyl group, and L, $R^1$ to $R^5$ are as described herein.

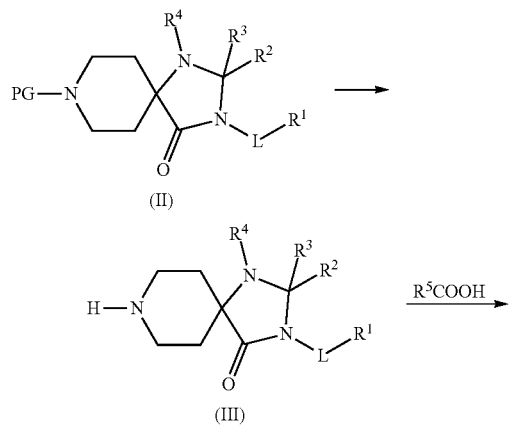

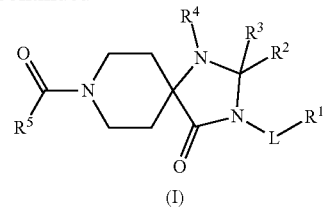

If one of the starting materials, intermediates or compounds of formula (I) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 5$^{th}$ Ed., 2014, John Wiley & Sons, N.Y.) can be introduced before the critical step applying methods well known in the art. Such protecting groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., (chiral) HPLC or crystallization. Racemic compounds can e.g., be separated into their antipodes via diastereomeric salts by crystallization with optically pure acids or by separation of the antipodes by specific chromatographic methods using either a chiral adsorbent or a chiral eluent.

Scheme 1

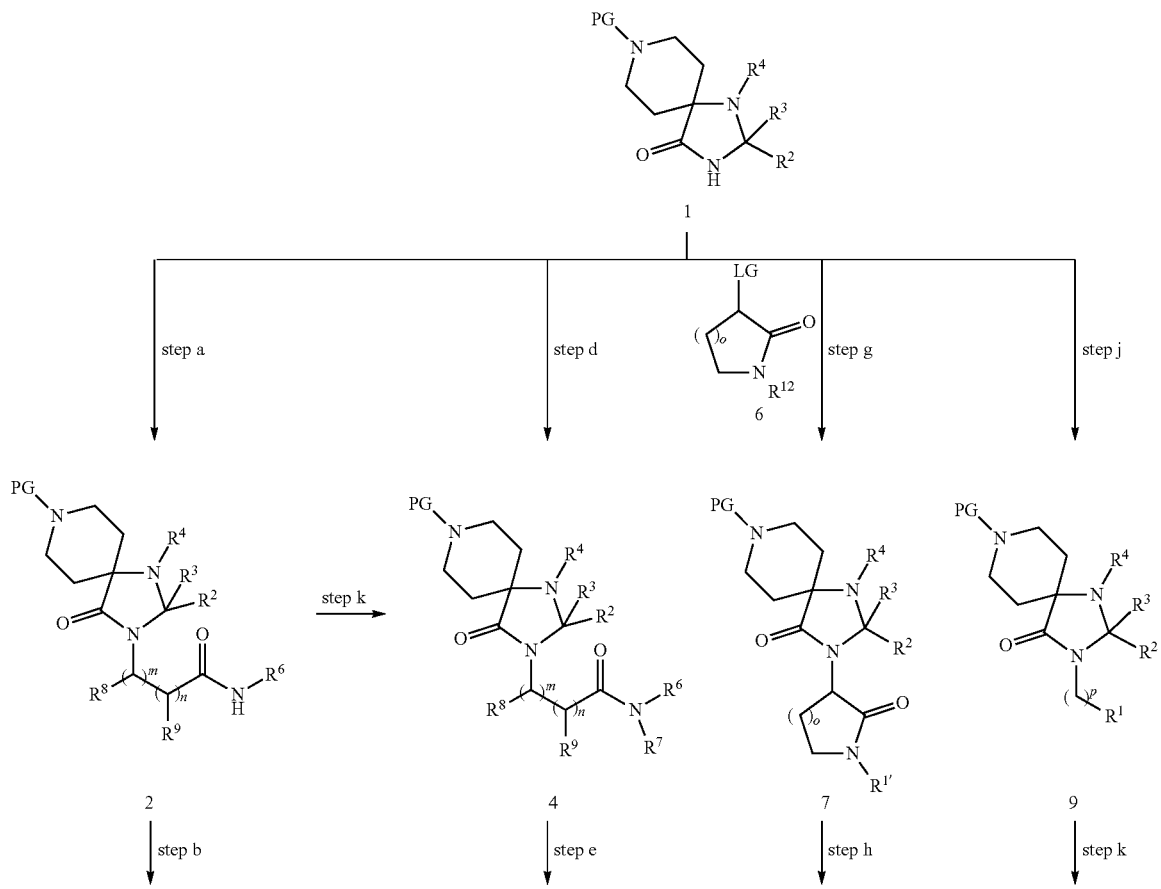

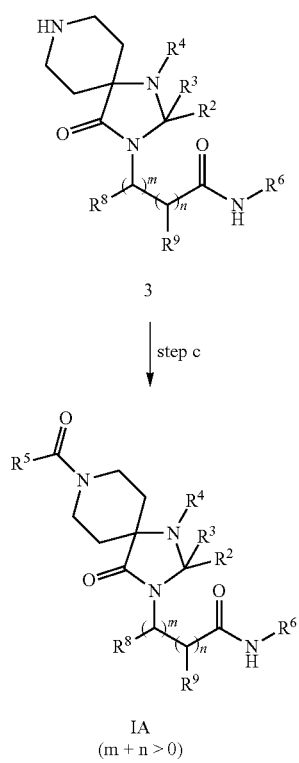
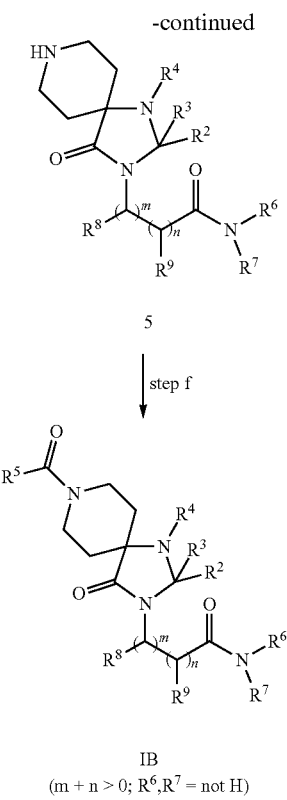
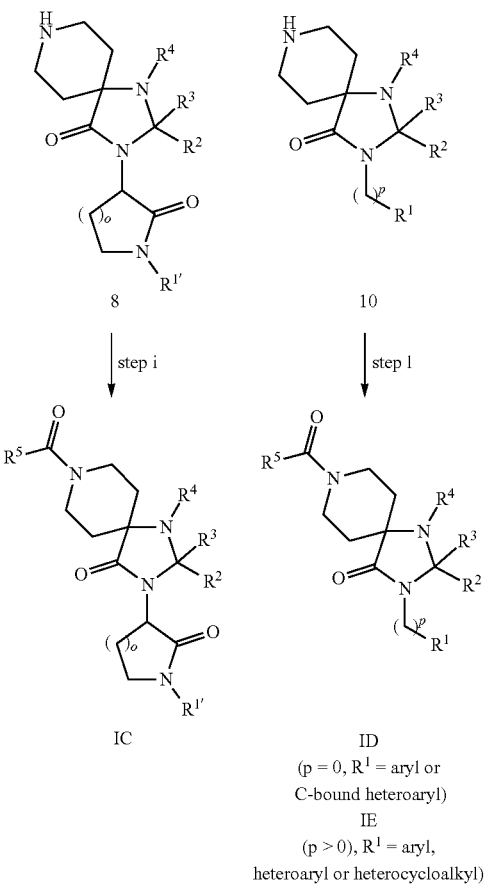

PG = Protective group

Compounds of formula IA-IE can be synthesized according to literature procedures and as depicted in Scheme 1, wherein o is 1 or 2, p is 0, 1 or 2, PG is a protecting group and $R^2$ to $R^9$, n and m are as described herein.

Compounds of formula IA can be prepared for example by alkylation of intermediates 1 in which PG signifies a suitable protecting group such as a benzyl or tert-butyloxycarbonyl group with compounds of the type $LG(CHR^8)_m(CHR^9)_nC(O)NHR^6$ (LG signifies a leaving group such as Cl, Br, I, $OSO_2$alkyl, $OSO_2$fluoroalkyl or $OSO_2$aryl) in an appropriate solvent such as N,N'-dimethylformamide and using an appropriate base such as cesium carbonate at temperatures ranging from 0° C. to the reflux temperature of the solvent to give intermediates 2 (step a).

Removal of the protecting group from intermediates 2 by methods known to those skilled in the art, as described in literature and as described for example in "Protective Groups in Organic Chemistry" by T. W. Greene and P. G. M. Wutts, $5^{th}$ Ed., 2014, John Wiley & Sons, N.Y. (e.g., a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 3 (step b).

Reaction of intermediates 3 with carboxylic acids of the type $R^5COOH$, furnishes compounds IA (step c). Amide couplings of this type are widely described in the literature and can be accomplished by the usage of coupling reagents such as CDI, DCC, HATU, HBTU, HOBT, TBTU or Mukaiyama reagent in a suitable solvent e.g., DMF, DMA, DCM or dioxane, optionally in the presence of a base (e.g., $NEt_3$, DIPEA (Huenig's base) or DMAP). Alternatively, the optionally protected carboxylic acids $R^5COOH$ can be converted into their acid chlorides by treatment with, e.g. thionyl chloride, neat or optionally in a solvent such as DCM. Reaction of the acid chloride with intermediates 3 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds IA (step c).

Compounds of formula IB can be prepared in for example by alkylation of intermediates 1 in which PG signifies a suitable protecting group such as a benzyl or tert-butyloxycarbonyl group with compounds of the type $LG(CHR^8)_m(CHR^9)_nC(O)NR^6R^7$ in which LG signifies a leaving group such as Cl, Br, I, $OSO_2$alkyl, $OSO_2$fluoroalkyl or $OSO_2$aryl in an appropriate solvent such as N,N'-dimethylformamide and using an appropriate base such as cesium carbonate at temperatures ranging from 0° C. to the reflux temperature of the solvent or solvent mixture to give intermediates 4 (step d).

Removal of the protecting group from intermediates 4 by methods known to those skilled in the art and as described for example in "Protective Groups in Organic Chemistry" by T. W. Greene and P. G. M. Wutts, $5^{th}$ Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 5 (step e).

Reaction of intermediates 5 with carboxylic acids of the type $R^5COOH$ furnishes compounds IB (step f). Amide couplings of this type are widely described in the literature and can be accomplished by the usage of coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., $NEt_3$, DIPEA (Huenig's base) or DMAP). Alternatively, the optionally protected carboxylic acids $R^5COOH$ can be converted into their acid chlorides by treatment with, e.g. thionyl chloride, neat or optionally in a solvent such as DCM. Reaction of the acid chloride with intermediates 5 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds IB (step f).

Compounds IB can alternatively be prepared by alkylation of intermediates 2 with compounds $R^7$-LG in which LG signifies a suitable leaving group such as bromo (or another leaving group such as chloro, iodo or $OSO_2$alkyl, $OSO_2$fluoroalkyl, $OSO_2$aryl) using an appropriate base and solvent such as sodium hydride in tetrahydrofuran to furnish intermediates 4 (step k). Subsequent deprotection and acylation as described before under step e and step f furnishes compounds IB.

Compounds of formula IC can be prepared in for example by alkylation of intermediates 1 with β-, γ- or δ-lactams 6 (n=1, 2 or 3, respectively; either commercially available or prepared by methods known in the art) in which LG signifies a suitable leaving group such as bromo (or another leaving group such as chloro, iodo or $OSO_2$alkyl, $OSO_2$fluoroalkyl, $OSO_2$aryl) using an appropriate base and solvent such as sodium hydride in tetrahydrofuran to furnish compounds 7 (step g).

Removal of the protecting group from intermediates 7 by methods known to those skilled in the art and as described for example in "Protective Groups in Organic Chemistry" by T. W. Greene and P. G. M. Wutts, $5^{th}$ Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 8 (step h).

Reaction of intermediates 8 with carboxylic acids of the type $R^5COOH$ furnishes compounds IC (step i). Amide couplings of this type are widely described in the literature and can be accomplished by the usage of coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., $NEt_3$, DIPEA (Huenig's base) or DMAP). Alternatively, the optionally protected carboxylic acids $R^5COOH$ can be converted into their acid chlorides by treatment with, e.g. thionyl chloride, neat or optionally in a solvent such as DCM. Reaction of the acid chloride with intermediates 5 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds IC (step i).

Compounds of formula ID in which p=0 and $R^1$ signifies an optionally substituted phenyl or optionally substituted heteroaryl ring can be prepared for example from intermediates 1 as described in Scheme 1. Reaction of intermediates 1 with compounds $R^1LG$ in which LG represents a suitable leaving group such iodo or bromo (or another leaving group such as $OSO_2$alkyl, $OSO_2$fluoroalkyl or $OSO_2$aryl) using an appropriate base and solvent such as $K_2CO_3$ in dioxane in the presence of DMEDA and Cu(I) at temperatures between RT and the boiling point of the solvent yields compounds 9 (p=0, step j). Microwave heating may be applied to accelerate the reaction or drive the reaction to completion.

Removal of the protecting group in intermediates 9 by methods known to those skilled in the art and as described for example in "Protective Groups in Organic Chemistry" by T. W. Greene and P. G. M. Wutts, $5^{th}$ Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 10 (p=0, step k).

Reaction of intermediates 10 with carboxylic acids of the type $R^5COOH$ furnishes compounds ID (p=0, step i). Amide couplings of this type are widely described in the literature and can be accomplished by the usage of coupling reagents such as, e.g., CDI, DCC, HATU, HOBT, TBTU or Mukaiyama reagent in a suitable solvent, e.g., DMF, DMA, DCM or dioxane, optionally in the presence of a base (e.g., $NEt_3$, DIPEA (Huenig's base) or DMAP). Alternatively, the optionally protected carboxylic acids $R^5COOH$ can be converted into their acid chlorides by treatment with, e.g. thionyl chloride, neat or optionally in a solvent such as DCM. Reaction of the acid chloride with intermediates 10 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds ID (p=0, step l).

Compounds of formula IE in which p=1 and $R^1$ signifies an optionally substituted phenyl or optionally substituted heteroaryl ring can be prepared from intermediates 1 as depicted in Scheme 1. Alkylation of intermediates 1 with compounds $R^1CH_2LG$ in which LG represents a suitable leaving group such as chloro, bromo, iodo (or another leaving group such as $OSO_2$alkyl, $OSO_2$fluoroalkyl or $OSO_2$aryl) using an appropriate base and solvent such as sodium hydride in tetrahydrofuran yields compounds 9 (p=1, step j).

Removal of the protecting group in intermediates 9 by methods known to those skilled in the art and as described for example in "Protective Groups in Organic Chemistry" by T. W. Greene and P. G. M. Wutts, $5^{th}$ Ed., 2014, John Wiley & Sons, N.Y. (e.g. a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 10 (p=1, step k).

Acylation of intermediates 10 with carboxylic acids of the type $R^5COOH$ furnishes compounds IE (step l). Amide couplings of this type are widely described in the literature and can be accomplished by the usage of coupling reagents such as, e.g., CDI, DCC, HATU, HBTU, HOBT, TBTU or Mukaiyama reagent in a suitable solvent, e.g., DMF, DMA, DCM or dioxane, optionally in the presence of a base (e.g., NEt$_3$, DIPEA (Huenig's base) or DMAP). Alternatively, the optionally protected carboxylic acids R$^5$COOH can be converted into their acid chlorides by treatment with, e.g. thionyl chloride, neat or optionally in a solvent such as DCM. Reaction of the acid chloride with intermediates 10 in an appropriate solvent such as DCM or DMF and a base, e.g. NEt$_3$, Huenig's base, pyridine, DMAP or lithium bis(trimethylsilyl)amide at temperatures ranging from 0° C. to the reflux temperature of the solvent or solvent mixture yields compounds IE (p=1, step l).

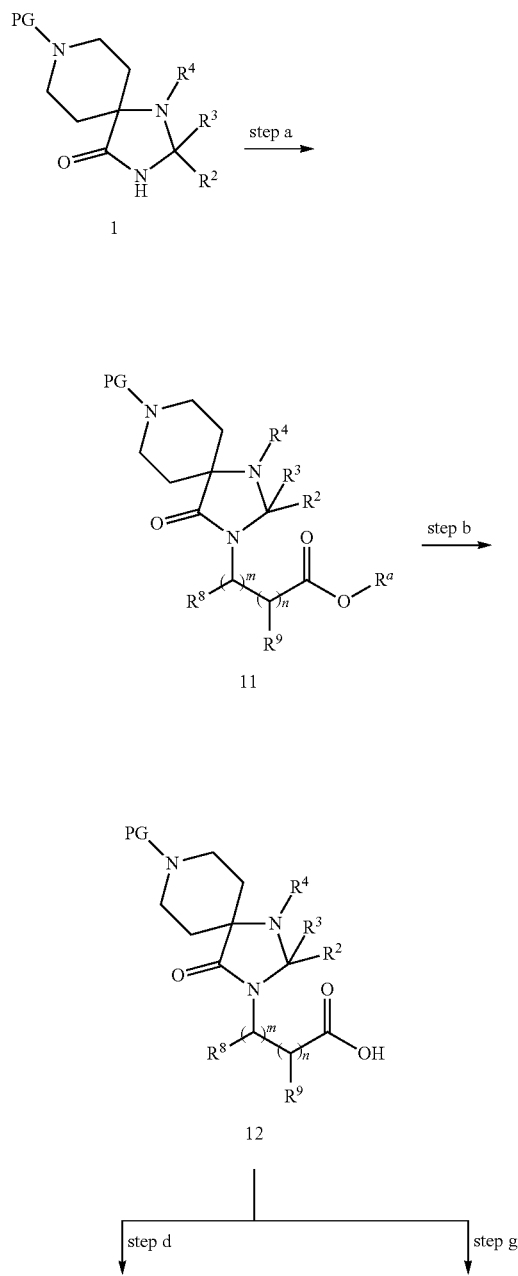

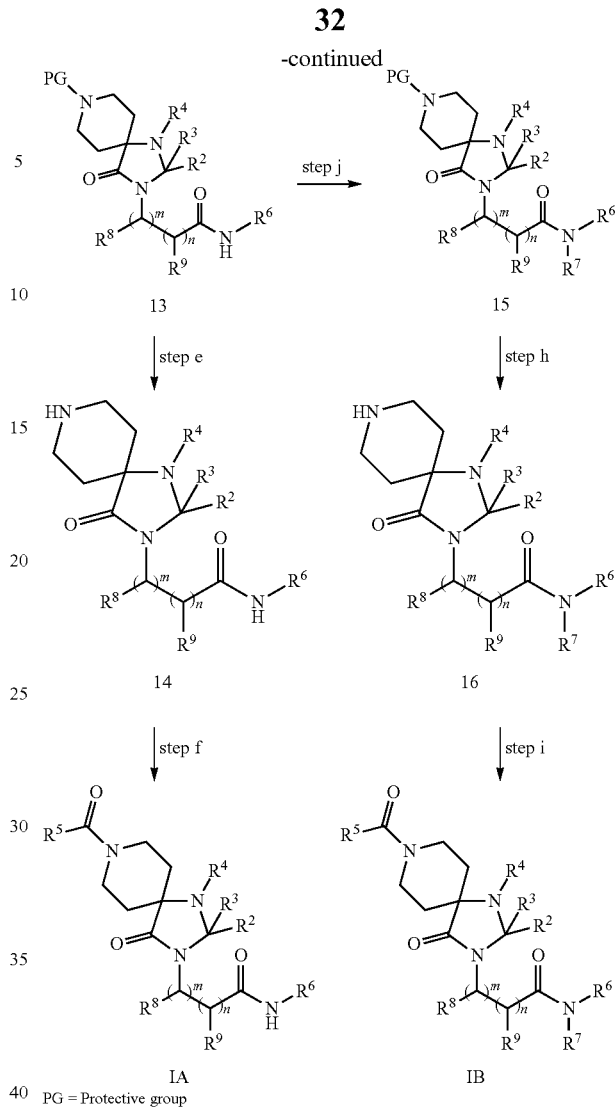

PG = Protective group

Compounds of formula IA and IB can be alternatively prepared as described in Scheme 2, wherein PG is a protecting group and R$^2$ to R$^9$, n and m are as described herein.

Alkylation of intermediates 1 with esters of the type LG(CHR$^8$)$_m$(CHR$^9$)$_n$CO$_2$R$^a$ in which R$^a$ signifies an ester protecting group, e.g. methyl, ethyl or tert-butyl and LG signifies a suitable leaving group such as Cl, Br, I, OSO$_2$alkyl, OSO$_2$fluoroalkyl or OSO$_2$aryl using an appropriate base and solvent such as sodium hydride in dioxane at temperatures ranging from 0° C. to the reflux temperature of the solvent yields intermediates 11 (step a).

Cleavage of the ester functionality in intermediates 11 under basic (e.g. methyl or ethyl esters with lithium or sodium hydroxide in polar solvents such as methanol, H$_2$O or THF or mixtures of said solvents) or under acidic conditions (e.g. a tert-butyl ester using concentrated hydrochloric acid in tetrahydrofuran or formic acid in an appropriate solvent such as alcohols like isopropanol) furnishes compounds 12 (step b). Further esters include, but are not limited to, e.g. allyl or benzyl esters that can be cleaved by methods known to those skilled in the art and as described for example in "Protective Groups in Organic Chemistry" by T. W. Greene and P. G. M. Wutts, 5$^{th}$ Ed., 2014, John Wiley & Sons, N.Y.

Intermediates 12 can be converted into intermediates 13 by reacting intermediates 12 with amines $R^6NH_2$ (either commercially available or prepared by methods well known in the art). Amide couplings of this type are widely described in the literature and can be accomplished by the usage of coupling reagents such as, e.g. CDI, DCC, HATU, HBTU, HOBT, TBTU or Mukaiyama reagent in a suitable solvent, e.g., DMF, DMA, DCM or dioxane, optionally in the presence of a base (e.g. $NEt_3$, DIPEA or DMAP). Alternatively, the carboxylic acid functionality in compounds 12 can be converted into an acid chloride by treatment with, e.g. thionyl chloride, neat or optionally in a solvent such as DCM. Reaction of the acid chloride with amines $R^6NH_2$ in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields intermediates 13 (step d).

Intermediates 13 can be converted into intermediates 14 (step e) and further into compounds IA (step f) by methods known in the art and using the reagents and applying the reaction conditions described before, e.g. in Scheme 1 step b and step c.

Compounds IB can be prepared from intermediates 12 and amines $R^6R^7NH$ (either commercially available or prepared by methods well known in the art) by methods known in the art and using the reagents and applying the reaction conditions described before to give intermediates 15 (step g).

Intermediates 15 can be transformed into intermediates 16 (step h) that can be further converted into compounds IB (step i) by methods known in the art and using the reagents and applying the reaction conditions described before, e.g. in Scheme 1 step e and step f.

Intermediates 15 can be also prepared from intermediates 13 applying methods known in the art, for example by alkylating the secondary amide functionality in 15 with compounds $R^7$-LG in which LG signifies a suitable leaving group such as bromo (or another leaving group such as chloro, iodo or $OSO_2$alkyl, $OSO_2$fluoroalkyl or $OSO_2$aryl) using an appropriate base and solvent such as sodium hydride in tetrahydrofuran (step j).

In case substituents $R^5$, $R^8$ and $R^9$ in compounds IA-IE carry protecting groups these can be removed by methods known to those skilled in the art and as described for example in "Protective Groups in Organic Chemistry" by T. W. Greene and P. G. M. Wutts, $5^{th}$ Ed., 2014, John Wiley & Sons, N.Y. to furnish the final compounds.

A person skilled in the art will acknowledge that the sequence of reactions steps as depicted in Scheme 1 and Scheme 2 may be varied depending on reactivity and nature of the intermediates.

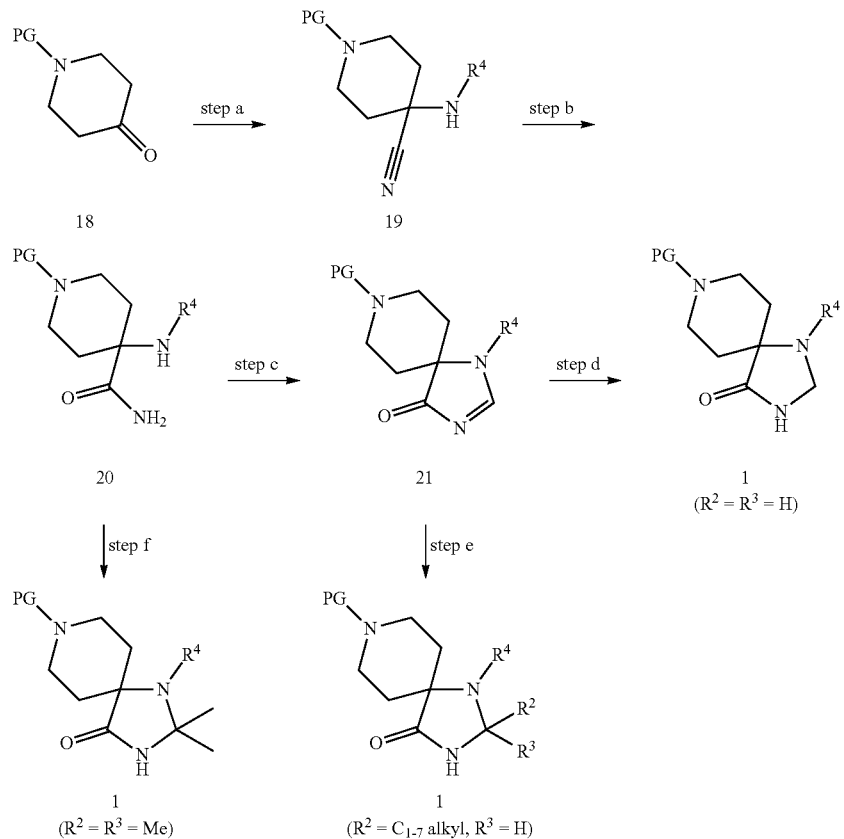

Scheme 3.

PG = Protective group

If intermediates 1 are commercially not available they can be prepared according to procedures described in literature and as depicted in Scheme 3, wherein PG is a protecting group and $R^2$ to $R^4$ are as described herein.

Intermediates 1 in which $R^2=R^3=H$ are described in e.g., WO2001/094346, WO2010/037081, M. C. O'Reilly et al., J. Med. Chem. 2013, 56(6), 2695 or R. R. Lavieri et al., J. Med. Chem. 2010, 53(18), 6706. For example, reaction of commercially available piperidin-4-ones 18 in which PG signifies a suitable protecting group such as a benzyl or a tert-butyloxycarbonyl group are reacted with a suitable cyano source such as trimethylsilyl- or potassium cyanide under acidic conditions e.g., using acetic acid to give intermediates 19 (step a).

Hydrolysis of the nitrile functionality in intermediates 19 using for example sulfuric acid yields 4-anilino-4-carboxamide-piperidine intermediates 20 (step b).

Intermediates 20 can by cyclized using for example trimethyl- or triethyl-orthoformate (or alternatively N,N-dimethylformamide dimethyl acetal) in the presence of e.g., acetic acid at elevated temperatures to give the 1,3,8-triazaspiro[4.5]dec-2-en-4-ones 21 (step c). Microwave heating may be applied to accelerate the reaction or drive the reaction to completion.

Intermediates 21 can be further reduced for example using sodium borohydride in a suitable solvent such as methanol to furnish intermediates 1 in which $R^2=R^3=H$.

Intermediates 1 in which one of $R^2$ or $R^3$ is $C_{1-7}$ alkyl and the other is hydrogen can be prepared in analogy to methods described in literature e.g., EP921125, WO 2001/094346 or WO 2005/040166. Reaction of intermediates 21 with a Grignard reagent $R^2MgX$ in which $R^2$ signifies $C_{1-7}$ alkyl or optionally substituted phenyl group and X means chloro or bromo in an appropriate solvent such as THF optionally in the presence of a catalyst such as copper(I)chloride at temperatures ranging from −78° to RT yields intermediates 1 in which $R^2$ or $R^3$ is $C_{1-7}$ alkyl or optionally substituted phenyl group (step e).

Intermediates 1 in which $R^2$ and $R^3$ signify a methyl group can be synthesized in analogy to literature procedures (e.g. WO2005/040166), for example by reaction of intermediates 20 with 2-methoxyprop-1-ene or 2,2-dimethoxypropane in the presence of e.g., p-toluenesulfonic acid in a suitable solvent such as toluene at temperatures ranging from RT to the boiling point of the solvent or solvent mixture. Microwave heating may be applied to accelerate the reaction or drive the reaction to completion (step f).

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C, Handbook of Pharmaceutical Excipients (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Therapeutic Uses

As described above, the compounds of formula (I) and their pharmaceutically acceptable salts possess valuable pharmacological properties and have been found to be inhibitors of the Discoidin Domain Receptor 1 (DDR1).

The compounds of the present invention can be used, either alone or in combination with other drugs, for the treatment or prevention of diseases related to DDR1. These diseases include, but are not limited to renal conditions, liver conditions, inflammatory conditions, vascular conditions, cardiovascular conditions, fibrotic diseases, cancer and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitis/systemic diseases as well as acute and chronic kidney transplant rejection. Renal conditions also includes early and advanced Alport syndrome.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma. Further conditions of the respiratory system include, but are not limited to, other diffuse parenchymal lung diseases of different etiologies including iatrogenic drug-induced fibrosis, occupational and/or environmental induced fibrosis, systemic diseases and vasculitis, granulomatous diseases (sarcoidosis, hypersensitivity pneumonia), collagen vascular disease, radiation induced fibrosis.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma and progression and metastatic aggressiveness thereof.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the compounds of formula (I) or their pharmaceutically acceptable salts and esters can be used for the treatment or prophylaxis of organ or skin fibrosis.

In a particular embodiment, the fibrotic disease is renal tubulo-interstitial fibrosis or glomerulosclerosis.

In a particular embodiment, the fibrotic disease is early or progressive renal tubule-interstitial fibrosis and glomerular damage induced by Alport syndrome.

In a particular embodiment, the fibrotic disease induce by patients affected by Alport syndrome.

In a particular embodiment of the invention, the compounds of the present invention are used for the treatment or prevention of early or advanced Alport syndrome.

In a particular embodiment, the fibrotic disease is non-alcoholic liver steatosis, liver fibrosis or liver cirrhosis.

In a particular embodiment, the fibrotic disease is idiopathic pulmonary fibrosis.

In a particular embodiment, the fibrotic disease is encapsulating peritonitis

In a particular embodiment, the cancer includes, but is not limited to, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma and progression and metastatic aggressiveness thereof.

Compounds of formula (I) as described herein can also be used in combination with any other cancer drug even if the compound on its own might not be tumor static or induce cancer regression but as a combination treatment to reduce metastasis and prevent cancer drug resistance.

A particular embodiment of the invention also relates to a pharmaceutical composition comprising a compound of formula (I) as described herein and at least one pharmaceutically acceptable excipient.

A particular embodiment of the invention also relates to a compound of formula (I) as described herein for use as therapeutically active substances.

A particular embodiment of the invention also relates to a compound of formula (I) as described herein for use in the treatment or prevention of diseases which are related to DDR1, particularly for use in the treatment or prevention of renal conditions, liver conditions, inflammatory conditions, vascular conditions, cardiovascular conditions, fibrotic diseases, cancer and acute and chronic organ transplant rejection.

A particular embodiment of the invention also relates to a compound of formula (I) as described herein for use in the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

In another embodiment, the invention relates to a method for the treatment or prevention of diseases which are related to DDR1, which method comprises administering a compound of formula (I) as described herein to a human being or animal.

In another embodiment, the invention relates to a method for the treatment or prevention of renal conditions, liver conditions, inflammatory conditions, vascular conditions, cardiovascular conditions, fibrotic diseases, cancer and acute and chronic organ transplant rejection, which method comprises administering a compound of formula (I) as described herein to a human being or animal.

In another embodiment, the invention relates to a method for the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof, which method comprises administering a compound of formula (I) as described herein to a human being or animal.

The invention also embraces the use of a compound of formula (I) as described herein for the treatment or prevention of diseases which are related to DDR1.

The invention also embraces the use of a compound of formula (I) as described herein for the treatment or prevention of renal conditions, liver conditions, inflammatory conditions, vascular conditions, cardiovascular conditions, fibrotic diseases, cancer and acute and chronic organ transplant rej ection.

The invention also embraces the use of a compound of formula (I) as described herein for the treatment or prevention of acute kidney injury, chronic kidney disease, contrast agent-induced nephropathy, diabetic nephropathy, acute kidney transplant rej ection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

The invention also relates to the use of a compound of formula (I) as described herein for the preparation of medicaments useful for the treatment or prevention of diseases which are related to DDR1.

The invention also relates to the use of a compound of formula (I) as described herein for the preparation of medicaments useful for the treatment or prevention of renal conditions, liver conditions, inflammatory conditions, vascular conditions, cardiovascular conditions, fibrotic diseases, cancer and acute and chronic organ transplant rejection.

The invention also relates to the use of a compound of formula (I) as described herein for the preparation of medicaments useful for the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

EXAMPLES

The following examples 1-90 are provided for illustration of the invention. They should not be considered as limiting the scope of the invention, but merely as being representative thereof.

Abbreviations:

AcOH=acetic acid, ACN=MeCN, Boc anhydride=di-tert-butyl dicarbonate, CAS RN=chemical abstracts registration number, CO=carbon monoxide, CuCl=copper (I) chloride, CuI=copper (I) iodide, DCE=1,2-dichloroethane, DCM=dichloromethane, DMAP=4-dimethylaminopyridine, DME=dimethoxyethane, DMEDA=N,N'-dimethylethylendiamine, DMF=N,N-dimethylformamide, DIPEA=N,N-diisopropylethylamine, DPPF=1,1'-bis(diphenylphosphanyl)ferrocene, EDCI=1-ethyl-3-(3-dimethylaminopropyl)carbodiimide, EtOH=ethanol, dppf=1,1 bis(diphenylphosphino)ferrocene, EI=electron impact, ESI=electrospray ionization, EtOAc=ethyl acetate, h=hour(s), $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=N,N,N',N'-tetramethyl-O-(1H-benzotriazol-1-yl)uronium hexafluorophosphate, HCl=hydrogen chloride, HOBt=1-hydroxybenzotriazole, HPLC=high performance liquid chromatography, iPrMgCl=isopropylmagnesium chloride, ISP=ion spray positive (mode), ISN=ion spray negative (mode), min=minutes, $K_2CO_3$=potassium carbonate, $LiAlH_4$ or LAH=lithium aluminium hydride, LiHMDS=lithium bis(trimethylsilyl)amide, LiOH=lithium hydroxide, MeOH=methanol, $MgSO_4$=magnesium sulfate, min=minute(s), MPLC=medium performance liquid chromatography, MS=mass spectrum, NaH=sodium hydride, nBuLi=n-butyllithium, NaHCO$_3$=sodium hydrogen carbonate, NaOH=sodium hydroxide, Na$_2$CO$_3$=sodium carbonate, Na$_2$SO$_4$=sodium sulfate, Na$_2$S$_2$O$_3$=sodium thiosulfate, NH$_4$Cl=ammonium chloride, NH$_4$OAc=ammonium acetate, KOH=potassium hydroxide, PG=protecting group, Pd—C=palladium on activated carbon, PdCl$_2$(dppf)-CH$_2$Cl$_2$=1,1'-bis(diphenylphosphino)-ferrocene-palladium (II)dichloride dichloromethane complex, Pd(OAc)$_2$=palladium(II) acetate, Pd(PPh$_3$)$_4$=tetrakis(triphenylphosphine) palladium(0), Pd$_2$(dba)$_3$=tris(dibenzylideneacetone) dipalladium(0), prep.=preparative, PyBOP=(benzotriazol-1-yl-oxytripyrrolidinophosphonium-hexafluorophosphate), RT=room temperature, S-PHOS=2-dicyclohexylphosphino-2',6'-dimethoxybiphenyl, TEA=triethylamine, TFA=trifluroacetic acid, THF=tetrahydrofuran, TMEDA=N,N,N',N'-tetramethylethylenediamine, TMS-CN=trimethylsily cyanide, pTsOH=p-toluenesulfonic acid, X-Phos=2-dicyclohexylphosphino-2',4',6'-triisopropylbiphenyl, Zn=zinc, ZnCl2=zinc chloride.

Example 1

(2-[1-(4-Fluoro-phenyl)-4-oxo-8-(1H-pyrazolo[3,4-b]pyridine-5 carbonyl)-1,3,8-triaza-spiro[4.5]dec-3-yl]-N-(2,2,2-trifluoro-ethyl)-acetamide)

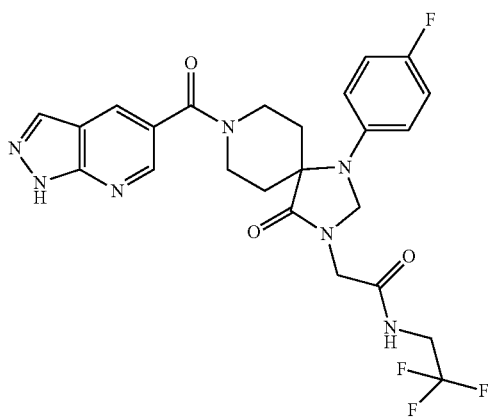 [SMILES: O=C(CN1CN(c2ccc(F)cc2)C2(CCN(C(=O)c3cnc4[nH]ncc4c3)CC2)C1=O)NCC(F)(F)F]

To a stirred solution of 2-[1-(4-fluoro-phenyl)-4-oxo-1,3,8-triaza-spiro[4.5]dec-3-yl]-N-(2,2,2-trifluoro-ethyl)-acetamide (100 mg, 0.26 mmol) in DMF (4 mL) were added 1H-pyrazolo[3,4-b]pyridine-5-carboxylic acid (50.41 mg, 0.31 mmol, CAS RN 952182-02-4), DIPEA (0.18 mL, 1.03 mmol), and PyBOP (335.31 mg, 0.64 mmol) and the reaction mixture was stirred at 25° C. for 4 h. The reaction mixture was quenched with H$_2$O and extracted with EtOAc. The combined organic layers were dried over Na$_2$SO$_4$, filtered and evaporated. The residue was purified by prep. HPLC (NH$_4$OAc/ACN) to get the title compound as an off-white solid (44 mg, 32%). MS (ESI): m/z=534.2 [M+H]$^+$.

Intermediate a) 2-[1-(4-Fluoro-phenyl)-4-oxo-1,3,8-triaza-spiro[4.5]dec-3-yl]-N-(2,2,2-trifluoro-ethyl)-acetamide To a stirred solution of 2-[8-benzyl-1-(4-fluoro-phenyl)-4-oxo-1,3,8-triaza-spiro[4.5]dec-3-yl]-N-(2,2,2-trifluoro-ethyl)-acetamide (300 mg, 0.63 mmol) in MeOH (5 mL) was added Pd/C (60 mg) and the reaction mixture was stirred at 25° C. for 16 h under hydrogen atmosphere. The reaction mixture was filtered through a celite bed and washed with 10% MeOH in DCM (25 mL). The Filtrate was evaporated to give the title compound as an off-white solid (230 mg, 94%). MS (ESI): m/z=389.2 [M+H]$^+$.

Intermediate b) 2-[8-Benzyl-1-(4-fluoro-phenyl)-4-oxo-1,3,8-triaza-spiro[4.5]dec-3-yl]-N-(2,2,2-trifluoro-ethyl)-acetamide To a stirred solution of 8-benzyl-1-(4-fluoro-phenyl)-1,3,8-triaza-spiro[4.5]decan-4-one (450 mg, 1.33 mmol) in DMF (5 mL) was added NaH (47.78 mg, 1.99 mmol) at 0° C. and the reaction mixture was stirred at 25° C. for 1 h. Then 2-chloro-N-(2,2,2-trifluoro-ethyl)-acetamide (279.62 mg, 1.59 mmol, CAS RN 170655-44-4) in DMF (5 mL) was added and the reaction mixture was stirred at 25° C. for 16 h. The reaction mixture was quenched with saturated aqueous NH$_4$Cl solution and extracted with EtOAc. The combined organic layers were dried over Na$_2$SO$_4$, filtered and evaporated. The resulting residue was purified by silica gel flash chromatography (2% to 3% MeOH in DCM) to give the title compound as a brown semi solid (300 mg, 47%). MS (ESI): m/z=479.4 [M+H]$^+$.

Intermediate c) 8-Benzyl-1-(4-fluoro-phenyl)-1,3,8-triaza-spiro[4.5]decan-4-one

To a stirred solution of 8-benzyl-1-(4-fluoro-phenyl)-1,3,8-triaza-spiro[4.5]dec-2-en-4-one (600 mg, 1.78 mmol) in MeOH (15 mL) was added NaBH$_4$ (168.38 mg, 4.45 mmol) at 0° C. and reaction mixture was stirred at 25° C. for 4 h. Reaction mixture was quenched with H$_2$O; solvent was evaporated and extracted with DCM (2×20 mL). The combined organic layers were dried over Na$_2$SO$_4$, filtered and evaporated under reduced pressure. The resulting residue was washed with Et$_2$O and pentane to give the title compound as an off-white solid (450 mg, 74%). MS (ESI): m/z=340.4 [M+H]$^+$.

Intermediate d) 8-Benzyl-1-(4-fluoro-phenyl)-1,3,8-triaza-spiro[4.5]dec-2-en-4-one 1-Benzyl-4-(4-fluoro-phenylamino)-piperidine-4-carboxamide (2 g, 6.10 mmol), triethyl orthoformate (2.58 mL, CAS RN 122-51-0) and AcOH (1.3 mL) were heated to 170° C. in microwave for 40 min. The reaction mixture was diluted with H$_2$O, basified with aqueous ammonia solution and extracted with DCM (2×25 mL). The combined organic layers were dried over Na$_2$SO$_4$, filtered and evaporated. The resulting residue was purified by silica gel flash chromatography (2% to 3% MeOH in DCM) to give the title compound as a brown liquid (600 mg, 29%). MS (ESI): m/z=340.2 [M+H]$^+$.

Intermediate e) 1-Benzyl-4-(4-fluoro-phenylamino)-piperidine-4-carboxamide

1-Benzyl-4-(4-fluoro-phenylamino)-piperidine-4-carbonitrile (6.8 g, 22.00 mmol) was stirred in concentrated H$_2$SO$_4$ (22 mL) at 25° C. for 16 h. The reaction mixture was poured onto ice, the pH was adjusted to 9 using 5N NaOH solution and extracted with DCM (2×30 mL). The combined organic layers were washed with brine, dried over Na$_2$SO$_4$, filtered and evaporated to give the title compound as an off-white solid (6.5 g, 90%). MS (ESI): m/z=327.9 [M+H]⁺.

Intermediate f) 1-Benzyl-4-(4-fluoro-phenylamino)-piperidine-4-carbonitrile

To a solution of 1-benzyl-piperidin-4-one (5 g, 26.42 mmol, CAS RN 3612-20-2) and 4-fluoro-phenylamine (2.79 mL, 29.06 mmol, CAS RN 371-40-4) in AcOH (20 mL) was added trimethylsilyl cyanide (3.31 mL, 26.42 mmol, CAS RN 7677-24-9) and the reaction mixture was stirred at 25° C. for 16 h. The reaction mixture was poured onto ice, the pH adjusted to 9 using 5N NaOH solution and the aqueous mixture was extracted with DCM (2×100 mL). The combined organic layer were washed with brine, dried over Na₂SO₄, filtered and evaporated. The residue was washed with Et₂O to give the title compound as an off-white solid (6.8 g, 83%). MS (ESI): m/z=310.4 [M+H]⁺.

Example 2

2-[1-(3-Fluoro-phenyl)-4-oxo-8-(1H-pyrazolo[3,4-b]pyridine-5-carbonyl)-1,3,8-triaza-spiro[4.5]dec-3-yl]-N-(2,2,2-trifluoro-ethyl)-acetamide

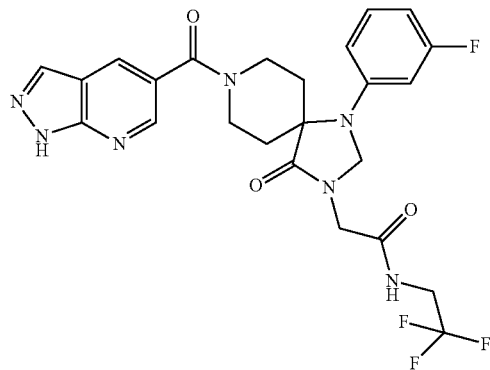 [SMILES: O=C(CN1CN(c2cccc(F)c2)C2(CCN(C(=O)c3cnc4[nH]ncc4c3)CC2)C1=O)NCC(F)(F)F]

The title compound was obtained in analogy to example 1, from 2-[1-(3-fluoro-phenyl)-4-oxo-1,3,8-triaza-spiro[4.5]dec-3-yl]-N-(2,2,2-trifluoro-ethyl)-acetamide and 1H-pyrazolo[3,4-b]pyridine-5-carboxylic acid (CAS RN 952182-02-4) as an off-white solid. MS (EI): m/z=534.2 [M+H]⁺.

Intermediate a) 2-[1-(3-Fluoro-phenyl)-4-oxo-1,3,8-triaza-spiro[4.5]dec-3-yl]-N-(2,2,2-trifluoro-ethyl)-acetamide The title compound was obtained in analogy to example 1, intermediate a, from 2-[8-benzyl-1-(3-fluoro-phenyl)-4-oxo-1,3,8-triaza-spiro[4.5]dec-3-yl]-N-(2,2,2-trifluoro-ethyl)-acetamide as an off-white semi solid. MS (EI): m/z=389.2 [M+H]⁺.

Intermediate b) 2-[8-Benzyl-1-(3-fluoro-phenyl)-4-oxo-1,3,8-triaza-spiro[4.5]dec-3-yl]-N-(2,2,2-trifluoro-ethyl)-acetamide The title compound was obtained in analogy to example 1, intermediate b, from 8-benzyl-1-(3-fluoro-phenyl)-1,3,8-triaza-spiro[4.5]decan-4-one and 2-chloro-N-(2,2,2-trifluoro-ethyl)-acetamide (CAS RN 170655-44-4) as an off-white semi solid. MS (EI): m/z=478.9 [M+H]⁺.

Intermediate c) 8-Benzyl-1-(3-fluoro-phenyl)-1,3,8-triaza-spiro[4.5]decan-4-one

The title compound was obtained in analogy to example 1, intermediate c, from 1-benzyl-4-(3-fluoro-phenylamino)-piperidine-4-carboxamide as a yellow solid. MS (EI): m/z=340.2 [M+H]⁺.

Intermediate d) 1-Benzyl-4-(3-fluoro-phenylamino)-piperidine-4-carboxamide

The title compound was obtained in analogy to example 1, intermediate e, from 1-benzyl-4-(3-fluoro-phenylamino)-piperidine-4-carbonitrile as an off-white solid. MS (EI): m/z=328.3 [M+H]⁺.

Intermediate e) 1-Benzyl-4-(3-fluoro-phenylamino)-piperidine-4-carbonitrile

The title compound was obtained in analogy to example 1, intermediate f, from 1-benzyl-piperidin-4-one (CAS RN 3612-20-2) and 3-fluoro-phenylamine (CAS RN 372-19-0) as an off-white solid. MS (EI): m/z=310.4 [M+H]⁺.

Example 3

2-[1-(2-Fluoro-phenyl)-4-oxo-8-(1H-pyrazolo[3,4-b]pyridine-5-carbonyl)-1,3,8-triaza-spiro[4.5]dec-3-yl]-N-(2,2,2-trifluoro-ethyl)-acetamide

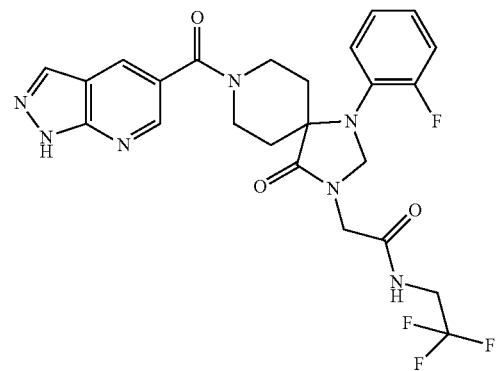 [SMILES: O=C(CN1CN(c2ccccc2F)C2(CCN(C(=O)c3cnc4[nH]ncc4c3)CC2)C1=O)NCC(F)(F)F]

The title compound was obtained in analogy to example 1, from 2-[1-(2-fluoro-phenyl)-4-oxo-1,3,8-triaza-spiro[4.5]dec-3-yl]-N-(2,2,2-trifluoro-ethyl)-acetamide and 1H-pyrazolo[3,4-b]pyridine-5-carboxylic acid (CAS RN 952182-02-4) as an off-white solid. MS (EI): m/z=534.1 [M+H]⁺.

Intermediate a) 2-[1-(2-Fluoro-phenyl)-4-oxo-1,3,8-triaza-spiro[4.5]dec-3-yl]-N-(2,2,2-trifluoro-ethyl)-acetamide The title compound was obtained in analogy to example 1, intermediate a, from 2-[8-benzyl-1-(2-fluoro-phenyl)-4-oxo-1,3,8-triaza-spiro[4.5]dec-3-yl]-N-(2,2,2-trifluoro-ethyl)-acetamide as an off-white solid. MS (EI): m/z=389.2 [M+H]⁺.

Intermediate b) 2-[8-Benzyl-1-(2-fluoro-phenyl)-4-oxo-1,3,8-triaza-spiro[4.5]dec-3-yl]-N-(2,2,2-trifluoro-ethyl)-acetamide The title compound was obtained in analogy to example 1, intermediate b, from 8-benzyl-1-(2-fluoro-phenyl)-1,3,8- triaza-spiro[4.5]decan-4-one and 2-chloro-N-(2,2,2-trifluoro-ethyl)-acetamide (CAS RN 170655-44-4) as an off-white solid. MS (EI): m/z=478.6 [M+H]⁺.

Intermediate c) 8-Benzyl-1-(2-fluoro-phenyl)-1,3,8-triaza-spiro[4.5]decan-4-one

The title compound was obtained in analogy to example 1, intermediate c, from 8-benzyl-1-(2-fluoro-phenyl)-1,3,8-triaza-spiro[4.5]dec-2-en-4-one as a colorless liquid. MS (EI): m/z=339.9 [M+H]⁺.

Intermediate d) 8-Benzyl-1-(2-fluoro-phenyl)-1,3,8-triaza-spiro[4.5]dec-2-en-4-one 1-Benzyl-4-(2-fluoro-phenylamino)-piperidine-4-carboxamide (1 g, 3.06 mmol) and N,N-dimethylformamide dimethyl acetal (6.5 mL, 48.93 mmol, CAS RN 4637-24-5) were heated to 120° C. for 48 h. The reaction mixture was diluted with H₂O, basified with aqueous NaHCO₃ solution and extracted with DCM (2×25 mL). The combined organic layers were dried over Na₂SO₄, filtered and evaporated to get the title compound as a brown liquid. MS (EI): m/z=338.3 [M+H]⁺.

Intermediate e) 1-Benzyl-4-(2-fluoro-phenylamino)-piperidine-4-carboxamide

The title compound was obtained in analogy to example 1, intermediate e, from 1-benzyl-4-(2-fluoro-phenylamino)-piperidine-4-carbonitrile as an off-white solid. MS (EI): m/z=327.9 [M+H]⁺.

Intermediate f) 1-Benzyl-4-(2-fluoro-phenylamino)-piperidine-4-carbonitrile

The title compound was obtained in analogy to example 1, intermediate f, from 1-benzyl-piperidin-4-one (CAS RN 3612-20-2) and 2-fluoro-phenylamine (CAS RN 348-54-9) as an off-white solid. MS (EI): m/z=310.0 [M+H]⁺.

Example 4

2-(1-(3,4-Dichlorophenyl)-8-(1H-indazole-5-carbonyl)-4-oxo-1,3,8-triazaspiro[4.5]decan-3-yl)-N-(2,2,2-trifluoroethyl)acetamide tert-Butyl 5-[1-(3,4-dichlorophenyl)-4-oxo-1,3,8-triazaspiro[4.5]decane-8-carbonyl]indazole-1-carboxylate (80 mg, 147 µmol), 2-chloro-N-(2,2,2-trifluoroethyl)acetamide (28.8 mg, 164 µmol, CAS RN 170655-44-4) and cesium carbonate (80 mg, 246 µmol) were treated with DMF (2 mL). The reaction mixture was heated to 80° C. for 30 min. An additional amount of 2-chloro-N-(2,2,2-trifluoroethyl) acetamide (28.8 mg, 164 µmol, CAS RN 170655-44-4) was added. The reaction mixture was stirred at 50° C. overnight. The reaction mixture was diluted with EtOAc, then washed with H₂O. The organic phase was collected and dried over Na₂SO₄, filtered and evaporated. The crude product was treated with 2 M HCl in EtOAc and stirred for 72 h at RT. The crude reaction mixture was concentrated in vacuo. The residue was purified by prep. HPLC to get title compound as a white solid (21 mg, 24.5%), MS (ESI): m/z=583 [M+H]⁺.

Intermediate a) tert-Butyl 5-[1-(3,4-dichlorophenyl)-4-oxo-1,3,8-triazaspiro[4.5]decane-8-carbonyl]indazole-1-carboxylate 1-(3,4-Dichlorophenyl)-1,3,8-triazaspiro[4.5]decan-4-one (120 mg, 400 µmol), 1-(tert-butoxycarbonyl)-1H-indazole-5-carboxylic acid (105 mg, 400 µmol, CAS RN 61700-61-6), HBTU (152 mg, 400 µmol), TEA (121 mg, 167 µL, 1.2 mmol) were dissolved in DCM (15 mL). Molecular sieve (4 Å) was added, and the reaction mixture was stirred at RT overnight. The whole reaction mixture was filtered. Silica gel was added to the filtrate and concentrated in vacuo. The resulting residue was purified by silica gel flash chromatography (0% to 10% MeOH in DCM) to give the title compound as a yellow gum (24 mg, 24.8%) MS (ESI): m/z=506 [M+H]⁺.

Intermediate b) 1-(3,4-Dichlorophenyl)-1,3,8-triazaspiro[4.5]decan-4-one

The title compound 1-(3,4-dichlorophenyl)-1,3,8-triazaspiro[4.5]decan-4-one was obtained in analogy to general procedures described in the literature (e.g. S. Ceccarelli, WO2005/040166).

Example 5

2-(1-(4-Chlorophenyl)-8-(1H-indazole-5-carbonyl)-4-oxo-1,3,8-triazaspiro[4.5]decan-3-yl)-N-(2,2,2-trifluoroethyl)acetamide

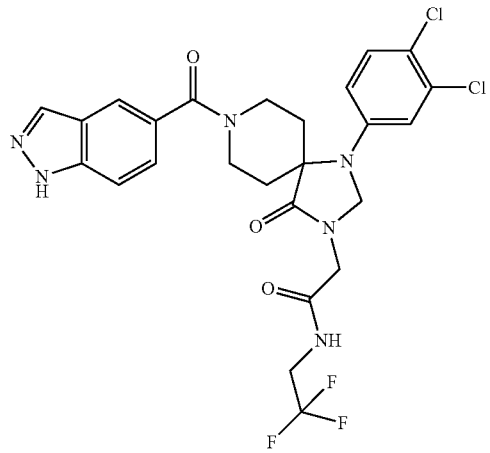 [SMILES: O=C(CN1CN(c2ccc(Cl)c(Cl)c2)C2(CCN(C(=O)c3ccc4[nH]ncc4c3)CC2)C1=O)NCC(F)(F)F]

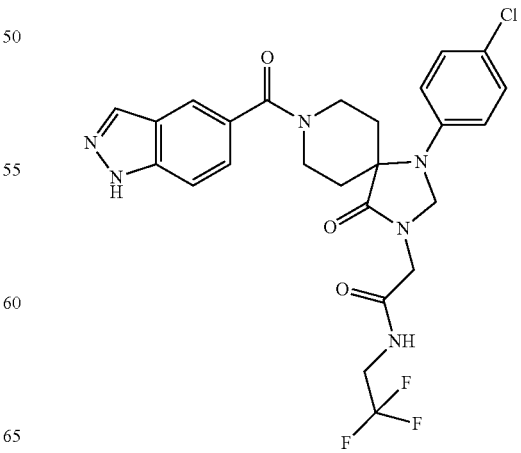

tert-Butyl 5-(1-(4-chlorophenyl)-4-oxo-1,3,8-triazaspiro[4.5]decane-8-carbonyl)-1H-indazole-1-carboxylate (68 mg, 100 µmol) was dissolved in DMF (1 mL). Cesium carbonate (65.2 mg, 200 µmol) followed by 2-chloro-N-(2,2,2-trifluoroethyl)acetamide (17.6 mg, 100 µmol, CAS RN 170655-44-4) were added. The reaction mixture was allowed to warm up to RT, and then continued to stir for 15 h. EtOAc and H₂O were added. The combined organic layers were dried over Na₂SO₄, filtered and evaporated. The crude product was treated with 2 M HCl in EtOAc and stirred overnight at RT. The pH of the reaction solution was neutralized with 1 M NaOH solution. The organic phase was separated, dried over Na₂SO₄, filtered and evaporated. The residue was purified by prep. HPLC to get the title compound as a light yellow gum (9.4 mg, 14.6%); MS (ESI): m/z=549 [M+H]⁺.

Intermediate a) tert-Butyl 5-[1-(4-chlorophenyl)-4-oxo-1,3,8-triazaspiro[4.5]decane-8-carbonyl]indazole-1-carboxylate 1-(4-Chlorophenyl)-1,3,8-triazaspiro[4.5]decan-4-one (100 mg, 376 µmol), 1-(tert-butoxycarbonyl)-1H-indazole-5-carboxylic acid (98.7 mg, 376 µmol, CAS RN 61700-61-6), HBTU (143 mg, 376 µmol), TEA (114 mg, 157 µL, 1.13 mmol) were dissolved in DCM (12 mL). The reaction mixture was stirred overnight at RT. The reaction mixture was filtered. Silica gel was added to the filtrate and concentrated in vacuo. The resulting residue was purified by silica gel flash chromatography (0% to 10% MeOH in DCM) to give the title compound as a white solid (120 mg, 46.9%); MS (ESI): m/z=510 [M+H]⁺.

Intermediate b) 1-(4-Chlorophenyl)-1,3,8-triazaspiro[4.5]decan-4-one

The title compound 1-(4-chlorophenyl)-1,3,8-triazaspiro[4.5]decan-4-one was obtained in analogy to general procedures described in the literature (e.g. S. Ceccarelli, WO2005/040166).

Example 6

2-(8-(1H-Indazole-5-carbonyl)-4-oxo-1-phenyl-1,3,8-triazaspiro[4.5]decan-3-yl)-N-phenylacetamide

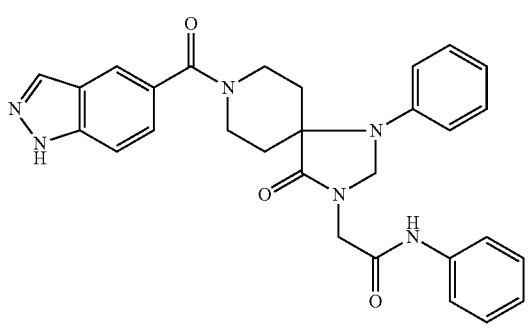 [SMILES: O=C(CN1CN(c2ccccc2)C2(CCN(C(=O)c3ccc4[nH]ncc4c3)CC2)C1=O)Nc1ccccc1]

2-(4-Oxo-1-phenyl-1,3,8-triazaspiro[4.5]decan-3-yl)-N-phenylacetamide hydrochloride (74 mg, 125 µmol) was partially dissolved in anhydrous DMF (2.2 mL). TEA (315 mg, 434 µL, 3.11 mmol) followed by 1H-indazole-5-carbonyl chloride (45 mg, 125 µmol) were added. The reaction mixture was stirred overnight at 35° C. under an argon atmosphere. The suspension was diluted with EtOAc (30 mL), and washed with H₂O (5×5 mL). The combined organic phases were concentrated in vacuo. The residue was purified by preparative HPLC (NH₄OAc/CH₃CN) to give the title compound as a white powder (13 mg, 20.5%). MS (ESI): m/z=509.2 [M+H]⁺.

Intermediate a) 1H-Indazole-5-carbonyl chloride

1H-Indazole-5-carboxylic acid (130 mg, 802 µmol, CAS RN 61700-61-6) was suspended in DCM (4 mL). Oxalyl chloride (153 mg, 105 µL, 1.2 mmol) was added followed by DMF (50 µL). The reaction mixture was stirred at RT for 1 h and then concentrated in vacuo to give the title compound as a yellow solid (164 mg) which was used as is for the subsequent reaction.

Intermediate b) 2-(4-Oxo-1-phenyl-1,3,8-triazaspiro[4.5]decan-3-yl)-N-phenyl-acetamide; hydrochloride A solution of tert-butyl 4-oxo-3-(2-oxo-2-(phenylamino)ethyl)-1-phenyl-1,3,8-triazaspiro[4.5]decane-8-carboxylate (347 mg, 747 µmol) in DCM (5 mL) was added 2 M HCl in EtOAc (8.68 mL, 17.4 mmol) at 0° C. The reaction mixture was stirred overnight at RT. The crude reaction mixture was concentrated in vacuo to give the title compound as a yellow solid (444 mg, 100%). MS (ESI): m/z=365 [M+H]⁺.

Intermediate c) tert-Butyl 3-(2-anilino-2-oxo-ethyl)-4-oxo-1-phenyl-1,3,8-triazaspiro[4.5]decane-8-carboxylate 2-(8-(tert-Butoxycarbonyl)-4-oxo-1-phenyl-1,3,8-triazaspiro[4.5]decan-3-yl)acetic acid (700 mg, 1.8 mmol, CAS RN 180386-35-0) was dissolved in anhydrous DCM (5 mL). HBTU (886 mg, 2.34 mmol) followed by TEA (909 mg, 1.25 mL, 8.99 mmol) were added. The reaction mixture was stirred for 30 min before aniline (251 mg, 2.7 mmol) was added. The reaction mixture was stirred for 48 h at RT under an argon atmosphere. The crude reaction mixture was concentrated in vacuo and the residue was purified by flash chromatography on silica gel (10% to 60% EtOAc in n-heptane) to give the title compound as a yellow solid (627 mg, 75%). MS (ESI): m/z=463 [M+H]⁺.

Example 7

2-(8-(1H-Indazole-5-carbonyl)-4-oxo-1-phenyl-1,3,8-triazaspiro[4.5]decan-3-yl)-N-(2,2,2-trifluoroethyl)acetamide

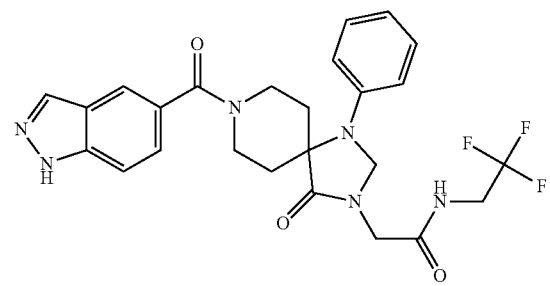 [SMILES: O=C(CN1CN(c2ccccc2)C2(CCN(C(=O)c3ccc4[nH]ncc4c3)CC2)C1=O)NCC(F)(F)F]

The title compound was obtained in analogy to example 6, intermediate c, using 2,2,2-trifluoroethanamine (CAS RN 753-90-2) instead of aniline (CAS RN 62-53-3) to give an off-white solid. MS (ESI): m/z=515 [M+H]+.

Example 8

2-(8-(1H-Indazole-5-carbonyl)-4-oxo-1-phenyl-1,3,8-triazaspiro[4.5]decan-3-yl)-N-(2-morpholinoethyl)acetamide

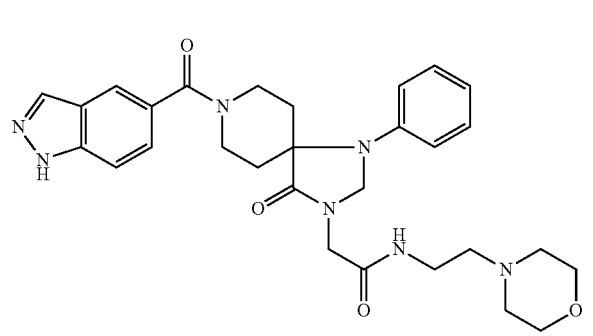 [SMILES: O=C(CN1CN(c2ccccc2)C2(CCN(C(=O)c3ccc4[nH]ncc4c3)CC2)C1=O)NCCN1CCOCC1]

The title compound was obtained in analogy to example 6, intermediate c, using 2-morpholinoethanamine (CAS RN 2038-03-1) instead of aniline (CAS RN 62-53-3) as a white powder. MS (ESI): m/z=546 [M+H]+.

Example 9

(rac,trans)-2-(8-(1H-Indazole-5-carbonyl)-4-oxo-1-phenyl-1,3,8-triazaspiro[4.5]decan-3-yl)-N-(2-phenylcyclopropyl)acetamide

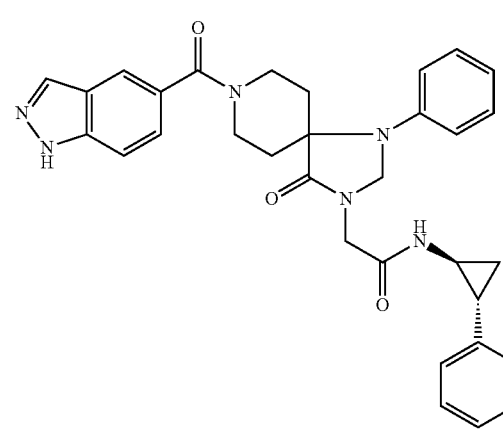

The title compound was obtained in analogy to example 6, intermediate c, using (rac,trans)-2-phenylcyclopropanamine (CAS RN 155-09-9) instead of aniline (CAS RN 62-53-3) as a white powder. MS (ESI): m/z=549 [M+H]+.

Example 10

8-(1H-Indazole-5-carbonyl)-3-(2-morpholino-2-oxoethyl)-1-phenyl-1,3,8-triazaspiro[4.5]decan-4-one

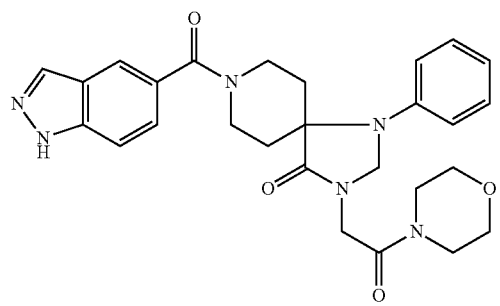 [SMILES: O=C(CN1CN(c2ccccc2)C2(CCN(C(=O)c3ccc4[nH]ncc4c3)CC2)C1=O)N1CCOCC1]

The title compound was obtained in analogy to example 6, intermediate c, using morpholine (CAS RN 110-91-8) instead of aniline (CAS RN 62-53-3) as a white solid. MS (ESI): m/z=503 [M+H]+.

Example 11

2-(8-(1H-Indazole-5-carbonyl)-4-oxo-1-phenyl-1,3,8-triazaspiro[4.5]decan-3-yl)-N-(pyridin-3-yl)acetamide

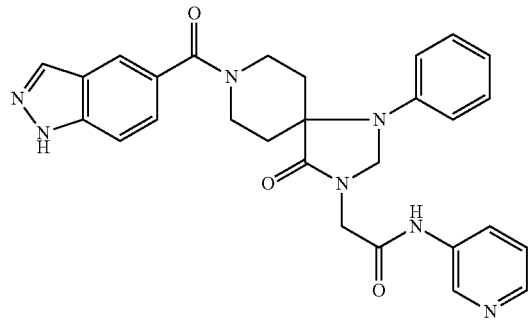 [SMILES: O=C(CN1CN(c2ccccc2)C2(CCN(C(=O)c3ccc4[nH]ncc4c3)CC2)C1=O)Nc1cccnc1]

The title compound was obtained in analogy to example 6, intermediate c, using pyridin-3-amine (CAS RN 462-08-8) instead of aniline (CAS RN 62-53-3) as a white solid. MS (ESI): m/z=510 [M+H]+.

Example 12

2-(8-(1H-Indazole-5-carbonyl)-4-oxo-1-phenyl-1,3,8-triazaspiro[4.5]decan-3-yl)-N-(pyridin-4-yl)acetamide

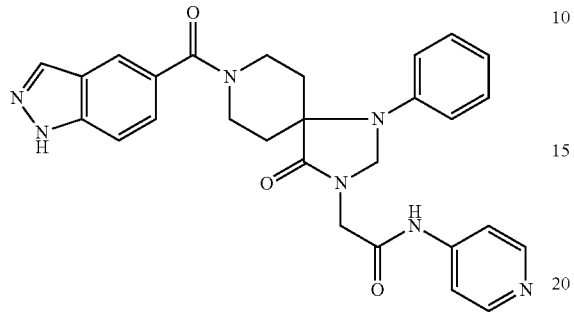

The title compound was obtained in analogy to example 6, intermediate c, using pyridin-4-amine (CAS RN 504-24-5) instead of aniline (CAS RN 62-53-3) as a white solid. MS (ESI): m/z=508 [M−H]+.

Example 13

2-(8-(1H-Indazole-5-carbonyl)-4-oxo-1-phenyl-1,3,8-triazaspiro[4.5]decan-3-yl)-N-(3-morpholinophenyl)acetamide

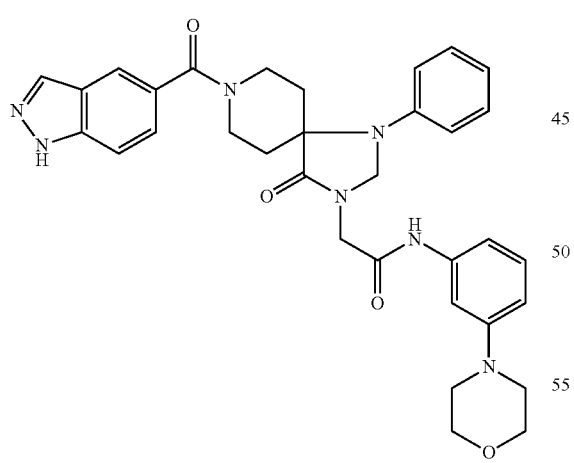

The title compound was obtained in analogy to example 6, intermediate c, using 3-morpholinoaniline (CAS RN 159724-40-0) instead of aniline (CAS RN 62-53-3) as a white solid. MS (ESI): m/z=594 [M+H]+.

Example 14

2-(8-(1H-Indazole-5-carbonyl)-4-oxo-1-phenyl-1,3,8-triazaspiro[4.5]decan-3-yl)-N-(3-(trifluoromethoxy)phenyl)acetamide

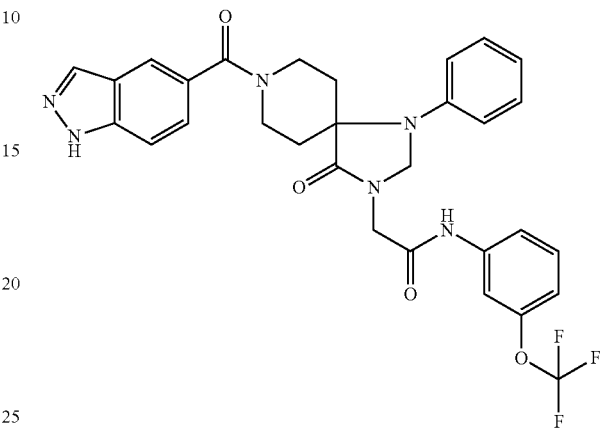

The title compound was obtained in analogy to example 6, intermediate c, using 3-(trifluoromethoxy)aniline (CAS RN 1535-73-5) instead of aniline (CAS RN 62-53-3) as a white solid. MS (ESI): m/z=593 [M+H]+.

Example 15

2-(8-(1H-Indazole-5-carbonyl)-4-oxo-1-phenyl-1,3,8-triazaspiro[4.5]decan-3-yl)-N-(pyridin-2-yl)acetamide

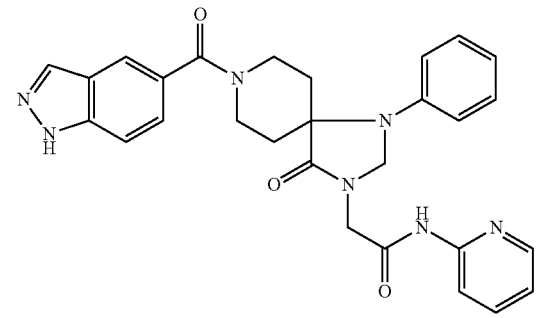 [SMILES: O=C(CN1CN(c2ccccc2)C2(CCN(C(=O)c3ccc4[nH]ncc4c3)CC2)C1=O)Nc1ccccn1]

The title compound was obtained in analogy to example 6, intermediate c, using pyridin-2-amine (CAS RN 504-29-0) instead of aniline (CAS RN 62-53-3) as a yellow solid. MS (ESI): m/z=510 [M+H]+.

Example 16

2-(8-(1H-Indazole-6-carbonyl)-4-oxo-1-phenyl-1,3,8-triazaspiro[4.5]decan-3-yl)-N-phenylacetamide

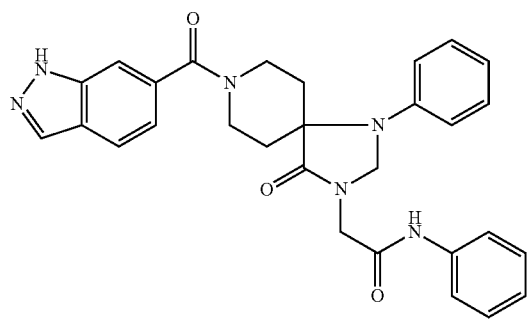 [SMILES: O=C(CN1CN(c2ccccc2)C2(CCN(C(=O)c3ccc4cn[nH]c4c3)CC2)C1=O)Nc1ccccc1]

The title compound was obtained in analogy to example 6, from 2-(4-Oxo-1-phenyl-1,3,8-triazaspiro[4.5]decan-3-yl)-N-phenylacetamide hydrochloride and 1H-indazole-6-carbonyl chloride (prepared from 1H-indazole-6-carboxylic acid (CAS RN 704-91-6) in analogy to example 6, intermediate a) as yellow solid. MS (ESI): m/z=509 [M+H]$^+$.

Example 17

2-[8-(3-Amino-1H-indazole-6-carbonyl)-4-oxo-1-phenyl-1,3,8-triazaspiro[4.5]decan-3-yl]-N-(2,2,2-trifluoroethyl)acetamide

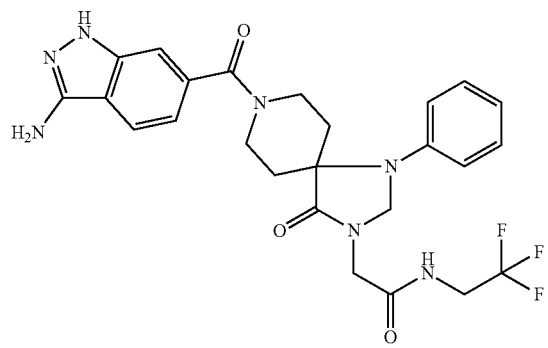 [SMILES: Nc1n[nH]c2cc(C(=O)N3CCC4(CC3)C(=O)N(CC(=O)NCC(F)(F)F)CN4c3ccccc3)ccc12]

To a solution of 2-(4-oxo-1-phenyl-1,3,8-triazaspiro[4.5]decan-3-yl)-N-(2,2,2-trifluoroethyl)acetamide hydrochloride (50 mg, 123 µmol) in DMF (2.5 mL) were added 3-amino-1H-indazole-6-carboxylic acid (23.9 mg, 135 µmol, CAS RN 871709-92-1), HBTU (71.7 mg, 189 µmol) and TEA (137 mg, 188 µL, 1.35 mmol). The reaction mixture was stirred overnight at room temperature under an argon atmosphere. The reaction mixture was filtered, evaporated and the residue purified by prep. HPLC (NH$_4$OAc/ACN) to provide the title compound as colorless needles (8 mg, 11.2%). MS (ESI): m/z=530 [M+H]$^+$.

Intermediate a) 2-(4-Oxo-1-phenyl-1,3,8-triazaspiro[4.5]decan-3-yl)-N-(2,2,2-trifluoroethyl)acetamide hydrochloride tert-Butyl 4-oxo-3-(2-oxo-2-(2,2,2-trifluoroethyl)amino)ethyl)-1-phenyl-1,3,8-triazaspiro[4.5]decane-8-carboxylate (1.355 g, 2.88 mmol) was treated with 2 M HCl in EtOAc (50.4 mL, 101 mmol) and stirred overnight at RT under an argon atmosphere. The white precipitate was filtered off to provide the titled compound as a white solid (961 mg, 81.9%). MS (ESI): m/z=371 [M+H]$^+$.

Intermediate b) tert-Butyl 4-oxo-3-[2-oxo-2-(2,2,2-trifluoroethylamino)ethyl]-1-phenyl-1,3,8-triazaspiro[4.5]decane-8-carboxylate 2-(8-(tert-Butoxycarbonyl)-4-oxo-1-phenyl-1,3,8-triazaspiro[4.5]decan-3-yl)acetic acid (1 g, 2.57 mmol, CAS RN 180386-35-0) was dissolved in anhydrous DCM (20 mL). HBTU (1.27 g, 3.34 mmol) followed by TEA (1.3 g, 1.79 mL, 12.8 mmol) were added. After 30 min, 2,2,2-trifluoroethanamine (509 mg, 409 µL, 5.14 mmol, CAS RN 753-90-2) was added. The reaction mixture was stirred overnight at RT under an argon atmosphere. After evaporation the brown oil was dissolved in EtoAc, treated with silica gel and concentrated under vacuo. The compound was purified by silica gel chromatography on a 24 g column using a MPLC system eluting with a gradient of n-heptane:EtOAc (100:0 to 0:100) to get the title compound as a colorless viscous oil (1.355 g, 100%), MS (ESI): m/z=471 [M+H]$^+$.

Example 18

2-(4-Oxo-1-phenyl-8-(tetrazolo[1,5-a]pyridine-6-carbonyl)-1,3,8-triazaspiro[4.5]decan-3-yl)-N-(2,2,2-trifluoroethyl)acetamide

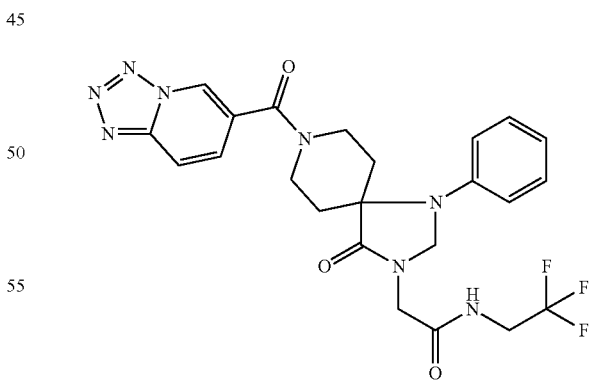

The title compound was obtained in analogy to example 17, from 2-(4-oxo-1-phenyl-1,3,8-triazaspiro[4.5]decan-3-yl)-N-(2,2,2-trifluoroethyl)acetamide hydrochloride and tetrazolo[1,5-a]pyridine-6-carbonyl chloride (prepared in analogy from tetrazolo[1,5-a]pyridine-6-carboxylic acid (CAS RN 7477-13-6) to example 6, intermediate a) as a white solid. MS (ESI): m/z=517 [M+H]$^+$.

Example 19

2-[8-(1H-Indazole-6-carbonyl)-4-oxo-1-phenyl-1,3,8-triazaspiro[4.5]decan-3-yl]-N-(2,2,2-trifluoroethyl)acetamide

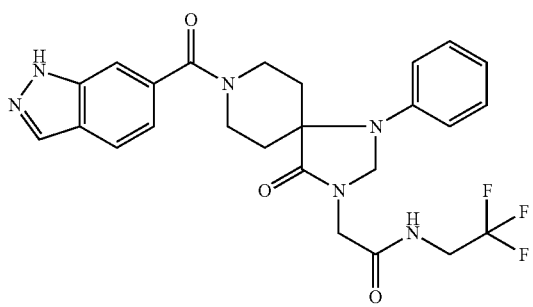 [SMILES: O=C(CN1CN(c2ccccc2)C2(CCN(C(=O)c3ccc4cn[nH]c4c3)CC2)C1=O)NCC(F)(F)F]

The title compound was obtained in analogy to example 17, from 2-(4-oxo-1-phenyl-1,3,8-triazaspiro[4.5]decan-3-yl)-N-(2,2,2-trifluoroethyl)acetamide hydrochloride and 1H-indazole-6-carbonyl chloride (prepared in analogy from 1H-indazole-6-carboxylic acid (CAS RN 704-91-6) to example 6, intermediate a) as a white solid. MS (ESI): m/z=515 [M+H]$^+$.

Example 20

2-(4-Oxo-1-phenyl-8-(1H-pyrazolo[3,4-c]pyridine-5-carbonyl)-1,3,8-triazaspiro[4.5]decan-3-yl)-N-(2,2,2-trifluoroethyl)acetamide

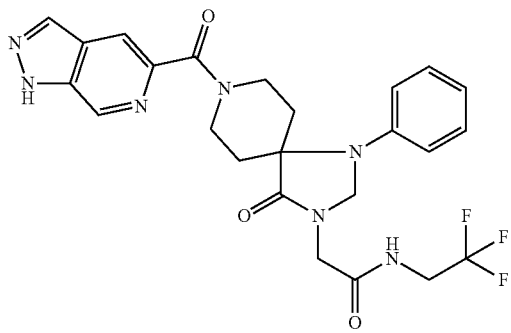 [SMILES: O=C(CN1CN(c2ccccc2)C2(CCN(C(=O)c3cc4cn[nH]c4cn3)CC2)C1=O)NCC(F)(F)F]

The title compound was obtained in analogy to example 17, from 2-(4-oxo-1-phenyl-1,3,8-triazaspiro[4.5]decan-3-yl)-N-(2,2,2-trifluoroethyl)acetamide hydrochloride and 1H-pyrazolo[3,4-c]pyridine-5-carbonyl chloride (prepared in analogy from 1H-pyrazolo[3,4-c]pyridine-5-carboxylic acid (CAS RN 1256824-45-9) to example 6, intermediate a) as an off-white solid. MS (ESI): m/z=516 [M+H]$^+$.

Example 21

2-(8-(Imidazo[1,5-a]pyridine-6-carbonyl)-4-oxo-1-phenyl-1,3,8-triazaspiro[4.5]decan-3-yl)-N-(2,2,2-trifluoroethyl)acetamide

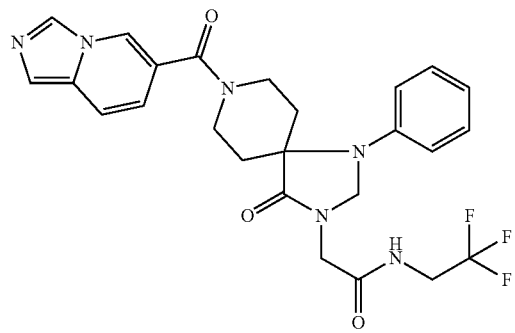 [SMILES: O=C(CN1CN(c2ccccc2)C2(CCN(C(=O)c3ccc4cncn4c3)CC2)C1=O)NCC(F)(F)F]

The title compound was obtained in analogy to example 17, from 2-(4-oxo-1-phenyl-1,3,8-triazaspiro[4.5]decan-3-yl)-N-(2,2,2-trifluoroethyl)acetamide hydrochloride and imidazo-[1,5]-pyridine-6-carbonyl chloride (prepared in analogy from imidazo-[1,5]-pyridine-6-carboxylic acid (CAS RN 256935-76-9) to example 6, intermediate a) as a white solid. MS (ESI): m/z=515 [M+H]$^+$.

Example 22

2-[4-Oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide

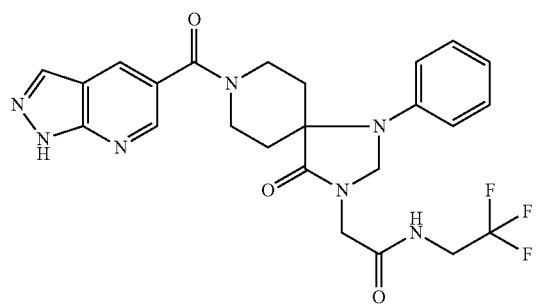 [SMILES: O=C(CN1CN(c2ccccc2)C2(CCN(C(=O)c3cnc4[nH]ncc4c3)CC2)C1=O)NCC(F)(F)F]

2-(4-Oxo-1-phenyl-8-(1H-pyrazolo[3,4-b]pyridine-5-carbonyl)-1,3,8-triazaspiro[4.5]decan-3-yl)acetic acid (32 mg, 73.7 μmol) was dissolved in anhydrous DCM (5 mL). HBTU (36.3 mg, 95.8 μmol) followed by TEA (37.3 mg, 51.3 μL, 368 μmol) were added. After 30 min, 2,2,2-trifluoroethylamine (10.9 mg, 110 μmol, CAS RN 753-90-2) was added. The reaction mixture was stirred overnight at RT under an argon atmosphere, and then concentrated in vacuo. The residue was purified by prep HPLC to give the title compound as a white solid (4.5 mg, 11.9%). MS (ESI): m/z=516 [M+H]$^+$.

Intermediate a) 2-(4-Oxo-1-phenyl-8-(1H-pyrazolo[3,4-b]pyridine-5-carbonyl)-1,3,8-triazaspiro[4.5]decan-3-yl)acetic acid Methyl 2-(4-oxo-1-phenyl-8-(1H-pyrazolo[3,4-b]pyridine-5-carbonyl)-1,3,8-triazaspiro[4.5]decan-3-yl)acetate (116 mg, 259 µmol) was dissolved in THF (3 mL). 3 M NaOH solution (862 µL, 2.59 mmol) was added and the solution stirred overnight at ambient temperature. The reaction mixture was diluted with EtOAc (20 mL) and washed with 1M HCl solution (10 mL) and brine. The combined organic layers were dried over $Na_2SO_4$, filtered and evaporated under reduced pressure to give the title compound as a light yellow solid (110 mg, 97.9%). MS (ESI): m/z=435 [M+H]$^+$.

Intermediate b) Methyl 2-(4-oxo-1-phenyl-8-(1H-pyrazolo[3,4-b]pyridine-5-carbonyl)-1,3,8-triazaspiro[4.5]decan-3-yl)acetate 1H-Pyrazolo[3,4-b]pyridine-5-carboxylic acid (300 mg, 1.84 mmol, CAS RN 952182-02-4) was suspended in DCM (4 mL). Oxalyl chloride (351 mg, 242 µL, 2.77 mmol) was added followed by a catalytic amount of DMF (50 µL). After 4 h, the acid chloride suspension was added dropwise to a stirred solution of methyl 2-(4-oxo-1-phenyl-1,3,8-triazaspiro[4.5]decan-3-yl)acetate (560 mg, 1.85 mmol) and TEA (1.87 g, 2.57 mL, 18.5 mmol) in DCM (15 mL). The reaction mixture was stirred overnight at RT under an argon atmosphere. The reaction mixture was washed with $H_2O$ and brine. The combined organic layers were dried over $Na_2SO_4$, filtered and evaporated under reduced pressure to give the title compound as a light brown gum (996 mg, 83.6%) MS (ESI): m/z=449 [M+H]$^+$.

Intermediate c) Methyl 2-(4-oxo-1-phenyl-1,3,8-triazaspiro[4.5]decan-3-yl)acetate tert-Butyl 3-(2-methoxy-2-oxo-ethyl)-4-oxo-1-phenyl-1,3,8-triazaspiro[4.5]decane-8-carboxylate (5.15 g, 12.8 mmol) was dissolved in DCM (5 mL). TFA (14.8 g, 10 mL, 130 mmol) was added. The reaction mixture was stirred overnight at RT, and then poured slowly onto an aqueous $NaHCO_3$ solution and extracted twice with DCM. The combined organic layers were dried over $Na_2SO_4$, filtered and evaporated under reduced pressure to give the title compound as a light yellow foam (4.61 g, 98.8%). MS (ESI): m/z=304 [M+H]$^+$.

Intermediate d) tert-Butyl 3-(2-methoxy-2-oxo-ethyl)-4-oxo-1-phenyl-1,3,8-triazaspiro[4.5]decane-8-carboxylate 2-(8-(tert-Butoxycarbonyl)-4-oxo-1-phenyl-1,3,8-triazaspiro[4.5]decan-3-yl)acetic acid (5 g, 12.8 mmol, CAS RN 180386-35-0) was dissolved in MeOH (174 mL) and cooled to 0° C. 2 M trimethylsilyldiazomethane in n-hexane (12.8 mL, 25.7 mmol) was added dropwise. The reaction mixture was allowed to warm up to RT and stirred overnight under an argon atmosphere. The reaction mixture was cooled down to 0° C. 2 M Trimethylsilyldiazomethane in n-hexane was added dropwise until the reaction turned slightly yellow, and stirring was continued overnight at RT. Acetic acid (1 mL) was added dropwise at 0° C. The crude reaction solution was evaporated under reduced pressure to give the title compound as a colorless gum (5.15 g, 99.4%), MS (ESI): m/z=304 [M+H]$^+$.

Example 23

2-(4-Oxo-1-phenyl-8-(1H-pyrazolo[3,4-b]pyridine-5-carbonyl)-1,3,8-triazaspiro[4.5]decan-3-yl)-N-phenylacetamide

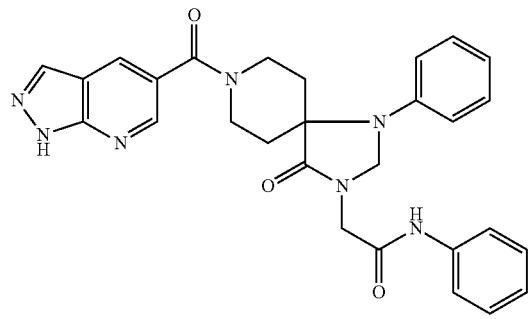 [SMILES: O=C(CN1CN(c2ccccc2)C2(CCN(C(=O)c3cnc4[nH]ncc4c3)CC2)C1=O)Nc1ccccc1]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and aniline (CAS RN 62-53-3) as a white solid. MS (ESI): m/z=510 [M+H]$^+$.

Example 24

2-(4-Oxo-1-phenyl-8-(1H-pyrazolo[3,4-b]pyridine-5-carbonyl)-1,3,8-triazaspiro[4.5]decan-3-yl)-N-(pyridin-2-yl)acetamide

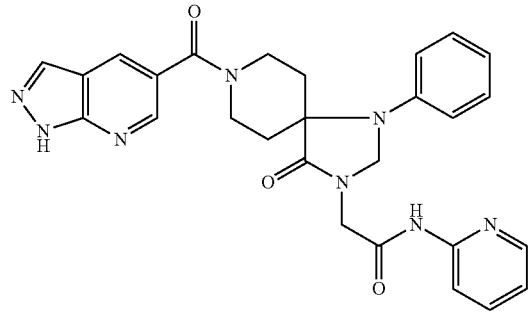 [SMILES: O=C(CN1CN(c2ccccc2)C2(CCN(C(=O)c3cnc4[nH]ncc4c3)CC2)C1=O)Nc1ccccn1]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and pyridin-2-amine (CAS RN 504-29-0) as a white solid. MS (ESI): m/z=509 [M+H]$^+$.

Example 25

8-(1H-benzotriazole-5-carbonyl)-3-(2-morpholino-2-oxo-ethyl)-1-phenyl-1,3,8-triazaspiro[4.5]decan-4-one

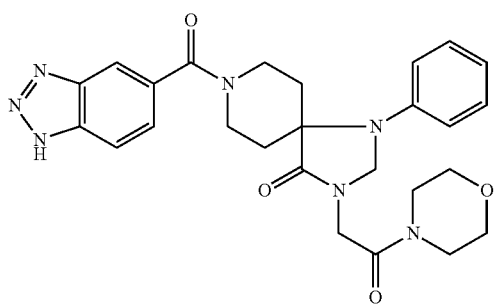 [SMILES: O=C(CN1CN(c2ccccc2)C2(CCN(C(=O)c3ccc4[nH]nnc4c3)CC2)C1=O)N1CCOCC1]

2-(8-(1H-benzotriazole-5-carbonyl)-4-oxo-1-phenyl-1,3,8-triazaspiro-(4.5)-decan-3-yl) acetic acid (63 mg, 145 µmol) was dissolved in anhydrous DMF (1 ml). HBTU (66 mg, 174 µmol) followed by morpholine (12.6 mg, 145 µmol, CAS RN 110-91-8) and TEA (44 mg, 435 µmol) were added. Reaction mixture was stirred at 35° C. overnight. The reaction mixture was filtered. The filtrate was purified by prep. HPLC to give the title compound as a white solid (11 mg, 15.1%). MS (ESI): m/z=504 [M+H]+.

Intermediate a) 2-(8-(1H-Benzotriazole-5-carbonyl)-4-oxo-1-phenyl-1,3,8-triazaspiro-(4.5)-decan-3-yl) acetic acid Methyl 2-[8-(1H-benzotriazole-5-carbonyl)-4-oxo-1-phenyl-1,3,8-triazaspiro[4.5]decan-3-yl]acetate (132 mg, 294 µmol) was dissolved in THF (3 mL). 2 M NaOH solution (1.47 mL, 2.94 mmol) was added. The reaction mixture was stirred at RT overnight. H2O was added followed by EtOAc. The organic phase was concentrated to give a brown solid (127 mg, 99.3%). The crude product was used as is for the next step without further purification.

Intermediate b) Methyl 2-[8-(1H-benzotriazole-5-carbonyl)-4-oxo-1-phenyl-1,3,8-triazaspiro[4.5]decan-3-yl]acetate Methyl 2-(4-oxo-1-phenyl-1,3,8-triazaspiro[4.5]decan-3-yl)acetate (258 mg, 850 example 22, intermediate c) was dissolved in DCM (5 ml). TEA (258 mg, 2.55 mmol) was added followed by 1H-benzotriazole-5-carbonyl chloride (200 mg, 1.1 mmol, CAS RN 46053-85-4). The reaction mixture was stirred at RT overnight. Water was added. The organic phase was concentrated in vacuo to give a yellow solid (132 mg, 34.6%) which was used as is for the next step without further purification. MS (ESI): m/z=449.3 [M+H]+.

Example 26

2-(8-(1H-Benzo[d][1,2,3]triazole-5-carbonyl)-4-oxo-1-phenyl-1,3,8-triazaspiro[4.5]decan-3-yl)-N-(2,2,2-trifluoroethyl)acetamide

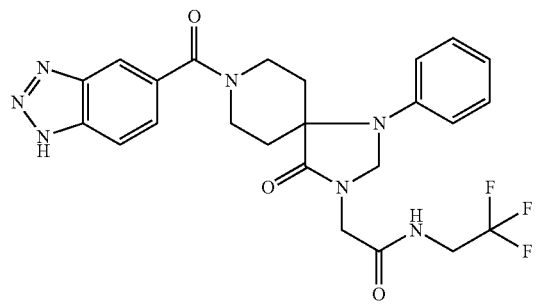 [SMILES: O=C(CN1CN(c2ccccc2)C2(CCN(C(=O)c3ccc4[nH]nnc4c3)CC2)C1=O)NCC(F)(F)F]

The title compound was obtained in analogy to example 25, from 2-(8-(1H-benzotriazole-5-carbonyl)-4-oxo-1-phenyl-1,3,8-triazaspiro-(4.5)-decan-3-yl) acetic acid (example 25, intermediate a) and 2,2,2-trifluoroethylamine (CAS RN 753-90-2) as a white solid. MS (ESI): m/z=516 [M+H]+.

Example 27

N-Methyl-2-(4-oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide

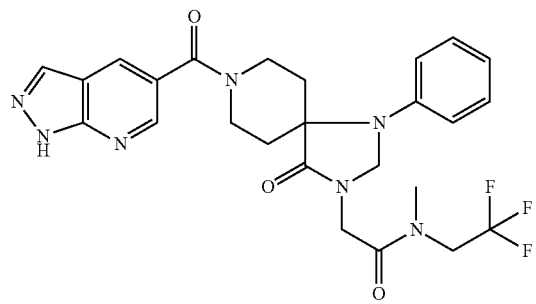 [SMILES: CN(CC(F)(F)F)C(=O)CN1CN(c2ccccc2)C2(CCN(C(=O)c3cnc4[nH]ncc4c3)CC2)C1=O]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and 2,2,2-trifluoro-N-methyl-ethanamine hydrochloride (CAS RN 2730-52-1) as a white solid. MS (ESI): m/z=530 [M+H]+.

Example 28

3-(2-(4-Methylpiperazin-1-yl)-2-oxoethyl)-1-phenyl-8-(1H-pyrazolo[3,4-b]pyridine-5-carbonyl)-1,3,8-triazaspiro[4.5]decan-4-one

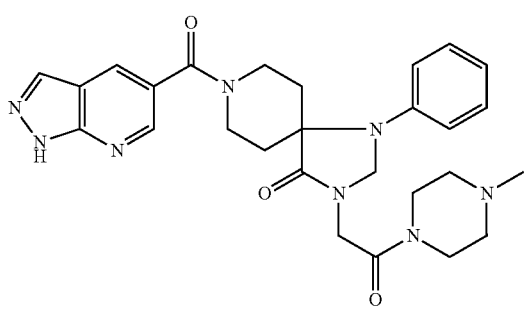 [SMILES: CN1CCN(C(=O)CN2CN(c3ccccc3)C3(CCN(C(=O)c4cnc5[nH]ncc5c4)CC3)C2=O)CC1]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and 1-methylpiperazine (CAS RN 109-01-3) as a white solid. MS (ESI): m/z=517 [M+H]$^+$.

Example 29

3-(2-(1,1-Dioxidothiomorpholino)-2-oxoethyl)-1-phenyl-8-(1H-pyrazolo[3,4-b]pyridine-5-carbonyl)-1,3,8-triazaspiro[4.5]decan-4-one

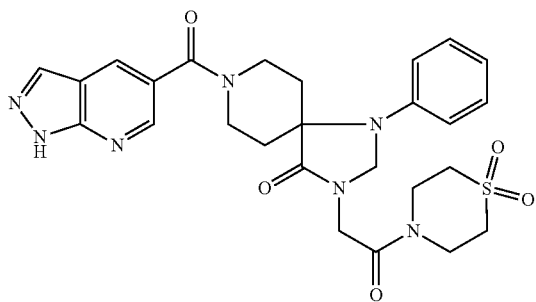 [SMILES: O=C(CN1CN(c2ccccc2)C2(CCN(C(=O)c3cnc4[nH]ncc4c3)CC2)C1=O)N1CCS(=O)(=O)CC1]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and thiomorpholine 1,1-dioxide (CAS RN 39093-93-1) as a white solid. MS (ESI): m/z=552 [M+H]$^+$.

Example 30

N-(Adamantan-1-yl)-2-(4-oxo-1-phenyl-8-(1H-pyrazolo[3,4-b]pyridine-5-carbonyl)-1,3,8-triazaspiro[4.5]decan-3-yl)acetamide

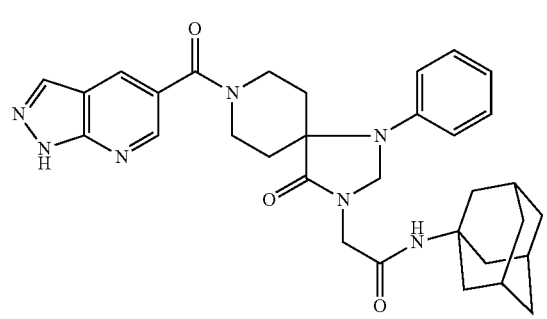 [SMILES: O=C(CN1CN(c2ccccc2)C2(CCN(C(=O)c3cnc4[nH]ncc4c3)CC2)C1=O)NC12CC3CC(CC(C3)C1)C2]

The title compound was obtained in analogy to example 22, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and 1-adamantamine (CAS RN 768-94-5) as a white solid. MS (ESI): m/z=568 [M+H]$^+$.

Example 31

2-[8-(1H-Indazole-5-carbonyl)-4-oxo-1-phenyl-1,3,8-triazaspiro[4.5]decan-3-yl]-N-methyl-acetamide

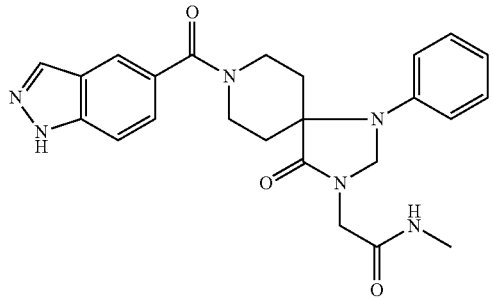 [SMILES: CNC(=O)CN1CN(c2ccccc2)C2(CCN(C(=O)c3ccc4[nH]ncc4c3)CC2)C1=O]

To a solution of 1H-indazole-5-carboxylic acid (100 mg, 0.62 mmol, CAS RN 61700-61-6) in anhydrous DMF (4 mL) was added N-methyl-2-(4-oxo-1-phenyl-1,3,8-triazaspiro[4.5]decan-3-yl)acetamide (271.6 mg, 0.80 mmol) and TEA (188.2 mg, 1.86 mmol), and the solution was stirred at RT for 15 min. A 50% solution of propylphosphonic anhydride in EtOAc (0.7 mL, 0.68 mmol) was added, and the reaction mixture was stirred at 15° C. for 15 h. The solvent was removed and the crude product was purified by prep. HPLC to give the title compound (50 mg, 18.1%). MS (ESI): m/z=447 [M+H]$^+$.

Intermediate a) N-Methyl-2-(4-oxo-1-phenyl-1,3,8-triazaspiro[4.5]decan-3-yl)acetamide To a solution of tert-butyl 3-[2-(methylamino)-2-oxoethyl]-4-oxo-1-phenyl-1,3,8-triazaspiro[4.5]decane-8-carboxylate (0.92 g, 2.28 mmol) in DCM (4 mL) was added HCl/EtOAc (10 mL) dropwise at 0° C. The reaction mixture was stirred at 15° C. for 3 hours. The solvent was evaporated to give the title product (0.7 g salt, crude). $^1$H NMR:

MeOH-d4 400 MHz δ=7.34 (t, J=7.9 Hz, 2H), 7.07 (d, J=8.3 Hz, 2H), 6.98 (t, J=7.3 Hz, 1H), 4.83 (s, 2H), 4.19-4.11 (m, 2H), 3.80 (dt, J=3.0, 12.9 Hz, 2H), 3.41 (dd, J=3.9, 12.4 Hz, 2H), 2.80 (s, 3H), 2.67.

Intermediate b) tert-Butyl 3-[2-(methylamino)-2-oxo-ethyl]-4-oxo-1-phenyl-1,3,8-triazaspiro[4.5]decane-8-carboxylate The solution of tert-butyl 3-(2-ethoxy-2-oxo-ethyl)-4-oxo-1-phenyl-1,3,8-triazaspiro[4.5]decane-8-carboxylate (1 g, 2.39 mmol) in methylamine in MeOH (10 mL) was stirred at 60° C. for 10 hours. The solvent was evaporated to give title product (800 mg, 83.3%). $^1$H NMR: CDCl$_3$ 400 MHz δ=7.30-7.25 (m, 2H), 6.91 (t, J=7.4 Hz, 1H), 6.81 (d, J=8.3 Hz, 2H), 6.03 (br. s., 1H), 4.83 (s, 2H), 4.15-3.91 (m, 4H), 3.55 (br. s., 2H), 2.87 (d, J=4.8 Hz, 3H), 2.51 (br. s., 2H), 1.69 (d, J=7.5 Hz, 2H), 1.52 (s, 9H).

Intermediate c) tert-Butyl 3-(2-ethoxy-2-oxo-ethyl)-4-oxo-1-phenyl-1,3,8-triazaspiro[4.5]decane-8-carboxylate To a solution of tert-butyl 4-oxo-1-phenyl-1,3,8-triazaspiro[4.5]decane-8-carboxylate (3 g, 9.05 mmol, example 35, intermediate c) in dry THF (40 mL) was added NaH (0.43 g, 10.86 mmol) at 0° C. under N$_2$ atmosphere. Then the reaction mixture was stirred at 15° C. for 40 min and ethyl bromoacetate (1.66 g, 9.96 mmol) was added dropwise. The reaction mixture was stirred at 15° C. for 15 hours. The reaction mixture was quenched with ice-water, extracted with EtOAc which was washed with sat. NaHCO$_3$ solution and brine. Then the organic phase was concentrated to give the title product (2.5 g, 66.14%) which was used as is for the next step without further purification.

Example 32

3-(5-Chloro-2-fluorophenyl)-8-(1H-indazole-5-carbonyl)-1-phenyl-1,3,8-triazaspiro[4.5]decan-4-one

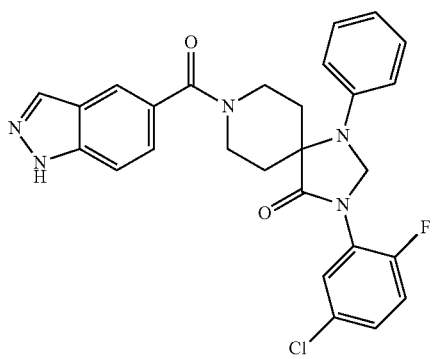 [SMILES: O=C(c1ccc2[nH]ncc2c1)N1CCC2(CC1)C(=O)N(c1cc(Cl)ccc1F)CN2c1ccccc1]

To a suspension of tert-butyl 5-(4-oxo-1-phenyl-1,3,8-triazaspiro[4.5]decane-8-carbonyl)indazole-1-carboxylate (100 mg, 210 μmol) and 4-chloro-1-fluoro-2-iodobenzene (129 mg, 505 μmol; CAS RN 116272-42-5) in dioxane (3 mL) were added K$_2$CO$_3$ (87.2 mg, 631 μmol), DMEDA (2.13 μL, 16.8 μmol) and CuI (1.6 mg, 8.41 μmol). The mixture was purged with argon and stirred at 160° C. in a sealed tube over 16 hours. Another 4-chloro-1-fluoro-2-iodobenzene (129 mg, 505 μmol; CAS RN 116272-42-5), DMEDA (2.13 μL, 16.8 μmol), CuI (1.6 mg, 8.41 μmol) and K$_2$CO$_3$ (87.2 mg, 631 μmol) were added and stirring was continued at 160° C. over 16 hours. The reaction mixture was cooled down to RT and filtered over a syringe microfilter. The filtrate was treated with silica gel and evaporated. The compound was purified by silica gel chromatography on a 4 g column using an MPLC (ISCO) system eluting with a gradient of DCM:MeOH (100:0 to 80:20). The product (25 mg) was purified by preparative HPLC (Gemini NX column) using a gradient of ACN:H$_2$O (containing 0.1% formic acid) (20:80 to 98:2). The obtained product was twice purified by silica gel chromatography on a 4 g and a 12 g column using an MPLC (ISCO) system eluting with a gradient of DCM:MeOH (100:0 to 80:20) to give the title compound as a colorless solid (6 mg; 5.66%). MS (ESI): m/z=504.16 [M+H]$^+$.

Intermediate a) tert-Butyl 5-(4-oxo-1-phenyl-1,3,8-triazaspiro[4.5]decane-8-carbonyl)indazole-1-carboxylate To a solution of 1-(tert-butoxycarbonyl)-1H-indazole-5-carboxylic acid (160 mg, 305 μmol; CAS RN 885954-14-3) and HBTU (127 mg, 336 μmol) in DMF (1.5 mL) were added 1-phenyl-1,3,8-triazaspiro[4.5]decan-4-one (77.6 mg, 336 μmol; CAS RN 1021-25-6) and TEA (128 μL, 915 μmol) and the light brown solution was stirred at RT over 3 hours. The product was purified by preparative HPLC (Gemini NX column) using a gradient of ACN:H$_2$O (containing 0.1% TEA) (20:80 to 98:2) to give the title compound as a colorless solid (0.102 g; 70.3%). MS (ESI): m/z=476.23 [M+H]$^+$.

Example 33

3-[(3-Cyclopropyl-1,2,4-oxadiazol-5-yl)methyl]-8-(1H-indazole-5-carbonyl)-1-phenyl-1,3,8-triazaspiro[4.5]decan-4-one

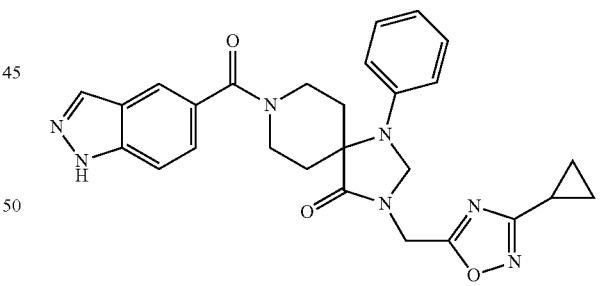

To a solution of 1H-indazole-5-carboxylic acid (25.2 mg, 156 μmol; CAS RN 61700-61-6), 3-[(3-cyclopropyl-1,2,4-oxadiazol-5-yl)methyl]-1-phenyl-1,3,8-triazaspiro[4.5]decan-4-one (50 mg, 141 μmol) and HBTU (59 mg, 156 μmol) in DMF (1 mL) was added TEA (59.2 μL, 424 μmol) and the reaction mixture was stirred at RT over 2.5 hours. The reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered and evaporated. The product was purified by preparative HPLC (Gemini NX column) using a gradient of ACN:H$_2$O (containing 0.1% TEA) (20:80 to 98:2) to give the title compound as a colorless foam (0.051 g; 72.5%). MS (ESI): m/z=498.23 [M+H]$^+$.

Intermediate a) 3-[(3-Cyclopropyl-1,2,4-oxadiazol-5-yl)methyl]-1-phenyl-1,3,8-triazaspiro[4.5]decan-4-one To a suspension of 1-phenyl-1,3,8-triazaspiro[4.5]decan-4-one (339 mg, 1.47 mmol; CAS RN 1021-25-6) in DMF (5 mL) was added NaH (55% in mineral oil, 64 mg, 1.47 mmol; CAS RN 7646-69-7) and the mixture was stirred at RT over 15 minutes. To the turbid, light yellow solution was added dropwise 5-(chloromethyl)-3-cyclopropyl-1,2,4-oxadiazole (232 mg, 1.47 mmol; CAS RN 119223-01-7) and the mixture was stirred at RT overnight. H$_2$O (29 µL, 1.61 mmol) was added and the product was purified by preparative HPLC (Gemini NX column) using a gradient of ACN:H$_2$O (containing 0.1% TEA) (20:80 to 98:2) to give the title compound as a colorless solid (0.172 g; 33.2%). MS (ESI): m/z=354.19 [M+H]$^+$.

Example 34

8-(1H-Indazole-5-carbonyl)-3-[(2-methyl-1,3-thiazol-4-yl)methyl]-1-phenyl-1,3,8-triazaspiro[4.5]decan-4-one

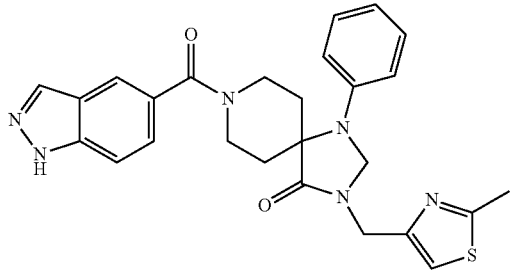 [SMILES: Cc1nc(CN2CN(c3ccccc3)C3(CCN(C(=O)c4ccc5[nH]ncc5c4)CC3)C2=O)cs1]

To a suspension of 1-phenyl-1,3,8-triazaspiro[4.5]decan-4-one (400 mg, 1.73 mmol; CAS RN 1021-25-6) in DMF (4 mL) was added NaH (55% in mineral oil, 83 mg, 1.9 mmol; CAS RN 7646-69-7) and the mixture was stirred at RT over 15 minutes. To the turbid, light yellow solution was added dropwise a solution of 4-(chloromethyl)-2-methylthiazole (255 mg, 1.73 mmol; CAS RN 39238-07-8) in DMF (1 mL) and the mixture was stirred at RT over 1.5 hours. The product was purified by preparative HPLC (Gemini NX column) using a gradient of ACN:H$_2$O (containing 0.1% TEA) (20:80 to 98:2). The residue was dissolved in DMF (2 mL) and 1H-indazole-5-carboxylic acid (123 mg, 756 µmol; CAS RN 61700-61-6), HBTU (315 mg, 832 µmol) and TEA (316 µL, 2.27 mmol) were added. The rapidly formed suspension was stirred at RT over 2.5 hours. The product was purified by preparative HPLC (Gemini NX column) using a gradient of ACN:H$_2$O (containing 0.1% TEA) (20:80 to 98:2) to give the title compound as a colorless solid (0.041 g; 11.1%). MS (ESI): m/z=487.19 [M+H]$^+$.

Example 35

8-(1H-Indazole-5-carbonyl)-3-[(1-methylimidazol-2-yl)methyl]-1-phenyl-1,3,8-triazaspiro[4.5]decan-4-one

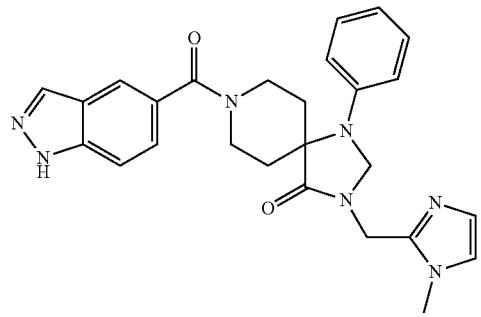 [SMILES: Cn1ccnc1CN1CN(c2ccccc2)C2(CCN(C(=O)c3ccc4[nH]ncc4c3)CC2)C1=O]

The title compound was obtained in analogy to example 33, from 3-[(1-methylimidazol-2-yl)methyl]-1-phenyl-1,3,8-triazaspiro[4.5]decan-4-one; trifluoroacetate and 1H-indazole-5-carboxylic acid (CAS RN 61700-61-6). The reaction solution was directly purified by preparative HPLC (Gemini NX column) using a gradient of ACN:H$_2$O (containing 0.1% TEA) (20:80 to 98:2) to give the title compound as a colorless solid. MS (ESI): m/z=470.23 [M+H]$^+$.

Intermediate a) 3-[(1-Methylimidazol-2-yl)methyl]-1-phenyl-1,3,8-triazaspiro[4.5]decan-4-one; trifluoroacetate To a solution of tert-butyl 3-[(1-methylimidazol-2-yl)methyl]-4-oxo-1-phenyl-1,3,8-triazaspiro[4.5]decane-8-carboxylate (180 mg, 423 µmol) in DCM (2 mL) was added TFA (652 µL, 8.46 mmol) and the clear, colorless solution was stirred at RT over 1 hour. The reaction mixture was evaporated. The reaction mixture was poured on half-saturated aqueous NaHCO$_3$ solution and EtOAc and the layers were separated. The aqueous layer was extracted five times with EtOAc. The combined organic layers were dried over MgSO$_4$, filtered and evaporated to give the title compound as a light brown solid (0.104 g; 75.6%). MS (ESI): m/z=326.20 [M–F$_3$CCOOH+H]$^+$.

Intermediate b) tert-Butyl 3-[(1-methylimidazol-2-yl)methyl]-4-oxo-1-phenyl-1,3,8-triazaspiro[4.5]decane-8-carboxylate A suspension of tert-butyl 4-oxo-1-phenyl-1,3,8-triazaspiro[4.5]decane-8-carboxylate (249 mg, 751 µmol), 2-(chloromethyl)-1-methyl-1H-imidazole hydrochloride (126 mg, 751 µmol; CAS RN 78667-04-6) and TEA (314 µL, 2.25 mmol) in DMF (2 mL) were stirred at RT overnight. After 16 hours, NaH (55% in mineral oil, 72.1 mg, 1.65 mmol; CAS RN 7646-69-7) was added. The reaction mixture was heated to 100° C. in a sealed tube over 4 hours. The reaction mixture was poured on half-saturated aqueous NH$_4$Cl solution and EtOAc and the layers were separated. The aqueous layer was extracted once with EtOAc. The organic layers were washed twice with H$_2$O and once with brine, dried over MgSO$_4$, filtered, treated with silica gel and evaporated. The compound was purified by silica gel chromatography on a 12 g column using an MPLC system eluting with a gradient of n-heptane:EtOAc (100:0 to 0:100)

to give the title compound as a colorless foam (0.184 g; 57.6%). MS (ESI): m/z=426.25 [M+H]+.

Intermediate c) tert-Butyl 4-oxo-1-phenyl-1,3,8-triazaspiro[4.5]decane-8-carboxylate To a mixture of 1-phenyl-1,3,8-triazaspiro[4.5]decan-4-one (4 g, 17.3 mmol; CAS RN 1021-25-6) in DCM (40 mL) and aqueous saturated NaHCO₃ solution (40 mL, 17.3 mmol) was added dropwise a solution of di-tert-butyl dicarbonate (4.15 g, 19 mmol) in DCM (20 mL) over 30 minutes. After stirring for another 45 minutes at RT the reaction mixture was poured on H₂O (200 mL) and EtOAc (200 mL) and the layers were separated. The aqueous layer was extracted once with EtOAc. The organic layers were washed with H₂O and with brine, dried over MgSO₄, filtered and evaporated. The residue was stirred with n-heptane (50 mL) over 15 minutes, filtered and washed with n-heptane to give the title compound as a colorless solid (4.42 g; 77.2%). MS (ESI): m/z=330.40 [M–H]⁻.

Example 36

8-(1H-Indazole-5-carbonyl)-3-[(2-methylpyrazol-3-yl)methyl]-1-phenyl-1,3,8-triazaspiro[4.5]decan-4-one

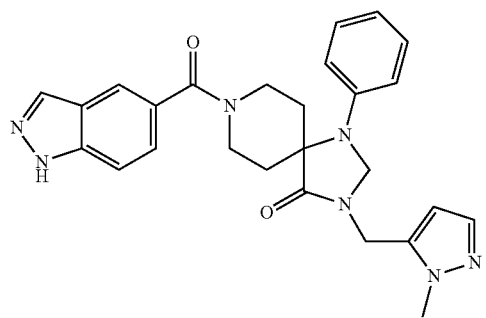 [SMILES: Cn1nccc1CN1CN(c2ccccc2)C2(CCN(C(=O)c3ccc4[nH]ncc4c3)CC2)C1=O]

To a solution of tert-butyl 3-[(2-methylpyrazol-3-yl)methyl]-4-oxo-1-phenyl-1,3,8-triazaspiro[4.5]decane-8-carboxylate (105 mg, 247 μmol) in DCM (1 mL) was added TFA (380 μL, 4.93 mmol) and the mixture was stirred at RT over 1.5 hours. The reaction mixture was evaporated. The residue was dissolved in DMF (1 mL) and treated with TEA (310 μL, 2.22 mmol), 1H-indazole-5-carboxylic acid (40 mg, 247 μmol; CAS RN 61700-61-6) and HBTU (93.6 mg, 247 μmol) and the mixture was stirred at RT over 18 hours. The product was purified by preparative HPLC (Gemini NX column) using a gradient of ACN:H₂O (containing 0.1% formic acid) (20:80 to 98:2) to give the title compound as a colorless solid (0.075 g; 64.7%). MS (ESI): m/z=470.23 [M+H]+.

Intermediate a) tert-Butyl 3-[(2-methylpyrazol-3-yl)methyl]-4-oxo-1-phenyl-1,3,8-triazaspiro[4.5]decane-8-carboxylate The title compound was obtained in analogy to example 35, intermediate b, from tert-butyl 4-oxo-1-phenyl-1,3,8-triazaspiro[4.5]decane-8-carboxylate (example 35, intermediate c), and 5-(chloromethyl)-1-methyl-1H-pyrazole (CAS RN 84547-63-7) by stirring at 100° C. for 72 hours. The compound was purified by silica gel chromatography on a 12 g column using an MPLC system eluting with a gradient of DCM:MeOH (100:0 to 90:10) to give the title compound as a colorless oil. MS (ESI): m/z=425.9 [M+H]+.

Example 37

8-(1H-Indazole-5-carbonyl)-3-[(3-methyl-1,2,4-oxadiazol-5-yl)methyl]-1-phenyl-1,3,8-triazaspiro[4.5]decan-4-one

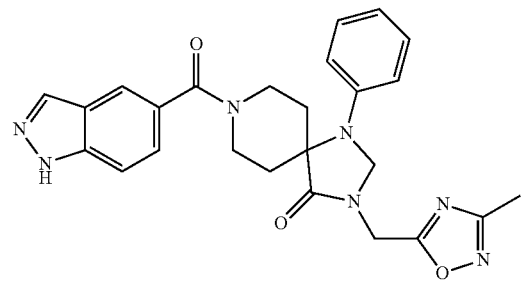 [SMILES: Cc1noc(CN2CN(c3ccccc3)C3(CCN(C(=O)c4ccc5[nH]ncc5c4)CC3)C2=O)n1]

The title compound was obtained in analogy to example 36, from tert-butyl 3-[(3-methyl-1,2,4-oxadiazol-5-yl)methyl]-4-oxo-1-phenyl-1,3,8-triazaspiro[4.5]decane-8-carboxylate and 1H-indazole-5-carboxylic acid (CAS RN 61700-61-6). The product was purified by preparative HPLC (Gemini NX column) using a gradient of ACN:H₂O (containing 0.1% TEA) (20:80 to 98:2) to give the title compound as a light brown solid. MS (ESI): m/z=472.21 [M+H]+.

Intermediate a) tert-Butyl 3-[(3-methyl-1,2,4-oxadiazol-5-yl)methyl]-4-oxo-1-phenyl-1,3,8-triazaspiro[4.5]decane-8-carboxylate The title compound was obtained in analogy to example 35, intermediate b, from 5-(chloromethyl)-3-methyl-1,2,4-oxadiazole (CAS RN 1192-81-0) and tert-butyl 4-oxo-1-phenyl-1,3,8-triazaspiro[4.5]decane-8-carboxylate (example 35, intermediate c) as a light yellow solid. MS (ESI): m/z=428.0 [M+H]+.

Example 38

8-(1H-Indazole-5-carbonyl)-3-[(5-methyl-1,3,4-oxadiazol-2-yl)methyl]-1-phenyl-1,3,8-triazaspiro[4.5]decan-4-one

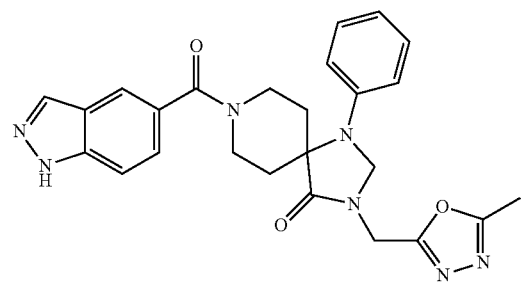 [SMILES: Cc1nnc(CN2CN(c3ccccc3)C3(CCN(C(=O)c4ccc5[nH]ncc5c4)CC3)C2=O)o1]

The title compound was obtained in analogy to example 36, from tert-butyl 3-[(5-methyl-1,3,4-oxadiazol-2-yl)

methyl]-4-oxo-1-phenyl-1,3,8-triazaspiro[4.5]decane-8-carboxylate (105 mg, 246 μmol) and 1H-indazole-5-carboxylic acid (39.8 mg, 246 μmol, CAS RN 61700-61-6). The product was purified by preparative HPLC (Gemini NX column) using a gradient of ACN:H₂O (containing 0.1% TEA) (20:80 to 98:2) to give the title compound as a colorless foam (0.070 g; 60.4%). MS (ESI): m/z=472.21 [M+H]⁺.

Intermediate a) tert-Butyl 3-[(5-methyl-1,3,4-oxadiazol-2-yl)methyl]-4-oxo-1-phenyl-1,3,8-triazaspiro[4.5]decane-8-carboxylate The title compound was obtained in analogy to example 35, intermediate b, from 2-(chloromethyl)-5-methyl-1,3,4-oxadiazole (CAS RN 3914-42-9) and tert-butyl 4-oxo-1-phenyl-1,3,8-triazaspiro[4.5]decane-8-carboxylate (example 35, intermediate c) without addition of TEA at 60° C. over 75 minutes as a colorless solid. MS (EI): m/z=427.227 [M].

Example 39

3-[[3-(4-Fluorophenyl)-1,2,4-oxadiazol-5-yl]methyl]-8-(1H-indazole-5-carbonyl)-1-phenyl-1,3,8-triazaspiro[4.5]decan-4-one

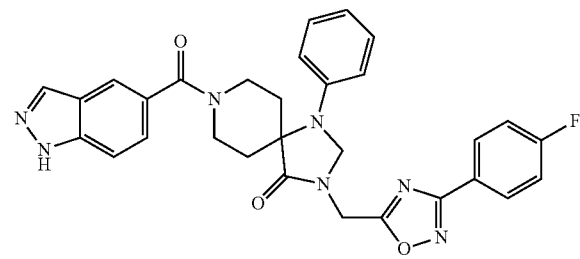 [SMILES: O=C(c1ccc2[nH]ncc2c1)N1CCC2(CC1)C(=O)N(Cc1nc(-c3ccc(F)cc3)no1)CN2c1ccccc1]

The title compound was obtained in analogy to example 36, from tert-butyl 3-[[3-(4-fluorophenyl)-1,2,4-oxadiazol-5-yl]methyl]-4-oxo-1-phenyl-1,3,8-triazaspiro[4.5]decane-8-carboxylate and 1H-indazole-5-carboxylic acid (CAS RN 61700-61-6) as a colorless foam. MS (ESI): m/z=552.22 [M+H]⁺.

Intermediate a) tert-Butyl 3-[[3-(4-fluorophenyl)-1,2,4-oxadiazol-5-yl]methyl]-4-oxo-1-phenyl-1,3,8-triazaspiro[4.5]decane-8-carboxylate The title compound was obtained in analogy to example 35, intermediate b, from 5-(chloromethyl)-3-(4-fluorophenyl)-1,2,4-oxadiazole (CAS RN 721428-34-8) and tert-butyl 4-oxo-1-phenyl-1,3,8-triazaspiro[4.5]decane-8-carboxylate (example 35, intermediate c) without addition of TEA at 60° C. over 75 minutes as a light yellow oil. MS (ESI): m/z=508.24 [M+H]⁺.

Example 40

3-[(5-Cyclopropyl-1,3,4-thiadiazol-2-yl)methyl]-8-(1H-indazole-5-carbonyl)-1-phenyl-1,3,8-triazaspiro[4.5]decan-4-one

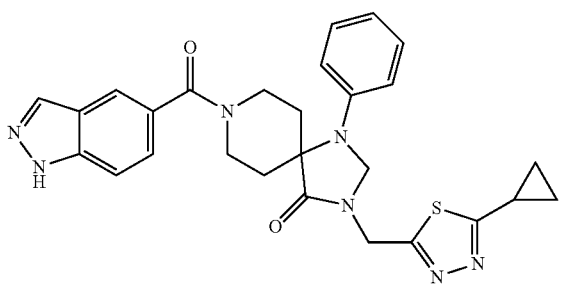 [SMILES: O=C(c1ccc2[nH]ncc2c1)N1CCC2(CC1)C(=O)N(Cc1nnc(C3CC3)s1)CN2c1ccccc1]

The title compound was obtained in analogy to example 36, from tert-butyl 3-[(5-cyclopropyl-1,3,4-thiadiazol-2-yl)methyl]-4-oxo-1-phenyl-1,3,8-triazaspiro[4.5]decane-8-carboxylate and 1H-indazole-5-carboxylic acid (CAS RN 61700-61-6) as a colorless foam. MS (ESI): m/z=514.20 [M+H]⁺.

Intermediate a) tert-Butyl 3-[(5-cyclopropyl-1,3,4-thiadiazol-2-yl)methyl]-4-oxo-1-phenyl-1,3,8-triazaspiro[4.5]decane-8-carboxylate The title compound was obtained in analogy to example 35, intermediate b, from 2-(chloromethyl)-5-cyclopropyl-1,3,4-thiadiazole (CAS RN 138300-59-1) and tert-butyl 4-oxo-1-phenyl-1,3,8-triazaspiro[4.5]decane-8-carboxylate (example 35, intermediate c) without addition of TEA at RT and stirring for 12 hours. The compound was purified by silica gel chromatography on a 10 g column using an MPLC (ISCO) system eluting with a gradient of DCM:MeOH (100:0 to 90:10) to give the title compound as a colorless gum. MS (ESI): m/z=470.22 [M+H]⁺.

Example 41

(3S,4R or 3R,4S)-2-[8-(1H-Indazole-5-carbonyl)-4-oxo-1-phenyl-1,3,8-triazaspiro[4.5]decan-3-yl]-N-(4-phenylpyrrolidin-3-yl)acetamide

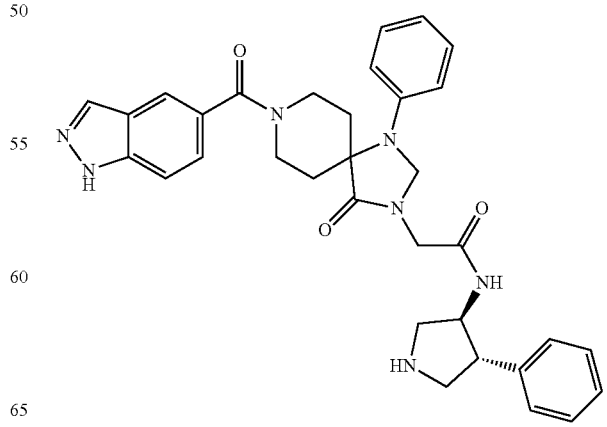

To a solution of 2-[8-(1H-indazole-5-carbonyl)-4-oxo-1-phenyl-1,3,8-triazaspiro[4.5]decan-3-yl]acetic acid (50 mg, 115 μmol) and (−)-tert-butyl 3-amino-4-phenylpyrrolidine-1-carboxylate (30.3 mg, 115 μmol) in DMF (1 mL) were added HBTU (43.7 mg, 115 μmol) and TEA (48.2 μL, 346 μmol) and the clear and colorless solution was stirred at RT over 4 hours. The reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered and evaporated. The residue was dissolved in DCM (1 mL) and treated with TFA (178 μl, 2.31 mmol) and the resulting solution was stirred at RT over 1.5 hours and then evaporated. The residue was taken up in DCM (1 mL) and TEA (322 μL, 2.31 mmol) was added under stirring, followed by evaporation. The product was purified by preparative HPLC (Gemini NX column) using a gradient of ACN:H$_2$O (containing 0.1% TEA) (20:80 to 98:2) to give the title compound as a colorless solid (0.029 g; 43.5%). MS (ESI): m/z=578.29 [M+H]$^+$.

Intermediate a) 2-[8-(1H-Indazole-5-carbonyl)-4-oxo-1-phenyl-1,3,8-triazaspiro[4.5]decan-3-yl]acetic acid To a solution of methyl 2-[8-(1H-indazole-5-carbonyl)-4-oxo-1-phenyl-1,3,8-triazaspiro[4.5]decan-3-yl]acetate (170 mg, 380 μmol) in dioxane (2 mL) and H$_2$O (2 mL) was added LiOH (17.5 mg, 418 μmol) and the solution was stirred at RT over 4 hours. Dioxane was removed by evaporation. HCl 1M in H$_2$O (456 μL, 456 μmol) was added dropwise and the resulting suspension was diluted with H$_2$O (1 mL) and filtered. The filter cake was washed with H$_2$O and dried overnight under high vacuum to give the title compound as a colorless solid (0.132 g; 80.2%). MS (ESI): m/z=434.18 [M+H]$^+$.

Intermediate b) Methyl 2-[8-(1H-indazole-5-carbonyl)-4-oxo-1-phenyl-1,3,8-triazaspiro[4.5]decan-3-yl]acetate The title compound was obtained in analogy to example 33, from methyl 2-(4-oxo-1-phenyl-1,3,8-triazaspiro[4.5]decan-3-yl)acetate (example 22, intermediate c) and 1H-indazole-5-carboxylic acid (CAS RN 61700-61-6). The reaction solution was directly purified by preparative HPLC (Gemini NX column) using a gradient of ACN:H$_2$O (containing 0.1% formic acid) (20:80 to 98:2) to give the title compound as a colorless solid. MS (ESI): m/z=448.20 [M+H]$^+$.

Intermediate c) (−)-tert-Butyl 3-amino-4-phenylpyrrolidine-1-carboxylate (rac,trans)-tert-Butyl (rac,trans)-3-amino-4-phenylpyrrolidine-1-carboxylate (3.4 g, 13 mol; CAS RN 1015070-53-7) was separated on a preparative chiral HPLC (Reprosil Chiral-NR column) using an isocratic mixture of EtOH (containing 0.5% NH$_4$OAc):n-heptane (20:80). The obtained fraction was evaporated. The residue was taken up in EtOAc and washed once with aqueous 2M Na$_2$CO$_3$ solution. The aqueous layer was extracted once with EtOAc. The organic layers were dried over MgSO$_4$, filtered and evaporated to give the title compound as colorless oil (1.396 g; 41.1%). MS (ESI): m/z=263.18 [M+H]$^+$. First eluting peak. Rotation is (−).

Example 42

(rac,trans)-2-[8-(1H-Indazole-5-carbonyl)-4-oxo-1-phenyl-1,3,8-triazaspiro[4.5]decan-3-yl]-N-[4-(3-methyl-1,2,4-oxadiazol-5-yl)pyrrolidin-3-yl]acetamide

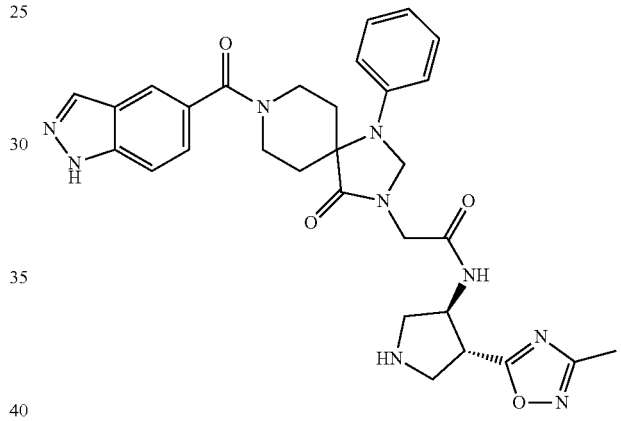

The title compound was obtained in analogy to example 41, from 2-(8-(1H-indazole-5-carbonyl)-4-oxo-1-phenyl-1,3,8-triazaspiro[4.5]decan-3-yl)acetic acid (example 41, intermediate a) and (rac,trans)-tert-butyl 3-amino-4-(3-methyl-1,2,4-oxadiazol-5-yl)pyrrolidine-1-carboxylate as a colorless solid. MS (ESI): m/z=584.27 [M+H]$^+$.

Intermediate a) (rac,trans)-tert-Butyl 3-amino-4-(3-methyl-1,2,4-oxadiazol-5-yl)pyrrolidine-1-carboxylate To a suspension of (rac,trans)-1-tert-butyl 3-ethyl 4-aminopyrrolidine-1,3-dicarboxylate hydrochloride (1.14 g, 3.87 mmol; CAS RN 1262849-90-0) and (Z)-N'-hydroxyacetimidamide (315 mg, 4.25 mmol; CAS RN 22059-22-9) in EtOH (12 mL) was added sodium ethoxide 21% in EtOH (2.89 mL, 7.74 mmol) and the mixture was stirred at 70° C. over 30 minutes. After cooling to RT, the reaction mixture was poured on brine and EtOAc and the layers were separated. The aqueous layer was extracted twice with EtOAc. The organic layers were dried over MgSO$_4$, filtered and evaporated. The residue was purified by silica gel chromatography on a 25 g column using an MPLC (ISCO) system eluting with a gradient of DCM:MeOH (100:0 to 90:10) to give the title compound as a light brown oil (0.224 g; 21.6%). MS (ESI): m/z=269.16 [M+H]$^+$.

Example 43

(RS)-2-[8-(1H-Indazole-5-carbonyl)-2-methyl-4-oxo-1-phenyl-1,3,8-triazaspiro[4.5]decan-3-yl]-N-(2,2,2-trifluoroethyl)acetamide

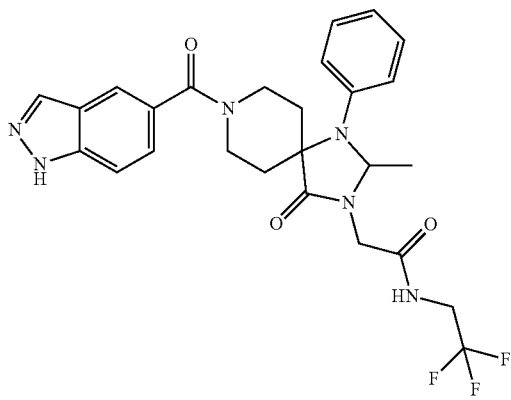 [SMILES: CC1N(CC(=O)NCC(F)(F)F)C(=O)C2(CCN(C(=O)c3ccc4[nH]ncc4c3)CC2)N1c1ccccc1]

To a solution of 8-benzyl-2-methyl-1-phenyl-1,3,8-triazaspiro[4.5]decan-4-one (64 mg, 191 µmol) (prepared as described in U.S. Pat. No. 3,238,216) in DMF (1 mL) was added NaH (55% in mineral oil, 9.99 mg, 229 µmol; CAS RN 7646-69-7) and the mixture was stirred at RT for 15 minutes before 2-chloro-N-(2,2,2-trifluoroethyl)acetamide (36.8 mg, 210 µmol; CAS RN 170655-44-4) was added and stirring was continued at RT for 17 hours. The reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered and evaporated. The residue was dissolved in MeOH (1.5 mL), treated with palladium on carbon 10% (10.2 mg, 95.4 µmol) and stirred under a hydrogen atmosphere of 1.5 bar over 4 hours. Another batch of palladium on carbon 10% (10.2 mg, 95.4 µmol) was added and stirring was continued over 72 hours under a hydrogen atmosphere of 1.65 bar. The reaction mixture was filtered over a microfilter, washed with MeOH and evaporated to dryness. The remaining light brown oil (75 mg) was dissolved in DMF (1 mL), treated with 1H-indazole-5-carboxylic acid (30.9 mg; CAS RN 61700-61-6), HBTU (72.4 mg, 191 µmol) and TEA (79.8 µL, 573 µmol) upon which the light brown solution turned rapidly into a suspension which was stirred at RT over 2 hours. The product was purified by preparative HPLC (Gemini NX column) using a gradient of ACN:H$_2$O (containing 0.1% TEA) (20:80 to 98:2) to give the title compound as a colorless solid (0.030 g; 29.8%). MS (ESI): m/z=529.22 [M+H]$^+$.

Example 44

3-[(2-tert-Butyl-5-methyl-1,3-oxazol-4-yl)methyl]-8-(1H-indazole-5-carbonyl)-1-phenyl-1,3,8-triazaspiro[4.5]decan-4-one

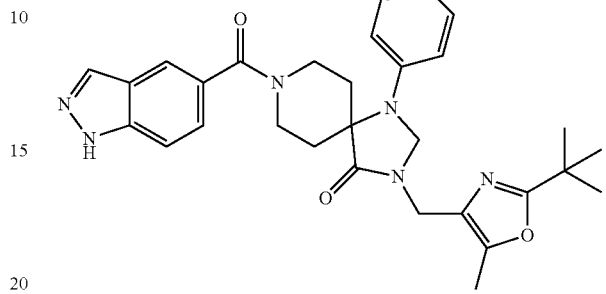

The title compound was obtained in analogy to example 36, from tert-butyl 3-[(2-tert-butyl-5-methyl-1,3-oxazol-4-yl)methyl]-4-oxo-1-phenyl-1,3,8-triazaspiro[4.5]decane-8-carboxylate and 1H-indazole-5-carboxylic acid (CAS RN 61700-61-6) as a colorless foam. MS (ESI): m/z=527.28 [M+H]$^+$.

Intermediate a) tert-Butyl 3-[(2-tert-butyl-5-methyl-1,3-oxazol-4-yl)methyl]-4-oxo-1-phenyl-1,3,8-triazaspiro[4.5]decane-8-carboxylate The title compound was obtained in analogy to example 36, intermediate a, from 2-(tert-butyl)-4-(chloromethyl)-5-methyloxazole (CAS RN 690684-13-0) and tert-butyl 4-oxo-1-phenyl-1,3,8-triazaspiro[4.5]decane-8-carboxylate (example 35, intermediate c) without addition of TEA at RT and stirring for 64 hours. The compound was purified by silica gel chromatography on a 4 g column using an MPLC system eluting with a gradient of n-heptane:EtOAc (100:0 to 50:50) to give the title compound as a colorless foam. MS (ESI): m/z=483.30 [M+H]$^+$.

Example 45

3-[(3-tert-Butyl-1,2,4-thiadiazol-5-yl)methyl]-8-(1H-indazole-5-carbonyl)-1-phenyl-1,3,8-triazaspiro[4.5]decan-4-one

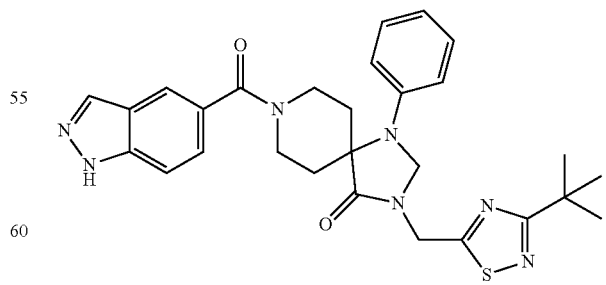

The title compound was obtained in analogy to example 36, from tert-butyl 3-[(3-tert-butyl-1,2,4-thiadiazol-5-yl)methyl]-4-oxo-1-phenyl-1,3,8-triazaspiro[4.5]decane-8-carboxylate and 1H-indazole-5-carboxylic acid (CAS RN 61700-61-6). The product was purified by preparative HPLC (Gemini NX column) using a gradient of ACN:H₂O (containing 0.1% TEA) (20:80 to 98:2) to give the title compound as a colorless solid. MS (ESI): m/z=530.23 [M+H]⁺.

Intermediate a) tert-Butyl 3-[(3-tert-butyl-1,2,4-thiadiazol-5-yl)methyl]-4-oxo-1-phenyl-1,3,8-triazaspiro[4.5]decane-8-carboxylate The title compound was obtained in analogy to example 35, intermediate b, from 3-(tert-butyl)-5-(chloromethyl)-1,2,4-thiadiazole (prepared as described in WO2005/68432) and tert-butyl 4-oxo-1-phenyl-1,3,8-triazaspiro[4.5]decane-8-carboxylate (example 35, intermediate c) without addition of TEA at RT over 64 hours to give the title compound as a yellow solid. MS (EI): m/z=485 [M].

Example 46

(3R,4S or 3S,4R)-2-[8-(1H-Indazole-5-carbonyl)-4-oxo-1-phenyl-1,3,8-triazaspiro[4.5]decan-3-yl]-N-(4-phenylpyrrolidin-3-yl)acetamide

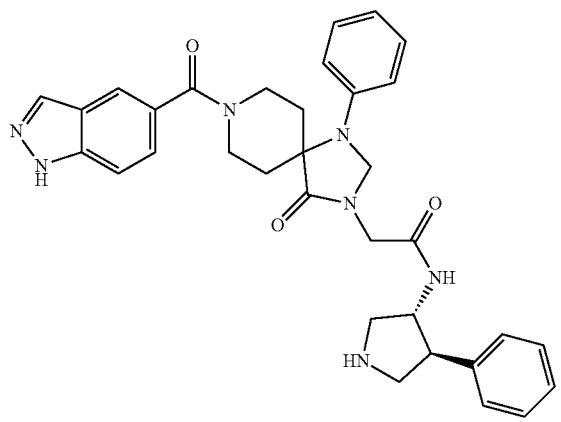 [SMILES: O=C(CN1CN(c2ccccc2)C2(CCN(C(=O)c3ccc4[nH]ncc4c3)CC2)C1=O)N[C@H]1CNC[C@@H]1c1ccccc1]

The title compound was obtained in analogy to example 41, from 2-(8-(1H-indazole-5-carbonyl)-4-oxo-1-phenyl-1,3,8-triazaspiro[4.5]decan-3-yl)acetic acid (example 41, intermediate a) and (+)-tert-butyl 3-amino-4-phenylpyrrolidine-1-carboxylate as a colorless solid. MS (ESI): m/z=578.29 [M+H]⁺.

Intermediate a) (+)-tert-Butyl 3-amino-4-phenylpyrrolidine-1-carboxylate

The title compound was obtained in analogy to example 41, intermediate c, from (rac,trans)-tert-butyl-3-amino-4-phenylpyrrolidine-1-carboxylate (CAS RN 1015070-53-7) as a colorless oil. MS (ESI): m/z=263.18 [M+H]⁺. Second eluting peak. Rotation is (+).

Example 47

(RS)-3-[2-Oxo-2-[3-(trifluoromethyl)pyrrolidin-1-yl]ethyl]-1-phenyl-8-(1H-pyrazolo[3,4-b]pyridine-5-carbonyl)-1,3,8-triazaspiro[4.5]decan-4-one

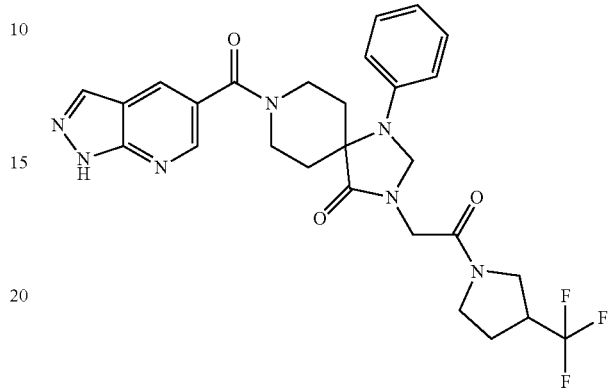

To a solution of 2-[4-oxo-1-phenyl-8-(1H-pyrazolo[3,4-b]pyridine-5-carbonyl)-1,3,8-triazaspiro[4.5]decan-3-yl] acetic acid (60 mg, 138 μmol, example 22, intermediate a), HBTU (62.9 mg, 166 μmol) and 3-(trifluoromethyl)pyrrolidine hydrochloride (24.2 mg, 138 μmol, CAS RN 644970-41-2) in DMF (1 mL) was added TEA (96.2 μL, 691 μmol) and the reaction mixture was stirred at RT for 8 hours. The product was purified by preparative HPLC (Gemini NX column) using a gradient of ACN:H₂O (containing 0.1% formic acid) (20:80 to 98:2) to give the title compound as a light brown solid (0.012 g; 15.6%). MS (ESI): m/z=554.21 [M+H]⁺.

Example 48

3-(1-Ethylpyrazol-3-yl)-8-(1H-indazole-5-carbonyl)-1-phenyl-1,3,8-triazaspiro[4.5]decan-4-one

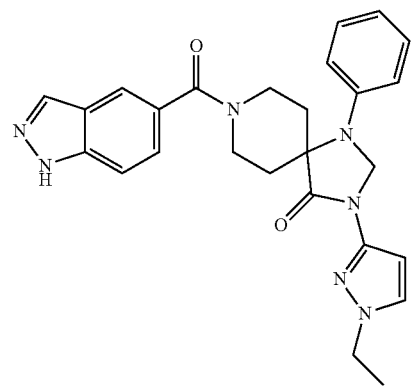 [SMILES: CCn1ccc(N2CN(c3ccccc3)C3(CCN(C(=O)c4ccc5[nH]ncc5c4)CC3)C2=O)n1]

The title compound was obtained in analogy to example 36, from tert-butyl 3-(1-ethylpyrazol-3-yl)-4-oxo-1-phenyl-1,3,8-triazaspiro[4.5]decane-8-carboxylate and 1H-indazole-5-carboxylic acid (CAS RN 61700-61-6). The product was purified by preparative HPLC (Gemini NX column)

using a gradient of ACN:H₂O (containing 0.1% TEA) (20:80 to 98:2) to give the title compound as a colorless solid. MS (ESI): m/z=470.23 [M+H]⁺.

Intermediate a) tert-Butyl 3-(1-ethylpyrazol-3-yl)-4-oxo-1-phenyl-1,3,8-triazaspiro[4.5]decane-8-carboxylate To a suspension of tert-butyl 4-oxo-1-phenyl-1,3,8-triazaspiro[4.5]decane-8-carboxylate (100 mg, 302 μmol, example 35, intermediate c) and 1-ethyl-3-iodo-1H-pyrazole (67 mg, 302 μmol, CAS RN 1202781-34-7) in dioxane (2 mL) were added K₂CO₃ (125 mg, 905 μmol), DMEDA (6.11 μL, 48.3 μmol, CAS RN 110-70-3) and CuI (4.6 mg, 24.1 μmol) and the mixture was purged with argon. The suspension was heated to 100° C. and stirred at this temperature over 14 hours. The reaction mixture was filtered over a microfilter, the filtrate was washed with a small volume of EtOAc and MeOH, treated with silica gel and evaporated. The compound was purified by silica gel chromatography on a 4 g column using an MPLC (ISCO) system eluting with a gradient of n-heptane:EtOAc (100:0 to 50:50) to give the title compound as a colorless solid (0.107 g; 83.3%). MS (ESI): m/z=426.25 [M+H]⁺.

Example 49

3-(1-Ethylpyrazol-4-yl)-8-(1H-indazole-5-carbonyl)-1-phenyl-1,3,8-triazaspiro[4.5]decan-4-one

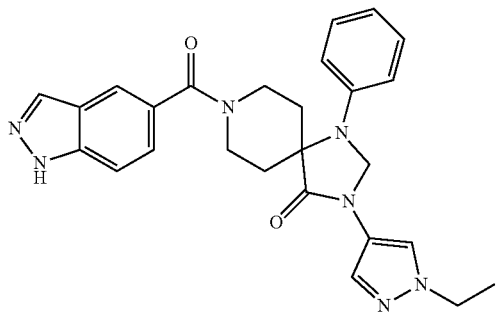 [SMILES: CCn1cc(N2CN(c3ccccc3)C3(CCN(C(=O)c4ccc5[nH]ncc5c4)CC3)C2=O)cn1]

The title compound was obtained in analogy to example 36, from tert-butyl 3-(1-ethylpyrazol-4-yl)-4-oxo-1-phenyl-1,3,8-triazaspiro[4.5]decane-8-carboxylate and 1H-indazole-5-carboxylic acid (CAS RN 61700-61-6) as a light brown solid. MS (ESI): m/z=470.23 [M+H]⁺.

Intermediate a) tert-Butyl 3-(1-ethylpyrazol-4-yl)-4-oxo-1-phenyl-1,3,8-triazaspiro[4.5]decane-8-carboxylate The title compound was obtained in analogy to example 48, intermediate a, from 1-ethyl-4-iodo-1H-pyrazole (CAS RN 172282-34-7) and tert-butyl 4-oxo-1-phenyl-1,3,8-triazaspiro[4.5]decane-8-carboxylate (example 35, intermediate c) at 100° C. over 80 hours as a light brown oil. MS (ESI): m/z=426.25 [M+H]⁺.

Example 50

3-(1,5-Dimethylpyrazol-3-yl)-8-(1H-indazole-5-carbonyl)-1-phenyl-1,3,8-triazaspiro[4.5]decan-4-one

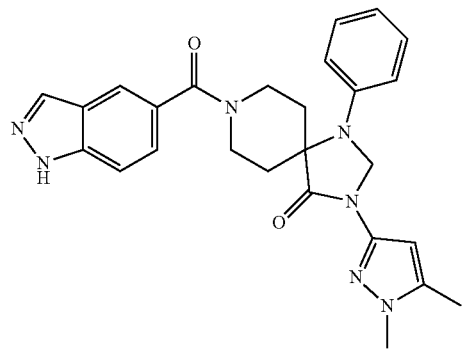 [SMILES: Cc1cc(N2CN(c3ccccc3)C3(CCN(C(=O)c4ccc5[nH]ncc5c4)CC3)C2=O)nn1C]

The title compound was obtained in analogy to example 36, from tert-butyl 3-(1,5-dimethylpyrazol-3-yl)-4-oxo-1-phenyl-1,3,8-triazaspiro[4.5]decane-8-carboxylate and 1H-indazole-5-carboxylic acid (CAS RN 61700-61-6) as a light brown foam. MS (ESI): m/z=470.23 [M+H]⁺.

Intermediate a) tert-Butyl 3-(1,5-dimethylpyrazol-3-yl)-4-oxo-1-phenyl-1,3,8-triazaspiro[4.5]decane-8-carboxylate The title compound was obtained in analogy to example 48, intermediate a, from tert-butyl 4-oxo-1-phenyl-1,3,8-triazaspiro[4.5]decane-8-carboxylate (example 35, intermediate c) and 3-bromo-1,5-dimethyl-1H-pyrazole (CAS RN 5744-80-9) at 120° C. over 19 hours as a colorless solid. MS (ESI): m/z=426.25 [M+H]⁺.

Example 51

3-(2,5-Dimethylpyrazol-3-yl)-8-(1H-indazole-5-carbonyl)-1-phenyl-1,3,8-triazaspiro[4.5]decan-4-one

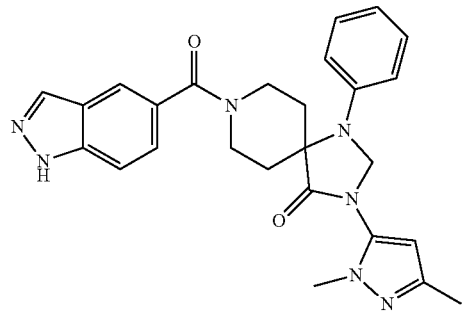 [SMILES: Cc1cc(N2CN(c3ccccc3)C3(CCN(C(=O)c4ccc5[nH]ncc5c4)CC3)C2=O)n(C)n1]

The title compound was obtained in analogy to example 36, from tert-butyl 3-(2,5-dimethylpyrazol-3-yl)-4-oxo-1-phenyl-1,3,8-triazaspiro[4.5]decane-8-carboxylate and 1H-indazole-5-carboxylic acid (CAS RN 61700-61-6) as a colorless solid. MS (ESI): m/z=470.23 [M+H]⁺.

Intermediate a) tert-Butyl 3-(2,5-dimethylpyrazol-3-yl)-4-oxo-1-phenyl-1,3,8-triazaspiro[4.5]decane-8-carboxylate The title compound was obtained in analogy to example 48, intermediate a, from 5-bromo-1,3-dimethyl-1H-pyrazole (CAS RN 5744-70-7) and tert-butyl 4-oxo-1-phenyl-1,3,8-triazaspiro[4.5]decane-8-carboxylate (example 35, intermediate c) and stirring at 120° C. over 17 hours. Colorless gum. MS (ESI): m/z=426.25 [M+H]+.

Example 52

3-(2,4-Dimethyl-1,3-thiazol-5-yl)-8-(1H-indazole-5-carbonyl)-1-phenyl-1,3,8-triazaspiro[4.5]decan-4-one

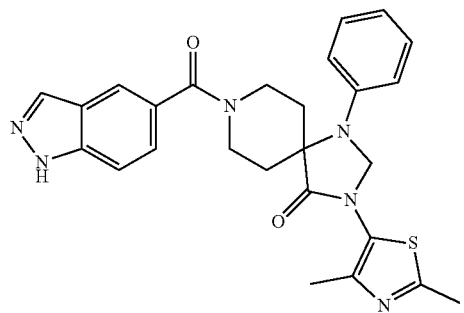 [SMILES: Cc1nc(C)c(N2CN(c3ccccc3)C3(CCN(C(=O)c4ccc5[nH]ncc5c4)CC3)C2=O)s1]

The title compound was obtained in analogy to example 36, from tert-butyl 3-(2,4-dimethyl-1,3-thiazol-5-yl)-4-oxo-1-phenyl-1,3,8-triazaspiro[4.5]decane-8-carboxylate and 1H-indazole-5-carboxylic acid (CAS RN 61700-61-6) as a colorless solid. MS (ESI): m/z=487.19 [M+H]+.

Intermediate a) tert-Butyl 3-(2,4-dimethyl-1,3-thiazol-5-yl)-4-oxo-1-phenyl-1,3,8-triazaspiro[4.5]decane-8-carboxylate The title compound was obtained in analogy to example 48, intermediate a, from 5-bromo-2,4-dimethylthiazole (CAS RN 28599-52-2) and tert-butyl 4-oxo-1-phenyl-1,3,8-triazaspiro[4.5]decane-8-carboxylate (example 35, intermediate c) as a colorless gum. MS (ESI): m/z=443.21 [M+H]+.

Example 53

(RS)-1-[2-[8-(1H-Indazole-5-carbonyl)-4-oxo-1-phenyl-1,3,8-triazaspiro[4.5]decan-3-yl]acetyl]pyrrolidine-3-carbonitrile

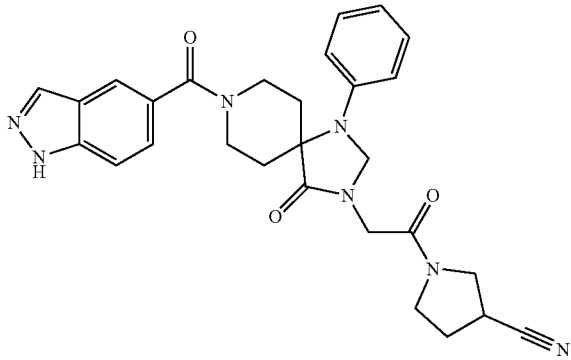 [SMILES: N#CC1CCN(C(=O)CN2CN(c3ccccc3)C3(CCN(C(=O)c4ccc5[nH]ncc5c4)CC3)C2=O)C1]

The title compound was obtained in analogy to example 47, from pyrrolidine-3-carbonitrile hydrochloride (CAS RN 10603-53-9) and 2-(8-(1H-indazole-5-carbonyl)-4-oxo-1-phenyl-1,3,8-triazaspiro[4.5]decan-3-yl)acetic acid (example 41, intermediate a) as a colorless solid. MS (ESI): m/z=512.24 [M+H]+.

Example 54

(RS)-8-(1H-Indazole-5-carbonyl)-3-[2-oxo-2-[3-(1,2,4-triazol-1-yl)pyrrolidin-1-yl]ethyl]-1-phenyl-1,3,8-triazaspiro[4.5]decan-4-one

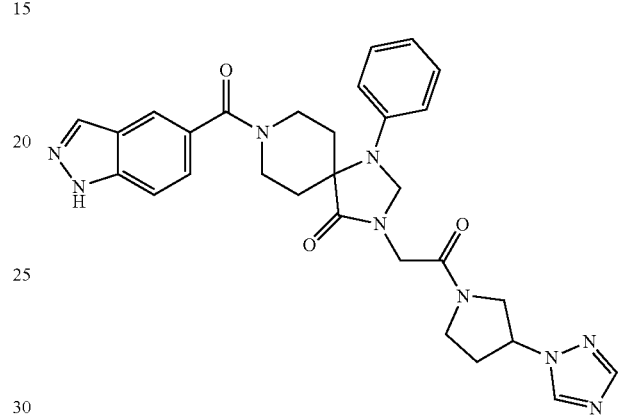

The title compound was obtained in analogy to example 47, from 1-(pyrrolidin-3-yl)-1H-1,2,4-triazole (prepared as described in US2009/221565) and 2-(8-(1H-indazole-5-carbonyl)-4-oxo-1-phenyl-1,3,8-triazaspiro[4.5]decan-3-yl) acetic acid (example 41, intermediate a) as a colorless solid. MS (ESI): m/z=554.26 [M+H]+.

Example 55

3-[2-(3,3-Dimethylpyrrolidin-1-yl)-2-oxoethyl]-8-(1H-indazole-5-carbonyl)-1-phenyl-1,3,8-triazaspiro[4.5]decan-4-one

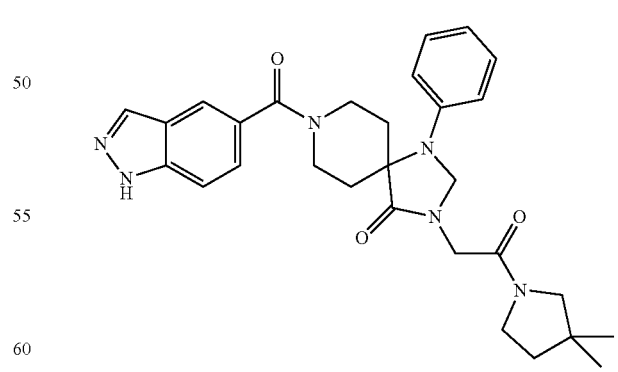

The title compound was obtained in analogy to example 47, from 3,3-dimethylpyrrolidine (CAS RN 3437-30-7) and 2-(8-(1H-indazole-5-carbonyl)-4-oxo-1-phenyl-1,3,8-triazaspiro[4.5]decan-3-yl)acetic acid (example 41, intermediate a) as a colorless solid. MS (ESI): m/z=515.28 [M+H]+.

Example 56

3-[2-(3,3-Difluoroazetidin-1-yl)-2-oxoethyl]-8-(1H-indazole-5-carbonyl)-1-phenyl-1,3,8-triazaspiro[4.5]decan-4-one

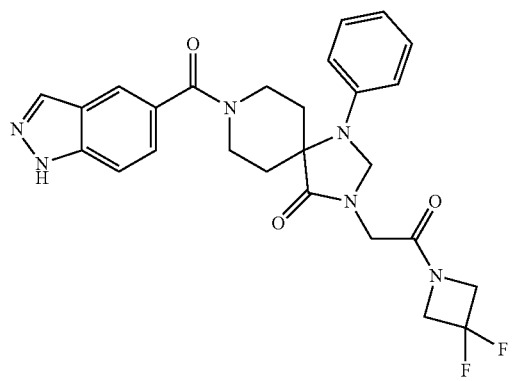 [SMILES: O=C(CN1CN(c2ccccc2)C2(CCN(C(=O)c3ccc4[nH]ncc4c3)CC2)C1=O)N1CC(F)(F)C1]

The title compound was obtained in analogy to example 47, from 3,3-difluoroazetidine hydrochloride (CAS RN 288315-03-7) and 2-(8-(1H-indazole-5-carbonyl)-4-oxo-1-phenyl-1,3,8-triazaspiro[4.5]decan-3-yl)acetic acid (example 41, intermediate a) as a colorless solid. MS (ESI): m/z=509.21 [M+H]$^+$.

Example 57

3-[2-[(3R)-3-(Dimethylamino)pyrrolidin-1-yl]-2-oxoethyl]-8-(1H-indazole-5-carbonyl)-1-phenyl-1,3,8-triazaspiro[4.5]decan-4-one

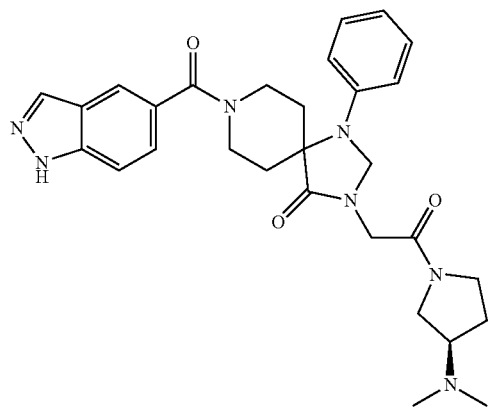 [SMILES: CN(C)[C@@H]1CCN(C(=O)CN2CN(c3ccccc3)C3(CCN(C(=O)c4ccc5[nH]ncc5c4)CC3)C2=O)C1]

The title compound was obtained in analogy to example 47, from (R)—N,N-dimethylpyrrolidin-3-amine (CAS RN 132958-72-6) and 2-(8-(1H-indazole-5-carbonyl)-4-oxo-1-phenyl-1,3,8-triazaspiro[4.5]decan-3-yl)acetic acid (example 41, intermediate a). The product was purified by preparative HPLC (Gemini NX column) using a gradient of ACN:H$_2$O (containing 0.1% TEA) (20:80 to 98:2) to give the title compound as a colorless solid. MS (ESI): m/z=530.29 [M+H]$^+$.

Example 58

(rac,cis)-3-[2-(2-Benzyl-1,3,3a,4,6,6a-hexahydropyrrolo[3,4-c]pyrrol-5-yl)-2-oxoethyl]-8-(1H-indazole-5-carbonyl)-1-phenyl-1,3,8-triazaspiro[4.5]decan-4-one

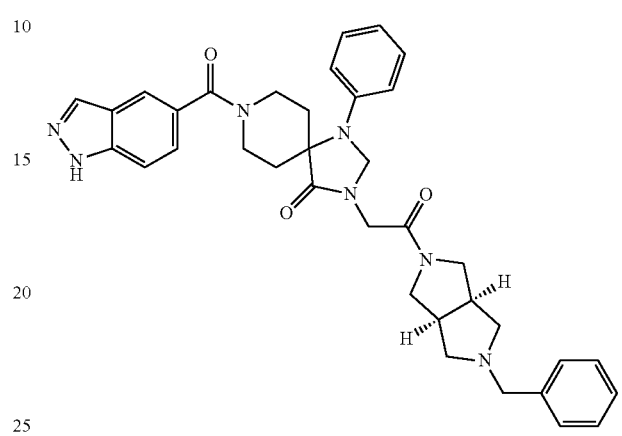

The title compound was obtained in analogy to example 47, from (rac,cis)-2-benzyloctahydropyrrolo[3,4-c]pyrrole (CAS RN 172739-04-7) and 2-(8-(1H-indazole-5-carbonyl)-4-oxo-1-phenyl-1,3,8-triazaspiro[4.5]decan-3-yl)acetic acid (example 41, intermediate a) as a colorless solid. MS (ESI): m/z=618.32 [M+H]$^+$.

Example 59

8-(1H-Indazole-5-carbonyl)-3-[2-[(2R)-2-(methoxymethyl)pyrrolidin-1-yl]-2-oxoethyl]-1-phenyl-1,3,8-triazaspiro[4.5]decan-4-one

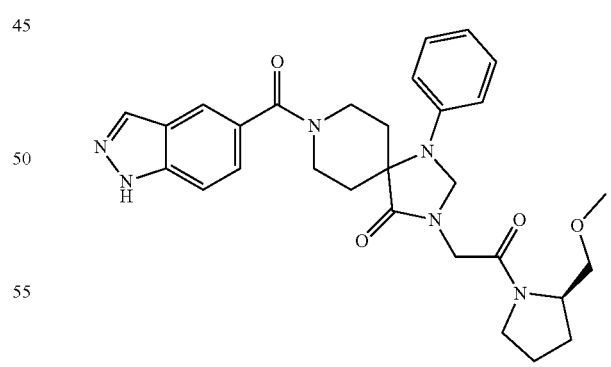

The title compound was obtained in analogy to example 47, from (R)-2-(methoxymethyl)pyrrolidine (CAS RN 84025-81-0) and 2-(8-(1H-indazole-5-carbonyl)-4-oxo-1-phenyl-1,3,8-triazaspiro[4.5]decan-3-yl)acetic acid (example 41, intermediate a) as a colorless foam. MS (ESI): m/z=531.27 [M+H]$^+$.

Example 60

(RS)-3-(2-Oxo-1-phenylpyrrolidin-3-yl)-1-phenyl-8-(1H-pyrazolo[3,4-b]pyridine-5-carbonyl)-1,3,8-triazaspiro[4.5]decan-4-one

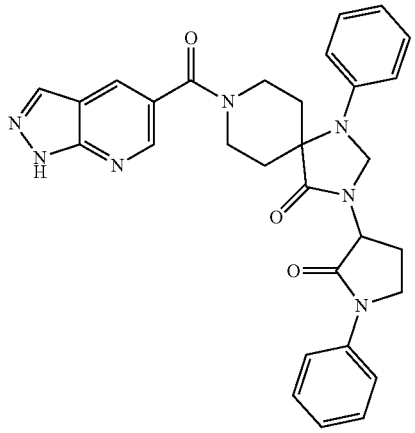 [SMILES: O=C(c1cnc2[nH]ncc2c1)N1CCC2(CC1)C(=O)N(C1CCN(c3ccccc3)C1=O)CN2c1ccccc1]

The title compound was obtained in analogy to example 36, from (RS)-tert-butyl 4-oxo-3-(2-oxo-1-phenylpyrrolidin-3-yl)-1-phenyl-1,3,8-triazaspiro[4.5]decane-8-carboxylate and 1H-pyrazolo[3,4-b]pyridine-5-carboxylic acid (CAS RN 952182-02-4). The product was purified by preparative HPLC (Gemini NX column) using a gradient of ACN:H$_2$O (containing 0.1% TEA) (20:80 to 98:2) to give the title compound as a colorless solid. MS (ESI): m/z=536.24 [M+H]$^+$.

Intermediate a) (RS)-tert-Butyl 4-oxo-3-(2-oxo-1-phenylpyrrolidin-3-yl)-1-phenyl-1,3,8-triazaspiro[4.5]decane-8-carboxylate To a turbid solution of tert-butyl 4-oxo-1-phenyl-1,3,8-triazaspiro[4.5]decane-8-carboxylate (100 mg, 302 μmol, example 35, intermediate c) in DMF (1 mL) was added NaH (55% in mineral oil, 13.2 mg, 302 μmol; CAS RN 7646-69-7) and the mixture was stirred at RT for 30 minutes. The resulting solution was added dropwise over 5 minutes to a stirred solution of (RS)-3-bromo-1-phenylpyrrolidin-2-one (72.4 mg, 302 μmol, CAS RN 77868-83-8) in DMF (1 mL) and the light brown solution was stirred at RT over 5.75 hours. The reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered, treated with silica gel and evaporated. The compound was purified twice by silica gel chromatography on a 4 g column using an MPLC system eluting with a gradient of n-heptane:EtOAc (100:0 to 50:50) to give the title compound as colorless solid (0.065 g; 43.9%). MS (ESI): m/z=391.21 [M−C$_4$H$_8$−CO$_2$+H]$^+$.

Example 61

N-(Oxetan-3-yl)-2-[4-oxo-1-phenyl-8-(1H-pyrazolo[3,4-b]pyridine-5-carbonyl)-1,3,8-triazaspiro[4.5]decan-3-yl]acetamide

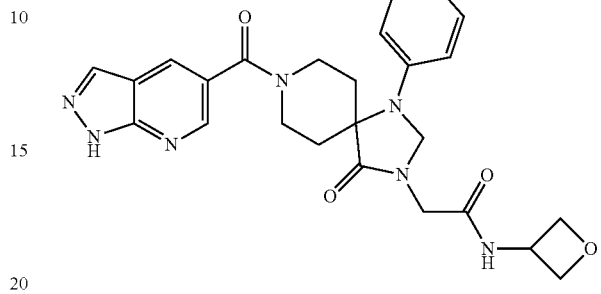

The title compound was obtained in analogy to example 47, from oxetan-3-amine (CAS RN 21635-88-1) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a). The product was purified by preparative HPLC (Gemini NX column) using a gradient of ACN:H$_2$O (containing 0.1% TEA) (20:80 to 98:2) to give the title compound as a colorless solid. MS (ESI): m/z=490.22 [M+H]$^+$.

Example 62

(RS)-3-(1-Methyl-2-oxopiperidin-3-yl)-1-phenyl-8-(1H-pyrazolo[3,4-b]pyridine-5-carbonyl)-1,3,8-triazaspiro[4.5]decan-4-one

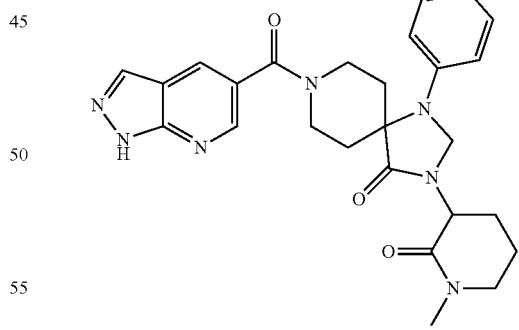

The title compound was obtained in analogy to example 36, from (RS)-tert-butyl 3-(1-methyl-2-oxopiperidin-3-yl)-4-oxo-1-phenyl-1,3,8-triazaspiro[4.5]decane-8-carboxylate and 1H-pyrazolo[3,4-b]pyridine-5-carboxylic acid (CAS RN 952182-02-4). The compound was purified by silica gel chromatography on a 4 g column using an MPLC (ISCO) system eluting with a gradient of DCM:MeOH (100:0 to 90:10) to give the title compound as a colorless solid. MS (ESI): m/z=488.24 [M+H]$^+$.

Intermediate (RS)-tert-Butyl 3-(1-methyl-2-oxopiperidin-3-yl)-4-oxo-1-phenyl-1,3,8-triazaspiro[4.5]decane-8-carboxylate

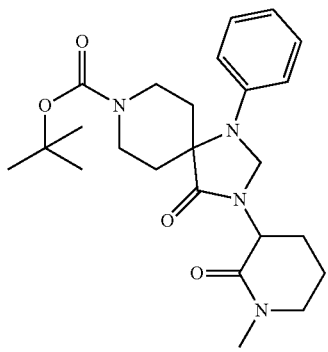 [SMILES: CN1CCCC(N2CN(c3ccccc3)C3(CCN(C(=O)OC(C)(C)C)CC3)C2=O)C1=O]

The title compound was obtained in analogy to example 60, intermediate a, from tert-butyl 4-oxo-1-phenyl-1,3,8-triazaspiro[4.5]decane-8-carboxylate (example 35, intermediate c) and 3-bromo-1-methylpiperidin-2-one (CAS RN 49785-85-5) as a colorless gum. MS (ESI): m/z=443.26 [M+H]$^+$.

Example 63

(rac,cis)-3-[2-(2-Benzyl-1,3,3a,4,6,6a-hexahydropyrrolo[3,4-c]pyrrol-5-yl)-2-oxoethyl]-1-phenyl-8-(1H-pyrazolo[3,4-b]pyridine-5-carbonyl)-1,3,8-triazaspiro[4.5]decan-4-one

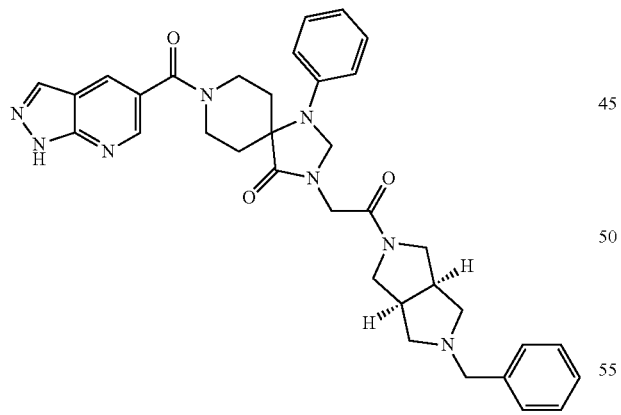

The title compound was obtained in analogy to example 36, from (rac,cis)-tert-butyl 3-(2-((5-benzylhexahydropyrrolo[3,4-c]pyrrol-2(1H)-yl)-2-oxoethyl)-4-oxo-1-phenyl-1,3,8-triazaspiro[4.5]decane-8-carboxylate and 1H-pyrazolo[3,4-b]pyridine-5-carboxylic acid (CAS RN 952182-02-4). The product was purified by preparative HPLC (Gemini NX column) using a gradient of ACN:H$_2$O (containing 0.1% TEA) (20:80 to 98:2) to give the title compound as a colorless solid. MS (ESI): m/z=619.31 [M+H]$^+$.

Intermediate a) (rac,cis)-tert-Butyl 3-(2-(5-benzylhexahydropyrrolo[3,4-c]pyrrol-2(1H)-yl)-2-oxoethyl)-4-oxo-1-phenyl-1,3,8-triazaspiro[4.5]decane-8-carboxylate The title compound was obtained in analogy to example 47, from 2-(8-(tert-butoxycarbonyl)-4-oxo-1-phenyl-1,3,8-triazaspiro[4.5]decan-3-yl)acetic acid (CAS RN 180386-35-0) and (rac,cis)-2-benzyloctahydropyrrolo[3,4-c]pyrrole (CAS RN 172739-04-7). The compound was purified by silica gel chromatography on a 4 g column using an MPLC system eluting with a gradient of DCM:MeOH (100:0 to 90:10) to give the title compound as light yellow foam. MS (ESI): m/z=574.34 [M+H]$^+$.

Example 64

3-[2-[(3S)-3-Fluoropyrrolidin-1-yl]-2-oxoethyl]-1-phenyl-8-(1H-pyrazolo[3,4-b]pyridine-5-carbonyl)-1,3,8-triazaspiro[4.5]decan-4-one

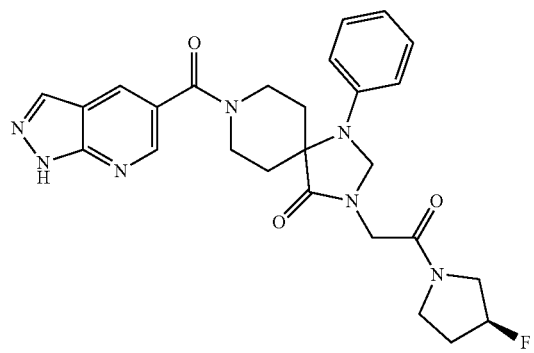 [SMILES: O=C(CN1CN(c2ccccc2)C2(CCN(C(=O)c3cnc4[nH]ncc4c3)CC2)C1=O)N1CC[C@H](F)C1]

The title compound was obtained in analogy to example 47, from (S)-3-fluoropyrrolidine hydrochloride (CAS RN 136725-54-7) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=506.23 [M+H]$^+$.

Example 65

3-[2-[(3R)-3-Fluoropyrrolidin-1-yl]-2-oxoethyl]-1-phenyl-8-(1H-pyrazolo[3,4-b]pyridine-5-carbonyl)-1,3,8-triazaspiro[4.5]decan-4-one

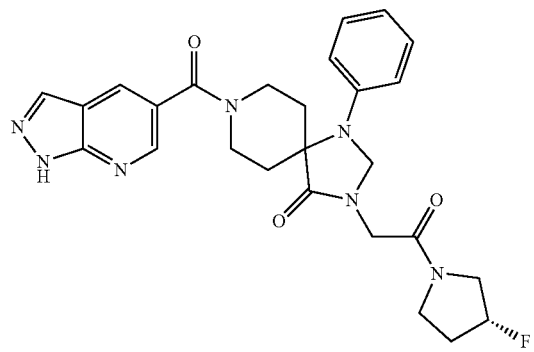 [SMILES: O=C(CN1CN(c2ccccc2)C2(CCN(C(=O)c3cnc4[nH]ncc4c3)CC2)C1=O)N1CC[C@@H](F)C1]

The title compound was obtained in analogy to example 47, from (R)-3-fluoropyrrolidine hydrochloride (CAS RN 679431-51-7) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=506.23 [M+H]⁻.

Example 66

(RS)-3-[2-(3-Methoxypyrrolidin-1-yl)-2-oxoethyl]-1-phenyl-8-(1H-pyrazolo[3,4-b]pyridine-5-carbonyl)-1,3,8-triazaspiro[4.5]decan-4-one

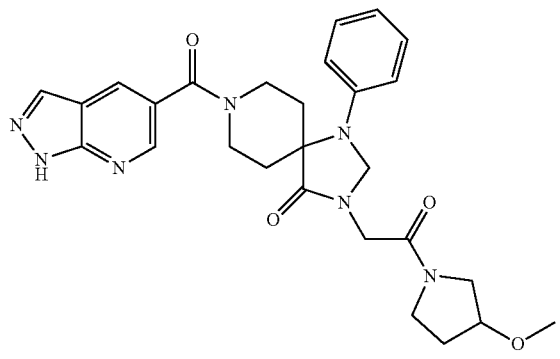 [SMILES: COC1CCN(C(=O)CN2CN(c3ccccc3)C3(CCN(C(=O)c4cnc5[nH]ncc5c4)CC3)C2=O)C1]

The title compound was obtained in analogy to example 47, from (RS)-3-methoxypyrrolidine hydrochloride (CAS RN 136725-50-3) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=518.25 [M+H]⁺.

Example 67

(RS)-3-[2-(3-Fluoro-3-methylpyrrolidin-1-yl)-2-oxoethyl]-1-phenyl-8-(1H-pyrazolo[3,4-b]pyridine-5-carbonyl)-1,3,8-triazaspiro[4.5]decan-4-one

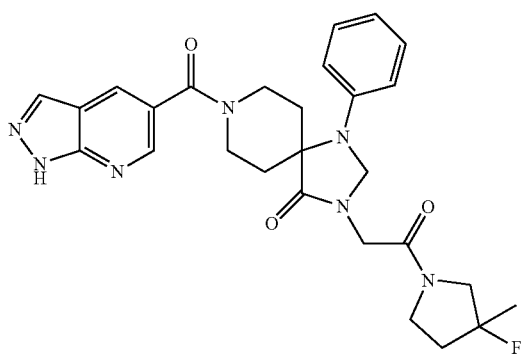 [SMILES: CC1(F)CCN(C(=O)CN2CN(c3ccccc3)C3(CCN(C(=O)c4cnc5[nH]ncc5c4)CC3)C2=O)C1]

The title compound was obtained in analogy to example 47, from (RS)-3-fluoro-3-methylpyrrolidine hydrochloride (Enamine Ltd.) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=520.25 [M+H]⁺.

Example 68

3-[2-(3,3-Difluoropyrrolidin-1-yl)-2-oxoethyl]-1-phenyl-8-(1H-pyrazolo[3,4-b]pyridine-5-carbonyl)-1,3,8-triazaspiro[4.5]decan-4-one

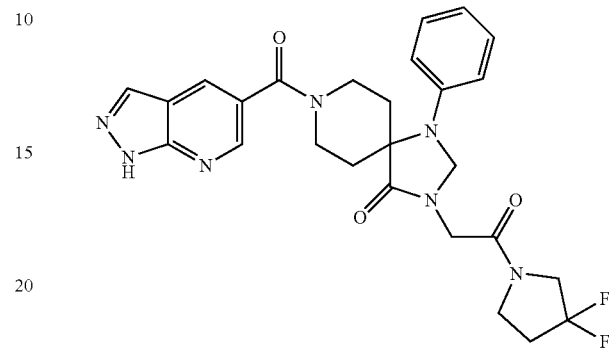

The title compound was obtained in analogy to example 47, from 3,3-difluoropyrrolidine hydrochloride (CAS RN 163457-23-6) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=524.22 [M+H]⁺.

Example 69

(RS)-3-[2-(2,2-Difluoro-5-azaspiro[2.4]heptan-5-yl)-2-oxoethyl]-1-phenyl-8-(1H-pyrazolo[3,4-b]pyridine-5-carbonyl)-1,3,8-triazaspiro[4.5]decan-4-one

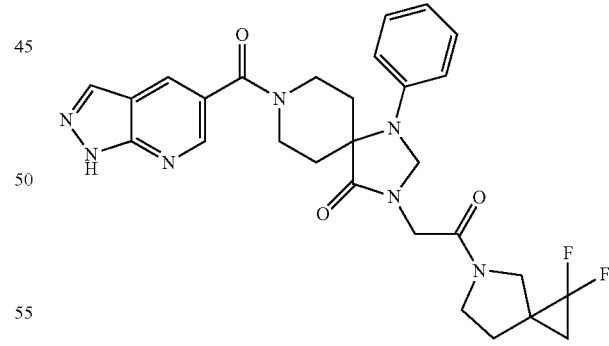

The title compound was obtained in analogy to example 47, from (RS)-1,1-difluoro-5-azaspiro[2.4]heptane hydrochloride (CAS RN 1215071-12-7) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=550.24 [M+H]⁺.

Example 70

(RS)-3-[2-(3-Hydroxy-3-methylpyrrolidin-1-yl)-2-oxoethyl]-1-phenyl-8-(1H-pyrazolo[3,4-b]pyridine-5-carbonyl)-1,3,8-triazaspiro[4.5]decan-4-one

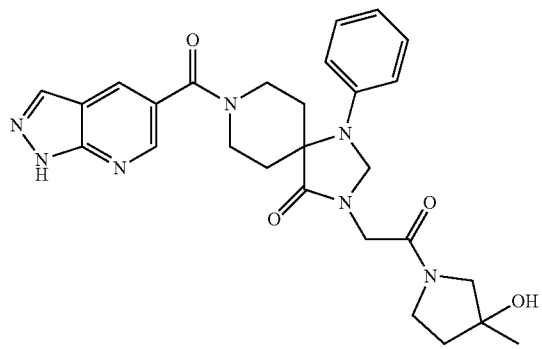 [SMILES: CC1(O)CCN(C(=O)CN2CN(c3ccccc3)C3(CCN(C(=O)c4cnc5[nH]ncc5c4)CC3)C2=O)C1]

The title compound was obtained in analogy to example 47, from (RS)-3-methylpyrrolidin-3-ol (CAS RN 125032-87-3) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=518.25 [M+H]+.

Example 71

(3-[2-(2-Oxa-5-azaspiro[3.4]octan-5-yl)-2-oxoethyl]-1-phenyl-8-(1H-pyrazolo[3,4-b]pyridine-5-carbonyl)-1,3,8-triazaspiro[4.5]decan-4-one

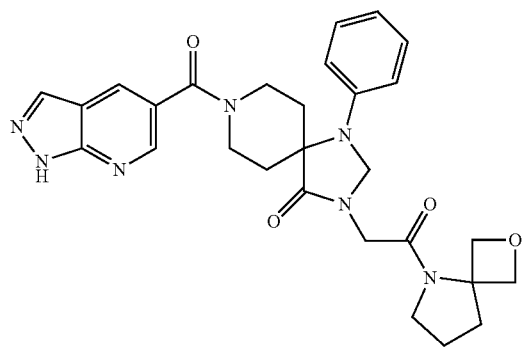 [SMILES: O=C(c1cnc2[nH]ncc2c1)N1CCC2(CC1)C(=O)N(CC(=O)N1CCCC13COC3)CN2c1ccccc1]

The title compound was obtained in analogy to example 47, from 2-oxa-5-azaspiro[3.4]octane (CAS RN 1215071-12-7) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=530.25 [M+H]+.

Example 72

3-[2-[(3R)-3-Hydroxypyrrolidin-1-yl]-2-oxoethyl]-1-phenyl-8-(1H-pyrazolo[3,4-b]pyridine-5-carbonyl)-1,3,8-triazaspiro[4.5]decan-4-one

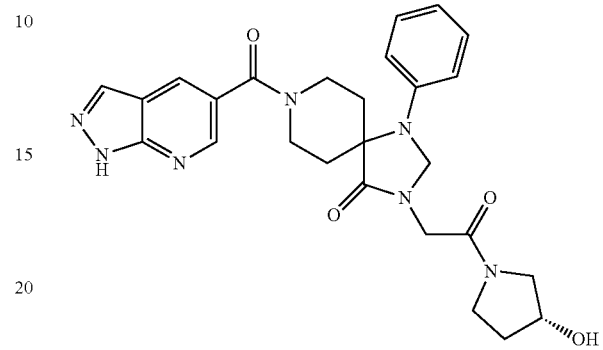

The title compound was obtained in analogy to example 47, from (R)-pyrrolidin-3-ol (CAS RN 2799-21-5) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=504.24 [M+H]+.

Example 73

3-[2-[(3S)-3-Hydroxypyrrolidin-1-yl]-2-oxoethyl]-1-phenyl-8-(1H-pyrazolo[3,4-b]pyridine-5-carbonyl)-1,3,8-triazaspiro[4.5]decan-4-one The title compound was obtained in analogy to example 47, from (S)-pyrrolidin-3-ol (CAS RN 100243-39-8) and 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) as a colorless solid. MS (ESI): m/z=504.24 [M+H]+.

Example 74

3-[2-[(3S)-3-(Dimethylamino)pyrrolidin-1-yl]-2-oxoethyl]-1-phenyl-8-(1H-pyrazolo[3,4-b]pyridine-5-carbonyl)-1,3,8-triazaspiro[4.5]decan-4-one

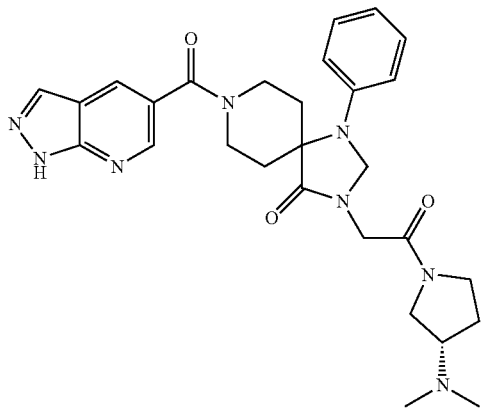 [SMILES: CN(C)[C@H]1CCN(C(=O)CN2CN(c3ccccc3)C3(CCN(C(=O)c4cnc5[nH]ncc5c4)CC3)C2=O)C1]

The title compound was obtained in analogy to example 47, from (S)—N,N-dimethylpyrrolidin-3-amine (CAS RN 132883-44-4) and 2-(4-oxo-1-phenyl-8-(1H-pyrazolo[3,4-b]pyridine-5-carbonyl)-1,3,8-triazaspiro[4.5]decan-3-yl) acetic acid (example 22, intermediate a). The product was purified by preparative HPLC (Gemini NX column) using a gradient of ACN:H$_2$O (containing 0.1% TEA) (20:80 to 98:2) to give the title compound as a colorless solid. MS (ESI): m/z=531.28 [M+H]$^+$.

Example 75

2-[4-Oxo-1-phenyl-8-(1H-pyrazolo[3,4-b]pyridine-5-carbonyl)-1,3,8-triazaspiro[4.5]decan-3-yl]-N-propan-2-yl-N-(2,2,2-trifluoroethyl)acetamide

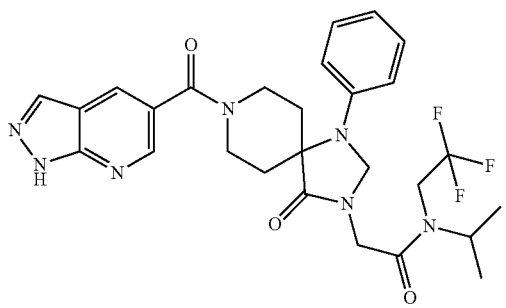 [SMILES: CC(C)N(CC(F)(F)F)C(=O)CN1CN(c2ccccc2)C2(CCN(C(=O)c3cnc4[nH]ncc4c3)CC2)C1=O]

To a solution of 2-(8-benzyl-4-oxo-1-phenyl-1,3,8-triazaspiro[4.5]decan-3-yl)-N-propan-2-yl-N-(2,2,2-trifluoroethyl)acetamide (32 mg, 63.7 µmol) in MeOH (1 mL) and EtOAc (0.5 mL) was added palladium 10% on carbon (6.78 mg, 63.7 µmol) and the suspension was hydrogenated at 1.7 bar over 4.5 hours. The mixture was filtered over a microfilter and the filtrate evaporated. The residue was taken up in DMF (1 mL), treated with 1H-pyrazolo[3,4-b]pyridine-5-carboxylic acid (10.4 mg, 63.7 µmol, CAS RN 952182-02-4), HBTU (24.1 mg, 63.7 µmol) and TEA (26.6 µL, 191 µmol) and the mixture was stirred overnight at RT. The product was purified by preparative HPLC (Gemini NX column) using a gradient of ACN:H$_2$O (containing 0.1% formic acid) (20:80 to 98:2) to give the title compound as a colorless solid (0.013 g; 36.6%). MS (ESI): m/z=558.24 [M+H]$^+$.

Intermediate a) 2-(8-Benzyl-4-oxo-1-phenyl-1,3,8-triazaspiro[4.5]decan-3-yl)-N-propan-2-yl-N-(2,2,2-trifluoroethyl)acetamide To a suspension of 2-(8-benzyl-4-oxo-1-phenyl-1,3,8-triazaspiro[4.5]decan-3-yl)acetic acid (100 mg, 264 µmol) and DMF (2.04 µL, 26.3 µmol) in DCM (1 mL) was added oxalyl chloride (34.6 µL, 395 µmol) and the light yellow turbid solution was stirred at RT over 1.5 hours. After complete evaporation, the residue was dissolved in DCM (1 mL) and added dropwise to a stirred suspension of N-(2,2,2-trifluoroethyl)propan-2-amine hydrochloride (93.6 mg, 527 µmol; Enamine Ltd.) and TEA (147 µL, 1.05 mmol) in DCM (1 mL) and the yellow suspension was stirred at RT over 2.5 hours. The reaction mixture was poured on H$_2$O and DCM and the layers were separated. The aqueous layer was extracted twice with DCM. The organic layers were dried over MgSO$_4$, filtered, treated with silica gel and evaporated. The compound was purified by silica gel chromatography on a 4 g column using an MPLC system eluting with a gradient of n-heptane:EtOAc (100:0 to 0:100). The product was purified by preparative HPLC (Gemini NX column) using a gradient of ACN:H$_2$O (containing 0.1% TEA) (20:80 to 98:2) to give the title compound as a colorless solid (0.037 g; 27.9%). MS (ESI): m/z=503.26 [M+H]$^+$.

Intermediate b) 2-(8-Benzyl-4-oxo-1-phenyl-1,3,8-triazaspiro[4.5]decan-3-yl)acetic acid The title compound was obtained in analogy to example 41, intermediate a, from ethyl 2-(8-benzyl-4-oxo-1-phenyl-1,3,8-triazaspiro[4.5]decan-3-yl)acetate as a colorless solid. MS (ESI): m/z=380.20 [M+H]$^+$.

Intermediate c) Ethyl 2-(8-benzyl-4-oxo-1-phenyl-1,3,8-triazaspiro[4.5]decan-3-yl)acetate To an ice-cold suspension of 8-benzyl-1-phenyl-1,3,8-triazaspiro[4.5]decan-4-one (1 g, 3.11 mmol, CAS RN 974-41-4) in dioxane (20 mL) was added NaH (55% in mineral oil, 136 mg, 3.11 mmol) and the mixture was stirred at 0° C. over 30 minutes. The ice-bath was removed and ethyl 2-iodoacetate (405 µL, 3.42 mmol) was added dropwise. The light yellow suspension was stirred overnight. The mixture was poured on H$_2$O and EtOAc and the layers were separated. The aqueous layer was extracted once with EtOAc. The organic layers were combined, dried over MgSO$_4$, filtered, treated with silica gel and evaporated. The compound was purified by silica gel chromatography on a 24 g column using an MPLC (ISCO) system eluting with a gradient of n-heptane:EtOAc (100:0 to 0:0) to give the title compound as a colorless gum (0.747 g; 58.9%). MS (ESI): m/z=408.23 [M+H]$^+$.

Example 76

N,N-Dimethyl-2-[4-oxo-1-phenyl-8-(1H-pyrazolo[3,4-b]pyridine-5-carbonyl)-1,3,8-triazaspiro[4.5]decan-3-yl]acetamide

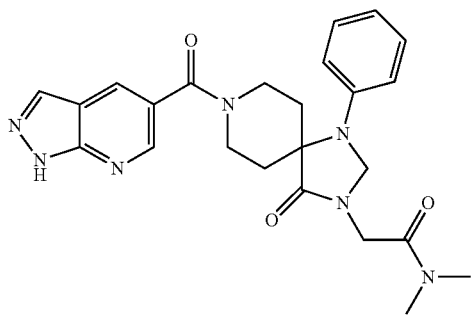 [SMILES: CN(C)C(=O)CN1CN(c2ccccc2)C2(CCN(C(=O)c3cnc4[nH]ncc4c3)CC2)C1=O]

The title compound was obtained in analogy to example 36, from tert-butyl 3-[2-(dimethylamino)-2-oxoethyl]-4-oxo-1-phenyl-1,3,8-triazaspiro[4.5]decane-8-carboxylate and 1H-pyrazolo[3,4-b]pyridine-5-carboxylic acid (CAS RN 952182-02-4) as a colorless solid. MS (ESI): m/z=462.23 [M+H]$^+$.

Intermediate a) tert-Butyl 3-[2-(dimethylamino)-2-oxoethyl]-4-oxo-1-phenyl-1,3,8-triazaspiro[4.5]decane-8-carboxylate The title compound was obtained in analogy to example 35, intermediate b, from tert-butyl 4-oxo-1-phenyl-1,3,8-triazaspiro[4.5]decane-8-carboxylate (example 35, intermediate c) and 2-chloro-N,N-dimethylacetamide (CAS RN 2675-89-0). The product was purified by preparative HPLC (Gemini NX column) using a gradient of ACN:H$_2$O (containing 0.1% formic acid) (20:80 to 98:2) to give the title compound as a colorless solid. MS (ESI): m/z=417.25 [M+H]$^+$.

Example 77

(RS)-3-[2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one

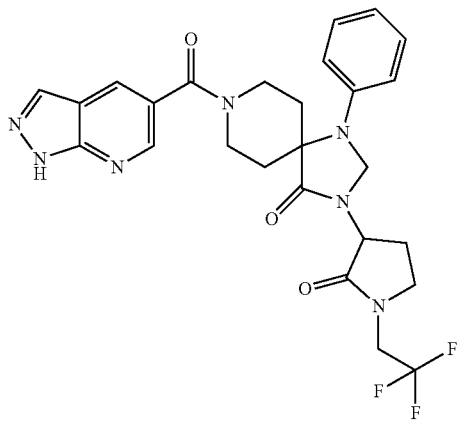 [SMILES: O=C(c1cnc2[nH]ncc2c1)N1CCC2(CC1)C(=O)N(C1CCN(CC(F)(F)F)C1=O)CN2c1ccccc1]

The title compound was obtained in analogy to example 36, from (RS)-tert-butyl 4-oxo-3-[2-oxo-1-(2,2,2-trifluoroethyl)pyrrolidin-3-yl]-1-phenyl-1,3,8-triazaspiro[4.5]decane-8-carboxylate and 1H-pyrazolo[3,4-b]pyridine-5-carboxylic acid (CAS RN 952182-02-4) as a colorless solid. MS (ESI): m/z=542.21 [M+H]$^+$.

Intermediate a) (RS)-tert-Butyl 4-oxo-3-[2-oxo-1-(2,2,2-trifluoroethyl)pyrrolidin-3-yl]-1-phenyl-1,3,8-triazaspiro[4.5]decane-8-carboxylate The title compound was obtained in analogy to example 60, intermediate a, from tert-butyl 4-oxo-1-phenyl-1,3,8-triazaspiro[4.5]decane-8-carboxylate (example 35, intermediate c) and (RS)-3-bromo-1-(2,2,2-trifluoroethyl)pyrrolidin-2-one (CAS RN 178946-24-2). The product was purified by preparative HPLC (Gemini NX column) using a gradient of ACN:H$_2$O (containing 0.1% formic acid) (20:80 to 98:2) to give the title compound as a colorless solid. MS (ESI): m/z=497.24 [M+H]$^+$.

Example 78

(RS)-3-(1-Cyclopropyl-2-oxopyrrolidin-3-yl)-1-phenyl-8-(1H-pyrazolo[3,4-b]pyridine-5-carbonyl)-1,3,8-triazaspiro[4.5]decan-4-one

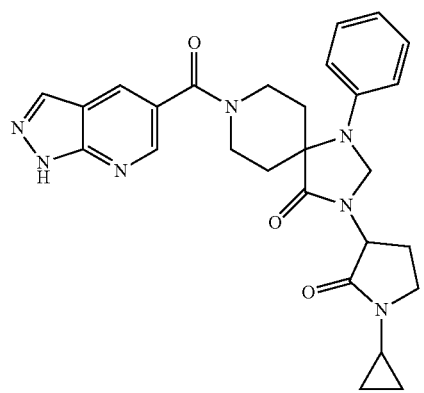 [SMILES: O=C(c1cnc2[nH]ncc2c1)N1CCC2(CC1)C(=O)N(C1CCN(C3CC3)C1=O)CN2c1ccccc1]

The title compound was obtained in analogy to example 36, from (RS)-tert-butyl 3-(1-cyclopropyl-2-oxopyrrolidin-3-yl)-4-oxo-1-phenyl-1,3,8-triazaspiro[4.5]decane-8-carboxylate and 1H-pyrazolo[3,4-b]pyridine-5-carboxylic acid (CAS RN 952182-02-4). The product was purified by preparative HPLC (Gemini NX column) using a gradient of ACN:H$_2$O (containing 0.1% TEA) (20:80 to 98:2) to give the title compound as a colorless solid. MS (ESI): m/z=500.24 [M+H]$^+$.

Intermediate a) (RS)-tert-Butyl 3-(1-cyclopropyl-2-oxopyrrolidin-3-yl)-4-oxo-1-phenyl-1,3,8-triazaspiro[4.5]decane-8-carboxylate The title compound was obtained in analogy to example 60, intermediate a, from tert-butyl 4-oxo-1-phenyl-1,3,8-triazaspiro[4.5]decane-8-carboxylate (example 35, intermediate c) and (RS)-3-bromo-1-cyclopropylpyrrolidin-2-one (CAS RN 148776-25-4). The compound was purified by silica gel chromatography on a 4 g column using an MPLC system eluting with a gradient of n-heptane:EtOAc (100:0 to 0:100) to give a title compound as a colorless solid. MS (ESI): m/z=355.21 [M–C$_4$H$_8$–CO$_2$+H]$^+$.

Example 79

8-(1H-Indazole-5-carbonyl)-1,3-diphenyl-1,3,8-tri-aza-spiro[4.5]decan-4-one

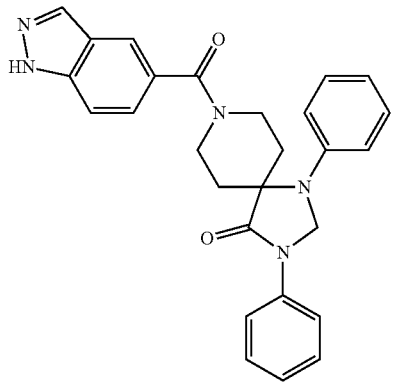 [SMILES: O=C(c1ccc2[nH]ncc2c1)N1CCC2(CC1)C(=O)N(c1ccccc1)CN2c1ccccc1]

To a solution of 1,3-diphenyl-1,3,8-triaza-spiro[4.5]decan-4-one (100 mg, 0.32 mmol) and 1H-indazole-5-carboxylic acid (53 mg, 0.32 mmol, CAS RN 915139-44-5) in anhydrous DMF (10 mL) were added HBTU (247 mg, 0.65 mmol, CAS RN 94790-37-1) and DIPEA (0.161 mL, 0.98 mmol, CAS RN 7087-68-5) under nitrogen atmosphere at RT. The mixture was stirred at RT for 16 h. Then solvent was removed under vacuum. The residue was diluted with EtOAc (30 mL), washed with H$_2$O (40 mL) and brine (30 mL). The organic part was dried over Na$_2$SO$_4$, filtered and concentrated. The resulting residue was purified by preparative HPLC (NH$_4$OAc/ACN) to give the title compound as white solid (45 mg, 31%). MS (ESI): m/z=452.2 [M+H]$^+$.

Intermediate a) 1,3-Diphenyl-1,3,8-triaza-spiro[4.5]decan-4-one

A solution of 8-benzyl-1,3-diphenyl-1,3,8-triaza-spiro[4.5]decan-4-one (238 mg, 0.599 mmol) in MeOH (30 mL) was purged with argon for 15 minutes. Then palladium on carbon 10% (50 mg; CAS RN 7440-05-3) was added and the reaction mixture was purged with argon for another 5 minutes. The mixture was degassed twice under vacuum and replacing each time the vacuum by hydrogen. Then the reaction mixture was stirred under hydrogen atmosphere for 3 h at RT. The reaction mixture was filtered through celite bed and washed with MeOH (20 mL). The filtrate was concentrated under reduced pressure to give the title compound (182 mg, 99%) as a white solid. MS (ESI): m/z=308.0 [M+H]$^+$.

Intermediate b) 8-Benzyl-1,3-diphenyl-1,3,8-triaza-spiro[4.5]decan-4-one

To a solution of 8-benzyl-1-phenyl-1,3,8-triaza-spiro[4.5]decan-4-one (100 mg, 0.31 mmol, CAS RN 974-41-4) in anhydrous dioxane (7 mL) were added iodo-benzene (0.083 mL, 0.747 mmol, CAS RN 591-50-4) and K$_2$CO$_3$ (129 mg, 0.93 mmol, CAS RN 584-08-7) and the flask was purged with argon for 20 minutes. DMEDA (0.003 mL, 0.025 mmol, CAS RN 110-70-3) and CuI (2 mg, 0.01 mmol, CAS RN 7681-65-4) were added and again degassed for another 10 minutes. The reaction mixture was stirred at 100° C. for 16 h. It was then cooled to RT, filtered through a celite pad and the filtrate was concentrated to get a residue which was dissolved in EtOAc (30 mL) and washed with H$_2$O (30 mL) and brine (20 mL). The organic layer was dried over Na$_2$SO$_4$, filtered and concentrated. The residue was purified by flash chromatography on silica gel (10% to 20% EtOAc in n-hexane) to get the title compound (120 mg, 97%) as colorless sticky solid. MS (ESI): m/z=397.8 [M+H]$^+$.

Example 80

3-(2-Fluoro-5-trifluoromethyl-phenyl)-8-(1H-indazole-5-carbonyl)-1-phenyl-1,3,8-triaza-spiro[4.5]decan-4-one

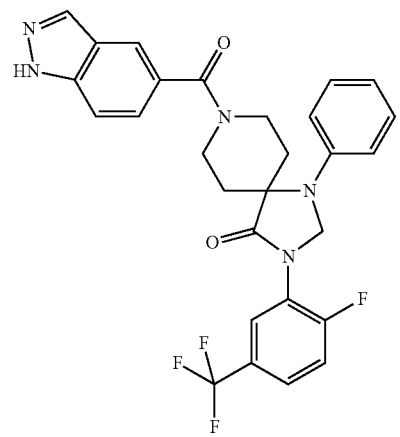 [SMILES: O=C(c1ccc2[nH]ncc2c1)N1CCC2(CC1)C(=O)N(c1cc(C(F)(F)F)ccc1F)CN2c1ccccc1]

The title compound was obtained in analogy to example 79, from 3-(2-fluoro-5-trifluoromethyl-phenyl)-1-phenyl-1,3,8-triaza-spiro[4.5]decan-4-one and 1H-indazole-5-carboxylic acid (CAS RN 915139-44-5) as a white solid. MS (EI): m/z=538.0 [M+H]$^+$.

Intermediate a) 3-(2-Fluoro-5-trifluoromethyl-phenyl)-1-phenyl-1,3,8-triaza-spiro[4.5]decan-4-one The title compound was prepared in analogy to example 79, intermediate a, from 8-benzyl-3-(2-fluoro-5-trifluoromethyl-phenyl)-1-phenyl-1,3,8-triaza-spiro[4.5]decan-4-one as a colorless sticky solid. MS (EI): m/z=394.0 [M+H]$^+$.

Intermediate b) 8-Benzyl-3-(2-fluoro-5-trifluoromethyl-phenyl)-1-phenyl-1,3,8-triaza-spiro[4.5]decan-4-one The title compound was prepared in analogy to example 79, intermediate b, from 8-benzyl-1-phenyl-1,3,8-triaza-spiro[4.5]decan-4-one (CAS RN 974-41-4) and 1-fluoro-2-iodo-4-trifluoromethyl-benzene (CAS RN 110192-48-8) as a colorless sticky solid. MS (EI): m/z=483.8 [M+H]$^+$.

Example 81

3-(2-Chloro-5-trifluoromethyl-phenyl)-8-(1H-indazole-5-carbonyl)-1-phenyl-1,3,8-triaza-spiro[4.5]decan-4-one

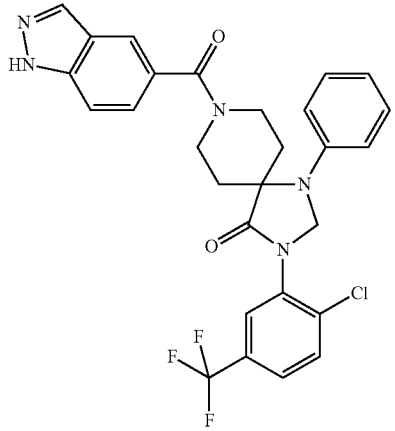 [SMILES: O=C(c1ccc2[nH]ncc2c1)N1CCC2(CC1)C(=O)N(c1cc(C(F)(F)F)ccc1Cl)CN2c1ccccc1]

The title compound was obtained in analogy to example 79, from 3-(2-chloro-5-trifluoromethyl-phenyl)-1-phenyl-1,3,8-triaza-spiro[4.5]decan-4-one and 1H-indazole-5-carboxylic acid (CAS RN 915139-44-5) as a white solid. MS (EI): m/z=554.1 [M+H]⁺.

Intermediate a) 3-(2-Chloro-5-trifluoromethyl-phenyl)-1-phenyl-1,3,8-triaza-spiro[4.5]decan-4-one To a solution of 8-benzyl-3-(2-chloro-5-trifluoromethyl-phenyl)-1-phenyl-1,3,8-triaza-spiro[4.5]decan-4-one (125 mg, 0.25 mmol) in DCE (10 mL) were added 1-chloroethyl chloroformate (0.03 mL, 0.275 mmol, CAS RN 50893-53-3) and DIPEA (0.04 mL, 0.25 mmol, CAS RN 7087-68-5) at 0° C. The reaction mixture was heated at 85° C. for 16 h. The solvent was evaporated, MeOH (10 mL) was added and the reaction mixture was heated at 65° C. for 3 h. The solvent was stripped off to afford the title compound (100 mg, 98%) as a brown liquid. MS (EI): m/z=409.8 [M+H]⁺.

Intermediate b) 8-Benzyl-3-(2-chloro-5-trifluoromethyl-phenyl)-1-phenyl-1,3,8-triaza-spiro[4.5]decan-4-one The title compound was prepared in analogy to example 79, intermediate b, from 8-benzyl-1-phenyl-1,3,8-triaza-spiro[4.5]decan-4-one (CAS RN 974-41-4) and 1-chloro-2-iodo-4-trifluoromethyl-benzene (CAS RN 672-57-1) as a colorless sticky solid. MS (EI): m/z=499.9 [M+H]⁺.

Example 82

3-(2-Fluoro-phenyl)-8-(1H-indazole-5-carbonyl)-1-phenyl-1,3,8-triaza-spiro[4.5]decan-4-one

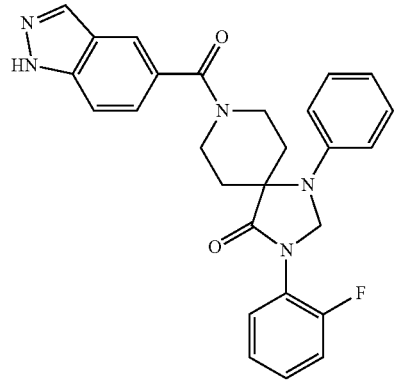 [SMILES: O=C(c1ccc2[nH]ncc2c1)N1CCC2(CC1)C(=O)N(c1ccccc1F)CN2c1ccccc1]

The title compound was obtained in analogy to example 79, from 3-(2-fluoro-phenyl)-1-phenyl-1,3,8-triaza-spiro[4.5]decan-4-one and 1H-indazole-5-carboxylic acid (CAS RN 915139-44-5) as a white solid. MS (EI): m/z=470.1 [M+H]⁺.

Intermediate a) 3-(2-Fluoro-phenyl)-1-phenyl-1,3,8-triaza-spiro[4.5]decan-4-one

The title compound was prepared in analogy to example 79, intermediate a, from 8-benzyl-3-(2-fluoro-phenyl)-1-phenyl-1,3,8-triaza-spiro[4.5]decan-4-one as a colorless sticky solid. MS (EI): m/z=326.1 [M+H]⁺.

Intermediate b) 8-Benzyl-3-(2-fluoro-phenyl)-1-phenyl-1,3,8-triaza-spiro[4.5]decan-4-one The title compound was prepared in analogy to example 79, intermediate b, from 8-benzyl-1-phenyl-1,3,8-triaza-spiro[4.5]decan-4-one (CAS RN 974-41-4) and 1-fluoro-2-iodo-benzene (CAS RN 348-52-7) as a colorless sticky solid. MS (EI): m/z=415.9 [M+H]⁺.

Example 83

1-Phenyl-8-(1H-pyrazolo pyridine-5-carbonyl)-3-(3-trifluoromethyl-phenyl)-1,3,8-triaza-spiro[4.5]decan-4-one

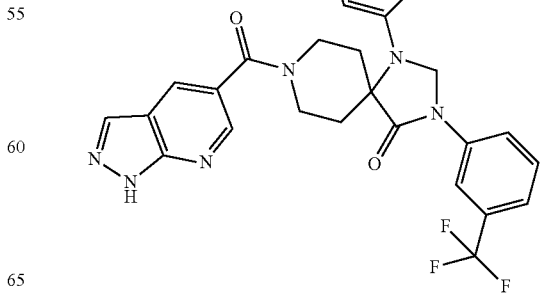

To a solution of 1-phenyl-3-(3-trifluoromethyl-phenyl)-1,3,8-triaza-spiro[4.5]decan-4-one (135 mg, 0.36 mmol) and 1H-pyrazolo[3,4-b]pyridine-5-carboxylic acid (59 mg, 0.36 mmol, CAS RN 952182-02-4) in anhydrous DCM (10 mL) were added PyBOP (281 mg, 0.539 mmol, CAS RN 128625-52-5) and DIPEA (0.18 mL, 0.72 mmol, CAS RN 7087-68-5) under nitrogen atmosphere at RT. The mixture was stirred at RT for 16 h. The reaction mixture was diluted with DCM (20 mL), washed with H$_2$O (30 mL) and brine (20 mL). The organic part was dried over Na$_2$SO$_4$, filtered and concentrated under reduced pressure. The residue was purified by preparative HPLC (NH$_4$OAc/ACN) to get the title compound (53 mg, 28%) as a white solid. MS (EI): m/z=519.3 [M–H]$^-$.

Intermediate a) 1-Phenyl-3-(3-trifluoromethyl-phenyl)-1,3,8-triaza-spiro[4.5]decan-4-one To a solution of 4-oxo-1-phenyl-3-(3-trifluoromethyl-phenyl)-1,3,8-triaza-spiro[4.5]decane-8-carboxylic acid tert-butyl ester ester (174 mg, 0.37 mmol) in DCM (10 mL) was added 4M HCl in dioxane (3 mL, CAS RN 7647-01-0) and the reaction mixture was stirred at 25° C. for 3 h. The solvent was evaporated under reduced pressure to deliver the desired product (136 mg, 99%) as a white solid. MS (EI): m/z=376.3 [M+H]$^+$.

Intermediate b) 4-Oxo-1-phenyl-3-(3-trifluoromethyl-phenyl)-1,3,8-triaza-spiro[4.5]decane-8-carboxylic acid tert-butyl ester ester The title compound was prepared in analogy to example 79, intermediate b, from 4-oxo-1-phenyl-1,3,8-triaza-spiro[4.5]decane-8-carboxylic acid tert-butyl ester (example 35, intermediate c) and 1-iodo-3-trifluoromethyl-benzene (CAS RN 401-81-0) as a colorless sticky solid. MS (EI): m/z=476.3 [M+H]$^+$.

Example 84

3-(2-Fluoro-4-trifluoromethyl-phenyl)-1-phenyl-8-(1H-pyrazolo pyridine-5-carbonyl)-1,3,8-triaza-spiro[4.5]decan-4-one

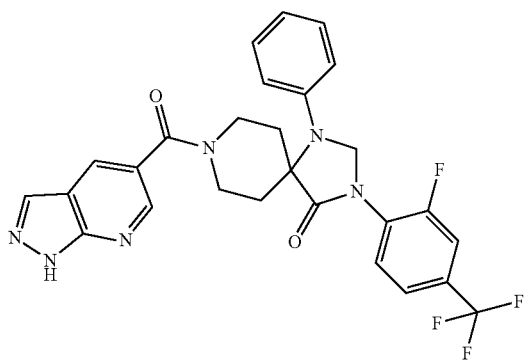 [SMILES: O=C(c1cnc2[nH]ncc2c1)N1CCC2(CC1)C(=O)N(c1ccc(C(F)(F)F)cc1F)CN2c1ccccc1]

The title compound was obtained in analogy to example 83, from 3-(2-fluoro-4-trifluoromethyl-phenyl)-1-phenyl-1,3,8-triaza-spiro[4.5]decan-4-one and 1H-pyrazolo[3,4-b]pyridine-5-carboxylic acid (CAS RN 952182-02-4) as a white solid. MS (EI): m/z=537.0 [M–H]$^-$.

Intermediate a) 3-(2-Fluoro-4-trifluoromethyl-phenyl)-1-phenyl-1,3,8-triaza-spiro[4.5]decan-4-one The title compound was prepared in analogy to example 83, intermediate c, from 3-(2-fluoro-4-trifluoromethyl-phenyl)-4-oxo-1-phenyl-1,3,8-triaza-spiro[4.5]decane-8-carboxylic acid tert-butyl ester as a white solid. MS (EI): m/z=394.2 [M+H]$^+$.

Intermediate b) 3-(2-Fluoro-4-trifluoromethyl-phenyl)-4-oxo-1-phenyl-1,3,8-triaza-spiro[4.5]decane-8-carboxylic acid tert-butyl ester The title compound was prepared in analogy to example 79, intermediate b, from 4-oxo-1-phenyl-1,3,8-triaza-spiro[4.5]decane-8-carboxylic acid tert-butyl ester (example 35, intermediate c) and 1-bromo-2-fluoro-4-trifluoromethyl-benzene (CAS RN 40161-54-4) as an off-white solid. MS (EI): m/z=494.1 [M+H]$^+$.

Example 85

3-(2-Fluoro-4-methyl-phenyl)-1-phenyl-8-(1H-pyrazolo[3,4-b]pyridine-5-carbonyl)-1,3,8-triaza-spiro[4.5]decan-4-one

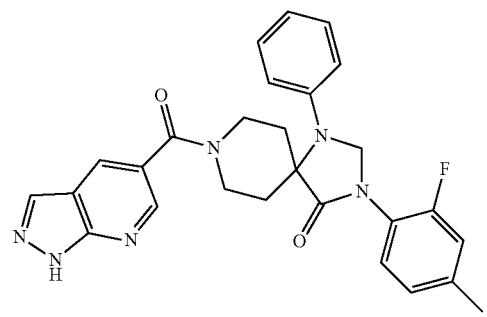 [SMILES: Cc1ccc(N2CN(c3ccccc3)C3(CCN(C(=O)c4cnc5[nH]ncc5c4)CC3)C2=O)c(F)c1]

The title compound was obtained in analogy to example 83, from 3-(2-fluoro-4-methyl-phenyl)-1-phenyl-1,3,8-triaza-spiro[4.5]decan-4-one and 1H-pyrazolo[3,4-b]pyridine-5-carboxylic acid (CAS RN 952182-02-4) as a white solid. MS (EI): m/z=485.3 [M+H]$^+$.

Intermediate a) 3-(2-Fluoro-4-methyl-phenyl)-1-phenyl-1,3,8-triaza-spiro[4.5]decan-4-one The title compound was prepared in analogy to example 83, intermediate a from 3-(2-fluoro-4-methyl-phenyl)-4-oxo-1-phenyl-1,3,8-triaza-spiro[4.5]decane-8-carboxylic acid tert-butyl ester as a white solid. MS (EI): m/z=340.0 [M+H]$^+$.

Intermediate b) 3-(2-Fluoro-4-methyl-phenyl)-4-oxo-1-phenyl-1,3,8-triaza-spiro[4.5]decane-8-carboxylic acid tert-butyl ester The title compound was prepared in analogy to example 79 intermediate b, from 4-oxo-1-phenyl-1,3,8-triaza-spiro[4.5]decane-8-carboxylic acid tert-butyl ester (example 35, intermediate c) and 2-fluoro-1-iodo-4-methyl-benzene (CAS RN 452-79-9) as an off-white solid. MS (EI): m/z=440.1 [M+H]$^+$.

Example 86

4-[4-Oxo-1-phenyl-8-(1H-pyrazolo[3,4-b]pyridine-5-carbonyl)-1,3,8-triaza-spiro[4.5]dec-3-yl]-benzonitrile

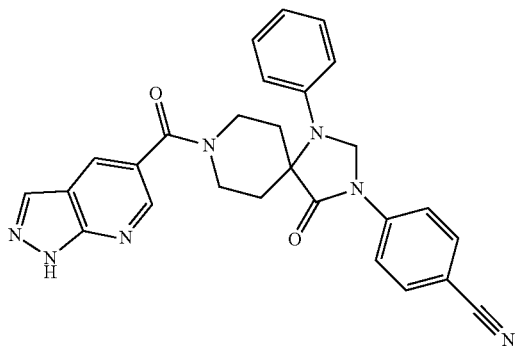 [SMILES: N#Cc1ccc(N2CN(c3ccccc3)C3(CCN(C(=O)c4cnc5[nH]ncc5c4)CC3)C2=O)cc1]

The title compound was obtained in analogy to example 83, from 4-(4-oxo-1-phenyl-1,3,8-triaza-spiro[4.5]dec-3-yl)-benzonitrile and 1H-pyrazolo[3,4-b]pyridine-5-carboxylic acid (CAS RN 952182-02-4) as a white solid. MS (EI): m/z=476.4 [M−H]⁻.

Intermediate a) 4-(4-Oxo-1-phenyl-1,3,8-triaza-spiro[4.5]dec-3-yl)-benzonitrile

The title compound was prepared in analogy to example 83, intermediate a, from 3-(4-cyano-phenyl)-4-oxo-1-phenyl-1,3,8-triaza-spiro[4.5]decane-8-carboxylic acid tert-butyl ester as a white solid. MS (EI): m/z=333.3 [M+H]⁺.

Intermediate b) 3-(4-Cyano-phenyl)-4-oxo-1-phenyl-1,3,8-triaza-spiro[4.5]decane-8-carboxylic acid tert-butyl ester The title compound was prepared in analogy to example 79, intermediate b, from 4-oxo-1-phenyl-1,3,8-triaza-spiro[4.5]decane-8-carboxylic acid tert-butyl ester (example 35, intermediate c) and 4-iodo-benzonitrile (CAS RN 3058-39-7) as an off-white solid. MS (EI): m/z=433.3 [M+H]⁺.

Example 87

3-(3-Chloro-phenyl)-1-phenyl-8-(1H-pyrazolo[3,4-b]pyridine-5-carbonyl)-1,3,8-triaza-spiro[4.5]decan-4-one

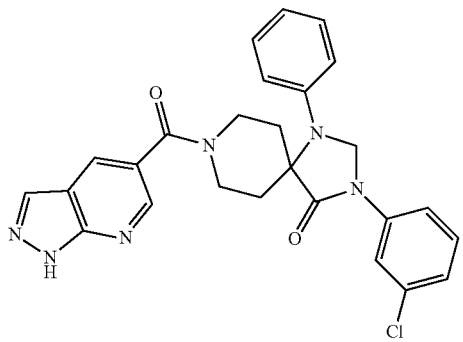 [SMILES: O=C(c1cnc2[nH]ncc2c1)N1CCC2(CC1)C(=O)N(c1cccc(Cl)c1)CN2c1ccccc1]

The title compound was obtained in analogy to example 83, from 3-(3-chloro-phenyl)-1-phenyl-1,3,8-triaza-spiro[4.5]decan-4-one and 1H-pyrazolo[3,4-b]pyridine-5-carboxylic acid (CAS RN 952182-02-4) as a white solid. MS (EI): m/z=487.2 [M+H]⁺.

Intermediate a) 3-(3-Chloro-phenyl)-1-phenyl-1,3,8-triaza-spiro[4.5]decan-4-one

The title compound was prepared in analogy to example 83, intermediate a, from 3-(3-chloro-phenyl)-4-oxo-1-phenyl-1,3,8-triaza-spiro[4.5]decane-8-carboxylic acid tert-butyl ester as a white solid. MS (EI): m/z=342.4 [M+H]⁺.

Intermediate b) 3-(3-Chloro-phenyl)-4-oxo-1-phenyl-1,3,8-triaza-spiro[4.5]decane-8-carboxylic acid tert-butyl ester The title compound was prepared in analogy to example 79, intermediate b, from 4-oxo-1-phenyl-1,3,8-triaza-spiro[4.5]decane-8-carboxylic acid tert-butyl ester (example 35, intermediate c) and 1-chloro-3-iodo-benzene (CAS RN 625-99-0) as a white solid. MS (EI): m/z=442.2 [M+H]⁺.

Example 88

3-(4-Chloro-2-fluoro-phenyl)-1-phenyl-8-(1H-pyrazolo[3,4-b]pyridine-5-carbonyl)-1,3,8-triaza-spiro[4.5]decan-4-one

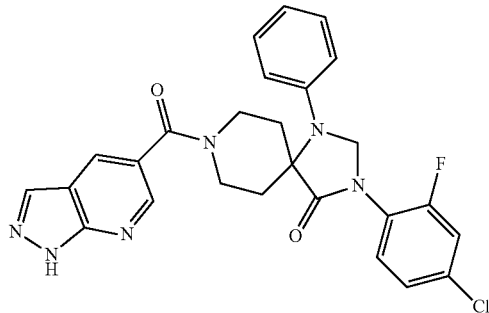 [SMILES: O=C(c1cnc2[nH]ncc2c1)N1CCC2(CC1)C(=O)N(c1ccc(Cl)cc1F)CN2c1ccccc1]

The title compound was obtained in analogy to example 83, from 3-(4-chloro-2-fluoro-phenyl)-1-phenyl-1,3,8-triaza-spiro[4.5]decan-4-one and 1H-pyrazolo[3,4-b]pyridine-5-carboxylic acid (CAS RN 952182-02-4) as a white solid. MS (EI): m/z=503.4 [M−H]⁻.

Intermediate a) 3-(4-Chloro-2-fluoro-phenyl)-1-phenyl-1,3,8-triaza-spiro[4.5]decan-4-one The title compound was prepared in analogy to example 83, intermediate a, from 3-(4-chloro-2-fluoro-phenyl)-4-oxo-1-phenyl-1,3,8-triaza-spiro[4.5]decane-8-carboxylic acid tert-butyl ester as a white solid. MS (EI): m/z=360.2 [M+H]⁺.

Intermediate b) 3-(4-Chloro-2-fluoro-phenyl)-4-oxo-1-phenyl-1,3,8-triaza-spiro[4.5]decane-8-carboxylic acid tert-butyl ester The title compound was prepared in analogy to example 79, intermediate b, from 4-oxo-1-phenyl-1,3,8-triaza-spiro[4.5]decane-8-carboxylic acid tert-butyl ester (example 35,

Example 89

3-(5-Chloro-2-fluoro-4-methyl-phenyl)-1-phenyl-8-(1H-pyrazolo[3,4-b]pyridine-5-carbonyl)-1,3,8-triaza-spiro[4.5]decan-4-one

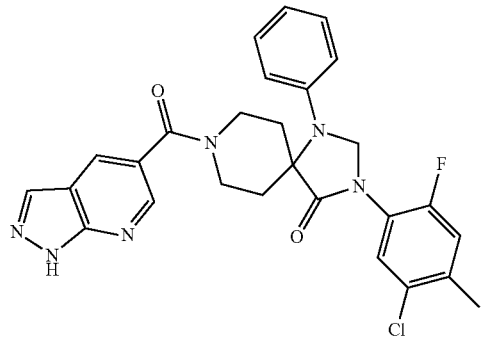 [SMILES: Cc1cc(F)c(N2CN(c3ccccc3)C3(CCN(C(=O)c4cnc5[nH]ncc5c4)CC3)C2=O)cc1Cl]

The title compound was obtained in analogy to example 83, from 3-(5-chloro-2-fluoro-4-methyl-phenyl)-1-phenyl-1,3,8-triaza-spiro[4.5]decan-4-one and 1H-pyrazolo[3,4-b]pyridine-5-carboxylic acid (CAS RN 952182-02-4) as a white solid. MS (EI): m/z=517.3 [M–H]⁻.

Intermediate a) 3-(5-Chloro-2-fluoro-4-methyl-phenyl)-1-phenyl-1,3,8-triaza-spiro[4.5]decan-4-one The title compound was prepared in analogy to example 83, intermediate a, from 3-(5-chloro-2-fluoro-4-methyl-phenyl)-4-oxo-1-phenyl-1,3,8-triaza-spiro[4.5]decane-8-carboxylic acid tert-butyl ester as a white solid. MS (EI): m/z=374.2 [M+H]⁺.

Intermediate b) 3-(5-Chloro-2-fluoro-4-methyl-phenyl)-4-oxo-1-phenyl-1,3,8-triaza-spiro[4.5]decane-8-carboxylic acid tert-butyl ester The title compound was prepared in analogy to example 79, intermediate b, from 4-oxo-1-phenyl-1,3,8-triaza-spiro[4.5]decane-8-carboxylic acid tert-butyl ester (example 35, intermediate c) and 1-bromo-5-chloro-2-fluoro-4-methyl-benzene (CAS RN 93765-83-4) as a white solid. MS (EI): m/z=474.2 [M+H]⁺.

Example 90

2-(3-((2-(8-(1H-indazole-5-carbonyl)-4-oxo-1-phenyl-1,3,8-triazaspiro[4.5]decan-3-yl)acetamido)methyl)phenyl)-N-methylacetamide

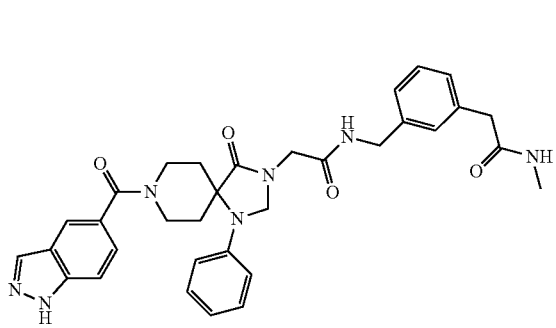 [SMILES: CNC(=O)Cc1cccc(CNC(=O)CN2CN(c3ccccc3)C3(CCN(C(=O)c4ccc5[nH]ncc5c4)CC3)C2=O)c1]

The title compound was obtained in analogy to example 17, from N-methyl-2-[3-[[[2-(4-oxo-1-phenyl-1,3,8-triazaspiro[4.5]decan-3-yl)acetyl]amino]methyl]phenyl]acetamide hydrochloride salt and 1H-indazole-5-carboxylic acid (CAS RN 61700-61-6) using HATU and DIPEA in THF as an off-white solid. MS (EI): m/z=594 [M+H]⁺.

Intermediate a) N-Methyl-2-[3-[[[2-(4-oxo-1-phenyl-1,3,8-triazaspiro[4.5]decan-3-yl)acetyl]amino]methyl]phenyl]acetamide; hydrochloride The title compound was prepared in analogy to example 6, intermediate b, from tert-butyl 3-[2-[[3-[2-(methylamino)-2-oxo-ethyl]phenyl]methylamino]-2-oxo-ethyl]-4-oxo-1-phenyl-1,3,8-triazaspiro[4.5]decane-8-carboxylate using 4M HCl in dioxane as a white solid. MS (EI): m/z=450 [M+H]⁺.

Intermediate b) tert-Butyl 3-[2-[[3-[2-(methylamino)-2-oxo-ethyl]phenyl]methylamino]-2-oxo-ethyl]-4-oxo-1-phenyl-1,3,8-triazaspiro[4.5]decane-8-carboxylate The title compound was prepared in analogy to example 22, from 2-(8-tert-butoxycarbonyl-4-oxo-1-phenyl-1,3,8-triazaspiro[4.5]decan-3-yl)acetic acid (CAS RN 180386-35-0) and 2-[3-(aminomethyl)phenyl]-N-methyl-acetamide hydrochloride salt using HATU and DIPEA in THF as a colorless oil. MS (EI): m/z=550 [M+H]⁺.

Intermediate c) 2-[3-(Aminomethyl)phenyl]-N-methyl-acetamide Hydrochloride Salt

The title compound was prepared in analogy to example 6, intermediate b, from tert-butyl N-[[3-[2-(methylamino)-2-oxo-ethyl]phenyl]methyl]carbamate using 4M HCl in dioxane as a colorless gum. MS (EI): m/z=215 [M+H]⁺.

Intermediate d) tert-Butyl N-[[3-[2-(methylamino)-2-oxo-ethyl]phenyl]methyl]carbamate The title compound was prepared in analogy to example 17, from 2-[3-[(tert-butoxycarbonylamino)methyl]phenyl]acetic acid (CAS RN 71420-95-6) and methylamine hydrochloride (CAS RN 593-51-1) using HATU and DIPEA in THF as an off-white solid. ¹H NMR (300 MHz, CDCl₃) δ ppm 7.28-7.36 (m, 1H), 7.12-7.24 (m, 3H), 5.35 (br. s., 1H), 4.87 (br. s., 1H), 4.32 (d, J=6.06 Hz, 2H), 3.56 (s, 2H), 2.76 (d, J=4.84 Hz, 3H), 1.46 (s, 9H).

Example 91

2-(4-Oxo-1-phenyl-8-(1H-pyrazolo[4,3-b]pyridine-5-carbonyl)-1,3,8-triazaspiro[4.5]decan-3-yl)-N-(2,2,2-trifluoroethyl)acetamide

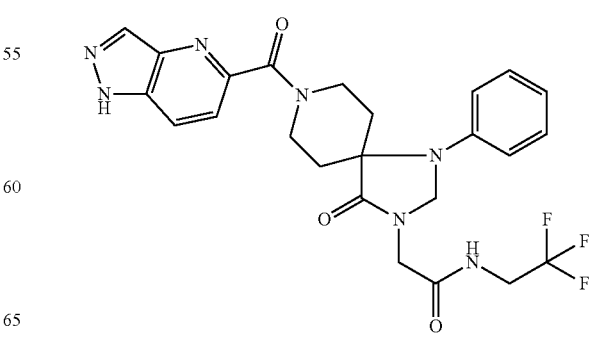

The title compound was obtained in analogy to example 17, from 2-(4-oxo-1-phenyl-1,3,8-triazaspiro[4.5]decan-3-yl)-N-(2,2,2-trifluoroethyl)acetamide (example 17, intermediate a) and 1H-pyrazolo[4,3-b]pyridine-5-carboxylic acid (CAS RN 1260670-03-8) in DCM as a white solid. MS (ESI): m/z=516 [M+H]⁺.

Example 92

2-[8-(2-Aminopyrimidine-5-carbonyl)-4-oxo-1-phenyl-1,3,8-triazaspiro[4.5]decan-3-yl]-N-(2,2,2-trifluoroethyl)acetamide

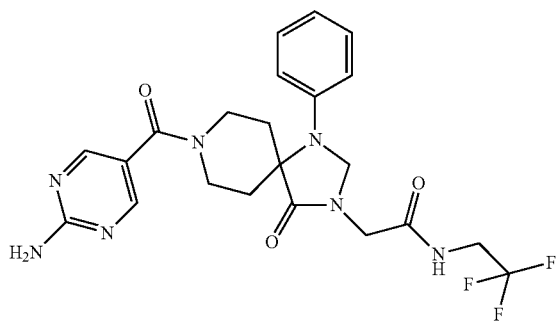 [SMILES: Nc1ncc(C(=O)N2CCC3(CC2)C(=O)N(CC(=O)NCC(F)(F)F)CN3c2ccccc2)cn1]

The title compound was obtained in analogy to example 17, from 2-(4-oxo-1-phenyl-1,3,8-triazaspiro[4.5]decan-3-yl)-N-(2,2,2-trifluoroethyl)acetamide (example 17, intermediate a) and 2-amino-pyrimidine-5-carboxylic acid (CAS RN 3167-50-8) in DCM as a white solid. MS (ESI): m/z=491.9 [M+H]⁺.

Example 93

N-(2-fluoroethyl)-2-[4-oxo-1-phenyl-8-(1H-pyrazolo[3,4-b]pyridine-5-carbonyl)-1,3,8-triazaspiro[4.5]decan-3-yl]acetamide

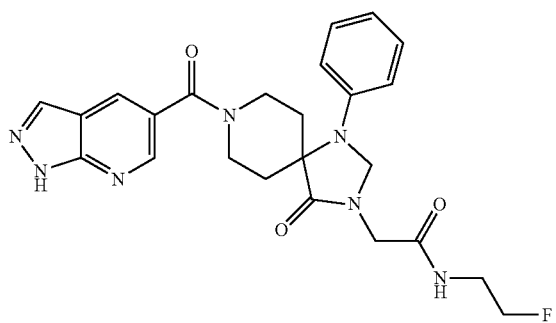 [SMILES: O=C(CN1CN(c2ccccc2)C2(CCN(C(=O)c3cnc4[nH]ncc4c3)CC2)C1=O)NCCF]

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and 2-fluoroethanamine hydrochloride (CAS RN 460-08-2) as a white solid. MS (ESI): m/z=480.2 [M+H]⁺.

Example 94

N-(2,2-Difluoroethyl)-2-[4-oxo-1-phenyl-8-(1H-pyrazolo[3,4-b]pyridine-5-carbonyl)-1,3,8-triazaspiro[4.5]decan-3-yl]acetamide

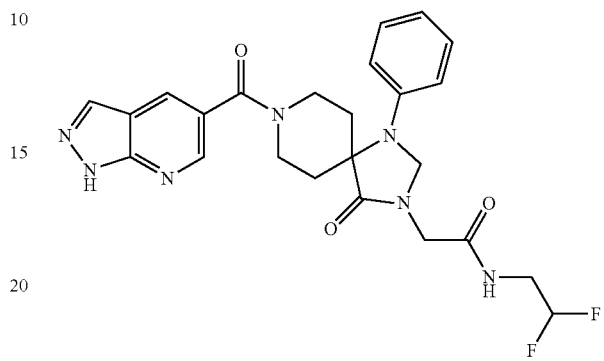

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and 2,2-difluoroethanamine hydrochloride (CAS RN 79667-91-7) as a white solid. MS (ESI): m/z=498.2 [M+H]⁺.

Example 95

3-(2-Oxo-2-pyrrolidin-1-ylethyl)-1-phenyl-8-(1H-pyrazolo[3,4-b]pyridine-5-carbonyl)-1,3,8-triazaspiro[4.5]decan-4-one

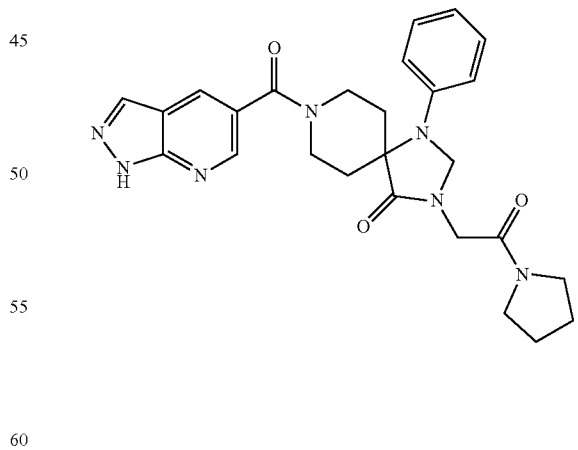

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and pyrrolidine (CAS RN 123-75-1) as a white solid. MS (ESI): m/z=488.2 [M+H]⁺.

Example 96

3-[2-[(3R)-3-(Dimethylamino)pyrrolidin-1-yl]-2-oxoethyl]-1-phenyl-8-(1H-pyrazolo[3,4-b]pyridine-5-carbonyl)-1,3,8-triazaspiro[4.5]decan-4-one

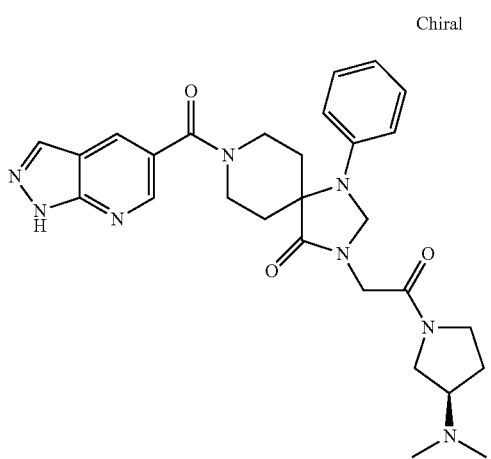 [SMILES: CN(C)[C@@H]1CCN(C(=O)CN2CN(c3ccccc3)C3(CCN(C(=O)c4cnc5[nH]ncc5c4)CC3)C2=O)C1]

Chiral

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and (R)—N,N-dimethylpyrrolidin-3-amine (CAS RN 132958-72-6) as a white solid. MS (ESI): m/z=531.3 [M+H]⁺.

Example 97

3-(2-Morpholino-2-oxoethyl)-1-phenyl-8-(1H-pyrazolo[3,4-b]pyridine-5-carbonyl)-1,3,8-triazaspiro[4.5]decan-4-one

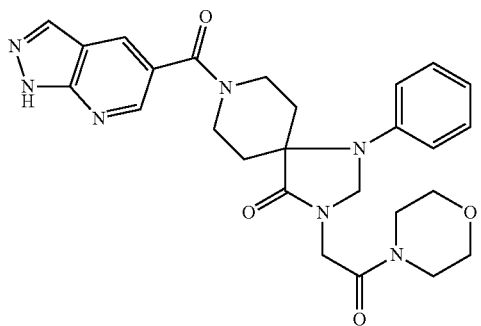 [SMILES: O=C(CN1CN(c2ccccc2)C2(CCN(C(=O)c3cnc4[nH]ncc4c3)CC2)C1=O)N1CCOCC1]

The title compound was obtained in analogy to example 17, from 3-(2-morpholino-2-oxo-ethyl)-1-phenyl-1,3,8-triazaspiro[4.5]decan-4-one and 1H-pyrazolo[3,4-b]pyridine-5-carboxylic acid (CAS RN 952182-02-4) using DCM as a white solid. MS (ESI): m/z=504 [M+H]⁺.

Intermediate a) 3-(2-Morpholino-2-oxo-ethyl)-1-phenyl-1,3,8-triazaspiro[4.5]decan-4-one The title compound was prepared in analogy to example 6, intermediate b, from tert-butyl 3-(2-morpholino-2-oxo-ethyl)-4-oxo-1-phenyl-1,3,8-triazaspiro[4.5]decane-8-carboxylate as a purple oil. MS (EI): m/z=359.3 [M+H]⁺.

Intermediate b) tert-Butyl 3-(2-morpholino-2-oxo-ethyl)-4-oxo-1-phenyl-1,3,8-triazaspiro[4.5]decane-8-carboxylate The title compound was prepared in analogy to example 25, from 2-(8-tert-butoxycarbonyl-4-oxo-1-phenyl-1,3,8-triazaspiro[4.5]decan-3-yl)acetic acid (CAS RN 180386-35-0) and morpholine (CAS RN 110-91-8) as a yellow oil. MS (EI): m/z=403 [M−C₄H₈]⁺.

Example 98

2-[4-Oxo-8-(1H-pyrazolo[3,4-b]pyridine-5-carbonyl)-1-pyridin-3-yl-1,3,8-triazaspiro[4.5]decan-3-yl]-N-(2,2,2-trifluoroethyl)acetamide

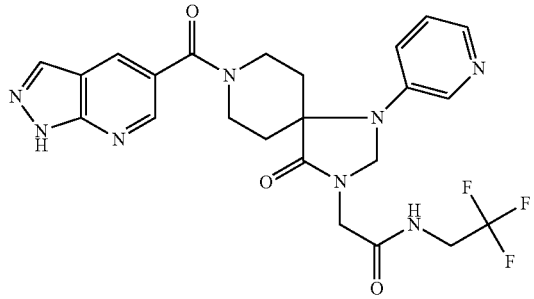 [SMILES: O=C(CN1CN(c2cccnc2)C2(CCN(C(=O)c3cnc4[nH]ncc4c3)CC2)C1=O)NCC(F)(F)F]

To a stirred solution of 2-[4-oxo-1-(pyridin-3-yl)-1,3,8-triazaspiro[4.5]decan-3-yl]-N-(2,2,2-trifluoroethyl)acetamide (100 mg, 0.27 mmol) in DMF (5 mL) were added 1H-pyrazolo[3,4-b]pyridine-5-carboxylic acid (44 mg, 0.27 mmol, CAS RN 952182-02-4), DIPEA (0.14 mL, 0.81 mmol, CAS RN 7087-68-5) and HATU (154 mg, 0.4 mmol, CAS RN 148893-10-1) at 25° C. and the reaction mixture was stirred at 25° C. for 16 h. The reaction mixture was quenched with water (20 mL) and extracted with DCM (2×80 mL). The combined organic layers were dried over Na₂SO₄, filtered and evaporated. The residue was purified by prep. HPLC to afford the title compound as an off-white solid (16 mg, 11%). MS (ESI): m/z=517.1 [M+H]⁺.

Intermediate a) 2-[4-Oxo-1-(pyridin-3-yl)-1,3,8-triazaspiro[4.5]decan-3-yl]-N-(2,2,2-trifluoroethyl)acetamide The title compound was prepared in analogy to example 1, intermediate a, from 2-[8-benzyl-4-oxo-1-(pyridin-3-yl)-1,3,8-triazaspiro[4.5]decan-3-yl]-N-(2,2,2-trifluoroethyl)acetamide as an off-white solid. MS (EI): m/z=372.3 [M+H]⁺.

Intermediate b) 2-[8-Benzyl-4-oxo-1-(pyridin-3-yl)-1,3,8-triazaspiro[4.5]decan-3-yl]-N-(2,2,2-trifluoroethyl)acetamide The title compound was prepared in analogy to example 1, intermediate b, from 8-benzyl-1-(pyridin-3-yl)-1,3,8-triazaspiro[4.5]decan-4-one as an off-white solid. MS (EI): m/z=462.4 [M+H]⁺.

Intermediate c) 8-Benzyl-1-(pyridin-3-yl)-1,3,8-triazaspiro[4.5]decan-4-one

To a stirred solution of 8-benzyl-1-(pyridin-3-yl)-1,3,8-triazaspiro[4.5]dec-2-en-4-one (450 mg, 1.41 mmol) in MeOH (10 mL) was added NaBH$_4$ (133.0 mg, 3.52 mmol, CAS RN 16940-66-2) at 0° C. and the reaction mixture was stirred at 25° C. for 4 h. The reaction mixture was quenched with H$_2$O (30 mL), the solvent was evaporated and the residue extracted with DCM (2×200 mL). The combined organic layers were dried over Na$_2$SO$_4$, filtered and evaporated. The resulting residue was purified by column chromatography over amine silica gel (1-2% MeOH/DCM) to get the title compound as a yellow solid (165 mg, 37%). MS: (ESI): m/z=323.2 [M+H]$^+$.

Intermediate d) 8-Benzyl-1-(pyridin-3-yl)-1,3,8-triazaspiro[4.5]dec-2-en-4-one To a stirred solution of 1-benzyl-4-(pyridin-3-ylamino)piperidine-4-carboxamide (500 mg, 1.613 mmol) in MeOH (5 mL) was added DMF-DMA (0.65 mL, 4.839 mmol, CAS RN 4637-24-5) at 25° C. and reaction mixture was stirred at 70° C. for 16 h. The solvent was evaporated, the residue was diluted with EtOAc (100 mL) and washed with H$_2$O (30 mL). The organic layer was dried over Na$_2$SO$_4$, filtered and evaporated to provide the title compound as brown sticky solid (452 mg). MS: (ESI): m/z=321.1 [M+H]$^+$.

Intermediate e) 1-Benzyl-4-(pyridin-3-ylamino)piperidine-4-carboxamide

To a stirred solution of 1-benzyl-4-(pyridin-3-ylamino)piperidine-4-carbonitrile (5 g, 17.12 mmol) in THF (40 mL) was added conc. H$_2$SO$_4$ (20 mL, CAS RN 7664-93-9) at 0° C. and the reaction mixture was stirred at 25° C. for 16 h. The reaction mixture was poured onto ice, basified using 5N aqueous NaOH solution to pH 9 and extracted with 10% MeOH in DCM (3×300 mL). The combined organic layers were dried over Na$_2$SO$_4$, filtered and evaporated. The crude product was purified by column chromatography over silica gel (2-5% MeOH/DCM) to yield the title compound as light yellow solid (2.3 g, 43%). MS: (ESI): m/z=311.2 [M+H]$^+$.

Intermediate f) 1-Benzyl-4-(pyridin-3-ylamino)piperidine-4-carbonitrile

To a stirred solution of 1-benzylpiperidin-4-one (10 g, 52.91 mmol, CAS RN 3612-20-2), pyridin-3-amine (5.47 g, 58.20 mmol, CAS RN 462-08-8) in AcOH (40 mL) was added TMS-CN (6.63 mL, 52.91 mmol, CAS RN 7677-24-9) at 25° C. and the reaction mixture was stirred at 25° C. for 16 h. The reaction mixture was poured onto ice and basified using 5M aqueous NaOH solution to pH 9 and extracted with DCM (2×300 mL). The combined organic layers were dried over Na$_2$SO$_4$, filtered and concentrated. The residue was washed with diethyl ether and dried under high vacuum to yield the title compound as a yellow solid (2.75 g, 18%). MS (ESI): m/z=293.2 [M+H]$^+$.

Example 99 tert-Butyl (3S)-3-[[2-[4-oxo-1-phenyl-8-(1H-pyrazolo[3,4-b]pyridine-5-carbonyl)-1,3,8-triazaspiro[4.5]decan-3-yl]acetyl]amino]pyrrolidine-1-carboxylate

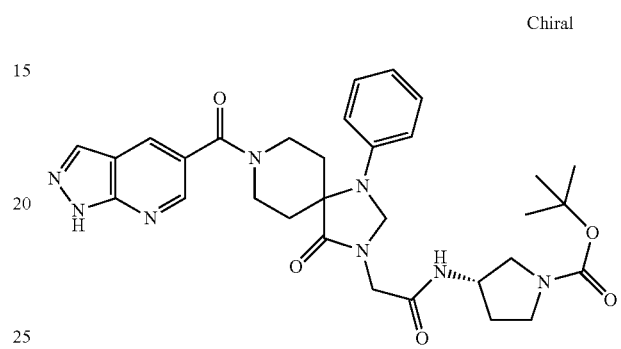

Chiral

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and (S)-tert-butyl 3-aminopyrrolidine-1-carboxylate (CAS RN 147081-44-5) in DCM as a white solid. MS (ESI): m/z=603 [M+H]$^+$.

Example 100 tert-Butyl (3R)-3-[[2-[4-oxo-1-phenyl-8-(1H-pyrazolo[3,4-b]pyridine-5-carbonyl)-1,3,8-triazaspiro[4.5]decan-3-yl]acetyl]amino]pyrrolidine-1-carboxylate

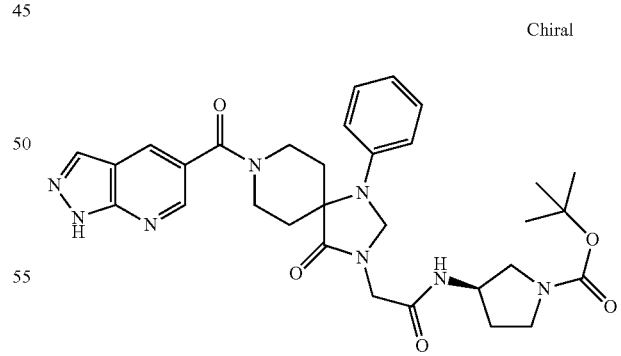

Chiral

The title compound was obtained in analogy to example 25, from 2-(4-oxo-1-phenyl-8-(1H-pyrazolo[3,4-b]pyridine-5-carbonyl)-1,3,8-triazaspiro[4.5]decan-3-yl)acetic acid (example 22, intermediate a) and (R)-tert-butyl 3-aminopyrrolidine-1-carboxylate (CAS RN 147081-49-0) in DCM as a white solid. MS (ESI): m/z=603 [M+H]$^+$.

Example 101

2-(8-(1H-Indazole-5-carbonyl)-4-oxo-1-phenyl-1,3,8-triazaspiro[4.5]decan-3-yl)-N-methyl-N-(2,2,2-trifluoroethyl)acetamide

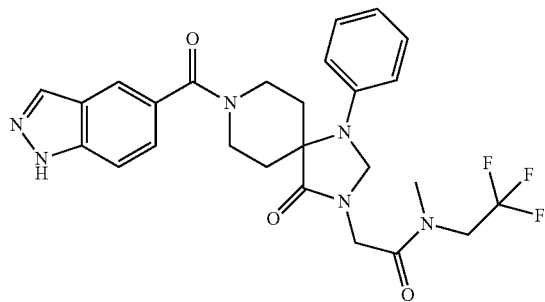 [SMILES: CN(CC(F)(F)F)C(=O)CN1CN(c2ccccc2)C2(CCN(C(=O)c3ccc4[nH]ncc4c3)CC2)C1=O]

The title compound was obtained in analogy to example 17, from N-methyl-2-(4-oxo-1-phenyl-1,3,8-triazaspiro[4.5]decan-3-yl)-N-(2,2,2-trifluoroethyl)acetamide hydrochloride salt and 1H-indazole-5-carboxylic acid (CAS RN 61700-61-6) in DCM as a light yellow solid. MS (ESI): m/z=529 [M+H]$^+$.

Intermediate a) N-Methyl-2-(4-oxo-1-phenyl-1,3,8-triazaspiro[4.5]decan-3-yl)-N-(2,2,2-trifluoroethyl)acetamide hydrochloride Salt The title compound was obtained in analogy to example 75, intermediate a, from 2-(8-(tert-butoxycarbonyl)-4-oxo-1-phenyl-1,3,8-triazaspiro[4.5]decan-3-yl)acetic acid (CAS RN 180386-35-0) and 2,2,2-trifluoro-N-methylethanamine (174 mg, 1.54 mmol, CAS RN 2730-67-8) as a purple gum. MS (ESI): m/z=385 [M+H]$^+$.

Example 102

N-Methyl-2-(4-oxo-1-phenyl-8-(1H-pyrazolo[3,4-c]pyridine-5-carbonyl)-1,3,8-triazaspiro[4.5]decan-3-yl)-N-(2,2,2-trifluoroethyl)acetamide

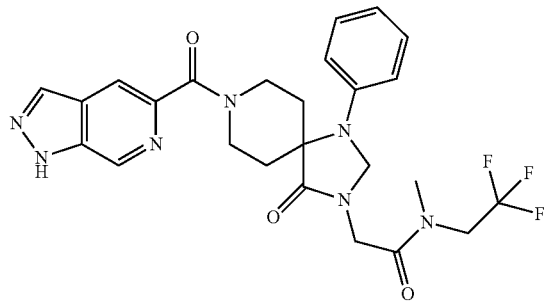 [SMILES: CN(CC(F)(F)F)C(=O)CN1CN(c2ccccc2)C2(CCN(C(=O)c3cc4cn[nH]c4cn3)CC2)C1=O]

The title compound was obtained in analogy to example 17, from N-methyl-2-(4-oxo-1-phenyl-1,3,8-triazaspiro[4.5]decan-3-yl)-N-(2,2,2-trifluoroethyl)acetamide hydrochloride salt (example 101, intermediate a) and 1H-pyrazolo[3,4-c]pyridine-5-carboxylic acid (CAS RN 1256824-45-9) in DCM as a white solid. MS (ESI): m/z=530 [M+H]$^+$.

Example 103

2-(8-(3-Methyl-1H-indazole-5-carbonyl)-4-oxo-1-phenyl-1,3,8-triazaspiro[4.5]decan-3-yl)-N-(2,2,2-trifluoroethyl)acetamide

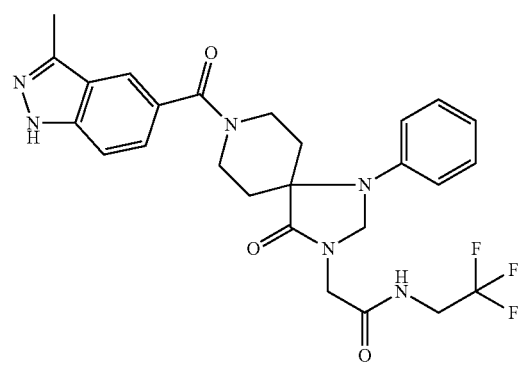 [SMILES: Cc1n[nH]c2ccc(C(=O)N3CCC4(CC3)C(=O)N(CC(=O)NCC(F)(F)F)CN4c3ccccc3)cc12]

The title compound was obtained in analogy to example 17, from 2-(4-oxo-1-phenyl-1,3,8-triazaspiro[4.5]decan-3-yl)-N-(2,2,2-trifluoroethyl)acetamide (example 17, intermediate a) and 3-methyl-1H-indazole-5-carboxylic acid (CAS RN 885223-58-5) in DCM as a white solid. MS (ESI): m/z=529 [M+H]$^+$.

Example 104

2-(8-(3-Amino-1H-indazole-5-carbonyl)-4-oxo-1-phenyl-1,3,8-triazaspiro[4.5]decan-3-yl)-N-(2,2,2-trifluoroethyl)acetamide

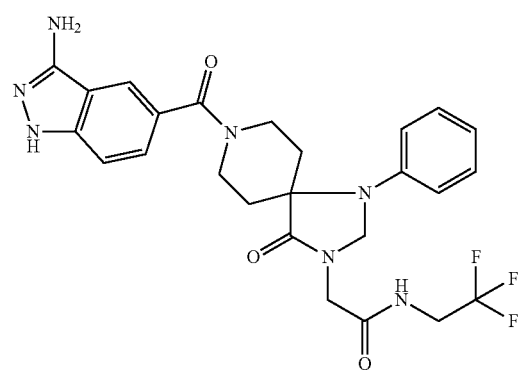 [SMILES: Nc1n[nH]c2ccc(C(=O)N3CCC4(CC3)C(=O)N(CC(=O)NCC(F)(F)F)CN4c3ccccc3)cc12]

The title compound was obtained in analogy to example 17, from 2-(4-oxo-1-phenyl-1,3,8-triazaspiro[4.5]decan-3-yl)-N-(2,2,2-trifluoroethyl)acetamide (example 17, intermediate a) and 3-amino-1H-indazole-5-carboxylic acid (CAS RN 871709-84-1) in DCM as a white solid. MS (ESI): m/z=530 [M+H]$^+$.

Example 105

2-[8-(1H-Indazole-5-carbonyl)-4-oxo-1-phenyl-1,3,8-triazaspiro[4.5]decan-3-yl]-N-(2,2,2-trifluoroethyl)propanamide

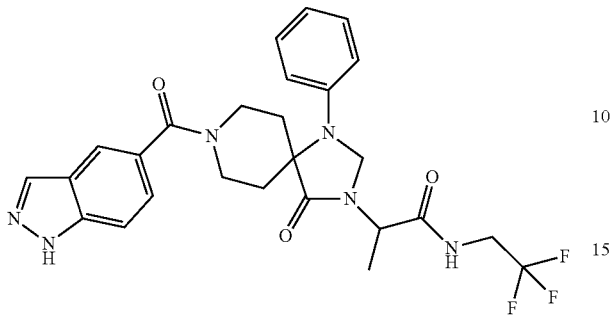

The title compound was obtained in analogy to example 17, from 2-(4-oxo-1-phenyl-1,3,8-triaza-spiro[4.5]dec-3-yl)-N-(2,2,2-trifluoro-ethyl)-propionamide and 1H-indazole-5-carboxylic acid (CAS RN 61700-61-6) as a white solid. MS (EI): m/z=528.9 [M+H]$^+$.

Intermediate a) 2-(4-Oxo-1-phenyl-1,3,8-triaza-spiro[4.5]dec-3-yl)-N-(2,2,2-trifluoro-ethyl)-propionamide The title compound was obtained in analogy to example 6, intermediate b, from 4-oxo-1-phenyl-3-[1-(2,2,2-trifluoro-ethylcarbamoyl)-ethyl]-1,3,8-triaza-spiro[4.5]-decane-8-carboxylic acid tert-butyl ester using 4M HCl in dioxane as a white solid. MS (EI): m/z=385 [M+H]$^-$.

Intermediate b) 4-Oxo-1-phenyl-3-[1-(2,2,2-trifluoro-ethylcarbamoyl)-ethyl]-1,3,8-triaza-spiro[4.5]-decane-8-carboxylic acid tert-butyl ester The title compound was obtained in analogy to example 1, intermediate b, from 4-oxo-1-phenyl-1,3,8-triaza-spiro[4.5]decane-8-carboxylic acid tert-butyl ester (CAS RN 138091-52-8) and 2-chloro-N-(2,2,2-trifluoro-ethyl)-propionamide (CAS RN 139126-57-1) as a brown solid. MS (EI): m/z=485.3 [M+H]$^+$.

Example 106

3-[(+)-2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one Chiral

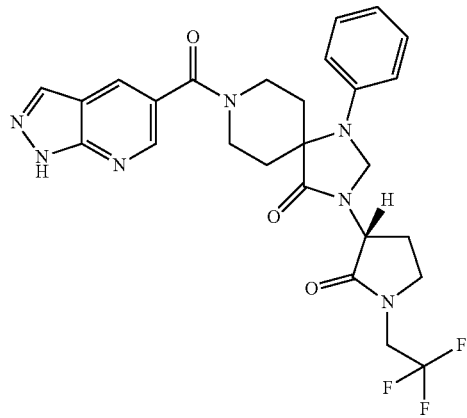

The title compound was obtained from racemic 3-[2-oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one (example 77) by preparative chiral HPLC (Chiralpak-AD column) using an isocratic mixture of EtOH (containing 0.5% NH$_4$OAc):n-heptane (40:60) as a light brown solid. MS (ESI): m/z=542.2 [M+H]$^+$.

Example 107

3-[(−)-2-Oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one Chiral

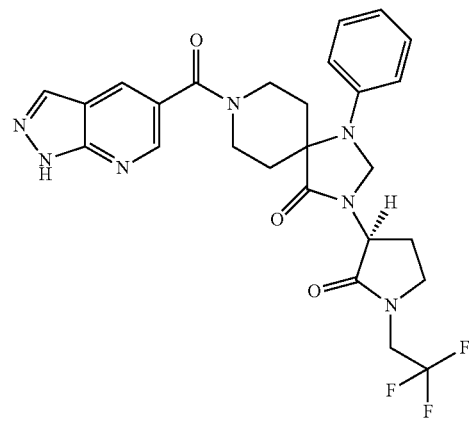

The title compound was obtained from racemic 3-[2-oxo-1-(2,2,2-trifluoroethyl)pyrrolidin-3-yl]-1-phenyl-8-(1H-pyrazolo[3,4-b]pyridine-5-carbonyl)-1,3,8-triazaspiro[4.5]decan-4-one (example 77) by preparative chiral HPLC (Chiralpak-AD column) using an isocratic mixture of EtOH (containing 0.5% NH$_4$OAc):n-heptane (40:60) as a light brown solid. MS (ESI): m/z=542.2 [M+H]$^+$.

Example 108

N-(6-Cyanopyridin-2-yl)-2-[4-oxo-1-phenyl-8-(1H-pyrazolo[3,4-b]pyridine-5-carbonyl)-1,3,8-triazaspiro[4.5]decan-3-yl]acetamide

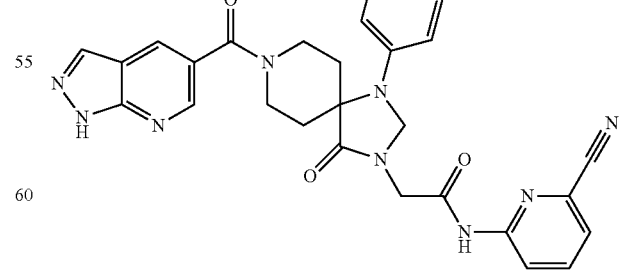

The title compound was obtained in analogy to example 75, intermediate a, from 2-[4-oxo-1-phenyl-8-(1H-pyrazolo[3,4-b]pyridine-5-carbonyl)-1,3,8-triazaspiro[4.5]decan-3- yl]acetic acid (example 22, intermediate a) and 6-aminopicolinonitrile (CAS RN 370556-44-8) using DMF as a solvent for the amide couling step, as a light brown solid. MS (ESI): m/z=536.2 [M+H]+.

Example 109

3-[(6-Methylpyridin-2-yl)methyl]-1-phenyl-8-(1H-pyrazolo[3,4-b]pyridine-5-carbonyl)-1,3,8-triazaspiro[4.5]decan-4-one

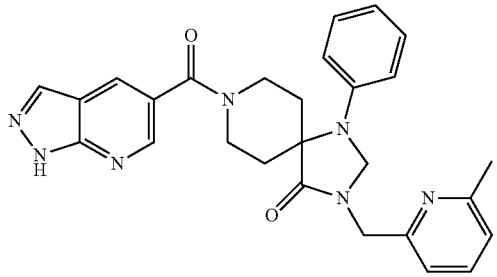 [SMILES: Cc1cccc(CN2CN(c3ccccc3)C3(CCN(C(=O)c4cnc5[nH]ncc5c4)CC3)C2=O)n1]

The title compound was obtained in analogy to example 36, from tert-butyl 2-[3-[(6-methyl-2-pyridyl)methyl]-4-oxo-1-phenyl-1,3,8-triazaspiro[4.5]decan-8-yl]-2-oxo-acetate and 1H-pyrazolo[3,4-b]pyridine-5-carboxylic acid (CAS RN 952182-02-4) as a light brown solid. MS (ESI): m/z=482.2 [M+H]+.

Intermediate a) tert-Butyl 3-[(6-methyl-2-pyridyl)methyl]-4-oxo-1-phenyl-1,3,8-triazaspiro[4.5]decane-8-carboxylate The title compound was obtained in analogy to example 35, intermediate b, from tert-butyl 4-oxo-1-phenyl-1,3,8-triazaspiro[4.5]decane-8-carboxylate (CAS RN 138091-52-8) and 2-(bromomethyl)-6-methylpyridine (CAS RN 68470-59-7) without TEA as a light brown oil. MS (EI): m/z=437.3 [M+H]+.

Example 110

6-[[4-Oxo-1-phenyl-8-(1H-pyrazolo[3,4-b]pyridine-5-carbonyl)-1,3,8-triazaspiro[4.5]decan-3-yl]methyl]pyridine-2-carbonitrile

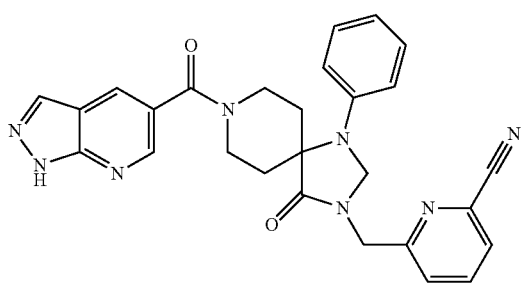 [SMILES: N#Cc1cccc(CN2CN(c3ccccc3)C3(CCN(C(=O)c4cnc5[nH]ncc5c4)CC3)C2=O)n1]

The title compound was obtained in analogy to example 36, from tert-butyl 3-[(6-cyano-2-pyridyl)methyl]-4-oxo-1-phenyl-1,3,8-triazaspiro[4.5]decane-8-carboxylate and 1H-pyrazolo[3,4-b]pyridine-5-carboxylic acid (CAS RN 952182-02-4) as a light brown solid. MS (ESI): m/z=493.2 [M+H]+.

Intermediate a) tert-Butyl 3-[(6-cyano-2-pyridyl)methyl]-4-oxo-1-phenyl-1,3,8-triazaspiro[4.5]decane-8-carboxylate The title compound was obtained in analogy to example 35, intermediate b, from tert-butyl 4-oxo-1-phenyl-1,3,8-triazaspiro[4.5]decane-8-carboxylate (CAS RN 138091-52-8) and 6-(chloromethyl)picolinonitrile (CAS RN 135450-23-6) without TEA as a light brown oil. MS (EI): m/z=448.2 [M+H]+.

Example 111

N-Cyclopropyl-2-[4-oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide

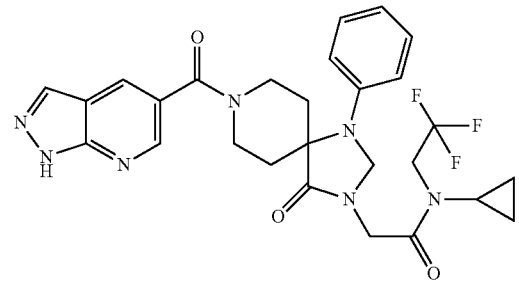 [SMILES: O=C(c1cnc2[nH]ncc2c1)N1CCC2(CC1)C(=O)N(CC(=O)N(CC(F)(F)F)C1CC1)CN2c1ccccc1]

The title compound was obtained in analogy to example 36, from tert-butyl 3-[2-[cyclopropyl(2,2,2-trifluoroethyl)amino]-2-oxo-ethyl]-4-oxo-1-phenyl-1,3,8-triazaspiro[4.5]decane-8-carboxylate and 1H-pyrazolo[3,4-b]pyridine-5-carboxylic acid (CAS RN 952182-02-4) as a white solid. MS (ESI): m/z=556.2 [M+H]+.

Intermediate a) tert-Butyl 3-[2-[cyclopropyl(2,2,2-trifluoroethyl)amino]-2-oxo-ethyl]-4-oxo-1-phenyl-1,3,8-triazaspiro[4.5]decane-8-carboxylate The title compound was obtained in analogy to example 75, intermediate a, from 2-(8-(tert-butoxycarbonyl)-4-oxo-1-phenyl-1,3,8-triazaspiro[4.5]decan-3-yl)acetic acid (CAS RN 180386-35-0) and N-(2,2,2-trifluoroethyl)cyclopropanamine hydrochloride (CAS RN 1169952-82-2) as a white solid. MS (EI): m/z=511.3 [M+H]+.

Example 112

1-[2-[4-Oxo-1-phenyl-8-(1H-pyrazolo[3,4-b]pyridine-5-carbonyl)-1,3,8-triazaspiro[4.5]decan-3-yl]acetyl]pyrrolidine-3-carbonitrile

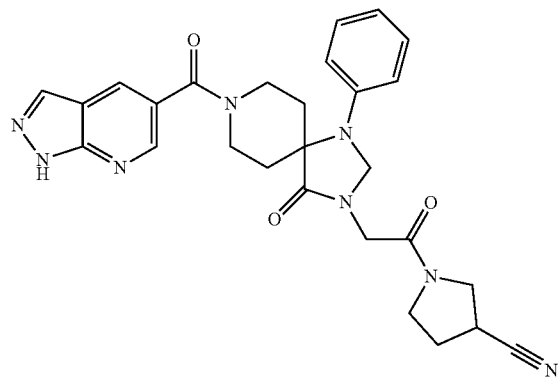 [SMILES: N#CC1CCN(C(=O)CN2CN(c3ccccc3)C3(CCN(C(=O)c4cnc5[nH]ncc5c4)CC3)C2=O)C1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and pyrrolidine-3-carbonitrile hydrochloride (CAS RN 10603-53-9) as a white solid. MS(ESI): m/z=513.2 [M+H]$^+$.

Example 113

(−)-2-[8-(1H-Indazole-5-carbonyl)-4-oxo-1-phenyl-1,3,8-triazaspiro[4.5]decan-3-yl]-N-(2,2,2-trifluoroethyl)propanamide

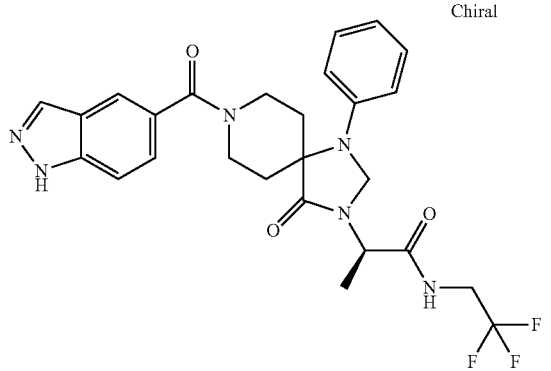 [SMILES: C[C@H](C(=O)NCC(F)(F)F)N1CN(c2ccccc2)C2(CCN(C(=O)c3ccc4[nH]ncc4c3)CC2)C1=O]

The title compound was obtained from racemic 2-[8-(1H-indazole-5-carbonyl)-4-oxo-1-phenyl-1,3,8-triazaspiro[4.5]decan-3-yl]-N-(2,2,2-trifluoroethyl)propanamide (example 105) by prep. chiral HPLC (Reprosil Chiral-NR column) using an isocratic mixture of EtOH (containing 0.5% NH$_4$OAc):n-heptane (40:60) as a white solid. MS (ESI): m/z=529.2 [M+H]$^+$.

Example 114

(+)-2-[8-(1H-indazole-5-carbonyl)-4-oxo-1-phenyl-1,3,8-triazaspiro[4.5]decan-3-yl]-N-(2,2,2-trifluoroethyl)propanamide

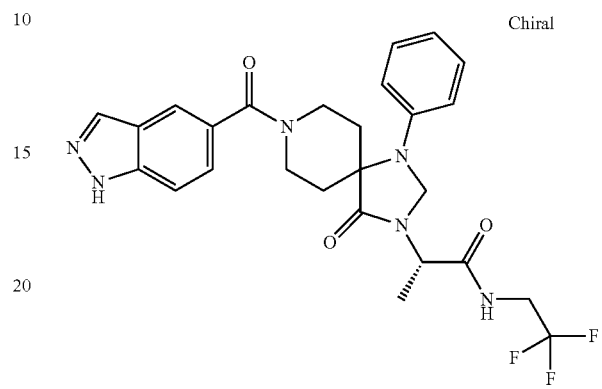

The title compound was obtained from racemic 2-[8-(1H-indazole-5-carbonyl)-4-oxo-1-phenyl-1,3,8-triazaspiro[4.5]decan-3-yl]-N-(2,2,2-trifluoroethyl)propanamide (example 105) by preparative chiral HPLC (Reprosil Chiral-NR column) using an isocratic mixture of EtOH (containing 0.5% NH$_4$OAc):n-heptane (40:60) as a white solid. MS (ESI): m/z=529.2 [M+H]$^+$.

Example 115

(S)-3-(2-Oxo-2-(2-(trifluoromethyl)pyrrolidin-1-yl)ethyl)-1-phenyl-8-(1H-pyrazolo[3,4-b]pyridine-5-carbonyl)-1,3,8-triazaspiro[4.5]decan-4-one

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (S)-2-(trifluoromethyl)pyrrolidine (CAS RN 119580-41-5) as a white solid. MS (ESI): m/z=556 [M+H]$^+$.

Example 116

(R)-3-(2-Oxo-2-(2-(trifluoromethyl)pyrrolidin-1-yl)ethyl)-1-phenyl-8-(1H-pyrazolo[3,4-b]pyridine-5-carbonyl)-1,3,8-triazaspiro[4.5]decan-4-one

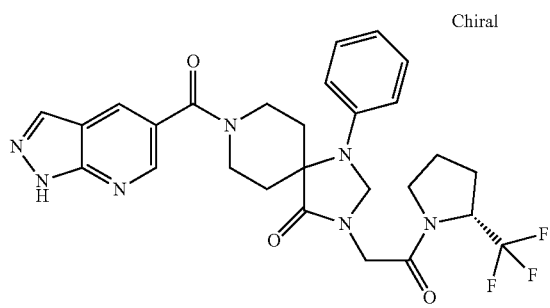 [SMILES: O=C(c1cnc2[nH]ncc2c1)N1CCC2(CC1)C(=O)N(CC(=O)N1CCC[C@@H]1C(F)(F)F)CN2c1ccccc1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (R)-2-(trifluoromethyl)pyrrolidine (CAS RN 1073556-31-6) as a white solid. MS(ESI): m/z=556 [M+H]$^+$.

Example 117 tert-Butyl 1-(2-(4-oxo-1-phenyl-8-(1H-pyrazolo[3,4-b]pyridine-5-carbonyl)-1,3,8-triazaspiro[4.5]decan-3-yl)acetyl)-1,6-diazaspiro[3.3]heptane-6-carboxylate

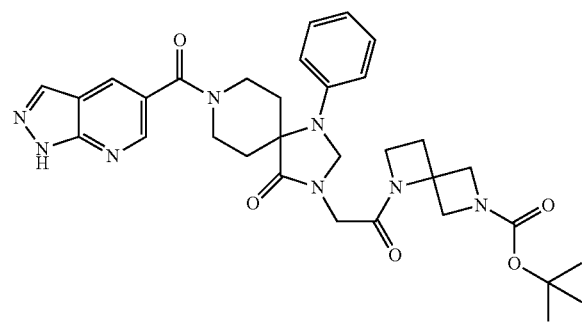 [SMILES: CC(C)(C)OC(=O)N1CC2(CCN2C(=O)CN2CN(c3ccccc3)C3(CCN(C(=O)c4cnc5[nH]ncc5c4)CC3)C2=O)C1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and tert-butyl 1,6-diazaspiro[3.3]heptane-6-carboxylate (CAS RN 1272412-72-2) as a white solid. MS(ESI): m/z=613 [M−H]$^−$.

Example 118

N-((rac,trans)-2-(3-((4-Methylpiperazin-1-yl)methyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide

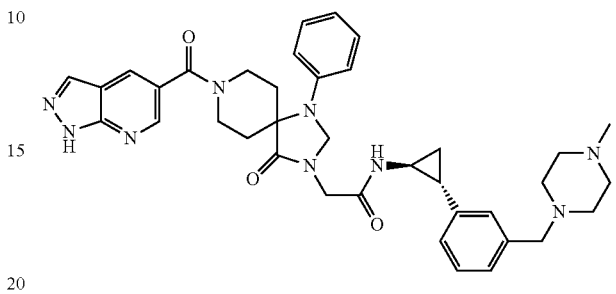

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (rac,trans)-2-(3-((4-methylpiperazin-1-yl)methyl)phenyl)cyclopropanamine as a white solid. MS (ESI): m/z=660 [M−H]$^−$.

Intermediate a) (rac,trans)-2-(3-((4-Methylpiperazin-1-yl)methyl)phenyl)cyclopropanamine The title compound was obtained in analogy to example 6, intermediate b, from tert-butyl N-[(rac,trans)-2-{3-[(4-methylpiperazin-1-yl)methyl]phenyl}cyclopropyl]carbamate using 4M HCl in dioxane as an off-white solid. MS: (ESI): m/z=246.0 [M+H]$^+$.

Intermediate b) tert-Butyl N-[(rac,trans)-2-{3-[(4-methylpiperazin-1-yl)methyl]phenyl}cyclopropyl]carbamate To a stirred solution of tert-butyl N-[(rac,trans)-2-(3-bromophenyl)cyclopropyl]carbamate (600 mg, 1.92 mmol) in dioxane (10 mL) and H$_2$O (1 mL) were added potassium 1-methyl-4-trifluoroboratomethylpiperazine (635 mg, 2.89 mmol, CAS RN 1015484-22-6) and K$_2$CO$_3$ (532 mg, 3.85 mmol, CAS RN 584-08-7) and reaction mixture was purged with argon for 15 min. Then X-Phos (36.8 mg, 0.077 mmol, CAS RN 564483-18-7) and Pd(OAc)$_2$ (8.6 mg, 0.038 mmol, CAS RN 3375-31-3) were added and the reaction mixture was again purged with argon for 10 min. The reaction mixture was stirred at 100° C. for 16 h and then diluted with H$_2$O (30 mL) and extracted with EtOAc (2×100 mL). The combined organic layers were dried over Na$_2$SO$_4$ and evaporated. The crude product was purified by column chromatography over amine silica gel (5-7% EtOAc/n-hexane) to get the title compound as a pale yellow liquid (300 mg, 45%). MS (ESI): m/z=346.2 [M+H]$^+$.

Intermediate c) tert-Butyl N-[(rac,trans)-2-(3-bromophenyl)cyclopropyl]carbamate To a stirred solution of (rac,trans)-2-(3-bromophenyl)cyclopropan-1-amine (2.5 g, 10.06 mmol, CAS RN 1314636-98-0) in DCM (50 mL) were added TEA (2.8 mL, 20.121 mmol) and boc anhydride (3.23 mL, 15.09 mmol, CAS RN 24424-99-5) under nitrogen atmosphere at RT and the reaction mixture was stirred at RT for 16 h. The reaction mixture was quenched with H₂O (100 mL) and extracted with DCM (2×250 mL). The combined organic layers were dried over Na₂SO₄ and evaporated. The residue was purified by column chromatography over silica gel (8-12% EtOAc/n-hexane) to get the title compound as an off-white solid (3 g, 95%). ¹H NMR (400 MHz, DMSO-d6) δ ppm 7.31 (m, 3H), 7.20 (t, J=7.72 Hz, 1H), 7.08 (d, J=7.6 Hz, 1H), 2.61 (m, 1H), 1.88 (m, 1H), 1.37 (s, 9H), 1.11 (m, 2H).

Example 119

2-[8-(1H-indazole-5-carbonyl)-2,2-dimethyl-4-oxo-1-phenyl-1,3,8-triazaspiro[4.5]decan-3-yl]-N-(2,2,2-trifluoroethyl)acetamide

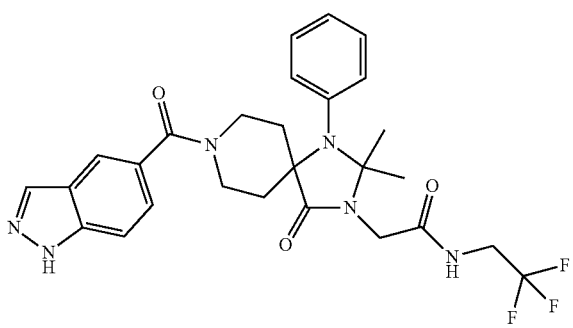 [SMILES: CC1(C)N(CC(=O)NCC(F)(F)F)C(=O)C2(CCN(C(=O)c3ccc4[nH]ncc4c3)CC2)N1c1ccccc1]

The title compound was obtained in analogy to example 17, from 2-(2,2-dimethyl-4-oxo-1-phenyl-1,3,8-triaza-spiro[4.5]dec-3-yl)-N-(2,2,2-trifluoro-ethyl)-acetamide and 1H-indazole-5-carboxylic acid (CAS RN 61700-61-6) as a white solid. MS (ESI): m/z=543.2 [M+H]⁺.

Intermediate a) 2-(2,2-Dimethyl-4-oxo-1-phenyl-1,3,8-triaza-spiro[4.5]dec-3-yl)-N-(2,2,2-trifluoro-ethyl)-acetamide The title compound was obtained in analogy to example 1, intermediate a, from 2-(8-benzyl-2,2-dimethyl-4-oxo-1-phenyl-1,3,8-triaza-spiro[4.5]dec-3-yl)-N-(2,2,2-trifluoro-ethyl)-acetamide as a brown oil. MS (EI): m/z=398.9 [M+H]⁺.

Intermediate b) 2-(8-Benzyl-2,2-dimethyl-4-oxo-1-phenyl-1,3,8-triaza-spiro[4.5]dec-3-yl)-N-(2,2,2-trifluoro-ethyl)-acetamide The title compound was obtained in analogy to example 1, intermediate b, from 8-benzyl-2,2-dimethyl-1-phenyl-1,3,8-triaza-spiro[4.5]decan-4-one and 2-chloro-N-(2,2,2-trifluoro-ethyl)-acetamide (CAS RN 170655-44-4) as a brown solid. MS (EI): m/z=488.8 [M+H]⁺.

Intermediate c) 8-Benzyl-2,2-dimethyl-1-phenyl-1,3,8-triaza-spiro[4.5]decan-4-one To a solution of 1-benzyl-4-phenylamino-piperidine-4-carboxylic acid amide (200 mg, 0.65 mmol; CAS RN 1096-03-3) in 2,2-dimethoxy-propane (10 mL, CAS RN 22094-18-4) was added p-TsOH monohydrate (246 mg, 1.29 mmol, CAS RN 6192-52-5). The reaction mixture was heated in a sealed tube at 80° C. for 6 h. Solvent was evaporated, the residue was dissolved in EtOAc (50 mL) and washed with saturated aqueous NaHCO₃ (20 mL). The organic layer was dried over Na₂SO₄, filtered and concentrated. The compound was purified by amine silica gel chromatography using an MPLC system eluting with a gradient of n-hexane:EtOAc (90:10 to 25:75) to get the title product along with other impurities as brown solid (105 mg). MS (EI): m/z=349.9 [M+H]⁺.

Example 120

N-(5-cyano-1,3-thiazol-2-yl)-2-[4-oxo-1-phenyl-8-(1H-pyrazolo[3,4-b]pyridine-5-carbonyl)-1,3,8-triazaspiro[4.5]decan-3-yl]acetamide

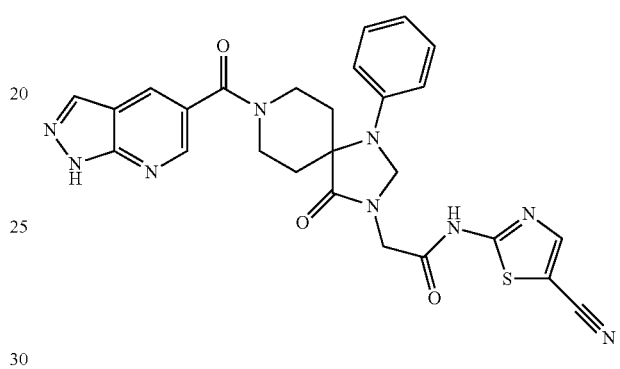

To a suspension of 2-(8-(tert-butoxycarbonyl)-4-oxo-1-phenyl-1,3,8-triazaspiro[4.5]decan-3-yl)acetic acid (150 mg, 385 μmol; CAS RN 180386-35-0) and oxalyl chloride (61.2 mg, 42.2 μL, 482 μmol; CAS RN 79-37-8) in DCM (1.5 mL) was added DMF (2.89 mg, 3.06 μL, 39.5 μmol) and the solution was stirred at RT over 1 hour. After complete evaporation, the residue was dissolved in DCM (1.5 mL) and added dropwise to a stirred suspension of 2-aminothiazole-5-carbonitrile (53 mg, 424 μmol; CAS RN 51640-52-9) and TEA (155 mg, 214 μL, 1.54 mmol) in DCM (1.5 mL) and the suspension was stirred at RT over 18 hours. The reaction mixture was poured on saturated aqueous NH₄Cl solution and DCM and the layers were separated. The aqueous layer was extracted twice with DCM. The organic layers were dried over MgSO₄, filtered, treated with silica gel and evaporated. The compound was purified by silica gel chromatography on a 4 g column using an MPLC system eluting with a gradient of n-heptane:EtOAc (100:0 to 0:100). The thus obtained crude product was dissolved in DCM (1 mL) and TFA (307 mg, 208 μL, 2.7 mmol) was added. After stirring at RT for 1.5 h, the mixture was evaporated. The residue was taken up in DMF (0.7 mL) and TEA (312 mg, 429 μL, 3.08 mmol), 1H-pyrazolo[3,4-b]pyridine-5-carboxylic acid (18.8 mg, 116 μmol; CAS RN 952182-02-4) and HBTU (43.8 mg, 116 μmol) were added the reaction mixture and stirred overnight at RT. The product was purified on a preparative HPLC (Gemini NX column) using a gradient of ACN:H₂O (containing 0.1% formic acid) (20:80 to 98:2) to give the title product as a white solid (0.021 g; 10.1%). MS (ESI): m/z=542.2 [M+H]⁺.

Example 121

N-[2-methyl-5-(trifluoromethyl)pyrazol-3-yl]-2-[4-oxo-1-phenyl-8-(1H-pyrazolo[3,4-b]pyridine-5-carbonyl)-1,3,8-triazaspiro[4.5]decan-3-yl]acetamide

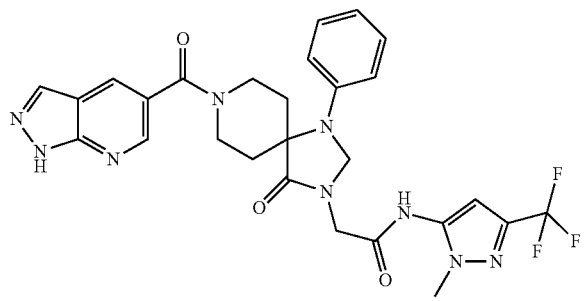 [SMILES: Cn1nc(C(F)(F)F)cc1NC(=O)CN1CN(c2ccccc2)C2(CCN(C(=O)c3cnc4[nH]ncc4c3)CC2)C1=O]

The title compound was obtained in analogy to example 36, from tert-butyl 3-[2-[[2-methyl-5-(trifluoromethyl)pyrazol-3-yl]amino]-2-oxo-ethyl]-4-oxo-1-phenyl-1,3,8-triazaspiro[4.5]decane-8-carboxylate and 1H-pyrazolo[3,4-b]pyridine-5-carboxylic acid (CAS RN 952182-02-4) as a white solid. MS (ESI): m/z=582.2 [M+H]$^+$.

Intermediate a) tert-Butyl 3-[2-[[2-methyl-5-(trifluoromethyl)pyrazol-3-yl]amino]-2-oxo-ethyl]-4-oxo-1-phenyl-1,3,8-triazaspiro[4.5]decane-8-carboxylate The title compound was obtained in analogy to example 75, intermediate a, from 2-(8-(tert-butoxycarbonyl)-4-oxo-1-phenyl-1,3,8-triazaspiro[4.5]decan-3-yl)acetic acid (CAS RN 180386-35-0) and 1-methyl-3-(trifluoromethyl)-1H-pyrazol-5-amine (CAS RN 149978-43-8) as a light brown gum. MS (EI): m/z=535.2 [M+H]$^+$.

Example 122

N-((rac,trans)-2-(3-(Morpholinomethyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide

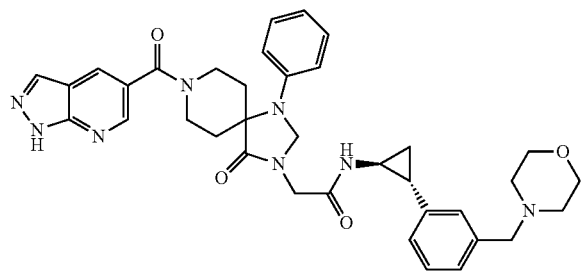 [SMILES: O=C(CN1CN(c2ccccc2)C2(CCN(C(=O)c3cnc4[nH]ncc4c3)CC2)C1=O)N[C@H]1C[C@@H]1c1cccc(CN2CCOCC2)c1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (rac,trans)-2-[3-(morpholinomethyl)phenyl]cyclopropanamine dihydrochloride salt as a white solid. MS (ESI): m/z=649 [M+H]$^+$.

Intermediate a) (rac,trans)-2-[3-(Morpholinomethyl)phenyl]cyclopropanamine; dihydrochloride The title compound was obtained in analogy to example 6, intermediate b, from tert-butyl N-[(rac,trans)-2-[3-(morpholin-4-ylmethyl)phenyl]cyclopropyl]carbamate using 4M HCl in dioxane as a pale yellow liquid. MS: (ESI): m/z=332.8 [M+H]$^+$.

Intermediate b) tert-Butyl N-[(rac,trans)-2-[3-(morpholin-4-ylmethyl)phenyl]cyclopropyl]carbamate To a stirred solution of tert-butyl N-[(rac,trans)-2-(3-bromophenyl)cyclopropyl]carbamate (600 mg, 1.92 mmol) in dioxane (10 mL) and H$_2$O (1 mL) were added potassium (morpholin-4-yl)methyltrifluoroborate (597 mg, 2.885 mmol, CAS RN 936329-94-1) and K$_2$CO$_3$ (532 mg, 3.85 mmol, CAS RN 584-08-7) and the reaction mixture was purged with argon for 15 min. Then X-Phos (36.8 mg, 0.077 mmol, CAS RN 564483-18-7) and Pd(OAc)$_2$ (8.6 mg, 0.038 mmol, CAS RN 375-31-3) were added to the reaction mixture and the reaction mixture was again purged with argon for 10 min. The reaction mixture was stirred at 100° C. for 16 h, then diluted with H$_2$O (30 mL) and extracted with EtOAc (2×100 mL). The combined organic layers were dried over Na$_2$SO$_4$, filtered and the filtrate was evaporated under vacuum. The residue was purified by column chromatography over amine silica gel (5-7% EtOAc/n-hexane) to afford the title compound as a pale yellow liquid (460 mg, 72%). MS (ESI): m/z=332.8 [M+H]$^+$.

Intermediate c) tert-Butyl N-[(rac,trans)-2-(3-bromophenyl)cyclopropyl]carbamate To a stirred solution of (rac, trans)-2-(3-bromophenyl)cyclopropan-1-amine (2.5 g, 10.06 mmol, MFCD11936660) in DCM (50 mL) were added TEA (2.8 mL, 20.121 mmol, CAS RN 121-44-8) and boc anhydride (3.23 mL, 15.09 mmol, CAS RN 24424-99-5) under nitrogen atmosphere at 25° C. and the reaction mixture was stirred at 25° C. for 16 h. The reaction mixture was quenched with H$_2$O (100 mL) and extracted with DCM (2×250 mL). The combined organic layers were dried over Na$_2$SO$_4$ and evaporated. The resulting crude product was purified by column chromatography over silica gel (8-12% EtOAc/n-hexane) to get the title compound as an off-white solid (3 g, 95%). $^1$H NMR (400 MHz, DMSO-d6) δ ppm 7.31 (m, 3H), 7.20 (t, J=7.72 Hz, 1H), 7.08 (d, J=7.6 Hz, 1H), 2.61 (m, 1H), 1.88 (m, 1H), 1.37 (s, 9H), 1.11 (m, 2H).

Example 123

N-(2-(2-((4-methylpiperazin-1-yl)methyl)phenyl)cyclopropyl)-2-(4-oxo-1-phenyl-8-(1H-pyrazolo[3,4-b]pyridine-5-carbonyl)-1,3,8-triazaspiro[4.5]decan-3-yl)acetamide

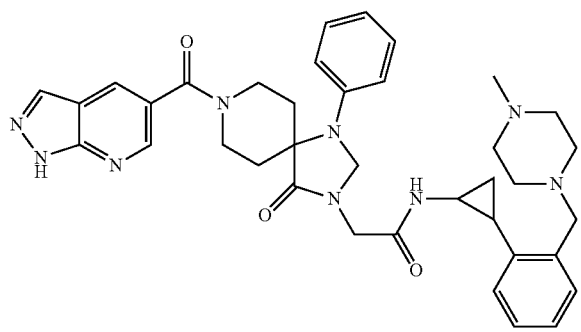 [SMILES: CN1CCN(Cc2ccccc2C2CC2NC(=O)CN2CN(c3ccccc3)C3(CCN(C(=O)c4cnc5[nH]ncc5c4)CC3)C2=O)CC1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 2-[2-[(4-methylpiperazin-1-yl)methyl]phenyl]cyclopropanamine trihydrochloride salt as a white solid. MS (ESI) m/z=662 [M+H]+.

Intermediate a) 2-[2-[(4-Methylpiperazin-1-yl)methyl]phenyl]cyclopropanamine trihydrochloride salt The title compound was obtained in analogy to example 6, intermediate b, from tert-butyl N-(2-{2-[(4-methylpiperazin-1-yl)methyl]phenyl}cyclopropyl) carbamate using 4M HCl in dioxane as an off-white solid. MS (ESI): m/z=246.3 [M+H]+.

Intermediate b) tert-Butyl N-(2-{2-[(4-methylpiperazin-1-yl)methyl]phenyl}cyclopropyl) carbamate The title compound was obtained in analogy to example 122, intermediate b, from tert-butyl N-[2-(3-bromophenyl)cyclopropyl]carbamate and potassium 1-methyl-4-trifluoroborato-methylpiperazine (CAS RN 1015484-22-6) as a pale yellow liquid. MS (ESI): m/z=346.2 [M+H]+.

Intermediate c) tert-Butyl N-[2-(3-bromophenyl)cyclopropyl]carbamate

The title compound was obtained in analogy to example 122, intermediate c, from 2-(2-bromophenyl)cyclopropan-1-amine hydrochloride (CAS RN 1354954-27-0) as an off-white solid. MS: (ESI): m/z=312.0 [M+H]+.

Example 124

3-(2-Oxo-2-(2-(trifluoromethyl)morpholino)ethyl)-1-phenyl-8-(1H-pyrazolo[3,4-b]pyridine-5-carbonyl)-1,3,8-triazaspiro[4.5]decan-4-one

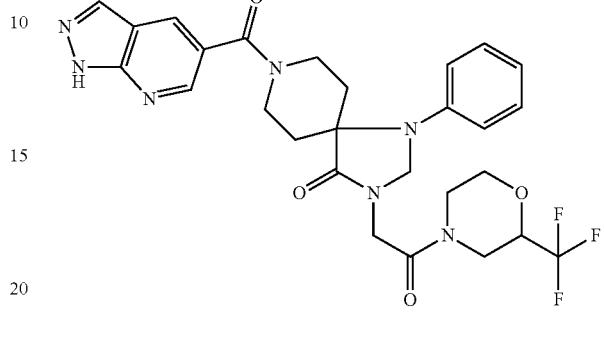

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 2-(trifluoromethyl)morpholine hydrochloride (CAS RN 1196152-51-8) as a white solid. MS (ESI): m/z=572 [M+H]+.

Example 125

2-(1-(3-Chlorophenyl)-4-oxo-8-(1H-pyrazolo[3,4-b]pyridine-5-carbonyl)-1,3,8-triazaspiro[4.5]decan-3-yl)-N-(2,2,2-trifluoroethyl)acetamide

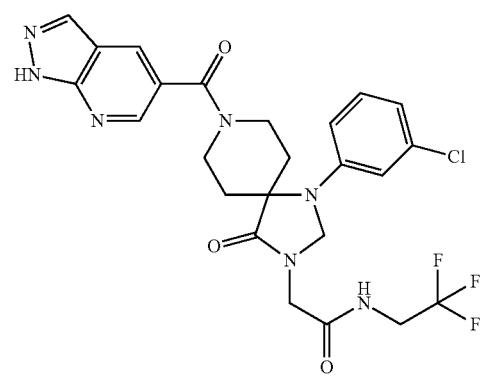 [SMILES: O=C(CN1CN(c2cccc(Cl)c2)C2(CCN(C(=O)c3cnc4[nH]ncc4c3)CC2)C1=O)NCC(F)(F)F]

The title compound was obtained in analogy to example 17, from 2-[1-(3-chlorophenyl)-4-oxo-1,3,8-triazaspiro[4.5]decan-3-yl]-N-(2,2,2-trifluoroethyl)acetamide and 1H-pyrazolo[3,4-b]pyridine-5-carboxylic acid (CAS RN 952182-02-4) as a white solid. MS (ESI): m/z=550 [M+H]+.

Intermediate a) 2-[1-(3-Chlorophenyl)-4-oxo-1,3,8-triazaspiro[4.5]decan-3-yl]-N-(2,2,2-trifluoroethyl)acetamide The title compound was obtained in analogy to example 81, intermediate a, from 2-[8-benzyl-1-(3-chlorophenyl)-4-oxo-1,3,8-triazaspiro[4.5]decan-3-yl]-N-(2,2,2-trifluoroethyl)acetamide as a white gum. MS (EI): m/z=405 [M+H]+.

Intermediate b) 2-[8-Benzyl-1-(3-chlorophenyl)-4-oxo-1,3,8-triazaspiro[4.5]decan-3-yl]-N-(2,2,2-trifluoroethyl)acetamide The title compound was obtained in analogy to example 1, intermediate b, from 8-benzyl-1-(3-chlorophenyl)-1,3,8-triazaspiro[4.5]decan-4-one (prepared as described in J. Med. Chem. 2010, 53, 6706-6719) and 2-chloro-N-(2,2,2-trifluoro-ethyl)-acetamide (CAS RN 170655-44-4) as a white solid. MS (EI): m/z=495.3 [M+H]$^+$.

Example 126

3-[2-(4-Cyclopropylpiperazin-1-yl)-2-oxoethyl]-1-phenyl-8-(1H-pyrazolo[3,4-b]pyridine-5-carbonyl)-1,3,8-triazaspiro[4.5]decan-4-one

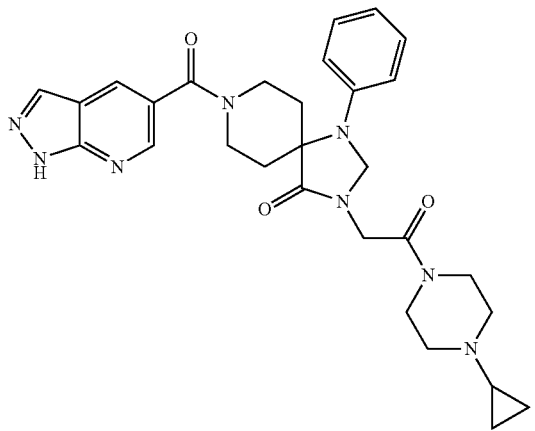 [SMILES: O=C(CN1CN(c2ccccc2)C2(CCN(C(=O)c3cnc4[nH]ncc4c3)CC2)C1=O)N1CCN(C2CC2)CC1]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 1-cyclopropylpiperazine dihydrochloride (CAS RN 139256-79-4) as a white solid. MS (ESI): m/z=543.3 [M+H]$^+$.

Example 127

3-[2-Oxo-2-(3,3,4-trimethylpiperazin-1-yl)ethyl]-1-phenyl-8-(1H-pyrazolo[3,4-b]pyridine-5-carbonyl)-1,3,8-triazaspiro[4.5]decan-4-one

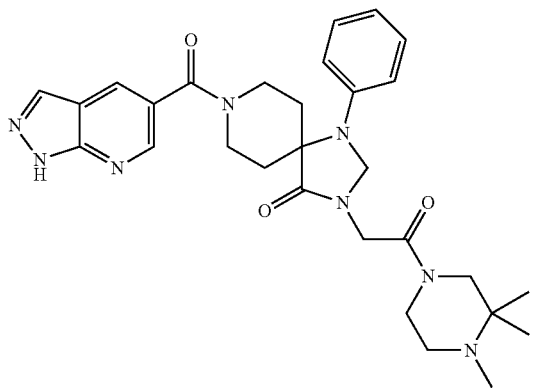 [SMILES: CN1CCN(C(=O)CN2CN(c3ccccc3)C3(CCN(C(=O)c4cnc5[nH]ncc5c4)CC3)C2=O)CC1(C)C]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 1,2,2-trimethylpiperazine hydrochloride (CAS RN 932047-03-5) as a white solid. MS(ESI): m/z=545.3 [M+H]$^+$.

Example 128

3-[2-Oxo-2-(3-pyrrolidin-1-ylpyrrolidin-1-yl)ethyl]-1-phenyl-8-(1H-pyrazolo[3,4-b]pyridine-5-carbonyl)-1,3,8-triazaspiro[4.5]decan-4-one

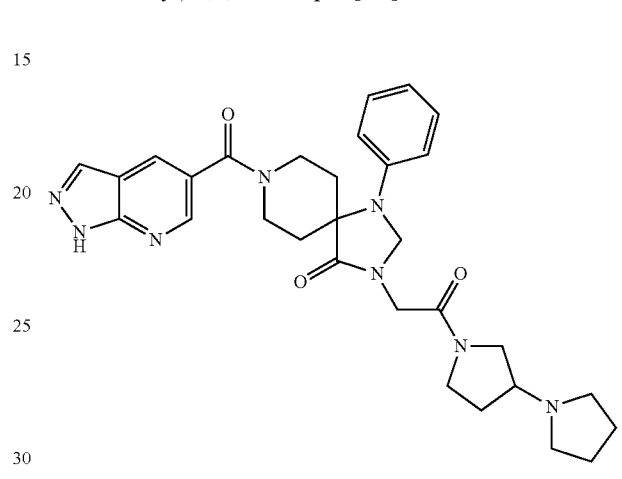

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 1,3'-bipyrrolidine dihydrochloride (CAS RN 957540-36-2) as a white solid. MS (ESI): m/z=557.3 [M+H]$^-$.

Example 129

3-[2-(4-Cyclopropyl-3-oxopiperazin-1-yl)-2-oxoethyl]-1-phenyl-8-(1H-pyrazolo[3,4-b]pyridine-5-carbonyl)-1,3,8-triazaspiro[4.5]decan-4-one

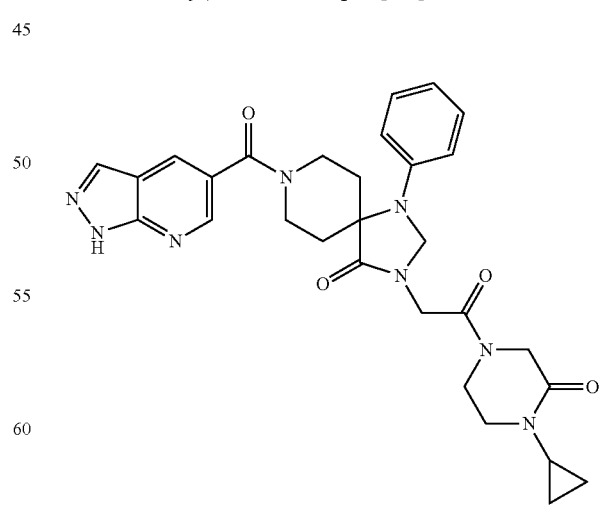

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 1-cyclopropylpiperazin-2-one (CAS RN 907972-23-0) as a white solid. MS (ESI): m/z=557.3 [M+H]⁻.

Example 130

3-[2-[(rac,cis)-3-Hydroxy-4-methylpyrrolidin-1-yl]-2-oxoethyl]-1-phenyl-8-(1H-pyrazolo[3,4-b]pyridine-5-carbonyl)-1,3,8-triazaspiro[4.5]decan-4-one

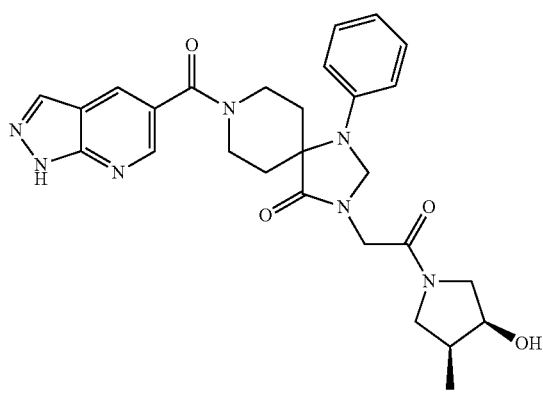 [SMILES: C[C@H]1CN(C(=O)CN2CN(c3ccccc3)C3(CCN(C(=O)c4cnc5[nH]ncc5c4)CC3)C2=O)C[C@H]1O]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (rac,cis)-4-methylpyrrolidin-3-ol hydrochloride (CAS RN 265108-43-8) as a white solid. MS (ESI): m/z=518.3 [M+H]⁺.

Example 131

3-[2-[(rac,trans)-3-Hydroxy-4-methylpyrrolidin-1-yl]-2-oxoethyl]-1-phenyl-8-(1H-pyrazolo[3,4-b]pyridine-5-carbonyl)-1,3,8-triazaspiro[4.5]decan-4-one

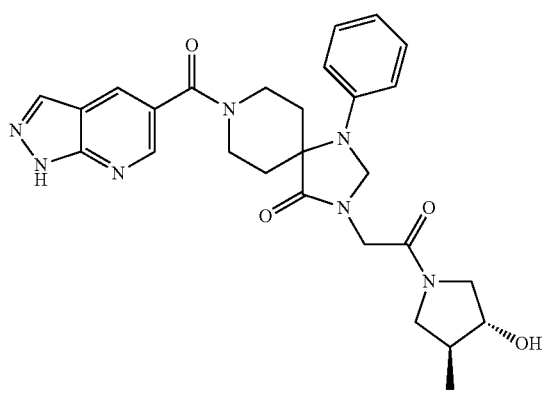 [SMILES: C[C@H]1CN(C(=O)CN2CN(c3ccccc3)C3(CCN(C(=O)c4cnc5[nH]ncc5c4)CC3)C2=O)C[C@@H]1O]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (rac,trans)-4-methylpyrrolidin-3-ol hydrochloride (CAS RN 265108-42-7) as a white solid. MS (ESI): m/z=518.3 [M+H]⁺.

Example 132

3-[2-[4-Methyl-3-(trifluoromethyl)piperazin-1-yl]-2-oxoethyl]-1-phenyl-8-(1H-pyrazolo[3,4-b]pyridine-5-carbonyl)-1,3,8-triazaspiro[4.5]decan-4-one

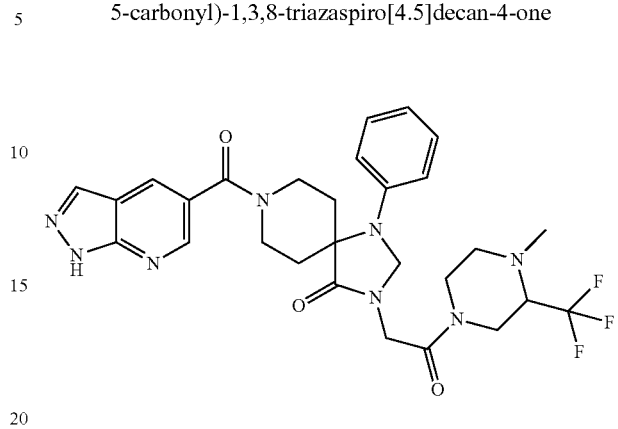

The title compound was obtained in analogy to example 17, from 3-[2-[4-methyl-3-(trifluoromethyl)piperazin-1-yl]-2-oxo-ethyl]-1-phenyl-1,3,8-triazaspiro[4.5]decan-4-one and 1H-pyrazolo[3,4-b]pyridine-5-carboxylic acid (CAS RN 952182-02-4) as a white solid. MS (ESI): m/z=585.3 [M+H]⁺.

Intermediate a) 3-[2-[4-Methyl-3-(trifluoromethyl)piperazin-1-yl]-2-oxo-ethyl]-1-phenyl-1,3,8-triazaspiro[4.5]decan-4-one The title compound was obtained in analogy to example 1, intermediate a, from 8-benzyl-3-[2-[4-methyl-3-(trifluoromethyl)piperazin-1-yl]-2-oxo-ethyl]-1-phenyl-1,3,8-triazaspiro[4.5]decan-4-one as a white foam. MS (ESI): m/z=440.2 [M+H]⁺.

Intermediate b) 8-Benzyl-3-[2-[4-methyl-3-(trifluoromethyl)piperazin-1-yl]-2-oxo-ethyl]-1-phenyl-1,3,8-triazaspiro[4.5]decan-4-one To a suspension of tert-butyl 4-(2-(8-benzyl-4-oxo-1-phenyl-1,3,8-triazaspiro[4.5]decan-3-yl)acetyl)-2-(trifluoromethyl)piperazine-1-carboxylate (340 mg, 552 μmol) in DCM (2 mL) was added TFA (1.26 g, 851 μL, 11 mmol) and stirring was continued at RT for 1 hour. The reaction mixture was completely evaporated, taken up in EtOAc and poured on saturated aqueous NH₄Cl solution. The layers were separated. The aqueous layer was extracted once with EtOAc. The organic layers were dried over MgSO₄, filtered and evaporated. The residue was dissolved in dioxane (4 mL) and formaldehyde (448 mg, 411 μL, 5.52 mmol) and sodium triacetoxyborohydride (293 mg, 1.38 mmol) were added. Stirring was continued at RT for 6 hours. The reaction mixture was poured on saturated aqueous NaHCO₃ solution and EtOAc and the layers were separated. The organic layer was dried over MgSO₄, filtered, treated with silica gel and evaporated. The compound was purified by silica gel chromatography on a 12 g column using an MPLC system eluting with a gradient of DCM:MeOH (100:0 to 80:20) to get the title compound as a light brown foam (0.224 g; 76.6%). MS (ESI): m/z=530.3 [M+H]⁺.

Intermediate c) tert-Butyl 4-(2-(8-benzyl-4-oxo-1-phenyl-1,3,8-triazaspiro[4.5]decan-3-yl)acetyl)-2-(trifluoromethyl)piperazine-1-carboxylate The title compound was obtained in analogy to example 25, from 2-(8-benzyl-4-oxo-1-phenyl-1,3,8-triazaspiro[4.5]

decan-3-yl)acetic acid (example 75, intermediate b) and tert-butyl 2-(trifluoromethyl)piperazine-1-carboxylate (CAS RN 886779-77-7) as a light brown foam. MS (ESI): m/z=616.3 [M+H]⁺.

Example 133

8-(1H-Indazole-5-carbonyl)-3-[2-[4-methyl-3-(trifluoromethyl)piperazin-1-yl]-2-oxoethyl]-1-phenyl-1,3,8-triazaspiro[4.5]decan-4-one

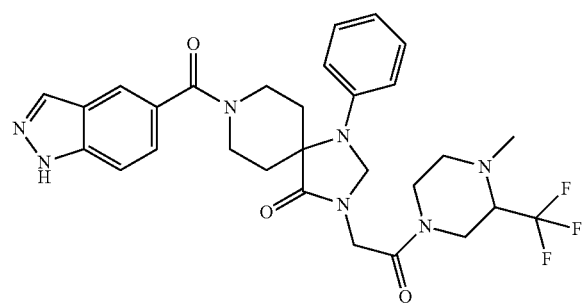 [SMILES: CN1CCN(C(=O)CN2CN(c3ccccc3)C3(CCN(C(=O)c4ccc5[nH]ncc5c4)CC3)C2=O)CC1C(F)(F)F]

The title compound was obtained in analogy to example 17, from 3-[2-[4-methyl-3-(trifluoromethyl)piperazin-1-yl]-2-oxo-ethyl]-1-phenyl-1,3,8-triazaspiro[4.5]decan-4-one (example 132, intermediate a) and 1H-indazole-5-carboxylic acid (CAS RN 61700-61-6) as a white solid. MS (ESI): m/z=584.3 [M+H]⁺.

Example 134

2-(4-Oxo-1-phenyl-8-(1H-pyrazolo[3,4-b]pyridine-5-carbonyl)-1,3,8-triazaspiro[4.5]decan-3-yl)-N-(6-(trifluoromethyl)pyridin-2-yl)acetamide

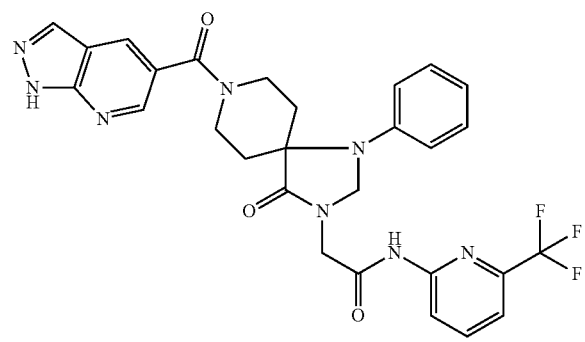 [SMILES: O=C(CN1CN(c2ccccc2)C2(CCN(C(=O)c3cnc4[nH]ncc4c3)CC2)C1=O)Nc1cccc(C(F)(F)F)n1]

The title compound was obtained in analogy to example 75, intermediate a, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 6-(trifluoromethyl)pyridin-2-amine (CAS RN 34486-24-3) as a white solid. MS (ESI): m/z=579.3 [M+H]⁺.

Example 135

3-[2-[3-(Aminomethyl)pyrrolidin-1-yl]-2-oxoethyl]-1-phenyl-8-(1H-pyrazolo[3,4-b]pyridine-5-carbonyl)-1,3,8-triazaspiro[4.5]decan-4-one

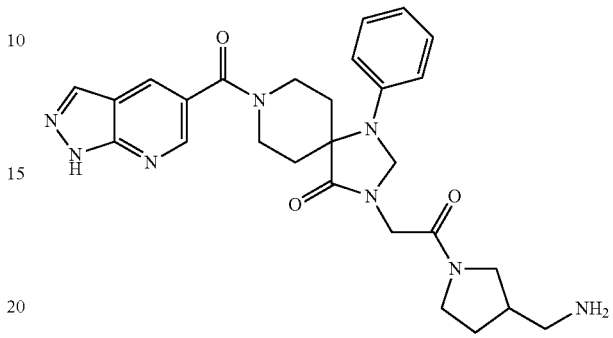

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and tert-butyl (pyrrolidin-3-ylmethyl)carbamate (CAS RN 149366-79-0) and treatment of the resulting intermediate with 4M HCl in dioxane, as a light brown foam. MS (ESI): m/z=517.3 [M+H]⁺.

Example 136

3-[2-[3-[2-(Dimethylamino)ethyl]pyrrolidin-1-yl]-2-oxoethyl]-1-phenyl-8-(1H-pyrazolo[3,4-b]pyridine-5-carbonyl)-1,3,8-triazaspiro[4.5]decan-4-one

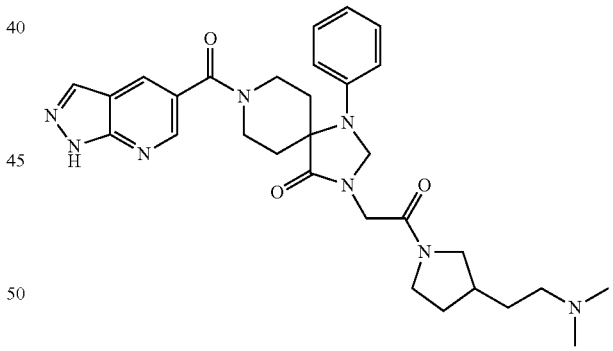

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and N,N-dimethyl-2-(pyrrolidin-3-yl)ethanamine as a white solid. MS (ESI): m/z=559.3 [M+H]⁺.

Intermediate a)
N,N-Dimethyl-2-(pyrrolidin-3-yl)ethanamine

The title compound was obtained in analogy to example 1, intermediate a, from benzyl 3-(2-(dimethylamino)ethyl)pyrrolidine-1-carboxylate (CAS RN 1420958-32-2) as a white oil. MS (EI): m/z=142.1 [M].

Example 137

N-(2-(Morpholinomethyl)phenyl)-2-(4-oxo-1-phenyl-8-(1H-pyrazolo[3,4-b]pyridine-5-carbonyl)-1,3,8-triazaspiro[4.5]decan-3-yl)acetamide

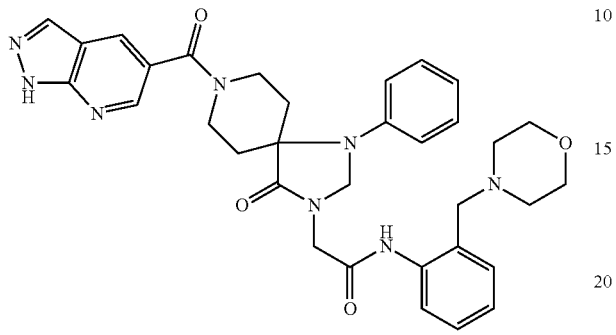

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 2-(morpholinomethyl)aniline (CAS RN 95539-61-0) as a white solid. MS (ESI): m/z=609.3 [M+H]$^+$.

Example 138

N-[2-(Dimethylamino)ethyl]-2-[4-oxo-1-phenyl-8-(1H-pyrazolo[3,4-b]pyridine-5-carbonyl)-1,3,8-triazaspiro[4.5]decan-3-yl]acetamide

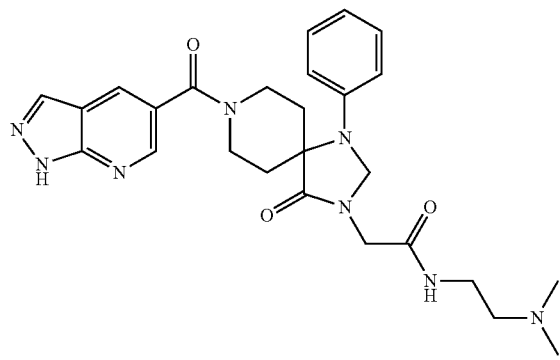 [SMILES: CN(C)CCNC(=O)CN1CN(c2ccccc2)C2(CCN(C(=O)c3cnc4[nH]ncc4c3)CC2)C1=O]

The title compound was obtained in analogy to example 25, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and N1,N1-dimethylethane-1,2-diamine (CAS RN 108-00-9) as a white solid. MS (ESI): m/z=505.3 [M+H]$^+$.

Example 139

N-[2-(Dimethylamino)ethyl]-2-[4-oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide

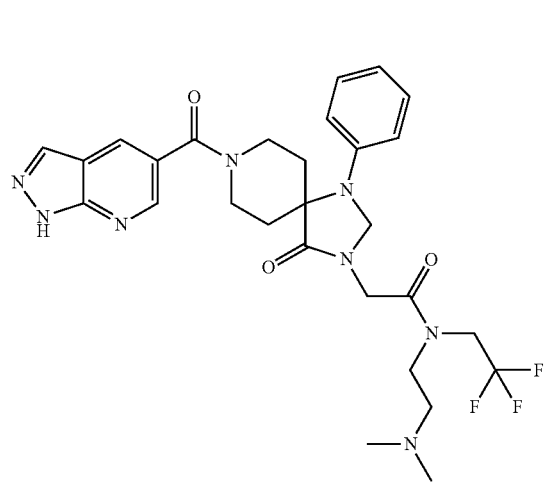 [SMILES: CN(C)CCN(CC(F)(F)F)C(=O)CN1CN(c2ccccc2)C2(CCN(C(=O)c3cnc4[nH]ncc4c3)CC2)C1=O]

The title compound was obtained in analogy to example 36, from tert-butyl 3-[2-[2-(dimethylamino)ethyl-(2,2,2-trifluoroethyl)amino]-2-oxo-ethyl]-4-oxo-1-phenyl-1,3,8-triazaspiro[4.5]decane-8-carboxylate and 1H-pyrazolo[3,4-b]pyridine-5-carboxylic acid (CAS RN 952182-02-4) as a white solid. MS (ESI): m/z=587.3 [M+H]$^+$.

Intermediate a) tert-Butyl 3-[2-[2-(dimethylamino)ethyl-(2,2,2-trifluoroethyl)amino]-2-oxo-ethyl]-4-oxo-1-phenyl-1,3,8-triazaspiro[4.5]decane-8-carboxylate To a solution of tert-butyl 4-oxo-3-(2-oxo-2-((2,2,2-trifluoroethyl)amino)ethyl)-1-phenyl-1,3,8-triazaspiro[4.5]decane-8-carboxylate (100 mg, 213 μmol, example 17, intermediate b) in ACN (1 mL) were added 2-bromo-N,N-dimethylethanamine hydrobromide (59.4 mg, 255 μmol; CAS RN 2862-39-7) and cesium carbonate (208 mg, 638 μmol) and the suspension was heated at 90° C. in a sealed tube for 16 hours. After cooling down, the reaction mixture was filtered over a microfilter. The filtrate was treated with silica gel and evaporated. The compound was purified by silica gel chromatography on a 4 g column using an MPLC (ISCO) system eluting with a gradient of DCM:MeOH (100:0 to 90:10) to get the title compound as a light brown gum (0.024 g; 20.8%). MS (ESI): m/z=542.3 [M+H]$^+$.

Example 140

(R)- or (S)-3-(2-Oxo-2-(2-(trifluoromethyl)morpholino)ethyl)-1-phenyl-8-(1H-pyrazolo[4,3-b]pyridine-5-carbonyl)-1,3,8-triazaspiro[4.5]decan-4-one

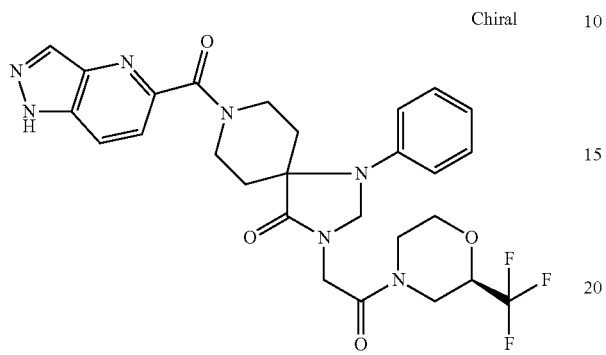

The title compound was obtained in analogy to example 17, from 3-[2-oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt and 1H-pyrazolo[4,3-b]pyridine-5-carboxylic acid (CAS RN 1260670-03-8) as a white solid. MS (ESI): m/z=572.2 [M+H]⁻.

Intermediate a) 3-[2-Oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt The title compound was obtained in analogy to example 21, intermediate c, from tert-butyl 4-oxo-3-[2-oxo-2-[(2R or 2S)-2-(trifluoromethyl)morpholin-4-yl]ethyl]-1-phenyl-1,3,8-triazaspiro[4.5]decane-8-carboxylate without extraction as a blue oil. MS (ESI): m/z=427.3 [M-TFA+H]⁺.

Intermediate b) tert-Butyl 4-oxo-3-[2-oxo-2-[(2R or 2S)-2-(trifluoromethyl)morpholin-4-yl]ethyl]-1-phenyl-1,3,8-triazaspiro[4.5]decane-8-carboxylate The title compound was obtained from racemic tert-butyl 4-oxo-3-[2-oxo-2-[2-(trifluoromethyl)morpholin-4-yl]ethyl]-1-phenyl-1,3,8-triazaspiro[4.5]decane-8-carboxylate by preparative chiral HPLC (Chiralpak-AD column) using an isocratic mixture of 2-propanol:n-heptane (20:80) as an off-white solid. MS (ESI): m/z=471.2 [M-C₄H₈+H]⁺.

Intermediate c) tert-Butyl 4-oxo-3-[2-oxo-2-[2-(trifluoromethyl)morpholin-4-yl]ethyl]-1-phenyl-1,3,8-triazaspiro[4.5]decane-8-carboxylate The title compound was obtained in analogy to example 25, from 2-(8-(tert-butoxycarbonyl)-4-oxo-1-phenyl-1,3,8-triazaspiro[4.5]decan-3-yl)acetic acid (CAS RN 180386-35-0) and 2-(trifluoromethyl)morpholine hydrochloride (CAS RN 1196152-51-8) as a light brown gum. MS (ESI): m/z=471.2 [M-C₄H₈+H]⁺.

Example 141

2-[4-Oxo-1-phenyl-8-(1H-pyrazolo[3,4-b]pyridine-5-carbonyl)-1,3,8-triazaspiro[4.5]decan-3-yl]-N-[1-(2,2,2-trifluoroethyl)pyrazol-3-yl]acetamide

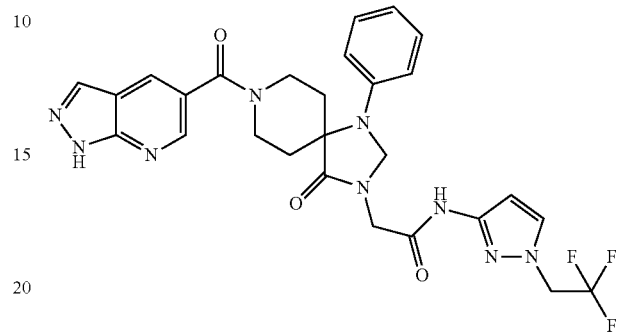

The title compound was obtained in analogy to example 75, intermediate a, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and 1-(2,2,2-trifluoroethyl)-1H-pyrazol-3-amine (CAS RN 947179-47-7) as a light yellow solid. MS (ESI): m/z=582.2 [M+H]⁺.

Example 142

(R)- or (S)-8-(1H-Indazole-5-carbonyl)-3-(2-oxo-2-(2-(trifluoromethyl)morpholino)ethyl)-1-phenyl-1,3,8-triazaspiro[4.5]decan-4-one

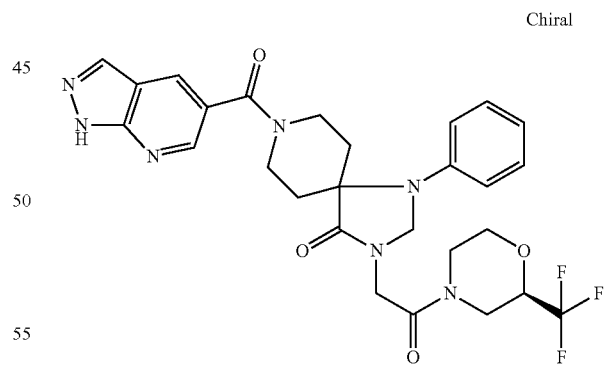

The title compound was obtained in analogy to example 17, from 3-[2-oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt (example 140, intermediate a) and 1H-pyrazolo[4,3-b]pyridine-5-carboxylic acid (CAS RN 952182-02-4) as a white solid. MS (ESI): m/z=572.2 [M+H]⁺.

Example 143

(R)- or (S)-8-(1H-indazole-5-carbonyl)-3-(2-oxo-2-(2-(trifluoromethyl)morpholino)ethyl)-1-phenyl-1,3,8-triazaspiro[4.5]decan-4-one Chiral

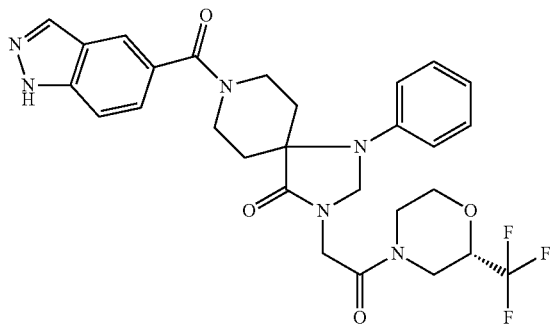

The title compound was obtained in analogy to example 17, from 3-[2-oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt and 1H-indazole-5-carboxylic acid (CAS RN 61700-61-6) as a white solid. MS (ESI): m/z=571.2 [M+H]$^+$.

Intermediate a) 3-[2-Oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt The title compound was obtained in analogy to example 21, intermediate c, from tert-butyl 4-oxo-3-[2-oxo-2-[(2R or 2S)-2-(trifluoromethyl)morpholin-4-yl]ethyl]-1-phenyl-1,3,8-triazaspiro[4.5]decane-8-carboxylate without extraction as a blue oil. MS (ESI): m/z=427.3 [M+H]$^+$ (free base).

Intermediate b) tert-Butyl 4-oxo-3-[2-oxo-2-[(2R or 2S)-2-(trifluoromethyl)morpholin-4-yl]ethyl]-1-phenyl-1,3,8-triazaspiro[4.5]decane-8-carboxylate The title compound was obtained from racemic tert-butyl 4-oxo-3-[2-oxo-2-[2-(trifluoromethyl)morpholin-4-yl]ethyl]-1-phenyl-1,3,8-triazaspiro[4.5]decane-8-carboxylate by preparative chiral HPLC (Chiralpak-AD column) using an isocratic mixture of 2-propanol:n-heptane (20:80) as an off-white solid. MS (ESI): m/z=471.2 [M−C$_4$H$_8$+H]$^+$.

Example 144

(S)- or (R)-3-(2-Oxo-2-(2-(trifluoromethyl)morpholino)ethyl)-1-phenyl-8-(1H-pyrazolo[3,4-b]pyridine-5-carbonyl)-1,3,8-triazaspiro[4.5]decan-4-one Chiral

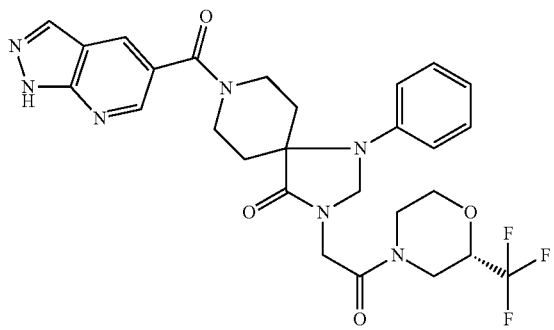

The title compound was obtained in analogy to example 17, from 3-[2-oxo-2-[(2S or 2R)-2-(trifluoromethyl)morpholin-4-yl]ethyl]-1-phenyl-1,3,8-triazaspiro[4.5]decan-4-one 2,2,2-trifluoroacetic acid salt (example 143, intermediate a) and 1H-pyrazolo[4,3-b]pyridine-5-carboxylic acid (CAS RN 952182-02-4) as a white solid. MS (ESI): m/z=572.2 [M+H]$^+$.

Example 145

(S)- or (R)-3-(2-Oxo-2-(2-(trifluoromethyl)morpholino)ethyl)-1-phenyl-8-(1H-pyrazolo[4,3-b]pyridine-5-carbonyl)-1,3,8-triazaspiro[4.5]decan-4-one Chiral

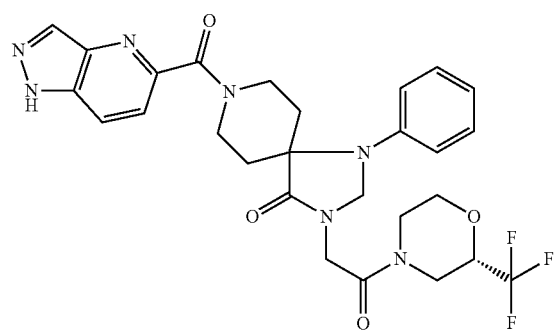

The title compound was obtained in analogy to example 17, from 3-[2-oxo-2-[(2S or 2R)-2-(trifluoromethyl)morpholin-4-yl]ethyl]-1-phenyl-1,3,8-triazaspiro[4.5]decan-4-one 2,2,2-trifluoroacetic acid salt (example 143, intermediate a) and 1H-pyrazolo[4,3-b]pyridine-5-carboxylic acid (CAS RN 1260670-03-8) as a white solid. MS (ESI): m/z=572.2 [M+H]$^+$.

Example 146

(R)- or (S)-3-(2-Oxo-2-(2-(trifluoromethyl)morpholino)ethyl)-1-phenyl-8-(1H-pyrazolo[3,4-c]pyridine-5-carbonyl)-1,3,8-triazaspiro[4.5]decan-4-one Chiral

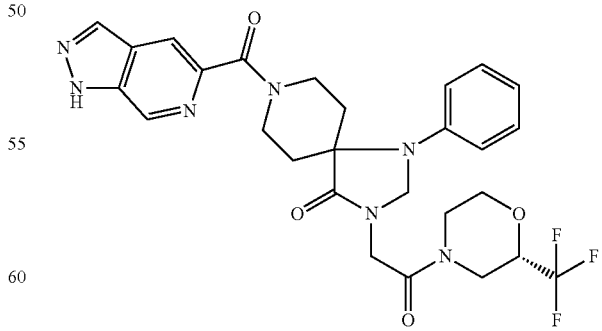

The title compound was obtained in analogy to example 17, from 3-[2-oxo-2-[(2R or 2S)-2-(trifluoromethyl)morpholin-4-yl]ethyl]-1-phenyl-1,3,8-triazaspiro[4.5]decan-4-one 2,2,2-trifluoroacetic acid salt (example 143, intermediate a) and 1H-pyrazolo[3,4-c]pyridine-5-carboxylic acid (CAS RN 1256824-45-9) as a white solid. MS (ESI): m/z=572.2 [M+H]$^+$.

Example 147

(S)- or (R)-3-(2-Oxo-2-(2-(trifluoromethyl)morpholino)ethyl)-1-phenyl-8-(1H-pyrazolo[3,4-c]pyridine-5-carbonyl)-1,3,8-triazaspiro[4.5]decan-4-one

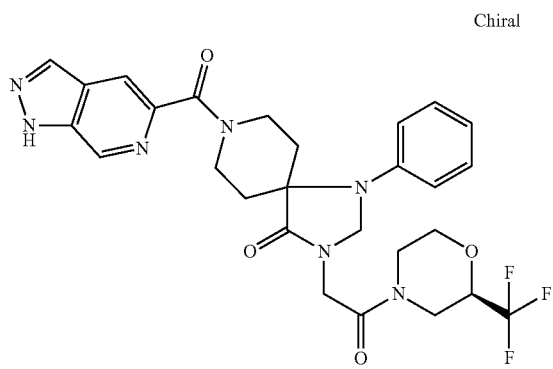 [SMILES: O=C(CN1CN(c2ccccc2)C2(CCN(C(=O)c3ccc4[nH]ncc4c3)CC2)C1=O)N1CCO[C@@H](C(F)(F)F)C1]

The title compound was obtained in analogy to example 17, from 3-[2-oxo-2-[(2S or 2R)-2-(trifluoromethyl)morpholin-4-yl]ethyl]-1-phenyl-1,3,8-triazaspiro[4.5]decan-4-one 2,2,2-trifluoroacetic acid salt (example 140, intermediate a) and 1H-pyrazolo[3,4-c]pyridine-5-carboxylic acid (CAS RN 1256824-45-9) as a white solid. MS (ESI): m/z=572.2 [M+H]$^+$.

Example 148

(S)- or (R)-8-(1H-indazole-5-carbonyl)-3-(2-oxo-2-(2-(trifluoromethyl)morpholino)ethyl)-1-phenyl-1,3,8-triazaspiro[4.5]decan-4-one

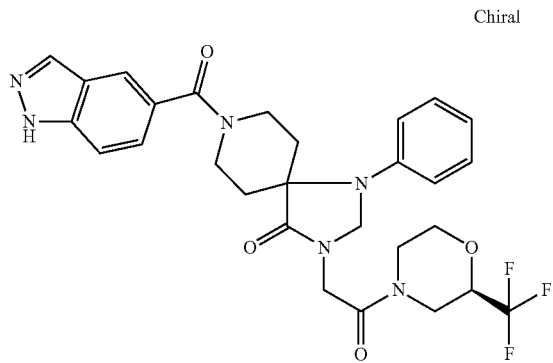

The title compound was obtained in analogy to example 17, from 3-[2-oxo-2-[(2S or 2R)-2-(trifluoromethyl)morpholin-4-yl]ethyl]-1-phenyl-1,3,8-triazaspiro[4.5]decan-4-one; 2,2,2-trifluoroacetic acid (example 140, intermediate a) and 1H-indazole-5-carboxylic acid (CAS RN 61700-61-6) as a white solid. MS (ESI): m/z=571.2 [M+H]$^+$.

Example 149 tert-Butyl (2R)- or (2S)-4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate

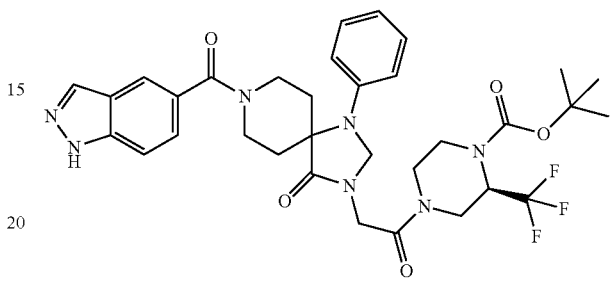

To a solution of (−)-tert-butyl 4-(2-(8-benzyl-4-oxo-1-phenyl-1,3,8-triazaspiro[4.5]decan-3-yl)acetyl)-2-(trifluoromethyl)piperazine-1-carboxylate (100 mg, 162 µmol) in EtOAc (1 mL) and MeOH (1 mL) was added palladium 10% on carbon (17.3 mg, 16.2 µmol) and the suspension was stirred for 15 hours under a hydrogen atmosphere at 1.9 bar. Hydrogen was replaced by argon and the suspension was filtered over a microfilter, washed with EtOAc and MeOH. The filtrate was evaporated, the residue was dissolved in DCM (1 mL) and treated with 1H-indazole-5-carboxylic acid (26.3 mg, 162 µmol, CAS RN 61700-61-6), HBTU (67.8 mg, 179 µmol) and TEA (65.7 mg, 90.6 µL, 650 µmol). The solution was stirred at RT for 4.5 hours. The reaction mixture was poured on half-saturated aqueous NH$_4$Cl solution and DCM and the layers were separated. The aqueous layer was extracted twice with DCM. The organic layers were dried over MgSO$_4$, filtered, treated with silica gel and evaporated. The compound was purified by silica gel chromatography on a 4 g column using an MPLC system eluting with a gradient of DCM:MeOH (100:0 to 90:10) to get the title compound as a light yellow solid (0.075 g; 69%). MS (ESI): m/z=670.30 [M+H]$^+$.

Intermediate a) (−)-tert-Butyl 4-(2-(8-benzyl-4-oxo-1-phenyl-1,3,8-triazaspiro[4.5]decan-3-yl)acetyl)-2-(trifluoromethyl)piperazine-1-carboxylate The title compound was obtained from racemic tert-butyl 4-(2-(8-benzyl-4-oxo-1-phenyl-1,3,8-triazaspiro[4.5]decan-3-yl)acetyl)-2-(trifluoromethyl)piperazine-1-carboxylate (example 132, intermediate c) by preparative chiral HPLC (Reprosil Chiral-NR column) using an isocratic mixture of EtOH (containing 0.5% NH$_4$OAc):n-heptane (30:70) as a off-white solid. MS (ESI): m/z=616.3 [M+H]$^+$.

Example 150 tert-Butyl (2S)- or (2R)-4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate

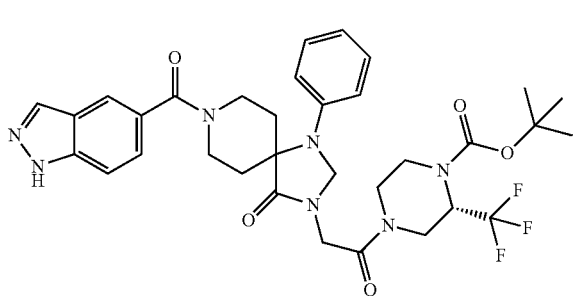

Chiral

The title compound was obtained in analogy to example 149, from (+)-tert-butyl 4-(2-(8-benzyl-4-oxo-1-phenyl-1,3,8-triazaspiro[4.5]decan-3-yl)acetyl)-2-(trifluoromethyl)piperazine-1-carboxylate and 1H-indazole-5-carboxylic acid (CAS RN 61700-61-6) as a light yellow solid (0.075 g; 69%). MS (ESI): m/z=670.30 [M+H]$^+$.

Intermediate a) (+)-tert-Butyl 4-(2-(8-benzyl-4-oxo-1-phenyl-1,3,8-triazaspiro[4.5]decan-3-yl)acetyl)-2-(trifluoromethyl)piperazine-1-carboxylate The title compound was obtained from racemic tert-butyl 4-(2-(8-benzyl-4-oxo-1-phenyl-1,3,8-triazaspiro[4.5]decan-3-yl)acetyl)-2-(trifluoromethyl)piperazine-1-carboxylate (example 132, intermediate c) by preparative chiral HPLC (Reprosil Chiral-NR column) using an isocratic mixture of EtOH (containing 0.5% NH$_4$OAc):n-heptane (30:70) as a off-white solid. MS (ESI): m/z=616.3 [M+H]$^+$.

Example 151

8-(1H-indazole-5-carbonyl)-3-[2-[(3R or 3S)-4-methyl-3-(trifluoromethyl)piperazin-1-yl]-2-oxo-ethyl]-1-phenyl-1,3,8-triazaspiro[4.5]decan-4-one

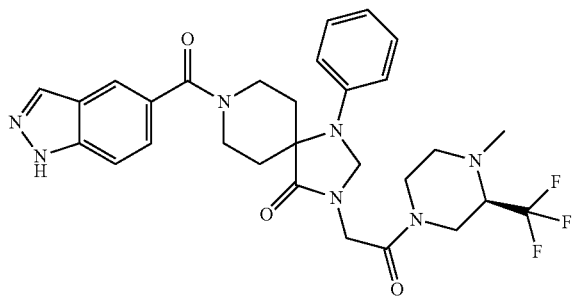

Chiral

The title compound was obtained in analogy to example 17, from 3-[2-[(3R or 3S)-4-methyl-3-(trifluoromethyl)piperazin-1-yl]-2-oxo-ethyl]-1-phenyl-1,3,8-triazaspiro[4.5]decan-4-one and 1H-indazole-5-carboxylic acid (CAS RN 61700-61-6) as a white solid. MS (ESI): m/z=584.3 [M+H]$^+$.

Intermediate a) 3-[2-[(3R or 3S)-4-Methyl-3-(trifluoromethyl)piperazin-1-yl]-2-oxo-ethyl]-1-phenyl-1,3,8-triazaspiro[4.5]decan-4-one The title compound was obtained in analogy to example 1, intermediate a, from 8-benzyl-3-[2-[(3R or 3S)-4-methyl-3-(trifluoromethyl)piperazin-1-yl]-2-oxo-ethyl]-1-phenyl-1,3,8-triazaspiro[4.5]decan-4-one as an off-white gum. MS (ESI): m/z=440.2 [M+H]$^+$.

Intermediate b) 8-Benzyl-3-[2-[(3R or 3S)-4-methyl-3-(trifluoromethyl)piperazin-1-yl]-2-oxo-ethyl]-1-phenyl-1,3,8-triazaspiro[4.5]decan-4-one The title compound was obtained in analogy to example 132, intermediate b, from (−)-tert-butyl 4-(2-(8-benzyl-4-oxo-1-phenyl-1,3,8-triazaspiro[4.5]decan-3-yl)acetyl)-2-(trifluoromethyl)piperazine-1-carboxylate (example 149, intermediate a) as a white gum. MS (ESI): m/z=530.3 [M+H]$^+$.

Example 152

8-(1H-Indazole-5-carbonyl)-3-[2-[(3S or 3R)-4-methyl-3-(trifluoromethyl)piperazin-1-yl]-2-oxo-ethyl]-1-phenyl-1,3,8-triazaspiro[4.5]decan-4-one

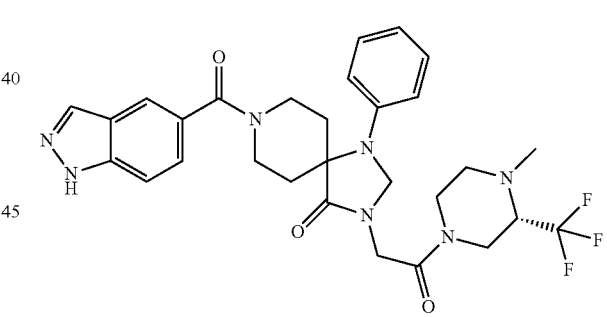

Chiral

The title compound was obtained in analogy to example 17, from 3-[2-[(3S or 3R)-4-methyl-3-(trifluoromethyl)piperazin-1-yl]-2-oxo-ethyl]-1-phenyl-1,3,8-triazaspiro[4.5]decan-4-one and 1H-indazole-5-carboxylic acid (CAS RN 61700-61-6) as a white solid (0.075 g; 69%). MS (ESI): m/z=584.3 [M+H]$^+$.

Intermediate a) 3-[2-[(3S or 3R)-4-Methyl-3-(trifluoromethyl)piperazin-1-yl]-2-oxo-ethyl]-1-phenyl-1,3,8-triazaspiro[4.5]decan-4-one The title compound was obtained in analogy to example 1, intermediate a, from 8-benzyl-3-[2-[(3S or 3R)-4-methyl-3-(trifluoromethyl)piperazin-1-yl]-2-oxo-ethyl]-1-phenyl-1,3,8-triazaspiro[4.5]decan-4-one as an off-white gum. MS (ESI): m/z=440.2 [M+H]$^+$.

Intermediate b) 8-Benzyl-3-[2-[(3S or 3R)-4-methyl-3-(trifluoromethyl)piperazin-1-yl]-2-oxo-ethyl]-1-phenyl-1,3,8-triazaspiro[4.5]decan-4-one The title compound was obtained in analogy to example 132, intermediate b, from (+)-tert-butyl 4-(2-(8-benzyl-4-oxo-1-phenyl-1,3,8-triazaspiro[4.5]decan-3-yl)acetyl)-2-(trifluoromethyl)piperazine-1-carboxylate (example 150, intermediate a) as a white gum. MS (ESI): m/z=530.3 [M+H]⁺.

Example 153

(R) or (S)-8-(1H-indazole-5-carbonyl)-3-(2-oxo-2-(3-(trifluoromethyl)piperazin-1-ynethyl)-1-phenyl-1,3,8-triazaspiro[4.5]decan-4-one Chiral

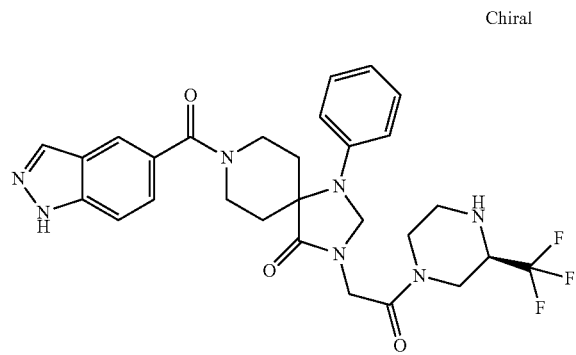 [SMILES: O=C(CN1CN(c2ccccc2)C2(CCN(C(=O)c3ccc4[nH]ncc4c3)CC2)C1=O)N1CCN[C@@H](C(F)(F)F)C1]

To a solution of tert-butyl (2R)- or (2S)-4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate (66 mg, 98.6 µmol, example 149) in DCM (1 mL) was added TFA (225 mg, 152 µL, 1.97 mmol) and the solution was stirred at RT for 2 h. The reaction mixture was evaporated. The reaction mixture was poured on saturated aqueous NaHCO₃ solution and DCM and the layers were separated. The aqueous layer was extracted twice with DCM. The organic layers were dried over MgSO₄, filtered, treated with silica gel and evaporated. The compound was purified by silica gel chromatography on a 4 g column using an MPLC system eluting with a gradient of DCM:MeOH (100:0 to 90:10) to furnish the title compound as a white solid (0.042 g; 74.8%). MS (ESI): m/z=570.2 [M+H]⁻.

Example 154

(S)- or (R)-8-(1H-indazole-5-carbonyl)-3-(2-oxo-2-(3-(trifluoromethyl)piperazin-1-yl)ethyl)-1-phenyl-1,3,8-triazaspiro[4.5]decan-4-one Chiral

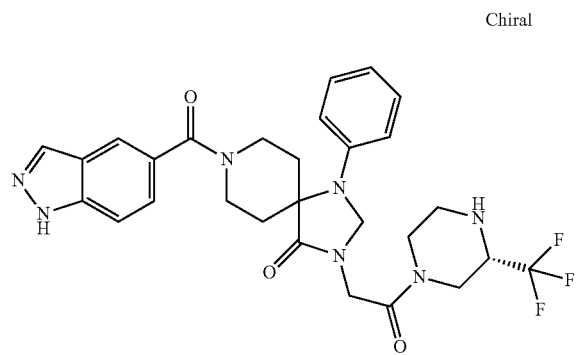 [SMILES: O=C(CN1CN(c2ccccc2)C2(CCN(C(=O)c3ccc4[nH]ncc4c3)CC2)C1=O)N1CCN[C@H](C(F)(F)F)C1]

The title compound was obtained in analogy to example 153, from tert-butyl (2S or 2R)-4-[2-[8-(1H-indazole-5-carbonyl)-4-oxo-1-phenyl-1,3,8-triazaspiro[4.5]decan-3-yl]acetyl]-2-(trifluoromethyl)piperazine-1-carboxylate (example 150) as a white solid. MS (ESI): m/z=570.2 [M+H]⁺.

Example 155

N-[2-(dimethylamino)ethyl]-2-[8-(1H-indazole-5-carbonyl)-4-oxo-1-phenyl-1,3,8-triazaspiro[4.5]decan-3-yl]-N-(2,2,2-trifluoroethyl)acetamide

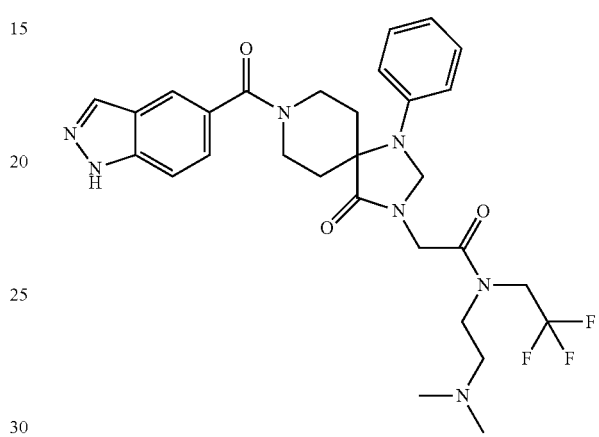

The title compound was obtained in analogy to example 36, from tert-butyl 3-[2-[2-(dimethylamino)ethyl-(2,2,2-trifluoroethyl)amino]-2-oxo-ethyl]-4-oxo-1-phenyl-1,3,8-triazaspiro[4.5]decane-8-carboxylate (example 139, intermediate a) and 1H-indazole-5-carboxylic acid (CAS RN 61700-61-6) as a white solid. MS (ESI): m/z=586.3 [M+H]⁺.

Example 156

N-(2-hydroxyethyl)-2-[8-(1H-indazole-5-carbonyl)-4-oxo-1-phenyl-1,3,8-triazaspiro[4.5]decan-3-yl]-N-(2,2,2-trifluoroethyl)acetamide

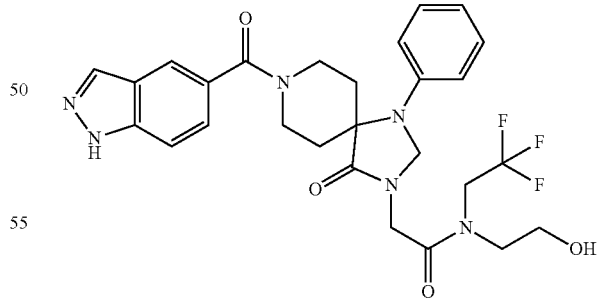

To a solution of [8-(1H-indazole-5-carbonyl)-4-oxo-1-phenyl-1,3,8-triaza-spiro[4.5]dec-3-yl]-acetic acid (150 mg, 0.35 mmol, example 41, intermediate a) in anhydrous THF (15 mL) were added 2-(2,2,2-trifluoro-ethylamino)-ethanol (99 mg, 0.69 mmol, CAS RN 371-99-3), 1-propanephosphonic acid cyclic anhydride (0.44 mL, 0.69 mmol, 50 w/v in EtOAc, CAS RN 68957-94-8) and DIPEA (0.11 mL, 0.69 mmol, CAS RN 7087-68-5). The reaction mixture was stirred at RT for 16 h. The reaction mixture was diluted with EtOAc (15 mL) and washed with water (30 mL). The organic part was washed with brine (20 mL), dried over Na₂SO₄, filtered and evaporated. The residue was purified by prep. HPLC (NH₄OAc/ACN) to get the title product (28 mg, 14%) as a white solid. MS (EI): m/z=559.2 [M+H]⁺.

Example 157

1-[2-[8-(1H-indazole-5-carbonyl)-4-oxo-1-phenyl-1,3,8-triazaspiro[4.5]decan-3-yl]acetyl]pyrrolidine-3-carboxamide

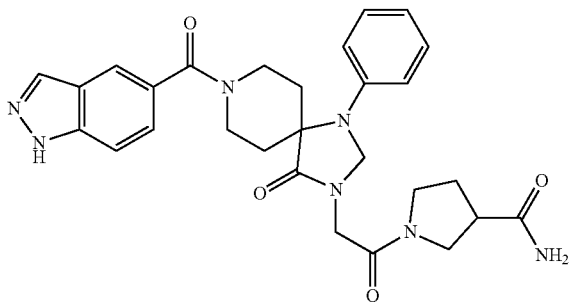 [SMILES: NC(=O)C1CCN(C(=O)CN2CN(c3ccccc3)C3(CCN(C(=O)c4ccc5[nH]ncc5c4)CC3)C2=O)C1]

The title compound was obtained in analogy to example 156, from [8-(1H-indazole-5-carbonyl)-4-oxo-1-phenyl-1,3,8-triaza-spiro[4.5]dec-3-yl]-acetic acid (example 41, intermediate a) and pyrrolidine-3-carboxamide hydrochloride (CAS RN 644972-57-6) as a white solid. MS (ESI): m/z=530.3 [M+H]⁺.

Example 158

N-(1-hydroxy-2-methylpropan-2-yl)-2-[8-(1H-indazole-5-carbonyl)-4-oxo-1-phenyl-1,3,8-triazaspiro[4.5]decan-3-yl]acetamide

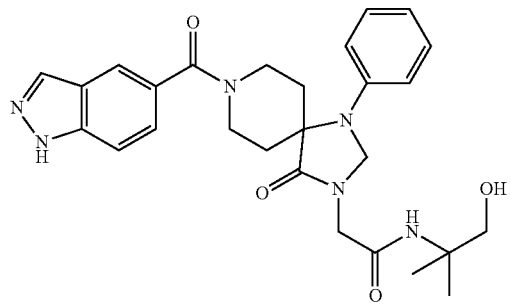

The title compound was obtained in analogy to example 25, from [8-(1H-indazole-5-carbonyl)-4-oxo-1-phenyl-1,3,8-triaza-spiro[4.5]dec-3-yl]-acetic acid (example 41, intermediate a) and 2-amino-2-methyl-propan-1-ol (CAS RN 124-68-5) as a white solid. MS (ESI): m/z=503.5 [M–H]⁻.

Example 159

2-[8-(1H-indazole-5-carbonyl)-4-oxo-1-phenyl-1,3,8-triazaspiro[4.5]decan-3-yl]-N-[1-(trifluoromethyl)cyclopropyl]acetamide

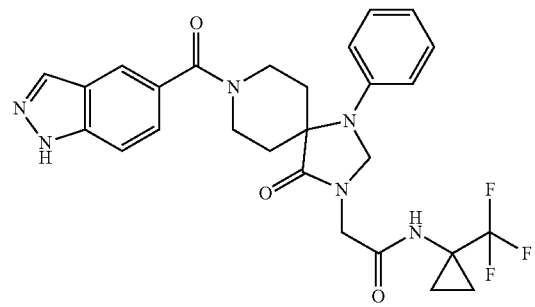 [SMILES: O=C(CN1CN(c2ccccc2)C2(CCN(C(=O)c3ccc4[nH]ncc4c3)CC2)C1=O)NC1(C(F)(F)F)CC1]

The title compound was obtained in analogy to example 156, from [8-(1H-indazole-5-carbonyl)-4-oxo-1-phenyl-1,3,8-triaza-spiro[4.5]dec-3-yl]-acetic acid (example 41, intermediate a) and 1-trifluoromethyl-cyclopropylamine hydrochloride (CAS RN 112738-67-7) as a white solid. MS (ESI): m/z=541.2 [M+H]⁺.

Example 160

N-(2-cyanopropan-2-yl)-2-[8-(1H-indazole-5-carbonyl)-4-oxo-1-phenyl-1,3,8-triazaspiro[4.5]decan-3-yl]acetamide

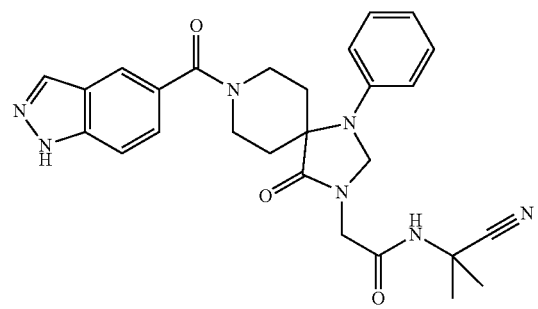 [SMILES: CC(C)(C#N)NC(=O)CN1CN(c2ccccc2)C2(CCN(C(=O)c3ccc4[nH]ncc4c3)CC2)C1=O]

The title compound was obtained in analogy to example 156, from [8-(1H-indazole-5-carbonyl)-4-oxo-1-phenyl-1,3,8-triaza-spiro[4.5]dec-3-yl]-acetic acid (example 41, intermediate a) and 2-amino-2-methyl-propionitrile (CAS RN 19355-69-2) as a white solid. MS (ESI): m/z=500.2 [M+H]⁺.

Example 161

N-(1-hydroxy-2-methylpropan-2-yl)-2-[4-oxo-1-phenyl-8-(1H-pyrazolo[3,4-b]pyridine-5-carbonyl)-1,3,8-triazaspiro[4.5]decan-3-yl]acetamide

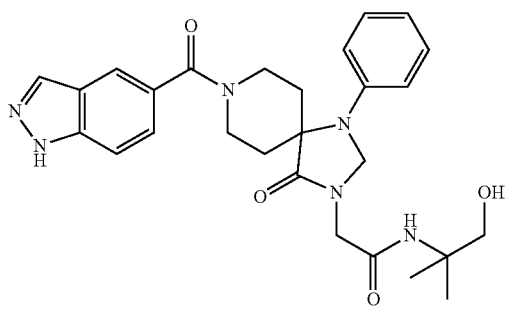 [SMILES: CC(C)(CO)NC(=O)CN1CN(c2ccccc2)C2(CCN(C(=O)c3ccc4[nH]ncc4c3)CC2)C1=O]

The title compound was obtained in analogy to example 25, from [4-oxo-1-phenyl-8-(1H-pyrazolo[3,4-b]pyridine-5-carbonyl)-1,3,8-triaza-spiro[4.5]dec-3-yl]-acetic acid (example 22, intermediate a) and 2-amino-2-methyl-propan-1-ol (CAS RN 124-68-5) as a white solid. MS (ESI): m/z=506.4 [M+H]$^+$.

Example 162

2-(8-(7-Methyl-1H-indazole-5-carbonyl)-4-oxo-1-phenyl-1,3,8-triazaspiro[4.5]decan-3-yl)-N-(2,2,2-trifluoroethyl)acetamide

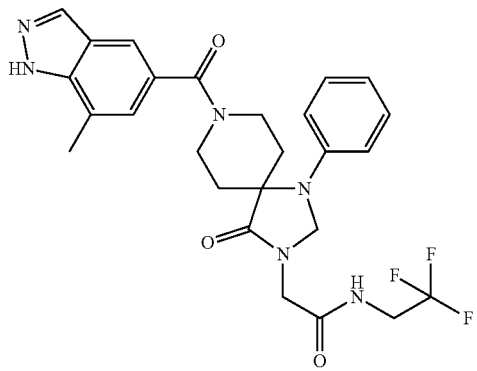 [SMILES: Cc1cc(C(=O)N2CCC3(CC2)C(=O)N(CC(=O)NCC(F)(F)F)CN3c2ccccc2)cc2cn[nH]c12]

The title compound was obtained in analogy to example 17, from 2-(4-oxo-1-phenyl-1,3,8-triazaspiro[4.5]decan-3-yl)-N-(2,2,2-trifluoroethyl)acetamide 2,2,2-trifluoro acetic acid salt and 7-methyl-1H-indazole-5-carboxylic acid (CAS RN 1031417-41-0) as a white solid. MS (ESI): m/z=529.3 [M+H]$^+$.

Intermediate a) 2-(4-Oxo-1-phenyl-1,3,8-triazaspiro[4.5]decan-3-yl)-N-(2,2,2-trifluoroethyl)acetamide 2,2,2-trifluoro acetic acid salt To a solution of tert-butyl 4-oxo-3-(2-oxo-24(2,2,2-trifluoroethyl)amino)ethyl)-1-phenyl-1,3,8-triazaspiro[4.5]decane-8-carboxylate (2.3 g, 4.89 mmol, example 17, intermediate b) in DCM (50 ml) was added 2,2,2-trifluoroacetic acid (5.57 g, 48.9 mmol). The reaction mixture stirred at RT overnight under an argon atmosphere. The reaction mixture was concentrated in vacuo to give a light green oil (4.7 g, 100%). MS(ESI): m/z=371.2 [M+H]$^+$ (free base).

Example 163

2-[1-(3-Bromophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide

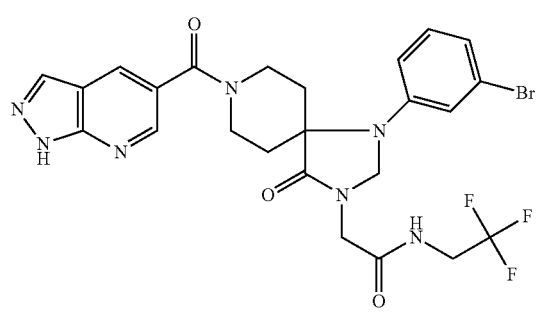 [SMILES: O=C(CN1CN(c2cccc(Br)c2)C2(CCN(C(=O)c3cnc4[nH]ncc4c3)CC2)C1=O)NCC(F)(F)F]

To a solution of 2-[1-(3-bromophenyl)-4-oxo-1,3,8-triazaspiro[4.5]decan-3-yl]-N-(2,2,2-trifluoroethyl)acetamide (90 mg, 0.2 mmol) and 1H-pyrazolo[3,4-b]pyridine-5-carboxylic acid (34.4 mg, 0.21 mmol, CAS RN 952182-02-4) in anhydrous DMF (2 mL) were added HOBt (28.5 mg, 0.21 mmol, CAS RN 2592-95-2), EDCI (42.27 mg, 0.22 mmol, CAS RN 25952-53-8) and DIPEA (0.11 ml, 0.601 mmol, CAS RN 7087-68-5) under nitrogen atmosphere at RT. The reaction mixture was stirred at RT for 16 h. Then the solvent was removed under reduced pressure. The residue was diluted with EtOAc (150 mL) and washed with H$_2$O (2×50 mL) and brine (50 mL). The organic part was dried over Na$_2$SO$_4$, filtered and concentrated. The resulting crude product was purified by prep. HPLC to get the title compound as an off-white solid (29.5 mg, 25%). MS (ESI): m/z=594.2 [M+H]$^+$.

Intermediate a) 2-[1-(3-Bromophenyl)-4-oxo-1,3,8-triazaspiro[4.5]decan-3-yl]-N-(2,2,2-trifluoroethyl)acetamide The title compound was obtained in analogy to example 81, intermediate a, from 2-[8-benzyl-1-(3-bromophenyl)-4-oxo-1,3,8-triazaspiro[4.5]decan-3-yl]-N-(2,2,2-trifluoroethyl)acetamide as a brown semi-solid. MS (ESI): m/z=449.2 [M+H]$^+$.

Intermediate b) 2-[8-Benzyl-1-(3-bromophenyl)-4-oxo-1,3,8-triazaspiro[4.5]decan-3-yl]-N-(2,2,2-trifluoroethyl)acetamide The title compound was obtained in analogy to example 1, intermediate b, from 8-benzyl-1-(3-bromophenyl)-1,3,8-triazaspiro[4.5]decan-4-one and 2-chloro-N-(2,2,2-trifluoroethyl)-acetamide (CAS RN 170655-44-4) as an off-white solid. MS (ESI): m/z=539.2 [M+H]$^+$.

Intermediate c) 8-Benzyl-1-(3-bromophenyl)-1,3,8-triazaspiro[4.5]decan-4-one

The title compound was obtained in analogy to example 98, intermediate c, from 8-benzyl-1-(3-bromophenyl)-1,3,8-triazaspiro[4.5]dec-2-en-4-one as an off-white solid. MS (ESI): m/z=400.0 [M+H]$^+$.

Intermediate d) 8-Benzyl-1-(3-bromophenyl)-1,3,8-triazaspiro[4.5]dec-2-en-4-one

The title compound was obtained in analogy to example 98, intermediate d, from 1-benzyl-4-[(3-bromophenyl)amino]piperidine-4-carboxamide as a brown liquid. MS (ESI): m/z=397.8 [M+H]$^+$.

Intermediate e) 1-Benzyl-4-[(3-bromophenyl)amino]piperidine-4-carboxamide

The title compound was obtained in analogy to example 98, intermediate e, from 1-benzyl-4-[(3-bromophenyl)amino]piperidine-4-carbonitrile as an off-white solid. MS (ESI): m/z=388.2 [M+H]$^+$.

Intermediate f) 1-Benzyl-4-[(3-bromophenyl)amino]piperidine-4-carbonitrile

The title compound was obtained in analogy to example 98, intermediate f, from 1-benzylpiperidin-4-one (CAS RN 3612-20-2) and 3-bromoaniline (CAS RN 591-19-5) as an off-white solid. MS (ESI): m/z=370.1 [M+H]$^+$.

Example 164

8-(1H-indazole-5-carbonyl)-3-[2-oxo-2-[2-(trifluoromethyl)piperazin-1-yl]ethyl]-1-phenyl-1,3,8-triazaspiro[4.5]decan-4-one

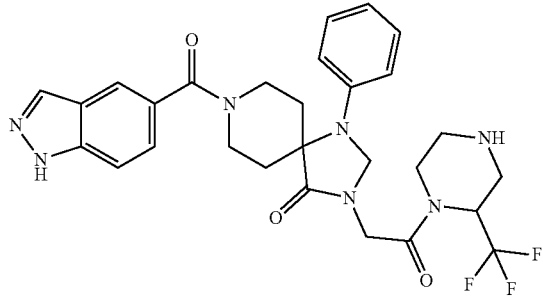 [SMILES: O=C(c1ccc2[nH]ncc2c1)N1CCC2(CC1)C(=O)N(CC(=O)N1CCNCC1C(F)(F)F)CN2c1ccccc1]

The title compound was obtained in analogy to example 1, intermediate a, from 3-[2-[4-benzyl-2-(trifluoromethyl)piperazin-1-yl]-2-oxoethyl]-8-(1H-indazole-5-carbonyl)-1-phenyl-1,3,8-triazaspiro[4.5]decan-4-one (example 165) as a white solid. MS (ESI): m/z=570.2 [M+H]$^+$.

Example 165

3-[2-[4-Benzyl-2-(trifluoromethyl)piperazin-1-yl]-2-oxoethyl]-8-(1H-indazole-5-carbonyl)-1-phenyl-1,3,8-triazaspiro[4.5]decan-4-one

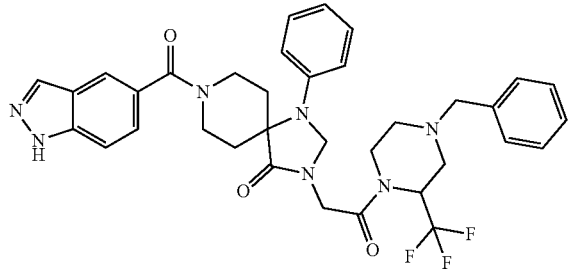 [SMILES: O=C(c1ccc2[nH]ncc2c1)N1CCC2(CC1)C(=O)N(CC(=O)N1CCN(Cc3ccccc3)CC1C(F)(F)F)CN2c1ccccc1]

The title compound was obtained in analogy to example 36, from tert-butyl 3-[2-[4-benzyl-2-(trifluoromethyl)piperazin-1-yl]-2-oxo-ethyl]-4-oxo-1-phenyl-1,3,8-triazaspiro[4.5]decane-8-carboxylate and 1H-indazole-5-carboxylic acid (CAS RN 61700-61-6) as a white solid. MS (ESI): m/z=660.3 [M+H]$^+$.

Intermediate a) tert-Butyl 3-[2-[4-benzyl-2-(trifluoromethyl)piperazin-1-yl]-2-oxo-ethyl]-4-oxo-1-phenyl-1,3,8-triazaspiro[4.5]decane-8-carboxylate The title compound was obtained in analogy to example 22, from 2-(8-tert-butoxycarbonyl-4-oxo-1-phenyl-1,3,8-triazaspiro[4.5]decan-3-yl)acetic acid (CAS RN 180386-35-0) and 1-benzyl-3-(trifluoromethyl)piperazine (CAS RN 167566-34-9) as a light brown foam. MS (ESI): m/z=616.3 [M+H]$^+$.

Example 166

8-(1H-Indazole-5-carbonyl)-3-[2-[4-methyl-2-(trifluoromethyl)piperazin-1-yl]-2-oxoethyl]-1-phenyl-1,3,8-triazaspiro[4.5]decan-4-one

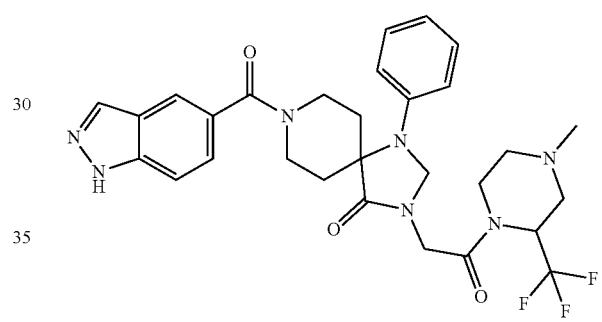

The title compound was obtained in analogy to example 36, from tert-butyl 3-[2-[4-methyl-2-(trifluoromethyl)piperazin-1-yl]-2-oxo-ethyl]-4-oxo-1-phenyl-1,3,8-triazaspiro[4.5]decane-8-carboxylate and 1H-indazole-5-carboxylic acid (CAS RN 61700-61-6) as a light brown solid. MS (ESI): m/z=584.3 [M+H]$^+$.

Intermediate a) tert-Butyl 3-[2-[4-methyl-2-(trifluoromethyl)piperazin-1-yl]-2-oxo-ethyl]-4-oxo-1-phenyl-1,3,8-triazaspiro[4.5]decane-8-carboxylate To a solution of tert-butyl 3-(2-(4-benzyl-2-(trifluoromethyl)piperazin-1-yl)-2-oxoethyl)-4-oxo-1-phenyl-1,3,8-triazaspiro[4.5]decane-8-carboxylate (200 mg, 325 µmol, example 165, intermediate a) in MeOH (1 mL) and EtOAc (1 mL) was added palladium 10% on carbon (31.1 mg, 29.2 µmol) and the mixture was stirred under a hydrogen atmosphere of 1.9 bar at RT for 18 h. The reaction mixture was filtered over a microfilter and the filtrate was evaporated. The product was dissolved in in dioxane (2 mL) and formaldehyde (37% solution in H$_2$O (264 mg, 242 µL, 3.25 mmol) and sodium triacetoxyborohydride (172 mg, 812 µmol) were added. Stirring was continued at RT for 2 hours. The reaction mixture was poured on saturated aqueous NaHCO$_3$ solution and EtOAc and the layers were separated. The aqueous layer was extracted with EtOAc. The organic layer was dried over MgSO$_4$, filtered, treated with silica gel and evaporated. The compound was purified by silica gel chromatography on a 4 g column using an MPLC system eluting with a gradient of n-heptane:EtOAc (100:0 to 0:100) to yield the title compound as a white gum (0.097 g; 55.3%). MS (ESI): m/z=540.28 [M+H]+.

Example 167

(S)-Methyl 4,4-difluoro-1-(2-(4-oxo-1-phenyl-8-(1H-pyrazolo[3,4-b]pyridine-5-carbonyl)-1,3,8-triazaspiro[4.5]decan-3-yl)acetyl)pyrrolidine-2-carboxylate

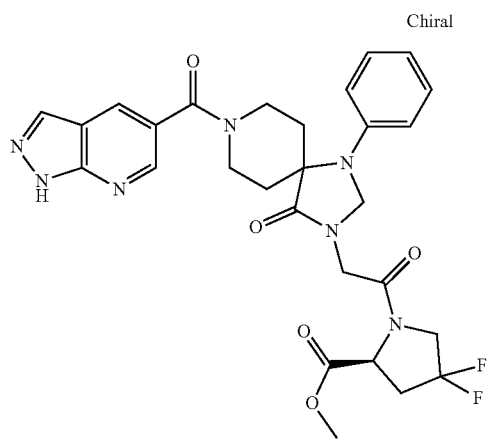 [SMILES: COC(=O)[C@@H]1CC(F)(F)CN1C(=O)CN1CN(c2ccccc2)C2(CCN(C(=O)c3cnc4[nH]ncc4c3)CC2)C1=O]

The title compound was obtained in analogy to example 75, intermediate a, from 2-[4-oxo-1-phenyl-8-(1H-pyrazolo[3,4-b]pyridine-5-carbonyl)-1,3,8-triazaspiro[4.5]decan-3-yl]acetic acid (example 22, intermediate a) and (S)-methyl 4,4-difluoropyrrolidine-2-carboxylate hydrochloride salt (CAS RN 126111-14-6) as a white solid. MS (ESI): m/z=582.3 [M+H]+.

Example 168

2-[4-Oxo-8-(1H-pyrazolo[3,4-b]pyridine-5-carbonyl)-1-[3-(trifluoromethyl)phenyl]-1,3,8-triazaspiro[4.5]decan-3-yl]-N-(2,2,2-trifluoroethyl)acetamide

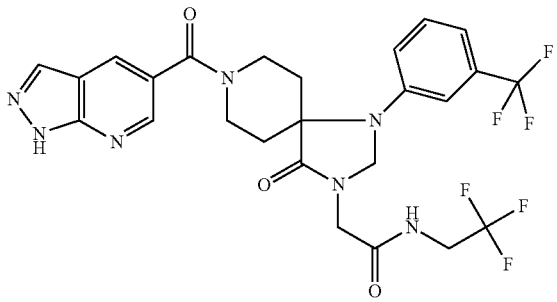 [SMILES: O=C(CN1CN(c2cccc(C(F)(F)F)c2)C2(CCN(C(=O)c3cnc4[nH]ncc4c3)CC2)C1=O)NCC(F)(F)F]

The title compound was obtained in analogy to example 163, from 2-[4-oxo-1-[3-(trifluoromethyl)phenyl]-1,3,8-triazaspiro[4.5]decan-3-yl]-N-(2,2,2-trifluoroethyl)acetamide and 1H-pyrazolo[3,4-b]pyridine-5-carboxylic acid (CAS RN 952182-02-4) as an off-white solid. MS (ESI): m/z=584.1 [M+H]+.

Intermediate a) 2-[4-Oxo-1-[3-(trifluoromethyl)phenyl]-1,3,8-triazaspiro[4.5]decan-3-yl]-N-(2,2,2-trifluoroethyl)acetamide The title compound was obtained in analogy to example 81, intermediate a, from 2-[8-benzyl-4-oxo-1-[3-(trifluoromethyl)phenyl]-1,3,8-triazaspiro[4.5]decan-3-yl]-N-(2,2,2-trifluoroethyl)acetamide as an off-white solid. MS (ESI): m/z=439.1 [M+H]+.

Intermediate b) 2-[8-Benzyl-4-oxo-1-[3-(trifluoromethyl)phenyl]-1,3,8-triazaspiro[4.5]decan-3-yl]-N-(2,2,2-trifluoroethyl)acetamide The title compound was obtained in analogy to example 1, intermediate b, from 8-benzyl-1-[3-(trifluoromethyl)phenyl]-1,3,8-triazaspiro[4.5]decan-4-one and 2-chloro-N-(2,2,2-trifluoroethyl)-acetamide (CAS RN 170655-44-4) as an off-white solid. MS (ESI): m/z=529 [M+H]+.

Intermediate c) 8-Benzyl-1-[3-(trifluoromethyl)phenyl]-1,3,8-triazaspiro[4.5]decan-4-one The title compound was obtained in analogy to example 98, intermediate c, from 8-benzyl-1-[3-(trifluoromethyl)phenyl]-1,3,8-triazaspiro[4.5]dec-2-en-4-one as an off-white solid. MS (ESI): m/z=390 [M+H]+.

Intermediate d) 8-Benzyl-1-[3-(trifluoromethyl)phenyl]-1,3,8-triazaspiro[4.5]dec-2-en-4-one The title compound was obtained in analogy to example 98, intermediate d, from 1-benzyl-4-{[3-(trifluoromethyl)phenyl]amino}piperidine-4-carboxamide as a brown liquid. MS (ESI): m/z=388.2 [M+H]+.

Intermediate e) 1-Benzyl-4-{[3-(trifluoromethyl)phenyl]amino}piperidine-4-carboxamide The title compound was obtained in analogy to example 98, intermediate e, from 1-benzyl-4-{[3-(trifluoromethyl)phenyl]amino}piperidine-4-carbonitrile as an off-white solid. MS (ESI): m/z=378.2 [M+H]+.

Intermediate f) 1-Benzyl-4-{[3-(trifluoromethyl)phenyl]amino}piperidine-4-carbonitrile The title compound was obtained in analogy to example 98, intermediate f, from 1-benzylpiperidin-4-one (CAS RN 3612-20-2) and 3-(trifluoro-methyl)aniline (CAS RN 98-16-8) as an off-white solid. MS (ESI): m/z=359.9 [M+H]+.

Example 169

2-[1-(3-Chloro-5-fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide

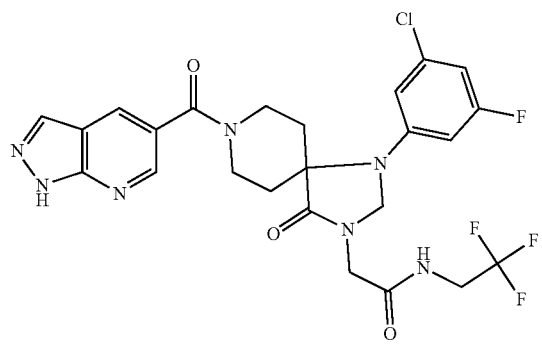 [SMILES: O=C(CN1CN(c2cc(F)cc(Cl)c2)C2(CCN(C(=O)c3cnc4[nH]ncc4c3)CC2)C1=O)NCC(F)(F)F]

The title compound was obtained in analogy to example 163, from 2-[1-(3-chloro-5-fluoro-phenyl)-4-oxo-1,3,8-triazaspiro[4.5]decan-3-yl]-N-(2,2,2-trifluoroethyl)acetamide and 1H-pyrazolo[3,4-b]pyridine-5-carboxylic acid (CAS RN 952182-02-4) as an off-white solid. MS (ESI): m/z=568.0 [M+H]$^+$.

Intermediate a) 2-[1-(3-Chloro-5-fluoro-phenyl)-4-oxo-1,3,8-triazaspiro[4.5]decan-3-yl]-N-(2,2,2-trifluoroethyl)acetamide The title compound was obtained in analogy to example 81, intermediate a, from 2-[8-benzyl-1-(3-chloro-5-fluoro-phenyl)-4-oxo-1,3,8-triaza-spiro[4.5]dec-3-yl]-N-(2,2,2-trifluoro-ethyl)-acetamide as a yellow solid. MS (ESI): m/z=423.1.1 [M+H]$^+$.

Intermediate b) 2-[8-Benzyl-1-(3-chloro-5-fluoro-phenyl)-4-oxo-1,3,8-triaza-spiro[4.5]dec-3-yl]-N-(2,2,2-trifluoro-ethyl)-acetamide The title compound was obtained in analogy to example 1, intermediate b, from 8-benzyl-1-(3-chloro-5-fluoro-phenyl)-1,3,8-triaza-spiro[4.5]decan-4-one and 2-chloro-N-(2,2,2-trifluoroethyl)-acetamide (CAS RN 170655-44-4) as an off-white solid. MS (ESI): m/z=513.0 [M+H]$^+$.

Intermediate c) 8-Benzyl-1-(3-chloro-5-fluoro-phenyl)-1,3,8-triaza-spiro[4.5]decan-4-one The title compound was obtained in analogy to example 98, intermediate c, from 8-benzyl-1-(3-chloro-5-fluoro-phenyl)-1,3,8-triaza-spiro[4.5]dec-2-en-4-one as an off-white solid. MS (ESI): m/z=374.2 [M+H]$^+$.

Intermediate d) 8-Benzyl-1-(3-chloro-5-fluoro-phenyl)-1,3,8-triaza-spiro[4.5]dec-2-en-4-one The title compound was obtained in analogy to example 98, intermediate d, from 1-benzyl-4-(3-chloro-5-fluoro-phenylamino)-piperidine-4-carboxylic acid amide as a brown liquid. MS(ESI): m/z=372.3.2 [M+H]$^+$.

Intermediate e) 1-Benzyl-4-(3-chloro-5-fluoro-phenylamino)-piperidine-4-carboxylic acid amide The title compound was obtained in analogy to example 98, intermediate e, from 1-benzyl-4-(3-chloro-5-fluoro-phenylamino)-piperidine-4-carbonitrile as an off-white solid. MS (ESI): m/z=361.8 [M+H]$^+$.

Intermediate f) 1-Benzyl-4-(3-chloro-5-fluoro-phenylamino)-piperidine-4-carbonitrile The title compound was obtained in analogy to example 98, intermediate f, from 1-benzylpiperidin-4-one (CAS RN 3612-20-2) and 3-chloro-5-fluoro-phenylamine (CAS RN 4863-91-6) as an off-white solid. MS (ESI): m/z=343.9 [M+H]$^+$.

Example 170

2-[1-(3-Cyanophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide

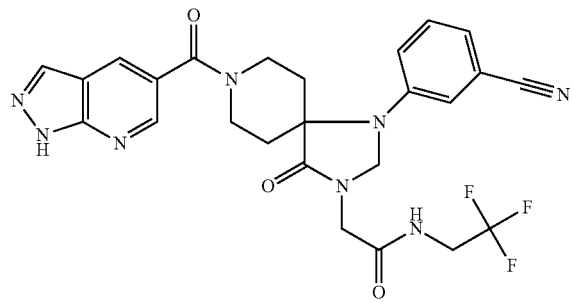 [SMILES: N#Cc1cccc(N2CN(CC(=O)NCC(F)(F)F)C(=O)C23CCN(C(=O)c2cnc4[nH]ncc4c2)CC3)c1]

The title compound was obtained in analogy to example 163, from 2-[1-(3-cyanophenyl)-4-oxo-1,3,8-triazaspiro[4.5]decan-3-yl]-N-(2,2,2-trifluoroethyl)acetamide and 1H-pyrazolo[3,4-b]pyridine-5-carboxylic acid (CAS RN 952182-02-4) as an off-white solid. MS (ESI): m/z=541.1 [M+H]$^+$.

Intermediate a) 2-[1-(3-Cyanophenyl)-4-oxo-1,3,8-triazaspiro[4.5]decan-3-yl]-N-(2,2,2-trifluoroethyl)acetamide The title compound was obtained in analogy to example 81, intermediate a, from 2-[8-benzyl-1-(3-cyanophenyl)-4-oxo-1,3,8-triazaspiro[4.5]decan-3-yl]-N-(2,2,2-trifluoroethyl)acetamide as a yellow solid. MS (ESI): m/z=396.2 [M+H]$^+$.

Intermediate b) 2-[8-Benzyl-1-(3-cyanophenyl)-4-oxo-1,3,8-triazaspiro[4.5]decan-3-yl]-N-(2,2,2-trifluoroethyl)acetamide To a stirred solution of 2-[8-benzyl-1-(3-bromophenyl)-4-oxo-1,3,8-triazaspiro[4.5]decan-3-yl]-N-(2,2,2-trifluoroethyl)acetamide (330 mg, 0.612 mmol, example 163, intermediate b) in DMF (4 mL) were added Zn(CN)$_2$ (144 mg, 1.224 mmol, CAS RN 557-21-1), DPPF (34 mg, 0.061 mmol, CAS RN 12150-46-8), Zn (10 mg, 0.153 mmol, CAS RN 7440-66-6) and the reaction mixture was purged with argon for 15 min. Then Pd$_2$(dba)$_3$ (28 mg, 0.031 mmol, CAS RN 51364-51-3) was added to reaction mixture and reaction mixture was again purged with argon for 10 min. The reaction mixture was stirred at 120° C. for 1 h in the microwave oven. Then the reaction mixture was filtered through celite and washed with DCM (80 mL) and the filtrate was evaporated. The crude product was purified by column chromatography over silica gel (3-5% MeOH/DCM) to furnish the title compound as a brown semi-solid (110 mg, 37%). MS (ESI): m/z=486.2 [M+H]$^+$.

Example 171

In Vitro Binding Assay for DDR1

An in vitro binding competition assay was performed to evaluate the effect of the compounds of present invention on DDR1 protein.

Binding Competition Assay:

This assay is based on the intracellular domain of the DDR1 protein which contains the kinase active site. The recombinant protein additionally carries a GST-tag that can be recognized by an Eu-labeled anti-GST antibody. A tracer compound binding to the active site is labeled with a dye so that a FRET donor acceptor pair can be formed. Excitation energy absorbed by the Europium complex (350 nm flash light or pulsed laser) is transferred to a suitable fluorescent dye, if it is in close proximity. Compounds binding competitively with the tracer molecule will displace the bound tracer molecules and reduce the FRET signal in a dose dependent manner. Due to the long lifetime of the Eu excited state, the emission of the donor and the acceptor can be measured in time-gated mode such that most of the intrinsic fluorescence contributions have already decayed. This results in high sensitivity, excellent reproducibility and high data quality. This sensitive detection method enables protein concentrations below 20 nM.

Protein, tracer and labeled antibody were obtained from commercial sources. The assay was performed in 384 low volume microtiter-plates with a final volume of 15 μl. Dose response curves were generated from 16 compound dilutions in DMSO as solvent compound dilutions, a solution containing protein and labeled antibody, and a solution containing the tracer which is added in the last step. The fluorescence of donor and acceptor were then measured after one hour incubation at room temperature. Every assay run was quality-controlled with dose response curves for two reference compounds.

Table 1 provides IC50 values for DDR1 inhibition obtained according to the above binding competition assay for particular compounds of the present invention.

Particular compounds of the present invention exhibit IC50 values for DDR1 inhibition≤1000 nM, obtained according to the above binding competition assay.

More particular compounds of the present invention exhibit IC50 values for DDR1 inhibition≤500 nM, obtained according to the above binding competition assay.

Most particular compounds of the present invention exhibit IC50 values for DDR1 inhibition≤100 nM, obtained according to the above binding competition assay.

TABLE 1

IC50 values for DDR1 inhibition measured using binding competition assay.

| Ex. No | Binding IC50 DDR1 [nM] |
|---|---|
| 1 | 436.1 |
| 2 | 12.7 |
| 3 | 209.9 |
| 4 | 504.3 |
| 5 | 1040.1 |
| 6 | 10.6 |
| 7 | 15.5 |
| 8 | 39.7 |
| 9 | 10.9 |
| 10 | 43 |
| 11 | 1456.4 |
| 12 | 778.8 |
| 13 | 946.8 |
| 14 | 922.8 |
| 15 | 15.4 |
| 16 | 496.5 |
| 17 | 83.3 |
| 18 | 7988 |
| 19 | 258.4 |
| 20 | 43.7 |
| 21 | 54.6 |
| 22 | 17.3 |
| 23 | 19.7 |
| 24 | 49.4 |
| 25 | 8858.9 |
| 26 | 345.4 |
| 27 | 29.6 |
| 28 | 1190.2 |
| 29 | 2616.5 |
| 30 | 27.1 |
| 31 | 1450.3 |
| 32 | 3105.7 |
| 33 | 13.8 |
| 34 | 114.2 |
| 35 | 896.9 |
| 36 | 7930.7 |
| 37 | 311.5 |
| 38 | 2650.2 |
| 39 | 155.2 |
| 40 | 64.1 |
| 41 | 472.6 |
| 42 | 3317.2 |
| 43 | 54.7 |
| 44 | 158.2 |
| 45 | 183.7 |
| 46 | 577.3 |
| 47 | 23.8 |
| 48 | 2107.3 |
| 49 | 3862.4 |
| 50 | 289.2 |
| 51 | 2308.1 |
| 52 | 1346.3 |
| 53 | 80.7 |
| 54 | 310.7 |
| 55 | 24.4 |
| 56 | 130.9 |
| 57 | 222.5 |
| 58 | 806.7 |
| 59 | 368.7 |
| 60 | 59.5 |
| 61 | 662.7 |
| 62 | 2986.6 |
| 63 | 2298.8 |
| 64 | 394.4 |
| 65 | 65.8 |
| 66 | 225.2 |
| 67 | 27.3 |
| 68 | 19.1 |
| 69 | 19.3 |
| 70 | 359.2 |
| 71 | 1834.5 |
| 72 | 1376.7 |

TABLE 1-continued

IC50 values for DDR1 inhibition measured using binding competition assay.

| Ex. No | Binding IC50 DDR1 [nM] |
|---|---|
| 73 | 1522.5 |
| 74 | 694.2 |
| 75 | 17.2 |
| 76 | 2279.3 |
| 77 | 87.7 |
| 78 | 565.1 |
| 79 | 4790.8 |
| 80 | 1170.4 |
| 81 | 1847.5 |
| 82 | 5019.3 |
| 83 | 2656.1 |
| 84 | 2351.9 |
| 85 | 1736.2 |
| 86 | 8209.5 |
| 87 | 7076.4 |
| 88 | 5851.5 |
| 89 | 2288.7 |
| 90 | 43.1 |
| 91 | 19.4 |
| 92 | 4914.4 |
| 93 | 322.3 |
| 94 | 65.4 |
| 95 | 183.7 |
| 96 | 530.2 |
| 97 | 265.3 |
| 98 | 1763.8 |
| 99 | 1433.6 |
| 100 | 922.4 |
| 101 | 18.7 |
| 102 | 110.6 |
| 103 | 25.0 |
| 104 | 21.0 |
| 105 | 34.9 |
| 106 | 80.7 |
| 107 | 2724.1 |
| 108 | 33.3 |
| 109 | 445.8 |
| 110 | 1095.3 |
| 111 | 12.4 |
| 112 | 219.1 |
| 113 | 22.0 |
| 114 | 669.7 |
| 115 | 17.7 |
| 116 | 238.9 |
| 117 | 6850.7 |
| 118 | 260.0 |
| 119 | 2133.8 |
| 120 | 80.0 |
| 121 | 103.1 |
| 122 | 426.3 |
| 123 | 45.6 |
| 124 | 34.3 |
| 125 | 12.9 |
| 126 | 404.0 |
| 127 | 564.5 |
| 128 | 1648.2 |
| 129 | 1027.5 |
| 130 | 455.8 |
| 131 | 272.3 |
| 132 | 69.5 |
| 133 | 19.3 |
| 134 | 63.1 |
| 135 | 4846.9 |
| 136 | 1473.2 |
| 137 | 23.1 |
| 138 | 5590.1 |
| 139 | 155.2 |
| 140 | 17.7 |
| 141 | 208.1 |
| 142 | 33.7 |
| 143 | 23.3 |
| 144 | 110.5 |
| 145 | 27.9 |
| 146 | 117.0 |
| 147 | 96.0 |
| 148 | 18.1 |
| 149 | 905.9 |
| 150 | 473.6 |
| 151 | 110.2 |
| 152 | 29.5 |
| 153 | 41.9 |
| 154 | 46.7 |
| 155 | 75.3 |
| 156 | 36.3 |
| 157 | 1559.4 |
| 158 | 143.9 |
| 159 | 17.2 |
| 160 | 33.2 |
| 161 | 549.6 |
| 162 | 17.8 |
| 163 | 59.9 |
| 164 | 196.8 |
| 165 | 517.7 |
| 166 | 83.5 |
| 167 | 106.4 |
| 168 | 2658.6 |
| 169 | 36.9 |
| 170 | 854.5 |

We claim:
1. A compound of formula (I)

wherein

L is —(CHR$^8$)$_m$—(CHR$^9$)$_n$—(CO)$_q$—

R$^1$ is —NR$^6$R$^7$, aryl or C$_{3-7}$ cycloalkyl, wherein each aryl and C$_{3-7}$ cycloalkyl is optionally substituted with one or more R$^{1'}$;

each R$^{1'}$ is independently selected from halogen, cyano, C$_{1-7}$ alkyl, halo-C$_{1-7}$ alkyl, C$_{3-7}$ cycloalkyl, C$_{3-7}$ cycloalkyl-C$_{1-7}$ alkyl, phenyl, benzyl, amino, hydroxy, C$_{1-7}$ alkoxy, halo-C$_{1-7}$ alkoxy, C$_{1-7}$ alkoxy-C$_{1-7}$ alkyl, oxo, —CH$_2$—OR$^{16}$, —C(O)—OR$^{16}$, —CH$_2$—NHR$^{16}$, —CH$_2$—CH$_2$—NR$^{17}$R$^{18}$, —CH$_2$—C(O)—NHR$^{16}$ and —C(O)—NHR$^{16}$;

or two R$^{1'}$ together are —(CR$^{12}$R$^{13}$)$_s$—;

R$^2$ is hydrogen, fluorine, C$_{1-7}$ alkyl, or halo-C$_{1-7}$ alkyl;

R$^3$ is hydrogen or C$_{1-7}$ alkyl;

R$^4$ is aryl optionally substituted by one or more R$^{4'}$;

each R$^{4'}$ is independently selected from halogen, cyano, C$_{1-7}$ alkyl, halo-C$_{1-7}$ alkyl, C$_{3-7}$ cycloalkyl, amino, hydroxy, C$_{1-7}$ alkoxy and halo-C$_{1-7}$ alkoxy;

R$^5$ is 1H-pyrazolo[3,4-b]pyridine which is optionally substituted with one or more R$^{5'}$;

each R$^{5'}$ is independently selected from halogen, cyano, C$_{1-7}$ alkyl, halo-C$_{1-7}$ alkyl, C$_{3-7}$ cycloalkyl, amino, hydroxy, C$_{1-7}$ alkoxy and —C(O)NH$_2$;

$R^6$ is $C_{1-7}$ alkyl, halo-$C_{1-7}$ alkyl, hydroxy-$C_{1-7}$ alkyl, $C_{1-7}$ alkoxy-$C_{1-7}$ alkyl, $C_{3-7}$ cycloalkyl, aryl, —$CH_2$—$CH_2$—$NR^{17}R^{18}$, wherein $C_{1-7}$ alkyl, $C_{3-7}$ cycloalkyl, aryl or benzyl are optionally substituted with one or more $R^{6'}$;

each $R^{6'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, halo-$C_{1-7}$ alkoxy, $C_{1-7}$ alkoxy-$C_{1-7}$ alkyl, oxo, —$CH_2$—$C(O)$—$NHR^{16}$, phenyl or benzyl said phenyl optionally substituted with $C_{1-7}$ alkyl;

$R^7$ is hydrogen, $C_{1-7}$ alkyl, $C_{3-7}$ cycloalkyl or halo-$C_{1-7}$ alkyl;

$R^8$ is hydrogen, $C_{1-7}$ alkyl, hydroxy-$C_{1-7}$ alkyl, $C_{1-7}$ alkoxy-$C_{1-7}$ alkyl, halo-$C_{1-7}$ alkoxy-$C_{1-7}$ alkyl, —$(CH_2)_r$-phenyl, or —$(CH_2)_r NR^{10}R^{11}$;

$R^9$ is hydrogen, $C_{1-7}$ alkyl, or halo-$C_{1-7}$ alkyl;

$R^{10}$ and $R^{11}$ are independently selected from hydrogen and $C_{1-7}$ alkyl;

$R^{12}$, $R^{13}$, $R^{14}$ and $R^{15}$ are each independently selected from hydrogen, halogen and $C_{1-7}$ alkyl;

$R^{16}$ is hydrogen, $C_{1-7}$alkyl, halo-$C_{1-7}$ alkyl or $C_{3-7}$ cycloalkyl;

$R^{17}$ and $R^{18}$ are selected from hydrogen and $C_{1-7}$ alkyl;

m is 0, 1 or 2;

n is 0, 1 or 2;

q is 0 or 1;

r is 0, 1 or 2;

s is 2, 3 or 4;

or a pharmaceutically acceptable salt thereof;

with the proviso that if $R^1$ is —$NR^6R^7$ then:

if q=0 then m+n≥2, or if q=1 then m+n≥1.

2. The compound of formula (I) according to claim 1, wherein m, n and q are each 0, m and q are both 0, n is 1 and $R^9$ is hydrogen- or m is 0, n and q are 1 and $R^9$ is hydrogen.

3. The compound of formula (I) according to claim 1 wherein m is 0, n and q are 1 and $R^9$ is hydrogen.

4. The compound of formula (I) according to claim 1 wherein $R^1$ is $NR^6R^7$ or aryl said aryl optionally substituted with one or more $R^{1'}$.

5. The compound of formula (I) according to claim 4, wherein $R^1$ is —$NR^6R^7$ or phenyl said phenyl optionally substituted with one, two or three $R^{1'}$.

6. The compound of formula (I) according to claim 1 wherein each $R^{1'}$ is independently selected from the group consisting of halogen, cyano, $C_{1-7}$ alkyl, halo-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, $C_{1-7}$ alkoxy-$C_{1-7}$ alkyl, oxo, phenyl and benzyl.

7. The compound of formula (I) according to claim 6 wherein each $R^{1'}$ is independently selected from the group consisting of fluoro, chloro, cyano, methyl, ethyl, tert-butyl, trifluoromethyl, trifluoroethyl, cyclopropyl, cyclopropylmethyl, dimethylamino, hydroxy, methoxy, methoxymethyl, oxo, phenyl and benzyl.

8. The compound of formula (I) according to claim 1 wherein $R^2$ is hydrogen.

9. The compound of formula (I) according to claim 1 wherein $R^3$ is hydrogen.

10. The compound of formula (I) according to claim 1 wherein $R^4$ is aryl optionally substituted by one or more $R^{4'}$.

11. The compound of formula (I) according to claim 1 wherein $R^4$ is phenyl optionally substituted with one or two halogen independently selected from fluoro and chloro.

12. The compound of formula (I) according to claim 11, wherein $R^4$ is phenyl.

13. The compound of formula (I) according to claim 1 wherein each $R^{4'}$ is independently selected from fluoro and chloro.

14. The compound of formula (I) according to claim 1 wherein $R^6$ is $C_{1-7}$ alkyl, halo-$C_{1-7}$ alkyl, $C_{3-7}$ cycloalkyl or aryl, each optionally substituted with one $R^{6'}$.

15. The compound of formula (I) according to claim 14, wherein $R^6$ is methyl, ethyl, trifluoroethyl, cyclopropyl, adamantyl, or phenyl, each optionally substituted with one $R^{6'}$.

16. The compound of formula (I) according to claim 15, wherein $R^6$ is trifluoroethyl.

17. The compound of formula (I) according to claim 1, wherein each $R^{6'}$ is independently selected from halo-$C_{1-7}$ alkoxy or phenyl.

18. The compound of formula (I) according to claim 17, wherein each $R^{6'}$ is independently selected from trifluoromethoxy or phenyl.

19. The compound of formula (I) according to claim 1, wherein $R^7$ is hydrogen or $C_{1-7}$ alkyl.

20. The compound of formula (I) according to claim 19, wherein $R^7$ is hydrogen, methyl or isopropyl.

21. The compound of formula (I) according to claim 1 which compound is selected from the group consisting of:

2-[1-(4-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(3-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(2-Fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-(4-Oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

2-(4-Oxo-1-phenyl-8-(1H-pyrazolo[3,4-b]pyridine-5-carbonyl)-1,3,8-triazaspiro[4.5]decan-3-yl)-N-phenyl acetamide;

N-Methyl-2-(4-oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide;

N-(Adamantan-1-yl)-2-(4-oxo-1-phenyl-8-(1H-pyrazolo[3,4-b]pyridine-5-carbonyl)-1,3,8-triazaspiro[4.5]decan-3-yl)acetamide;

2-[4-Oxo-1-phenyl-8-(1H-pyrazolo[3,4-b]pyridine-5-carbonyl)-1,3,8-triazaspiro[4.5]decan-3-yl]-N-propan-2-yl-N-(2,2,2-trifluoroethyl)acetamide;

N,N-Dimethyl-2-[4-oxo-1-phenyl-8-(1H-pyrazolo[3,4-b]pyridine-5-carbonyl)-1,3,8-triazaspiro[4.5]decan-3-yl]acetamide;

1-Phenyl-8-(1H-pyrazolo[3,4-b]pyridine-5-carbonyl)-3-[3-(trifluoromethyl)phenyl]-1,3,8-triazaspiro[4.5]decan-4-one;

3-[2-Fluoro-4-(trifluoromethyl)phenyl]-1-phenyl-8-(1H-pyrazolo[3,4-b]pyridine-5-carbonyl)-1,3,8-triazaspiro[4.5]decan-4-one;

3-(2-Fluoro-4-methylphenyl)-1-phenyl-8-(1H-pyrazolo[3,4-b]pyridine-5-carbonyl)-1,3,8-triazaspiro[4.5]decan-4-one;

4-[4-Oxo-1-phenyl-8-(1H-pyrazolo[3,4-b]pyridine-5-carbonyl)-1,3,8-triazaspiro[4.5]decan-3-yl]benzonitrile;

3-(3-Chlorophenyl)-1-phenyl-8-(1H-pyrazolo[3,4-b]pyridine-5-carbonyl)-1,3,8-triazaspiro[4.5]decan-4-one;

3-(4-Chloro-2-fluorophenyl)-1-phenyl-8-(1H-pyrazolo[3,4-b]pyridine-5-carbonyl)-1,3,8-triazaspiro[4.5]decan-4-one;

3-(5-Chloro-2-fluoro-4-methyl-phenyl)-1-phenyl-8-(1H-pyrazolo[3,4-b]pyridine-5-carbonyl)-1,3,8-triazaspiro[4.5]decan-4-one;

N-(2-fluoroethyl)-2-[4-oxo-1-phenyl-8-(1H-pyrazolo[3,4-b]pyridine-5-carbonyl)-1,3,8-triazaspiro[4.5]decan-3-yl]acetamide;

N-(2,2-difluoroethyl)-2-[4-oxo-1-phenyl-8-(1H-pyrazolo[3,4-b]pyridine-5-carbonyl)-1,3,8-triazaspiro[4.5]decan-3-yl]acetamide;

2-(1-(3-Chlorophenyl)-4-oxo-8-(1H-pyrazolo[3,4-b]pyridine-5-carbonyl)-1,3,8-triazaspiro[4.5]decan-3-yl)-N-(2,2,2-trifluoroethyl)acetamide;

N-[2-(dimethylamino)ethyl]-2-[4-oxo-1-phenyl-8-(1H-pyrazolo[3,4-b]pyridine-5-carbonyl)-1,3,8-triazaspiro[4.5]decan-3-yl]acetamide;

N-[2-(dimethylamino)ethyl]-2-[4-oxo-1-phenyl-8-(1H-pyrazolo[3,4-b]pyridine-5-carbonyl)-1,3,8-triazaspiro[4.5]decan-3-yl]-N-(2,2,2-trifluoroethyl)acetamide;

N-(1-hydroxy-2-methylpropan-2-yl)-2-[4-oxo-1-phenyl-8-(1H-pyrazolo[3,4-b]pyridine-5-carbonyl)-1,3,8-triazaspiro[4.5]decan-3-yl]acetamide;

2-[1-(3-Bromophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[4-Oxo-8-[3-pyrazolo[3,4-b]pyridine-5-carbonyl)-1-[3-(trifluoromethyl)phenyl]-1,3,8-triazaspiro[4.5]decan-3-yl]-N-(2,2,2-trifluoroethyl)acetamide;

2-[1-(3-Chloro-5-fluorophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide;

2-[1-(3-Cyanophenyl)-4-oxo-8-(1H-pyrazolo[3,4-b]pyridine-5-carbonyl)-1,3,8-triazaspiro[4.5]decan-3-yl]-N-(2,2,2-trifluoroethyl)acetamide; or, a pharmaceutically acceptable salt thereof.

22. The compound of claim 21 which compound is 2-(4-Oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide; or N-Methyl-2-(4-oxo-1-phenyl-8-(1H-pyrazolo[3,4-b]pyridine-5-carbonyl)-1,3,8-triazaspiro[4.5]decan-3-yl)-N-(2,2,2-trifluoroethyl)acetamide; or, a pharmaceutically acceptable salt thereof.

23. A pharmaceutical composition comprising a compound of formula (I) according to claim 1 and at least one pharmaceutically acceptable excipient.

\* \* \* \* \*